US010412939B2

(12) United States Patent
Siao et al.

(10) Patent No.: US 10,412,939 B2
(45) Date of Patent: Sep. 17, 2019

(54) RODENT MODEL OF PROSTATE CANCER

(71) Applicant: Regeneron Pharmaceuticals, Inc., Tarrytown, NY (US)

(72) Inventors: Chia-Jen Siao, New York, NY (US); Hoi-Ching Lee, Dumont, NJ (US); Zhe Li, Fort Lee, NJ (US); Ka-Man Venus Lai, Tarrytown, NY (US); Gavin Thurston, Briarcliff Manor, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 222 days.

(21) Appl. No.: 15/254,016

(22) Filed: Sep. 1, 2016

(65) Prior Publication Data

US 2017/0055505 A1 Mar. 2, 2017

Related U.S. Application Data

(60) Provisional application No. 62/213,389, filed on Sep. 2, 2015.

(51) Int. Cl.

*A01K 67/027* (2006.01)
*C12N 5/0735* (2010.01)
*C07K 7/08* (2006.01)
*C12N 15/85* (2006.01)

(52) U.S. Cl.

CPC ...... *A01K 67/0275* (2013.01); *A01K 67/0271* (2013.01); *C07K 7/08* (2013.01); *C12N 5/0606* (2013.01); *A01K 2207/12* (2013.01); *A01K 2217/05* (2013.01); *A01K 2217/052* (2013.01); *A01K 2227/105* (2013.01); *A01K 2267/0331* (2013.01); *A01K 2267/0393* (2013.01); *C07K 2319/50* (2013.01); *C07K 2319/61* (2013.01); *C12N 2015/8572* (2013.01); *C12N 2830/008* (2013.01); *C12N 2830/36* (2013.01)

(58) Field of Classification Search

CPC .................................................. A01K 67/0275
See application file for complete search history.

(56) References Cited

U.S. PATENT DOCUMENTS

2006/0101531 A1 5/2006 Vasioukhin et al.

OTHER PUBLICATIONS

Johnson et al. (2000, The Prostate, vol. 43, pp. 255-262) (Year: 2000).*
Masumori et al. (2001, Cancer Res., vol. 61, pp. 2239-2249) (Year: 2001).*
2004, Barthold S., Genetica, vol. 122, pp. 75-88 (Year: 2004).*
Hong et al. (2012, Stem Cells and Development, vol. 21(9), pp. 1571-1586) (Year: 2012).*
Tong et al. (2010, Nature, vol. 467(7312), pp. 211-213) (Year: 2010).*
Puccini et al. (2013, Cell Death and Differentiation, vol. 20, p. 964) (Year: 2013).*
Heimain-Patterson et al. (2011, Amyotrophic Lateral Schlerosis, vol. 00, pp. 1-8) (Year: 2011).*
Garcia-Arocena D. (2014, The Jackson Laboratory, Same Mutation, Different Phenotype?) (Year: 2014).*
Abbott D.E. et al., "Expressed Sequence Tag Profiling Identifies Developmental and Anatomic Partitioning of Gene Expression in the Mouse Prostate", Genome Biology 4(12):R79 (Nov. 2003).
Duan W. et al., "Knockin of SV40 Tag Oncogene in a Mouse Adenocarcinoma of the Prostate Model Demonstrates Advantageous Features Over the Transgenic Model", Oncogene 24(9):1510-1524 (Feb. 2005).
Ju H-L et al., "Transgenic Mouse Model Expressing P53R172H, Luciferase, EGFP, and KRASG12D in a Single Open Reading Frame for Live Imaging of Tumor", Scientific Reports 5:8053 (Jan. 2015).
Parisotto M. et al., "Genetically Engineered Mouse Models of Prostate Cancer", Molecular Oncology 7:190-205 (Apr. 2013).
Valenzuela D.M. et al., "High-Throughput Engineering of the Mouse Genome Coupled With High-Resolution Expression Analysis", Nature Biotechnology 21(6):652-659 (Jun. 2003).
International Search Report and Written Opinion dated Nov. 15, 2016 received in International Application No. PCT/US2016/049823.
Ahuja D. et al., "SV40 Large T Antigen Targets Multiple Cellular Pathways to Elicit Cellular Transformation", Oncogene 24:7729-7745 (2005).
Berman-Booty L.D. et al., "A Review of the Existing Grading Schemes and a Proposal for a Modified Grading Scheme for Prostatic Lesions in TRAMPMice", Toxicologic Pathology 40:5-17 (2012).
Chiaverotti T. et al., "Dissociation of Epithelial and Neuroendocrine Carcinoma Lineages in the Transgenic Adenocarcinoma of Mouse Prostate Model of Prostate Cancer", The American Journal of Pathology 172(1):236-246 (Jan. 2008).
Gingrich J.R. et al., "Metastatic Prostate Cancer in a Transgenic Mouse", Cancer Research 56:4096-4102 (Sep. 15, 1996).
Grabowska M.M. et al., "Mouse Models of Prostate Cancer: Picking the Best Model for the Question", Cancer Metastasis Rev. 33(0):377-397 (Sep. 2014).
Greenberg N.M. et al., "Prostate Cancer in a Transgenic Mouse", Proc. Natl. Acad. Sci. USA 92:3439-3443 (Apr. 1995).
Hill R. et al., "Heterogeneous Tumor Evolution Initiated by Loss of pRb Function in a Preclinical Prostate Cancer Model", Cancer Research 65(22):10243-10254 (Nov. 15, 2005).

(Continued)

*Primary Examiner* — Thaian N Ton
*Assistant Examiner* — David A. Montanari
(74) *Attorney, Agent, or Firm* — Scully, Scott, Murphy & Presser, P.C.; Yongjin Choi

(57) ABSTRACT

This disclosure provides a rodent model of prostate cancer. The rodents disclosed herein comprise a transgene that provides prostate-specific expression of an oncogenic protein (e.g, an SV40 tumor antigen) under the control of 5' and 3' regulatory regions of a mouse probasin gene. The rodents develop progressive forms of prostate tumor that resemble the development of human prostate cancer.

12 Claims, 9 Drawing Sheets
(8 of 9 Drawing Sheet(s) Filed in Color)

Specification includes a Sequence Listing.

(56) References Cited

OTHER PUBLICATIONS

Irshad S. et al., "Modeling Prostate Cancer in Mice: Something Old, Something New, Something Premalignant, Something Metastatic", Cancer Metastasis Review 32(1):109-122 (Jun. 2013).
Johnson M.A. et al., "Isolation and Characterization of Mouse Probasin: An Androgen-Regulated Protein Specifically Expressed in the Differentiated Prostate", The Prostate 43:255-262 (2000).
Kasper S. et al., "Development, Progression, and Androgen-Dependence of Prostate Tumors in Probasin-Large T Antigen Transgenic Mice: A Model for Prostate Cancer", Laboratory Investigation 78(3):i-xv (Mar. 1998).
Kim J H et al., "High Cleavage Efficiency of a 2A Peptide Derived from Porcine Teschovirus-1 in Human Cell Lines, Zebrafish and Mice", PLos One 6(4):e18556 (Apr. 2011).
Schoenborn J.R. et al., "Genomic Profiling Defines Subtypes of Prostate Cancer With the Potential for Therapeutic Stratification", Clinical Cancer Research 19(15):4058-4066 (Aug. 1, 2013).
Shen M.M. et al., "Molecular Genetics of Prostate Cancer: New Prospects for Old Challenges", Genes & Development 24:1967-2000 (2010).
Sleigh M.J. et al., "Mutants of SV40 With an Altered Small t Protein Are Reduced in Their Ability to Transform Cells", Cell 14:79-88 (May 1978).
Szymczak Al et al., "Development of 2A Peptide-Based Strategies in the Design of Multicistronic Vectors", Expert Opin Biol Ther. 5(5):627-638 (May 2005).
Van Santen V. et al., "Alternative Splicing of SV40 Early Pre-mRNA In Vitro", Nucleic Acids Research 14 (24):9911-9926 (1986).
Wu X. et al., "Current Mouse and Cell Models in Prostate Cancer Research", Endocrine-Related Cancer 20(4):R155-R170 (2013).
GenBank Accession No. AAB59924.1 (7 pages) (Dec. 14, 2000).
GenBank Accession No. AAB59925.1 (7 pages) (Dec. 14, 2000).
GenBank Accession No. J02400.1 (19 pages) (Dec. 14, 2000).

* cited by examiner

Representative prostate pathology in dorsal lateral lobes of Luci-TRAMP mice

Prostate pathology in anterior lobes of Luci-TRAMP mice

Luci-TRAMP

F1H4

Brown-black: anti-E-cadherin (cell-cell junction of epithelial cells)

RODENT MODEL OF PROSTATE CANCER

CROSS REFERENCE TO RELATED APPLICATION

This application claims the benefit of priority of U.S. Provisional Application No. 62/213,389 filed Sep. 2, 2015, the entire contents of which are incorporated herein by reference.

FIELD OF THE DISCLOSURE

This disclosure relates to a rodent model of prostate cancer. The rodents disclosed herein comprise a transgene that includes an SV40 tumor antigen coding sequence, operably linked to 5' and 3' regulatory regions of a mouse probasin gene. The rodents disclosed herein display prostate-specific expression of the transgene and develop progressive forms of prostate tumor that resemble the development of human prostate cancer.

INCORPORATION BY REFERENCE OF SEQUENCE LISTING

The sequence listing in the ASCII text file, named as 32350_10161US01_SequenceListing.txt of 440 KB, created on Aug. 24, 2016, and submitted to the United States Patent and Trademark Office via EFS-Web, is incorporated herein by reference.

BACKGROUND

Animal models of human diseases are important tools for understanding the pathological mechanisms underlying the diseases and for developing effective therapies. Prostate cancer will likely claim the lives of about 30,000 men in the United States this year alone, and more than 200,000 men will be newly diagnosed with the disease. Although mouse models of prostate cancer have been described in the art, they each have limitations. For example, transgenic mice that express an SV40 tumor antigen under the control of a rat probasin promoter exhibited a rapid disease progression, typically displaying prostate intraepithelial neoplasia ("PIN") by 6-12 weeks of age, and invasive carcinoma by 18-22 weeks of age. Such results differ from the characteristically slow development of carcinomas in humans. Further, prominent expression of the transgene has been detected in the ventral lobes in some of the mouse models, an area not analogous to the peripheral zone where human prostate carcinoma typically arises. In addition, the prevalence of neuroendocrine carcinomas in some of the mouse models also limits the relevance of those models to the small subpopulation of patients with neuroendocrine disease.

Therefore, there is a need for improved animal models of prostate cancer that faithfully recapitulate the pathological features of human prostate cancer.

SUMMARY

This disclosure provides a novel rodent model of prostate cancer. The rodents disclosed herein utilize 5' and 3' regulatory regions of a mouse probasin gene to direct prostate-specific expression of an oncogenic protein such as an SV40 tumor antigen or Myc. The rodents develop progressive forms of prostate tumor that recapitulate the development and progression of human prostate cancer.

In one aspect, this disclosure provides a rodent comprising a transgene in the genome, wherein the transgene comprises, from 5' to 3', a 5' regulatory region of a mouse probasin gene, a nucleic acid comprising a first nucleotide sequence encoding an oncogenic protein such as an SV40 tumor antigen or Myc, and a 3' regulatory region of a mouse probasin gene. The 5' regulatory region, the nucleic acid comprising a first nucleotide sequence encoding an oncogenic protein such as an SV40 tumor antigen, and the 3' regulatory region are operably linked to each other to effect prostate-specific expression of the oncogenic protein such as the SV40 tumor antigen or Myc in the rodent.

In some embodiments, the 5' regulatory region in a transgene includes a nucleotide sequence from a mouse probasin locus upstream of the transcriptional initiation site of the mouse probasin gene. In some embodiments, the 5' regulatory region in a transgene includes a nucleotide sequence from a mouse probasin locus immediately upstream of the transcriptional initiation site of the mouse probasin gene. In certain embodiments, the 5' regulatory region in a transgene includes a sequence of at least about 5 kb, 10 kb, or 25 kb upstream (e.g., immediately upstream) of the transcriptional initiation site of the mouse probasin gene. In some embodiments, the 5' regulatory region includes a 5' untranslated region (UTR) of a mouse probasin gene. In specific embodiments, the 5' regulatory region comprises the nucleotide sequence as set forth in SEQ ID NO: 6.

In some embodiments, the 3' regulatory region in a transgene includes a nucleotide sequence from a mouse probasin locus downstream of the transcriptional termination site of the mouse probasin gene. In some embodiments, the 3' regulatory region in a transgene includes a nucleotide sequence from a mouse probasin locus immediately downstream of the transcriptional termination site of the mouse probasin gene. In certain embodiments, the 3' regulatory region includes a sequence of at least about 5 kb, 25 kb, or 50 kb downstream (e.g., immediately downstream) of the transcriptional termination site of a mouse probasin gene. In some embodiments, the 3' regulatory region includes a 3' untranslated region (UTR) of a mouse probasin gene. In specific embodiments, the 3' regulatory region comprises the nucleotide sequence as set forth in SEQ ID NO: 7.

In some embodiments, the nucleic acid sequence encoding an SV40 tumor antigen in a transgene encodes an SV40 large T antigen or a functionally active fragment thereof. In some embodiments, the nucleic acid sequence encoding an SV40 tumor antigen in a transgene encodes an SV40 small t antigen or a functionally active fragment thereof. In other embodiments, the nucleotide sequence encoding an SV40 tumor antigen encodes an SV40 large T antigen or a functional active fragment thereof, and also encodes an SV40 small t antigen or a functional active fragment thereof. In specific embodiments, the nucleotide sequence encoding an SV40 tumor antigen comprises the sequence as set forth in SEQ ID NO: 1.

In some embodiments, the transgene further comprises a reporter gene. In specific embodiments, the reporter is a luciferase. In a particular embodiment, the reporter gene comprises the nucleotide sequence as set forth in SEQ ID NO: 3.

The reporter gene is operably linked to the oncogenic protein (e.g., an SV40 tumor antigen or Myc) coding sequence such that the expression of the reporter protein reflects the expression of the oncogenic protein (such as the SV40 tumor antigen or Myc). In some embodiments, the oncogenic protein (e.g., SV40 tumor antigen) coding sequence in a transgene is linked to a reporter gene in frame via a nucleotide sequence encoding a 2A peptide. In specific embodiments, the 2A peptide is selected from the group consisting of an F2A peptide, an E2A peptide, a P2A peptide and a T2A peptide. In particular embodiments, the 2A peptide is a T2A peptide that comprises the amino acid sequence of SEQ ID NO: 13.

In some embodiments, the transgene can include additional elements, for example, a selectable marker gene or cassette which permits selection and identification of a rodent cell that harbors the transgene.

In some embodiments, the transgene is integrated into an ectopic locus of the rodent gene. In certain embodiments, at least 1-10 copies (i.e., 1, 2, 3, 4, 5, 6, 7, 8, 9, 10 or more copies) of the transgene are integrated in one or more ectopic loci in the genome. In specific embodiments, multiple copies (2, 3, 4, 5, 6, 7, 8, 9, 10 or more copies) of the transgene are integrated in tandem in one ectopic locus in the genome. In a particular embodiment, 5 copies of the transgene are integrated in tandem in one ectopic locus in the genome. In other embodiments, the transgene is integrated into a target locus, e.g., an endogenous probasin locus.

In some embodiments, the rodent provided herein is a mouse or a rat. In specific embodiments, the rodent is a mouse. In some embodiments, the rodent is a mouse of a strain selected from a C57BL strain, a 129 strain, or a hybrid thereof. In specific embodiments, the rodent is a mouse of an F1H4 strain, which is a hybrid of C57BL/6 and 129.

In some embodiments, the rodents provided herein exhibit a combination of any of the expression and pathological features of human prostate cancer described herein, including, for example, the areas where the transgene encoding a reporter (e.g., luciferase) and an oncogenic protein (e.g., SV40 T antigen or Myc) is expressed, the period of time it takes to develop prostate intraepithelial neoplasia (PIN), the areas in the prostate where PIN develops, the period of time it takes to develop prostate adenocarcinoma, the areas in the prostate where adenocarcinoma develops, and the feature that the adenocarcinoma developed is not neuroendocrine carcinoma. In specific embodiments, the rodent begins to display prostate intraepithelial neoplasia in the prostate tissue at about 4-6 months of age. In some embodiments, the rodent begins to display adenocarcinoma at about 7-9 months of age. In certain embodiments, the adenocarcinoma developed in the rodent is not neuroendocrine carcinoma.

In another aspect, this disclosure provides a cell or tissue isolated from the rodent provided herein. Rodent tissues from which a cell can be isolated include, for example, thymus, spleen, gastrointestine, liver, lung, bladder, and prostate.

In still another aspect, this disclosure provides a rodent embryonic stem (ES) cell comprising a transgene in the genome, wherein the transgene comprises, from 5' to 3', a 5' regulatory region of a mouse probasin gene, a nucleic acid encoding an oncogenic protein such as an SV40 tumor antigen or Myc, and a 3' regulatory region of the mouse probasin gene, wherein the 5' regulatory region, the nucleic acid encoding an oncogenic protein such as an SV40 tumor antigen or Myc, and the 3' regulatory region are operably linked to each other. In some embodiments, the rodent ES cell is a mouse ES cell or a rat ES cell.

In a further aspect, this disclosure provides a method for making a rodent model of prostate cancer, comprising introducing into the genome of a rodent ES cell a transgene which comprises, from 5' to 3', a 5' regulatory region of a mouse probasin gene, a nucleic acid encoding an oncogenic protein such as an SV40 tumor antigen or Myc, and a 3' regulatory region of the mouse probasin gene, wherein the 5' regulatory region, the nucleic acid encoding an oncogenic protein such as an SV40 tumor antigen or Myc, and the 3' regulatory region are operably linked to each other, and selecting a modified rodent ES cell comprising the transgene in the genome; introducing the modified rodent ES cell into a host embryo of the rodent at a premorula stage; implanting the host embryo into a surrogate mother, and obtaining the rodent model of prostate cancer.

BRIEF DESCRIPTION OF THE DRAWINGS

The file of this application contains at least one drawing executed in color. Copies of this patent with color drawing(s) will be provided by the Patent and Trademark Office upon request and payment of the necessary fee.

In FIG. 3A, the F1H4 WT control mice did not exhibit any bioluminescence as they aged, while the luci-TRAMP mice showed increasing bioluminescence in their abdominal area as they aged. FIG. 3B is a representative example (mouse ID#1255743) of this abdominal bioluminescence, and, at 11 months of age, the bilateral urogenital expression of the luciferase gene is very obvious. The WT F1H4 control showed no bioluminescence, while the second control mice (R26-L-Luc2) showed bioluminescence in all organs and at all ages because the luciferase gene was expressed from the ubiquitous ROSA26 (R26) promoter. FIG. 3C shows detection of the luciferase gene in the lung and possibly liver and bone marrow (BM). qPCR assays (same as described in FIG. 2) were performed using indicated tissues, and the results showed that there was significant T-antigen transgene signal detected in the Luci-TRAMP lungs compared with either control strain lungs. The signals from Luci-TRAMP BM and liver were lower than the lungs, but statistically significant as compared with control tissues. The Luciferase qPCR results demonstrated statistically significant signals from the Luci-TRAMP lungs compared with F1H4 lungs. BM and liver signals were elevated from WT tissues but did not reach statistical significance. The results from R26-L-Luc2 mouse overwhelmed the signals from the Luci-TRAMP mice, and were omitted from the graph.

FIG. 4A shows prostatic intraepithelial neoplasia (PIN grades are listed in the labels for each sub-panel) from dorsolateral prostate lobes of luci-TRAMP mice. By 8 months of age, the hyperplasia have progressed to adenocarcinoma, albeit with intact basal borders. By 11 months of age, the stroma of the prostate became more and more infiltrated with stromal cells (possibly immune in character). In contrast, the WT F1H4 prostates showed some age-related hyperplasia at 11-16 months of age, but never to the point of luci-TRAMP prostates. FIG. 4B shows similar progression of luci-TRAMP anterior lobes from high-grade PIN to adenocarcinoma, compared with similar normal prostate epithelium in the WT control mice.

FIG. 5A shows immunostaining of prostate tissue samples using an anti-E-cadherin antibody. The brown-black deposition indicates where the antibody was specifically reacting with the protein which is expressed by luminal epithelial cells. FIG. 5B shows immunostaining of prostate tissue samples using an anti-synaptophysin antibody. The brown reaction product in the pancreas indicates islet cells which are neuroendocrine in nature. In contrast, neither the F1H4 WT nor the luci-TRAMP prostates of either lobe (DLP or AP) showed specific brown reaction product. The immunohistochemical protocol was performed according to standard procedures: paraffin sections were cut, deparaffinized, and reacted with the indicated antibody. A secondary antibody, against the host of the primary antibody and coupled to horseradish peroxidase was used to amplify the specific interaction. DAB [FIG. 5B] was used to visualize the immune complex.

Figure 1:
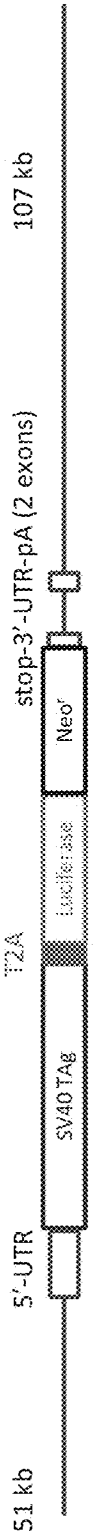
FIG. 1 depicts an example of a transgene and its components used in making a mouse model of prostate cancer. The transgene comprises, from 5' to 3', a 5' regulatory region of about 51 kb from a mouse probasin gene, a nucleic acid sequence encoding an SV40 tumor antigen, a nucleic acid sequence encoding a T2A peptide, a nucleic acid sequence encoding a luciferase reporter, a neomycin selection cassette, and a 3' regulatory region of about 107 kb from a mouse probasin gene.

SEQ ID NOS: 1-17 are summarized below, and the sequences are set forth at the end of this disclosure.

1 SV-40 T antigen coding sequence (encoding large T and small t antigens)
2 T2A coding sequence
3 Luciferase coding sequence
4 SV-40 late poly (A) sequence
5 Neomycin selection cassette
6 51 kb 5' regulatory region sequence of a mouse probasin gene
7 107 kb 3' regulatory region sequence of a mouse probasin gene
8 Amino acid sequence of SV40 Large T Antigen (GenBank: AAB59924.1)
9 Amino acid sequence of SV40 small t antigen (GenBank: AAB59925.1)
10 Amino acid sequence of peptide F2A
11 Amino acid sequence of peptide E2A
12 Amino acid sequence of peptide P2A
13 Amino acid sequence of peptide T2A
14 The LXCXE motif
15 Complete nucleotide sequence of a SV40 Tag-T2A-Luciferse transgene
16 5' sequence including the 5' untranslated region (5' UTR) of a mouse probasin gene
17 3' sequence including the 3' untranslated region (3' UTR) of a mouse probasin gene

DETAILED DESCRIPTION

This disclosure provides a novel rodent model of prostate cancer. The rodents disclosed herein contain a transgene that includes an oncogene or a nucleotide sequence encoding an oncogenic protein (such as an SV40 tumor antigen or Myc), operably linked to 5' and 3' regulatory regions of a mouse probasin gene. The rodents display prostate-specific expression of the transgene, and develop progressive forms of prostate tumor that resemble the development of human prostate cancer.

Transgenic mouse models of prostate cancer based on expression of SV40 tumor antigens driven by a rat probasin promoter have been described in the art. However, these transgenic mouse models have a number of limitations. For example, the transgenic mice generally have a rapid disease progression, typically displaying prostate intraepithelial neoplasia ("PIN") by 6-12 weeks of age, and invasive carcinoma by 18-22 weeks of age. The results differ from the characteristically slow development of carcinomas in humans. Further, prominent expression of the transgene has been detected in the ventral lobes in some of the mouse models, an area not analogous to the peripheral zone where human prostate carcinoma typically arises. In addition, the prevalence of neuroendocrine carcinomas in some of the mouse models also limits the relevance of those models to the small subpopulation of patients with neuroendocrine disease.

The rodents disclosed herein better recapitulate the pathological events occurring in human prostate cancer than the existing mouse models. For example, predominant expression of the transgene is detected in the dorsolateral lobes of the prostate in the rodents provided herein, an area analogous to the peripheral zone of human prostate where human prostate adenocarcinoma typically arises. Furthermore, the rodents provided herein develop progressive forms of prostate tumor that resemble the various stages of human prostate tumor, ranging from hyperplasia to high grade prostate intraepithelial neoplasia (or "HGPIN") to invasive adenocarcinoma, with a much slower rate of disease progression and longer life span than the transgenic mice reported in the art. In addition, adenocarcinoma developed in the rodent disclosed herein is not neuroendocrine in nature.

Without intending to be bound by any particular theory, it is believed that a 5' regulatory region and/or a 3' regulatory region of a mouse probasin gene, included in the transgene to direct the expression of an SV40 tumor antigen, may be an important factor for the observed advantages of the rodent model of this disclosure.

Transgene

The term "transgene" includes a nucleic acid molecule that is genetically engineered for introduction into a chromosome or extrachromosomal DNA of a recipient organism. "Transgene" also includes an exogenous nucleic acid integrated into a chromosomal or extrachromosomal DNA of an organism.

The transgenes disclosed herein for purposes of generating a transgenic rodent include from 5' to 3', a 5' regulatory region of a mouse probasin gene, a nucleic acid sequence encoding an SV40 tumor antigen, and a 3' regulatory region of a mouse probasin gene, operably linked to one another to effect prostate-specific expression of the SV40 tumor antigen in the rodent.

In some embodiments, the transgene includes additional elements, such as a reporter gene and a selectable marker gene, among others.

The term "operably linked" includes a linkage of nucleic acid elements in a functional relationship. A nucleic acid sequence is "operably linked" when it is placed into a functional relationship with another nucleic acid sequence. For instance, a promoter or enhancer, or a 5' regulatory region containing a promoter or enhancer, is operably linked to a coding sequence if it effects the transcription of the coding sequence. In the context of this disclosure, a 5' regulatory region of a mouse probasin gene and a 3' regulatory region of a mouse probasin gene are operably linked to a nucleic acid sequence encoding an SV40 tumor antigen to effect the initiation and termination of transcription of the nucleic acid encoding the SV40 tumor antigen.

The transgenes disclosed herein can be made using known methods. For example, a transgene can be assembled using bacterial homologous recombination and VELOCIGENE® technology (see, e.g., U.S. Pat. No. 6,586,251 and Valenzuela et al., High-throughput engineering of the mouse genome coupled with high-resolution expression analysis, 2003, *Nature Biotech.* 21(6):652-659). An example of a transgene provided herein comprises the nucleotide sequence as set forth in SEQ ID NO: 15.

The various elements of transgenes suitable for use in generating a rodent model of prostate cancer are described in further details below.

5' and 3' Regulatory Regions of a Mouse Probasin Gene

Probasin is a prostate-specific gene originally isolated from rat. The promoter of the rat probasin (rPB) gene has been shown to be capable of targeting heterologous genes specifically to the prostate in transgenic mice (Greenberg et al., *Proc. Natl. Acad. Sci. USA* 92: 3439-3443, 1995; Kasper et al., *Lab. Invest.* 78 (3): i-xv, 1998; Hill et al., *Cancer Res.* 65(22): 10243-10254, 2005). In these studies, the promoter region utilized is limited to a relatively short segment from the 5' region of the rat probasin gene (a 454 bp fragment (−426/+28) in Greenberg et al. (1995); a 11.5 kb fragment in Kasper et al. (1998); and a 458 bp fragment (−458) in Hill et al. (2005)).

In accordance with this disclosure, a 5' regulatory region and a 3' regulatory region from a mouse probasin gene are included in a transgene to direct prostate-specific expression of an SV40 tumor antigen.

By "prostate-specific expression" it is meant that the expression in the prostate is substantially higher than the expression in non-prostate tissues and organs, or the expression in non-prostate tissues and organs is insignificant compared to the expression in the prostate. By "substantially higher" it is meant that the expression in the prostate is at least 50%, 100%, 200%, 300%, 400%, 500%, 600%, 700%, 800%, 900%, or 1000%, higher than the expression in other tissues and organs. By "insignificant" it is meant that the expression in each such other tissue is not more than 20%, 10%, 5%, or 1% of the expression in the prostate.

The 5' and the 3' regulatory regions for use in a transgene herein include regulatory elements found in the 5' upstream region and the 3' downstream region of a mouse probasin gene and are sufficient to confer prostate-specific expression of a heterologous gene such as an SV40 tumor antigen coding sequence.

The term "regulatory elements" includes transcriptional regulatory sequences, which include both 5' transcriptional regulatory sequences such as promoter, enhancer, and suppressor elements, and 3' transcriptional regulatory sequences such as a transcriptional termination sequence. The term "regulatory elements" also includes regulatory sequences in the 5' untranslated region (5' UTR) and the 3' UTR that may affect the efficiency of transcription and the stability of transcript, as well the initiation of translation.

In accordance with this disclosure, the 5' regulatory sequence flanking the SV40 tumor antigen coding sequence in a transgene includes a nucleotide sequence from a mouse probasin locus upstream of the translational start (or start codon ATG) of the mouse probasin gene. In some embodiments, the 5' regulatory sequence flanking the SV40 tumor antigen coding sequence in a transgene includes a nucleotide sequence from a mouse probasin locus immediately upstream of the transcriptional start (or transcription initiation site) of the mouse probasin gene. The phrase "immediately upstream of the transcriptional start" means that the sequence (e.g., the 5' regulatory sequence) is upstream and within 35, 30, 25, 20, 15, 10, 5, 2, or 1 bp of the transcriptional start site of a mouse probasin gene. In some embodiments, the 5' regulatory sequence flanking the SV40 tumor antigen coding sequence in a transgene includes a sequence of about 1 kb, 2 kb, 3 kb, 4 kb, 5 kb, 6 kb, 7 kb, 8 kb, 9 kb, or 10 kb upstream (e.g., immediately upstream) of the transcriptional start of a mouse probasin gene. In other embodiments, the 5' sequence flanking the SV40 tumor antigen coding sequence includes a sequence of at least 10 kb, 11 kb, 12 kb, 13 kb, 14 kb, 15 kb, 16 kb, 17 kb, 18 kb, 19 kb, or 20 kb upstream (e.g., immediately upstream) of the transcriptional start of a mouse probasin gene. In still other embodiments, the 5' regulatory sequence flanking the SV40 tumor antigen coding sequence includes a sequence of at least 15 kb, 20 kb, 25 kb, 30 kb, 35 kb, 40 kb, 45 kb, or 50 kb upstream (e.g., immediately upstream) of the transcriptional start of a mouse probasin gene. In specific embodiments, the 5' sequence flanking the SV40 tumor antigen coding sequence includes a sequence of at least about 45 kb, 46 kb, 47 kb, 48 kb, 49 kb, or 50 kb upstream (e.g., immediately upstream) of the transcriptional start of a mouse probasin gene.

In some embodiments, the 5' regulatory sequence flanking the SV40 tumor antigen coding sequence in a transgene also includes a 5' UTR sequence of a mouse probasin gene. In certain embodiments, the 5' sequence flanking the SV40 tumor antigen coding sequence includes the entire 5' UTR sequence of a mouse probasin gene. In specific embodiments, the 5' UTR sequence of a mouse probasin gene included in the 5' regulatory sequence flanking the SV40 tumor antigen coding sequence comprises the nucleotide sequence as set forth in nucleotides 329-469 or 427-469 of SEQ ID NO: 16.

In specific embodiments, the 5' regulatory sequence flanking the SV40 tumor antigen coding sequence in a transgene comprises the polynucleotide sequence as set forth in SEQ ID NO: 6, a sequence having a substantial identity thereto, or a fragment thereof.

By "substantially identical" in the context of comparing two sequences, it is meant that the subject sequence has a sequence identity of at least 75%, 80%, 85%, 90%, 95%, 98% or greater to a reference sequence.

In certain embodiments, the 5' regulatory sequence flanking the SV40 tumor antigen coding sequence in a transgene comprises the polynucleotide sequence as set forth in SEQ ID NO: 6. In other embodiments, the 5' regulatory sequence flanking the SV40 tumor antigen coding sequence comprises a fragment of at least 15 kb, 20 kb, 25 kb, 30 kb, 35 kb, 40 kb, 45 kb, or 50 kb in length of SEQ ID NO: 6, preferably a fragment of any of the above mentioned lengths measured from the 3' end of SEQ ID NO: 6.

In accordance with this disclosure, the 3' regulatory sequence flanking the SV40 tumor antigen coding sequence in a transgene includes a nucleotide sequence from a mouse probasin locus downstream of the translational termination site of the mouse probasin gene. In some embodiments, the 3' regulatory sequence flanking the SV40 tumor antigen coding sequence in a transgene includes a nucleotide sequence from a mouse probasin locus immediately downstream of the transcriptional termination site of the mouse probasin gene. The phrase "immediately downstream of the transcriptional termination site" means that the sequence (e.g., the 3' regulatory sequence) is downstream and within 35, 30, 25, 20, 15, 10, 5, 2, or 1 bp of the transcriptional termination site of a mouse probasin gene.

In some embodiments, the 3' regulatory sequence flanking the SV40 tumor antigen coding sequence in a transgene includes a sequence of at least 500 bp, 1 kb, 2 kb, 3 kb, 4 kb, 5 kb, 6 kb, 7 kb, 8 kb, 9 kb, or 10 kb downstream (e.g., immediately downstream) of the transcriptional termination of a mouse probasin gene. In specific embodiments, the 3' sequence flanking the SV40 tumor antigen coding sequence includes a sequence of at least 10 kb, 20 kb, 30 kb, 40 kb, 50 kb, 60 kb, 70 kb, 80 kb, 90 kb or 100 kb downstream (e.g., immediately downstream) of the transcriptional termination of a mouse probasin gene. In other embodiments, the 3' sequence flanking the SV40 tumor antigen coding sequence includes a sequence of about 100 kb, 101 kb, 102 kb, 103 kb, 104 kb, 105 kb, 106 kb, or 107 kb downstream (e.g., immediately downstream) of the transcriptional termination of a mouse probasin gene.

In some embodiments, the 3' sequence flanking the SV40 tumor antigen coding sequence also includes a 3' UTR sequence of a mouse probasin gene. In certain embodiments, the 3' sequence flanking the SV40 tumor antigen coding sequence includes the entire 3' UTR sequence and an intron of a mouse probasin gene. In specific embodiments, the 3' sequence that includes the 3' UTR and an intronic sequence of a mouse probasin gene is set forth in nucleotides 4-3982 of SEQ ID NO: 17.

In specific embodiments, the 3' sequence flanking the SV40 tumor antigen coding sequence comprises the polynucleotide sequence as set forth in SEQ ID NO: 7, a sequence having a substantial identity thereto, or a fragment thereof.

In certain embodiments, the 3' sequence flanking the SV40 tumor antigen coding sequence comprises the polynucleotide sequence as set forth in SEQ ID NO: 7. In other embodiments, the 3' sequence flanking the SV40 tumor antigen coding sequence comprises a fragment of at least 20 kb, 30 kb, 40 kb, 50 kb, 60 kb, 70 kb, 80 kb, 90 kb, 100 kb, or 105 kb in length of SEQ ID NO: 7, preferably a fragment of any of the above mentioned lengths measured from the 5' end of SEQ ID NO: 7.

SV40 Tumor Antigen

In many embodiments, an oncogene or a nucleic acid encoding an oncogenic protein is used in this disclosure. In some embodiments, the oncogene is Myc (Grabowska et al., *Cancer Metastasis Rev.* 2014 September; 33(0): 377-397). In other embodiments, the oncogenic protein is an SV40 tumor antigen.

The simian virus 40 (SV40) genome consists of 5243 bp (see, e.g., GenBank Accession No. J02400.1) and is divided into three regions: an early coding region, a late coding region, and a regulatory region (Ahuja et al., *Oncogene* 24: 7729-7745 (2005)). The early coding region encodes three proteins that are expressed early in a productive infection: the large T antigen, the small t antigen, and the 17K T antigen (Ahuja et al. (2005), supra). The large T antigen and the small t antigen are produced from two mRNAs generated through alternative splicing from a common pre-mRNA transcript (van Santen et al., *Nucleic Acid Res.* 14 (24): 9911-9926 (1986). It has been established that the inhibition by the SV40 large T antigen of the p53 and retinoblastoma (Rb) family of tumor suppressors, and the action by the SV40 small t antigen on the pp2A phosphatase, are important to SV40 induced transformation (Ahuja et al. (2005), supra). Expression of SV40 tumor antigens, including truncated large T antigens, in transgenic mice, results in development of hyperplasia and carcinoma (Ahuja et al. (2005), supra; Hill et al., *Cancer Res.* 65: 10243-54, 2005).

The SV40 large T antigen consists of 708 amino acids, and the small t antigen consists of 174 amino acids. Both the large T and small t antigens share a J domain located in the N-terminal region of the proteins. The large T antigen has a number of additional domains including a Rb-protein-binding motif (LXCXE, SEQ ID NO: 14), and a nuclear localization signal (NLS). The small t antigen has a pp2A binding domain following the J domain. See Ahuja et al. (2005), supra.

The term "SV40 tumor antigen" includes a full-length (i.e., wild type) SV40 large T antigen or a functional active fragment thereof, a full-length (i.e., wild type) SV40 small t-antigen or a functional active fragment thereof, or a combination thereof. In other words, the nucleic acid sequence in a transgene encoding an SV40 tumor antigen can encode a full-length SV40 large T antigen or a functionally active fragment thereof (without a small t antigen), a full-length SV40 small t-antigen or a functionally active fragment thereof (without a large T antigen), or a combination thereof (e.g., the nucleic acid sequence codes for both an SV40 large T antigen and an SV40 small t antigen).

The term "functionally active fragment" refers to a fragment of a T antigen having one or more functions associated with a full-length (wild type) T antigen; for example, the function of a full-length T antigen associated with inducing transformation, or with initiating, promoting or sustaining tumor formation; the function of a large T antigen in inhibiting the activity of p53 or Rb; or the function of a small t antigen in binding and acting on pp2A. An example of a functional active fragment of a T antigen is the truncated large T antigen described in Hill et al. (2005), supra, which includes only the N-terminal 121 amino acids of a wild type large T antigen (without a small t antigen), also referred to as "T121." The T121 mutant antigen, which includes the J domain and the pRb-binding domain, is found sufficient to inactivate the pRb family proteins and to produce PIN and adenocarcinoma in mice (Hill et al. (2005), supra).

Other mutant SV40 T antigens have been described that also maintain the function of a wild-type SV40 T antigen in initiating, promoting or sustaining tumor formation. For example, an SV40 gene deletion mutant described by Kasper et al. (*Lab Invest.* 78 (3): i-xv, 1998) expresses only the large T antigen without the small t antigen and was also found to induce PIN and adenocarcinoma in mice.

In accordance with some embodiments, the nucleic acid sequence encoding an SV40 tumor antigen in a transgene encodes a full-length SV40 large T antigen or a functional active fragment thereof, without also encoding a small t-antigen. In certain embodiments, the large T antigen comprises the amino acid sequence of SEQ ID NO: 8 or a sequence substantially identical thereto. In specific embodiments, the nucleic acid sequence encoding an SV40 tumor antigen encodes a large T antigen comprising the amino acid sequence of SEQ ID NO: 8. In other specific embodiments, the nucleic acid sequence encoding an SV40 tumor antigen codes for a truncated large T antigen comprising the first 121 amino acids of SEQ ID NO: 8.

In some embodiments, the nucleic acid sequence encoding an SV40 tumor antigen in a transgene encodes a full-length SV40 small t antigen or a functional active fragment thereof, without also encoding a large T antigen. In certain embodiments, the small t antigen comprises the amino acid sequence of SEQ ID NO: 9 or a sequence substantially identical thereto. In specific embodiments, the nucleic acid sequence encoding an SV40 tumor antigen encodes a small t antigen having the amino acid sequence of SEQ ID NO: 9.

In still other embodiments, the nucleic acid sequence encoding an SV40 tumor antigen in a transgene encodes both a full-length SV40 large T antigen or a functional active fragment thereof, and a full-length SV40 small t-antigen or a functional active fragment thereof. In certain embodiments, the nucleic acid sequence encoding an SV40 tumor antigen encodes both a full-length SV40 large T antigen and a full-length SV40 small t-antigen. In a specific embodiment, the nucleic acid encoding an SV40 tumor antigen comprises the nucleotide sequence set forth in SEQ ID NO: 1 or a nucleotide sequence substantially identical thereto.

Reporter

In some embodiments, the transgenes disclosed herein also include a reporter gene encoding a reporter protein (or "reporter") that provides or is capable of generating a detectable signal. Suitable reporters for use in this disclosure include β-galactosidase, mPlum, mCherry, tdTomato, mStrawberry, J-Red, DsRed, mOrange, mKO, mCitrine, Venus, YPet, yellow fluorescent protein (YFP), enhanced yellow fluorescent protein (EYFP), Emerald, green fluorescent protein (GFP), enhanced green fluorescent protein (EGFP), CyPet, cyan fluorescent protein (CFP), Cerulean, T-Sapphire, luciferase, alkaline phosphatase, or a combination thereof.

In certain embodiments, the reporter is a luciferase. The term "luciferase" includes the class of oxidative enzymes that catalyze an oxidation reaction of the substrate, luciferin, and bioluminescence is emitted as a result of the oxidation reaction. Luciferases suitable for use herein include firefly luciferase from the firefly species *Photinus pyralis*, luciferases from other organisms, and functional derivatives thereof (such as functional derivatives made by genetic engineering techniques). A "functional derivative" of a wild type (or naturally-occurring) luciferase includes proteins that differ from a wild type luciferase by having one or more amino acid modifications (e.g., additions, deletions, or substitutions) and that substantially retain the enzymatic activity of the wild type luciferase. The phrase "substantially retain the enzymatic activity of the wild type luciferase" includes a difference in both directions of not more than 30%, 25%, 20%, 15%, 10%, 5, 2% or 1% when a functional derivative and a wild type luciferase are compared in their enzymatic activities. In some embodiments, a functional derivative of a wild type luciferase has an amino acid sequence substantially identical to the amino acid sequence of the wild type luciferase. In a specific embodiment, the reporter gene encodes a luciferase and comprises the nucleotide sequence as set forth in SEQ ID NO: 3 or a nucleotide sequence substantially identical to SEQ ID NO: 3.

Linkage Between an SV40 Tumor Antigen Coding Sequence and a Reporter Gene

A reporter gene sequence is placed in a transgene in operable linkage with a nucleic acid sequence encoding an SV40 tumor antigen, such that the expression of the reporter reflects and coincides with the expression of the SV40 tumor antigen. Operable linkage between an SV40 tumor antigen coding sequence and a reporter nucleic acid can be achieved in a number of ways known in the art, such as through the use of multicistronic expression strategies. Multicistronic expression vectors simultaneously express two or more separate proteins from the same mRNA (i.e., a transcript produced from the same promoter). Suitable strategies for multicistronic expression of proteins include the use of a 2A peptide and the use of an internal ribosome entry site ("IRES").

In some embodiments, an SV40 tumor antigen coding sequence and a reporter gene are linked to each other via a nucleic acid sequence encoding a 2A peptide. The SV40 tumor antigen coding sequence can be placed at the N-terminus of a 2A peptide coding sequence, and the reporter gene is placed at the C-terminus of the 2A peptide coding sequence. Alternatively, the SV40 tumor antigen coding sequence can be placed at the C-terminus of a 2A peptide coding sequence, and the reporter gene is placed at the N-terminus of the 2A peptide coding sequence.

2A peptides are small "self-cleaving" peptides, generally having 18-22 amino acids in length. It has been demonstrated that ribosomes skip the synthesis of a glycyl-prolyl peptide bond at the C-terminus of a 2A peptide, leading to the cleavage between a 2A peptide and its immediate downstream peptide (Kim et al., *PLoS One* 2011; 6(4): e18556). As a result, the "cleaved-off" downstream peptide has proline at its N-terminus. 2A-mediated cleavage is a universal phenomenon in all eukaryotic cells. 2A peptides have been identified from picornaviruses, insect viruses and type C rotaviruses (Szymczak et al., "*Development of* 2A peptide-based strategies in the design of multicistronic vectors," Expert Opin Biol Ther 5: 627-638 (2005)) and are suitable for use in this disclosure. In certain embodiments, the 2A peptide used in linking the SV40 tumor antigen and the reporter protein is a 2A peptide selected from FMDV 2A ("F2A"), equine rhinitis A virus (ERAV) 2A ("E2A"), porcine teschovirus-1 2A ("P2A"), or Thoseaasigna virus 2A ("T2A"). In particular embodiments, these 2A peptides have the following sequences:

```
F2A
                                    (SEQ ID NO: 10)
VKQTLNFDLLKLAGDVESNPGP

E2A
                                    (SEQ ID NO: 11)
QCTNYALLKLAGDVESNPGP

P2A
                                    (SEQ ID NO: 12)
ATNFSLLKQAGDVEENPGP

T2A
                                    (SEQ ID NO: 13)
EGRGSLLTCGDVEENPGP
```

In some embodiments, a T2A peptide is used to provide a linkage between an SV40 tumor antigen and a reporter protein. In one embodiment, the T2A peptide used herein comprises the amino acid sequence of SEQ ID NO: 13. In a specific embodiment, the T2A peptide is encoded by the nucleotide sequence of SEQ ID NO: 2.

In other embodiments, an SV40 tumor antigen coding sequence and a reporter nucleic acid sequence are linked to each other via an Internal Ribosome Entry Site (IRES). An IRES is a nucleotide sequence well documented in the art that allows for translation initiation in the middle of a mRNA, thereby providing translation of two or more protein products from a single mRNA molecule.

Other Elements in a Transgene

In some embodiments, the transgenes provided herein also include a nucleic acid sequence encoding a selection marker. Such selection markers include, but are not limited to, neomycin phosphotransferase (neo), hygromycin B phosphotransferase (hyg), puromycin-N-acetyltransferase (puro), blasticidin S deaminase (bsr), xanthine/guanine phosphoribosyl transferase (gpt), or herpes simplex virus thymidine kinase (HSV-k), or a combination thereof.

The selection marker nucleic acid can be contained in an expression cassette, wherein the nucleic acid sequence encoding the selection marker is operably linked to one or more promoters active in desired cells—for example, two promoters, with one active in a rodent cell such as a rodent ES cell, and the other active in a bacterial cell.

In some embodiments, the nucleic acid sequence encoding the selection marker is flanked with site-specific recombination target sequences that permit removal of the nucleic acid sequence between the site-specific recombination target sequences (e.g., the selection marker nucleic acid) following integration of a transgene. Site-specific recombination target sequences, which can flank the selection marker nucleic acid or any polynucleotide of interest can include, but are not limited to, loxP, lox511, lox2272, lox66, lox71, loxM2, lox5171, FRT, FRT11, FRT71, attp, att, rox, and a combination thereof.

In particular embodiments, the transgenes provided herein include a neomycin selection cassette that contains, from 5' to 3', a loxP (5') sequence, a TATA box-hUb (human ubiquitin promoter, an EM7 promoter, a neomycin phosphotransferase coding sequence, a polyA sequence, and a loxP (3') sequence. In a specific embodiment, the neomycin selection cassette comprises the nucleotide sequence as set forth in SEQ ID NO: 5 or a sequence substantially identical thereto. Once an ES cell clone comprising the transgene is selected, the neomycin selection cassette can be excised by introducing a Cre recombinase, e.g., via electroporation. Alternatively, the neomycin selection cassette can be removed by crossing the progeny generated from the ES clone with a deletor rodent strain that expresses a Cre recombinase.

In some embodiments, the transgenes provided herein also include an SV40 late region poly A sequence, placed at the 3' side of the SV40 tumor antigen coding sequence; and if a reporter nucleic acid is present, at the 3' side of the reporter nucleic acid. In a specific embodiment, the SV40 late region poly A sequence comprises the nucleotide sequence as set forth in SEQ ID NO: 4 or a sequence substantially identical thereto.

Rodent Models of Prostate Cancer

Rodents are provided that contain in their genome a transgene encoding an SV40 tumor antigen, operably linked to 5' and 3' regulatory regions of a mouse probasin gene. Such rodents express the transgene specifically in the prostate and display progressive forms of prostate tumors that resemble the development of human prostate cancer.

Transgenic mouse models of prostate cancer have been described in the art. For example, a transgenic adenocarcinoma of the mouse prostate (TRAMP) model has been described by Greenberg et al. (1995), supra, and Gingrich et al. (*Cancer Res.* 56: 4096-4102, 1996), and utilizes a prostate-specific rat probasin minimal promoter (−427/+28 bp) to drive expression of SV40 large T- and small t-antigens. The transgene is specifically expressed in the prostatic epithelium of TRAMP mice, with expression at significantly higher levels in the ventral lobes as compared to the dorsal, lateral and anterior lobes of the prostate (FIG. 1 of Greenberg et al. (1995)). TRAMP mice develop prostate intraepithelial neoplasia (PIN) by 6-12 weeks of age, which progresses to poorly differentiated and invasive adenocarcinoma in the dorsolateral lobes of the prostate by 20-24 weeks of age (Greenberg et al. (1995)). Adenocarcinomas formed in TRAMP mice develop metastases to distant sites (e.g., lymph nodes and lungs) (Gingrich et al. (1996), supra), but rarely to bone. A majority of adenocarcinomas developed in TRAMP mice are neuroendocrine in origin (Chiaverotti et al., *Am J Pathol.* 172(1): 236-246, 2008), a type of carcinoma representing only 10% of human prostate cancer patients. A TRAMP model derivative is described by Hill et al. (2005), supra, and utilizes a truncated rat probasin promoter segment (−458 bp) with two adenine and uridine-rich elements (or "AREs") replaced to drive expression of a truncated SV40 large T antigen. The transgene is expressed in the dorsal, anterior and ventral lobes of the prostate. Such TRAMP derivative mice develop PIN by 2 months of age, which progresses to carcinoma by 4 months of age. A LADY transgenic mouse model of prostate cancer is described by Kasper et al. (1998), supra, and utilizes a larger (11.5 kb) rat probasin promoter segment to drive a truncated SV40 large T-antigen, which leads to transgene expression in the prostate. LADY mice develop glandular hyperplasia and PIN by 5-10 weeks of age, followed by high-grade epithelial dysplasia and poorly undifferentiated adenocarcinoma by 20 weeks, primarily in the dorsolateral and anterior lobes of the prostate. LADY mice rarely develop metastasis to other organs. All of these transgenic mouse models have a rapid rate of disease progression, which differs from the characteristically slow development of carcinomas in humans. The prevalence of neuroendocrine carcinomas in TRAMP mice also limits the relevance of this mouse model to the small subpopulation of patients with neuroendocrine disease.

The rodents provided herein better recapitulate the pathological features of human prostate cancer than the models described in the art. For example, predominant expression of the transgene is detected in the dorsolateral lobes of the rodents, the area analogous to the peripheral zone of human prostate where human prostate adenocarcinoma typically arises. Furthermore, the rodents provided herein develop progressive forms of prostate tumors that resemble the various stages of human prostate cancer, ranging from hyperplasia to high grade prostate intraepithelial neoplasia (or "HGPIN") to adenocarcinoma, with a much slower rate of disease progression and longer life span as compared to TRAMP and LADY mice reported in the art. In addition, adenocarcinoma developed in the rodents disclosed herein is not neuroendocrine in nature.

In some embodiments, the transgene is expressed in the dorsolateral lobes and/or anterior lobes of the prostate of rodents. In some embodiments, the expression of the transgene in the dorsolateral lobes and/or anterior lobes is higher than in the ventral lobes of the prostate. In specific embodiments, the expression of the transgene in the dorsolateral lobes, the anterior lobes, or in the dorsolateral and anterior lobes combined, is substantially higher (i.e., at least 30%, 40%, 50%, 75%, 100% or greater) than the expression in the ventral lobes.

The rodents provided herein develop prostate intraepithelial neoplasia, or "PIN". PIN is typically characterized by proliferation of atypical cells within pre-existing glandular spaces without invasion (i.e., the basement membrane has not been breached). In some embodiments, the rodents begin to display PIN at about 3-7 months of age, or about 4-6 months of age. In certain embodiments, the rodents do not display PIN until at least about 2, 3, 4, 5 or 6 months of age. In some embodiments, the PIN developed in the rodents is in the dorsolateral lobes, or the dorsolateral and anterior lobes of the prostate. In specific embodiments, the PIN developed in the rodents is substantially in the dorsolateral and/or anterior lobes of the prostate, but substantially not in the ventral lobes of the prostate. The term "substantially"

means that at least 50%, 60%, 70%, 80%, 90% or greater of areas displaying PIN are in the dorsolateral and/or anterior lobes of the prostate, with not more than 50%, 40%, 30%, 20%, 10% or less of areas displaying PIN are in the ventral lobes of the prostate.

The rodents provided herein develop prostate adenocarcinoma. Adenocarcinoma is generally characterized by infiltrative and/or destructive proliferation of atypical cells. Generally speaking, the atypical cells have some degree of glandular differentiation. In some embodiments, the rodents begin to display prostate adenocarcinoma at about 7-9 months of age, or at about 8 months of age. In certain embodiments, the rodents do not display adenocarcinoma until at least about 6, 7, 8, 9 or 10 months of age. In some embodiments, the adenocarcinoma developed in the rodents is in the dorsolateral lobes, or dorsolateral and anterior lobes of the prostate. In specific embodiments, the adenocarcinoma developed in the rodents is substantially in the dorsolateral and/or anterior lobes of the prostate, but substantially not in the ventral lobes of the prostate. The term “substantially” means that at least 50%, 60%, 70%, 80%, 90% or greater of areas displaying adenocarcinoma are in the dorsolateral and/or anterior lobes of the prostate, with not more than 50%, 40%, 30%, 20%, 10% or less of areas in the prostate displaying adenocarcinoma being in the ventral lobes of the prostate.

In some embodiments, the reporter gene (e.g., a luciferase gene) is detected in another organ. In specific embodiments, the reporter gene is detected in an organ selected from bladder, liver, lung, kidney, heart, thymus, salivary gland, bone, or a combination thereof.

In some embodiments, the adenocarcinoma developed in the rodents provided herein is not neuroendocrine carcinoma. Neuroendocrine (NE) carcinoma is associated with distinct morphology and marker expression pattern (Chiaverotti et al. (2008), supra). For example, NE carcinomas are characterized by poorly differentiated and highly invasive lesions; form large masses that distort the ductal architecture, entrap normal or hyperplastic glands, usually involve multiple lobes; and often have large areas of necrosis. In immunostaining assays, NE carcinoma typically stains negative for androgen receptor (AR) or shows weak and diffuse cytoplasmic staining for AR, but stains positive for synaptophysin, contrasting sharply with normal and hyperplastic prostatic epithelia which stain negative for synaptophysin with strong nuclear staining for AR. In specific embodiments, the adenocarcinoma developed in the rodents provided herein does not express synaptophysin, i.e., stains negative for synaptophysin as determined by immunostaining for example, although positive for the epithelial marker, E-cadherin.

In some embodiments, the rodents provided herein exhibit a combination of any of the expression and pathological features described above, including, for example, the areas where the transgene is expressed, the period of time it takes to develop PIN, the areas in the prostate where PIN develops, the period of time it takes to develop prostate adenocarcinoma, the areas in the prostate where adenocarcinoma develops, and the feature that the adenocarcinoma developed is not neuroendocrine carcinoma. In many embodiments, the rodents may exhibit a combination of any one of the following features: (i) transgene expression in the dorsolateral lobes and/or anterior lobes of the prostate; (ii) not displaying PIN until at least about 2, 3, 4, 5 or 6 months of age, and in specific embodiments, beginning to display PIN at about 3-7 months of age, or about 4-6 months of age; (iii) displaying PIN in the dorsolateral lobes, or the dorsolateral and anterior lobes of the prostate, and in some embodiments, substantially in the dorsolateral and/or anterior lobes of the prostate, but substantially not in the ventral lobes of the prostate; (iv) not displaying adenocarcinoma until at least about 6, 7, 8, 9 or 10 months of age, and in specific embodiments, beginning to display prostate adenocarcinoma at about 7-9 months of age, or at about 8 months of age; (v) displaying adenocarcinoma in the dorsolateral lobes, or dorsolateral and anterior lobes of the prostate, and in specific embodiments, substantially in the dorsolateral and/or anterior lobes of the prostate, but substantially not in the ventral lobes of the prostate. In particular embodiments, disclosed herein is a rodent that begins to display PIN in the prostate tissue at about 4-6 months of age, and begins to display adenocarcinoma at about 7-9 months of age, wherein the adenocarcinoma developed in the rodent is not neuroendocrine carcinoma.

The rodents provided herein have a longer survival time as compared to TRAMP and LADY mice reported in the art, possibly because the rodents provided herein have a slower rate of disease progression and do not develop the more aggressive, neuroendocrine carcinoma. In some embodiments, the rodents provided herein live at least to 16, 18, 20, 22, or 24 months of age. In specific embodiments, the rodents live longer than 24 months of age.

The rodents provided herein include, for example, mice, rats, and hamsters. In some embodiments, the rodent is a mouse or a rat. In specific embodiments, the rodent is a mouse.

In some embodiments, the rodent is a mouse of a C57BL strain, for example, a C57BL strain selected from C57BL/A, C57BL/An, C57BL/GrFa, C57BL/KaLwN, C57BL/6, C57BL/6J, C57BL/6ByJ, C57BL/6NJ, C57BL/10, C57BL/10ScSn, C57BL/10Cr, and C57BL/Ola. In other embodiments, the rodent is a mouse of a 129 strain, for example, a 129 strain selected from the group consisting of 129P1, 129P2, 129P3, 129X1, 129S1 (e.g., 129S1/SV, 129S1/SvIm), 129S2, 129S4, 129S5, 129S9/SvEvH, 129/SvJae, 129S6 (129/SvEvTac), 129S7, 129S8, 129T1, 129T2 (see, e.g., Festing et al. (1999), *Mammalian Genome* 10:836; Auerbach et al. (2000), *Biotechniques* 29(5):1024-1028, 1030, 1032). In some embodiments, the rodent is a mouse that is a mix of an aforementioned 129 strain and an aforementioned C57BL/6 strain. In certain embodiments, the mouse is a mix (i.e., hybrid) of aforementioned 129 strains, or a mix of aforementioned C57BL strains, or a mix of a C57BL strain and a 129 strain. In certain embodiments, the mouse is a mix of a C57BL/6 strain with a 129 strain. In specific embodiments, the mouse is a VGF1 strain, also known as F1H4, which is a hybrid of C57BL/6 and 129. In other embodiments, the mouse is a BALB strain, e.g., BALB/c strain. In some embodiments, the mouse is a mix of a BALB strain and another aforementioned strain.

In some embodiments, the rodent is a rat. In certain embodiments, the rat is selected from a Wistar rat, an LEA strain, a Sprague Dawley strain, a Fischer strain, F344, F6, and Dark Agouti. In other embodiments, the rat is a mix of two or more strains selected from the group consisting of Wistar, LEA, Sprague Dawley, Fischer, F344, F6, and Dark Agouti.

Methods of Making a Transgenic Rodent

The rodents provided herein can be made using methods known in the art. In exemplary embodiments, a vector containing a transgene that encodes an SV40 tumor antigen operably linked to 5' and 3' regulatory regions of a mouse probasin gene can be constructed. For example, a BAC vector carrying a desirable transgene can be constructed utilizing bacterial artificial chromosome (BAC) clones and bacterial homologous recombination and VELOCIGENE® technology (see, e.g., U.S. Pat. No. 6,586,251 and Valenzuela et al. (2003), High-throughput engineering of the mouse genome coupled with high-resolution expression analysis, *Nature Biotech.* 21(6):652-659).

In some embodiments, a BAC vector carrying a transgene can be introduced into rodent embryonic stem (ES) by, e.g., electroporation. Both mouse ES cells and rat ES cells have been described in the art. See, e.g., U.S. Pat. Nos. 7,576,259, 7,659,442, 7,294,754, and US 2008-0078000 A1 (all of which are incorporated herein by reference) describe mouse ES cells and the VELOCIMOUSE® method for making a genetically modified mouse; and US 2014/0235933 A1 and US 2014/0310828 A1 (all of which are incorporated herein by reference) describe rat ES cells and methods for making a genetically modified rat.

ES cells having the transgene integrated in the genome can be selected. In some embodiments, ES cells having the transgene integrated into a target locus of a rodent are selected. Target loci include, for example, an endogenous rodent probasin locus (via homologous recombination mediated integration, for example). Targeting vectors that facilitate targeted integration can be designed and used for generating ES cells having targeted integration of the transgene. In other embodiments, ES cells having the transgene integrated into the genome are selected irrespective of the site(s) where the integration occurs; in other words, one or more copies of the transgene may be integrated at one or more ectopic sites (i.e., sites other than a target locus). In some embodiments, at least 1-10 copies copy of a transgene are integrated in the genome of an ES cell. In certain embodiments, multiple copies of a transgene, e.g., 2, 3, 4, 5, 6, 7, 8, 9, 10 or more copies of a transgene, are integrated in the genome of an ES cell. The multiple copies of the transgene can be integrated into one locus or multiple loci of the genome. In specific embodiments, multiple copies (i.e., 2, 3, 4, 5, 6, 7, 8, 9, 10 or more copies) of a transgene are integrated in tandem into one locus of the genome. ES cells having the transgene integrated in the genome are then used as donor ES cells for injection into a pre-morula stage embryo (e.g., 8-cell stage embryo) by using the VELOCIMOUSE® method (see, e.g., U.S. Pat. Nos. 7,576,259, 7,659,442, 7,294,754, and US 2008-0078000 A1), or methods described in US 2014/0235933 A1 and US 2014/0310828 A1. The embryo comprising the donor ES cells is incubated until blastocyst stage and then implanted into a surrogate mother to produce an F0 rodent fully derived from the donor ES cells. Rodent pups bearing the transgene can be identified by genotyping of DNA isolated from tail snips using a modification of allele (MOA) assay (Valenzuela et al., supra) that detects the presence of the transgene sequence. Pups positive for the transgene can be further screened based on prostate-specific expression of the transgene (e.g., the level of expression in the prostate relative to other tissues and organs, and the expression in various sections of the prostate such as in dorsal, lateral, anterior, and ventral lobes), and/or based on development and progression of prostate carcinoma (e.g., the onset and progression of PIN and carcinoma).

ES clones capable of generating rodents that demonstrate desirable phenotypes as described above can be identified. Desirable phenotypes include, e.g., prostate-specific expression of the transgene substantially in the dorsolateral and anterior lobes of the prostate, and having an onset of PIN at about 4-6 months of age and an onset of carcinoma at about 8 months of age. Such ES clones can be cultured and stored. In some embodiments, an ES clone contains at least one copy of the transgene integrated at a target locus (e.g., an endogenous probasin locus). In other embodiments, at least 1-10 copies of a transgene are integrated at one or more ectopic sites in the genome. In some embodiments, an ES clone contains multiple copies of a transgene, e.g., 2, 3, 4, 5, 6, 7, 8, 9, 10 or more copies of the transgene, integrated in the genome. In certain embodiments, multiple copies (2, 3, 4, 5, 6, 7, 8, 9, 10 or more copies) of a transgene are integrated into multiple loci of the genome. In certain other embodiments, multiple copies of the transgene are integrated in tandem into one locus, e.g., one ectopic locus, of the genome. In a specific embodiment, a mouse ES clone designated as Clone A-C10 (5×) is provided herein that have five copies of a transgene integrated in tandom into one locus of the genome, wherein the transgene includes a coding sequence for SV40Tag-T2A-luciferase, flanked by 5' and 3' regulatory regions of a mouse probasin gene.

In other embodiments, a transgenic rodent can be made without using ES cells. For example, the genome of a non-ES cell of a rodent (e.g., a fibroblast or an induced pluripotent cell) can be modified based on conventional transformation methods (e.g., electroporation), and the modified genome of such non-ES cell can be transferred to a suitable recipient cell, e.g., an oocyte, by employing the nuclear transfer technique. The modified cell (e.g., the modified oocyte) is then gestated under suitable conditions to form an embryo. See, e.g., Han et al., "*Nuclear Transfer in Mouse Oocytes and Embryos", Methods in Enzymology* 476: 171-184 (2010), and Zhou et al., "*Generation of Fertile Cloned Rats by Regulating Oocyte Activation", Science* 302: 1179 (2003).

Methods of Using the Transgenic Rodents

The rodents provided herein permit the development of methodologies for the identification, diagnosis and staging of prostate cancer, as well as a better understanding of the molecular mechanisms underlying the progression of prostate cancer. In addition, such rodents may be used in the screening and development of therapeutic agents for the prevention and treatment of prostate cancer.

The present description is further illustrated by the following examples, which should not be construed as limiting in any way. The contents of all cited references (including literature references, issued patents, and published patent applications as cited throughout this application) are hereby expressly incorporated by reference.

Example 1 Generation of Luci-TRAMP Mice

This example illustrates generation of transgenic mice, also referred to herein as Luci-TRAMP mice, which contain a transgene that includes a nucleic acid coding sequence for an SV40 tumor antigen-T2A-luciferase polypeptide, flanked by a 5' regulatory region and a 3' regulatory region of a mouse probasin gene.

A vector containing the transgene was constructed via bacterial homologous recombination and VELOCIGENE® technology (see, e.g., U.S. Pat. No. 6,586,251 and Valenzuela et al., High-throughput engineering of the mouse genome coupled with high-resolution expression analysis, 2003, *Nature Biotech.* 21(6):652-659). Briefly, a bacterial artificial chromosome (BAC) clone RP23-417B18, which contains a mouse probasin gene, was utilized and modified as follows. One fragment, comprised of 75 base pairs (bps) of the mouse 5'-UTR, the SV40-T-antigen (without a stop codon), followed by the T2A sequence, NcoI/XhoI/NheI restriction sites, and a stop codon and 89 bps of the mouse 3'-UTR, was synthesized by GenScript and cloned into the R6K backbone for propagation. The luciferase2 cDNA sequence and its own pA, was amplified from the Promega plasmid (pGL4) using primers that add flanking NcoI and XhoI restriction sites. The neomycin resistance cassette, flanked by XhoI and NheI sites, were co-ligated with the luciferase amplicon into the synthesized fragment. Bacterial homologous recombination to replace the mouse Pbsn gene (from start ATG codon to stop TAG codon) was mediated by the homologous sequences up- (75 bps) and down-stream (89 bps). After sequencing the junctions to ensure the recombination was seamless and restriction fragment analysis to ascertain expected size of the modified BAC, the BacVec was linearized and purified for electroporation.

The resulting modified BAC vector is graphically depicted in FIG. 1. The nucleotide sequences of the components of the modified BAC vector are set forth in SEQ ID NOs: 1-7.

This modified BAC vector was electroporated into VGF1 (also known as F1H4) C57BL6/129 F1 hybrid embryonic stem (ES) cells to create modified ES cells having the SV40-T2A-luciferase transgene integrated in the genome. Modified ES cells containing the SV40-T2A-luciferase transgene were selected based on their resistance to geneticin (G418).

Selected ES cell clones were then used as donor ES cells and microinjected into a pre-morula stage mouse embryo by the VELOCIMOUSE® method (see, e.g., U.S. Pat. Nos. 7,576,259, 7,659,442, 7,294,754, and US 2008-0078000 A1). The mouse embryo comprising the donor ES cells was incubated until blastocyst stage and then implanted into a surrogate mother to produce an F0 mouse fully derived form the donor ES cells. Mice bearing the transgene were identified by genotyping of DNA isolated from tail snips using a modification of allele (MOA) assay (Valenzuela et al., supra) that detected the presence of the transgene sequence. Pups positive for the transgene were further screened for prostate-specific expression of T-antigen and luciferase.

Figure 2:
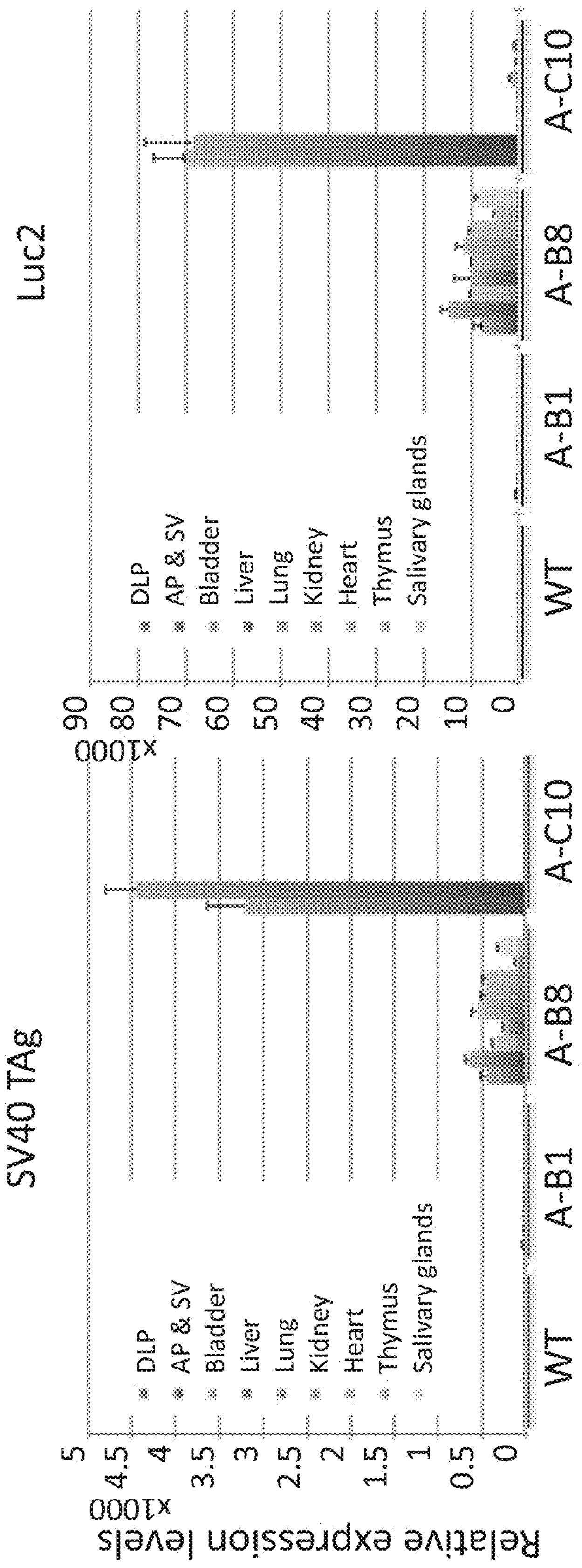
FIG. 2 illustrates identification of Luci-TRAMP ES clone A-C10 (5×) and prostate-specific expression of the transgene in mice derived from the ES clone. Transgene mRNA was evaluated using quantitative PCR (qPCR) with assays designed against the T-antigen and the luciferase transgenes. Tissues from mice of 8 weeks old were harvested and immersed immediately in RNALater reagent. Total RNA was extracted by the Regeneron DNA Core, and qPCR was performed according to PerkinElmer's instructions with minor modifications. WT, hybrid non-transgenic control mouse; A-B1, mouse with low/no-transgene expression; A-B8, mouse with moderate but mis-expressing the transgene; A-C10, Luci-TRAMP mouse with ~5 copies of the transgene expressed in only the dorsolateral prostate (DLP) and the anterior prostate (AP) and seminal vesicles (SV). The order of tissues represented by the bars in the graph is, from left to right, DLP, AP & SV, bladder, liver, lung, kidney, heart, thymus, and salivary gland.

Clone A-C10 (5×) was identified as an ES clone that produced mice which showed prostate-specific transgene expression at 8 weeks (FIG. 2). Transgene mRNA was evaluated using quantitative PCR (qPCR) with assays designed against the T-antigen and the luciferase transgenes. Tissues from mice at age 8 weeks were harvested and immersed immediately in RNALater reagent. Total RNA was extracted by the Regeneron DNA Core, and qPCR was performed according to PerkinElmer's instructions with minor modifications. WT, hybrid non-transgenic control mouse; A-B1, mouse with low/no-transgene expression; A-B8, mouse with moderate but mis-expressing the transgene; A-C10, Luci-TRAMP mouse with ~5 copies of the trasnsgene expressed in only the dorsolateral prostate (DLP) and the anterior prostate (AP and seminal vesicles (SV).

Example 2 Longitudinal Analysis of Luci-TRAMP Cohort

Luci-TRAMP mice generated from ES clone A-C10 (5×) were designated as MAID 2319 and used in the experiments described in this example. Mice designated as MAID 2363 contain the transgene "R26-L-luc2" at the Rosa 26 locus in the genome (which expresses a luciferase reporter in a non-tissue specific manner and wild type F1H4 mice, were used as controls.

A cohort of 35 MAID2319 mice (Luci-TRAMP) were kept to allow prostate tumor to develop, in parallel with an equivalent number of MAID 2363 mice (R26-L-Luc2) and F1H4 mice. 5 mice were removed from each group at 2, 4, 6, 8, 11, and 16 months, respectively, for in vivo luciferase imaging, pCT scan (to assess lean/fat/bone mass), histopathology analysis (starting from 4 months), and molecule phenotyping (RNA-seq and qPCR).

For the longitudinal study, at each indicated time point (inset below), all animals were given luciferin subcutaneously (150 mg/kg PerkinElmer), anesthetized by isofluorane, and scanned on a Lumina XR in vivo imaging system after 12-14 min. Living software was used to automatically draw ROIs with a contour perimeter and compute intensity signal (total flux) at a 5% threshold.

qPCR probes were designed using BioSearch Technologies and Regeneron in-house search parameters. Tissues were homogenized in TRIzol and chloroform was used for phase separation. The aqueous phase, containing total RNA, was purified using miRNeasy Mini Kit (Qiagen, Cat #217004) according to manufacturer's specifications. Genomic DNA was removed using MagMAX™Turbo™DNase Buffer and TURBO DNase reagents (Ambion by Life Technologies). mRNA was reverse-transcribed into cDNA using SuperScript® VILO™ Master Mix reagent (Invitrogen by Life Technologies, Cat#11755500). cDNA was amplified with the TaqMan® Gene Expression Master Mix reagent (Applied Biosystems by Life Technologies, Cat#4370074) using the ABI 7900HT Sequence Detection System (Applied Biosystems). Beta-actin was used as the internal control gene to normalize any cDNA input differences. WT (F H4) lung was used as a reference sample to calculate the fold difference of mRNA between samples. N=5 males per tissue per genotype. Statistical and graphical analyses were performed using GraphPad Prism software (version 3.0). Data were analyzed using Student's unpaired t-test. Results were considered statistically significant at P values<0.05. Error bars depict SD.

Figure 3A:
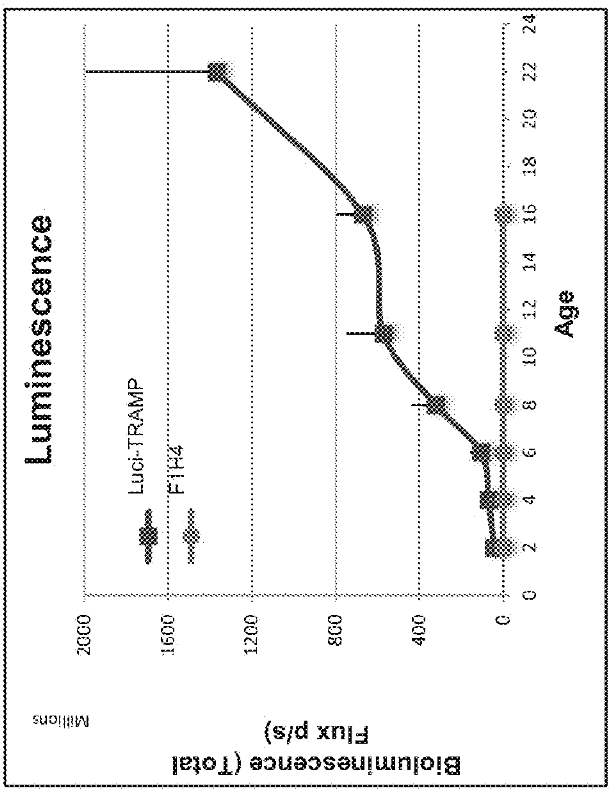
FIGS. 3A-3C show the longitudinal in vivo bioluminescence imaging of Luci-TRAMP mice at several ages over their life.
Figure 3B:
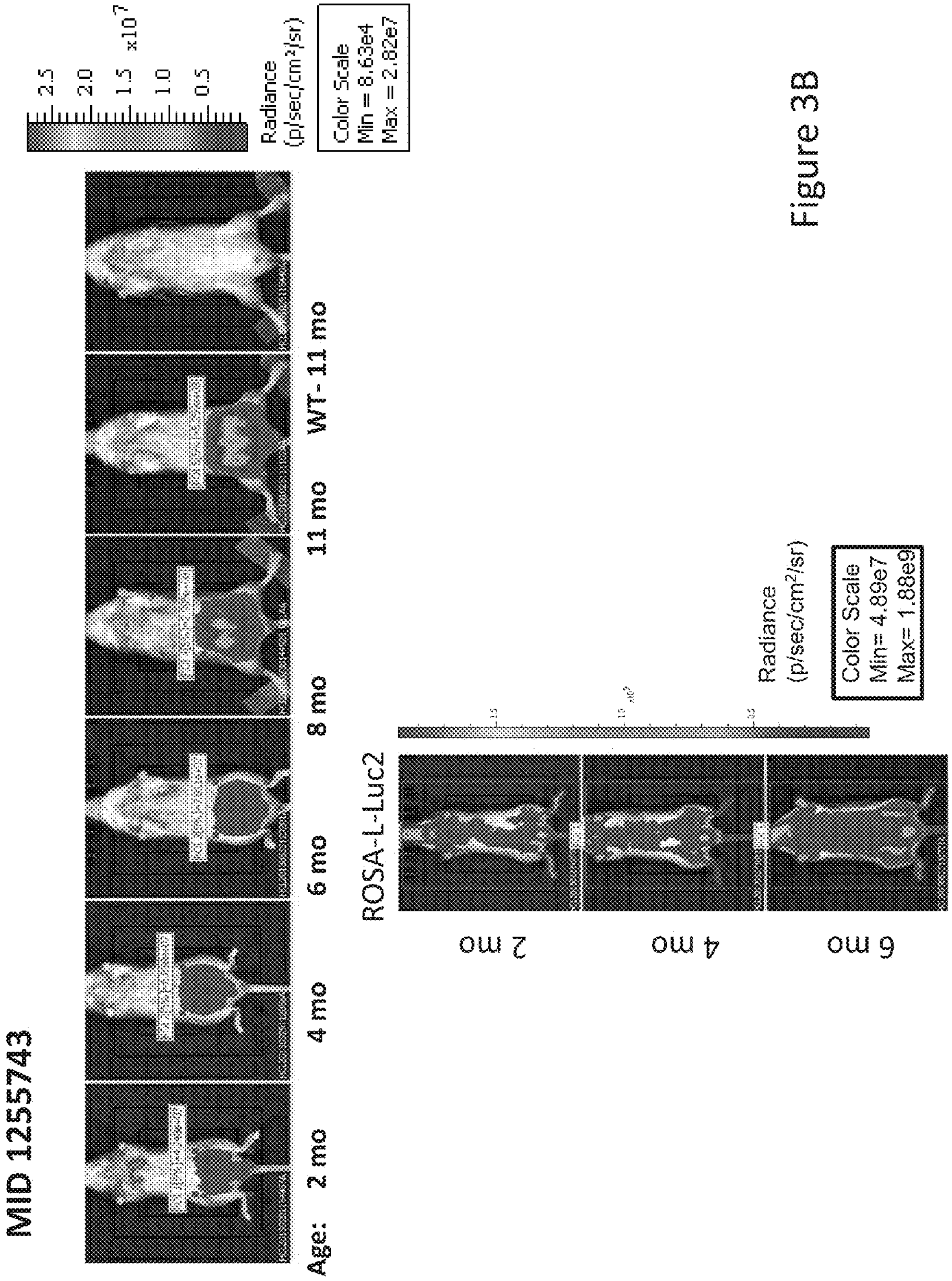
Figure 3C:
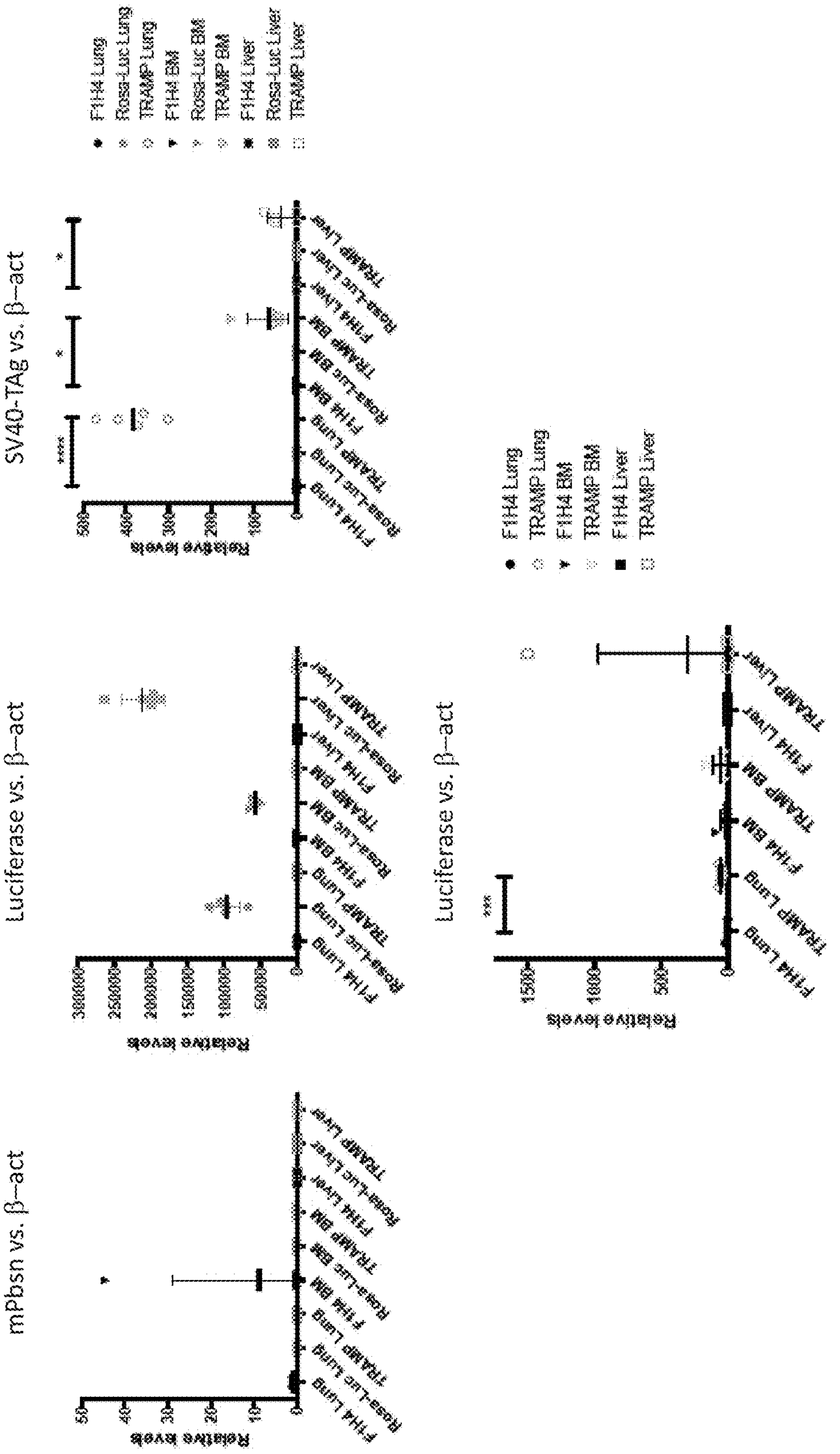

Results are shown in FIGS. 3A-3C. Prostate cancer progression revealed from the histopathology analysis was summarized in Table 1. The assignment of mPIN and adenocarcinoma was based on the following guideline.

mPIN: Proliferation of atypical cells within pre-existing glandular spaces, but lacking invasion (i.e., the basement membrane has not been breached). mPIN is differentiated from epithelial hyperplasia based on morphology (atypical) compatible with the particular GEM model. Progression of mPIN is associated with age, and has been demonstrated to advance to invasive carcinomas. Grading is based on increasing degrees of architectural or cytological abnormalities on a scale of 1-4:

mPIN1 (epithelial hyperplasia)=mild nuclear and/or cytoplasm atypia (independent of inflammation) with cells arranged single or double layers.

mPIN2=two or more layers of cells with nuclear atypia in tufts or papillary branches.

mPIN3=increased/more frequent atypia, with more extensive papillary branching that partially to completely fills the lumen.

mPIN4=marked/frequent atypia, with exuberant branching and distention of the gland spaces, but lacking clear invasion.

Adenocarcinoma: Infiltrative and/or destructive proliferation of atypical cells that have some degree of glandular differentiation. In mice, stromal desmoplasia and varying degrees of interstitial inflammation are associated with more advanced lesions.

Figure 4A:
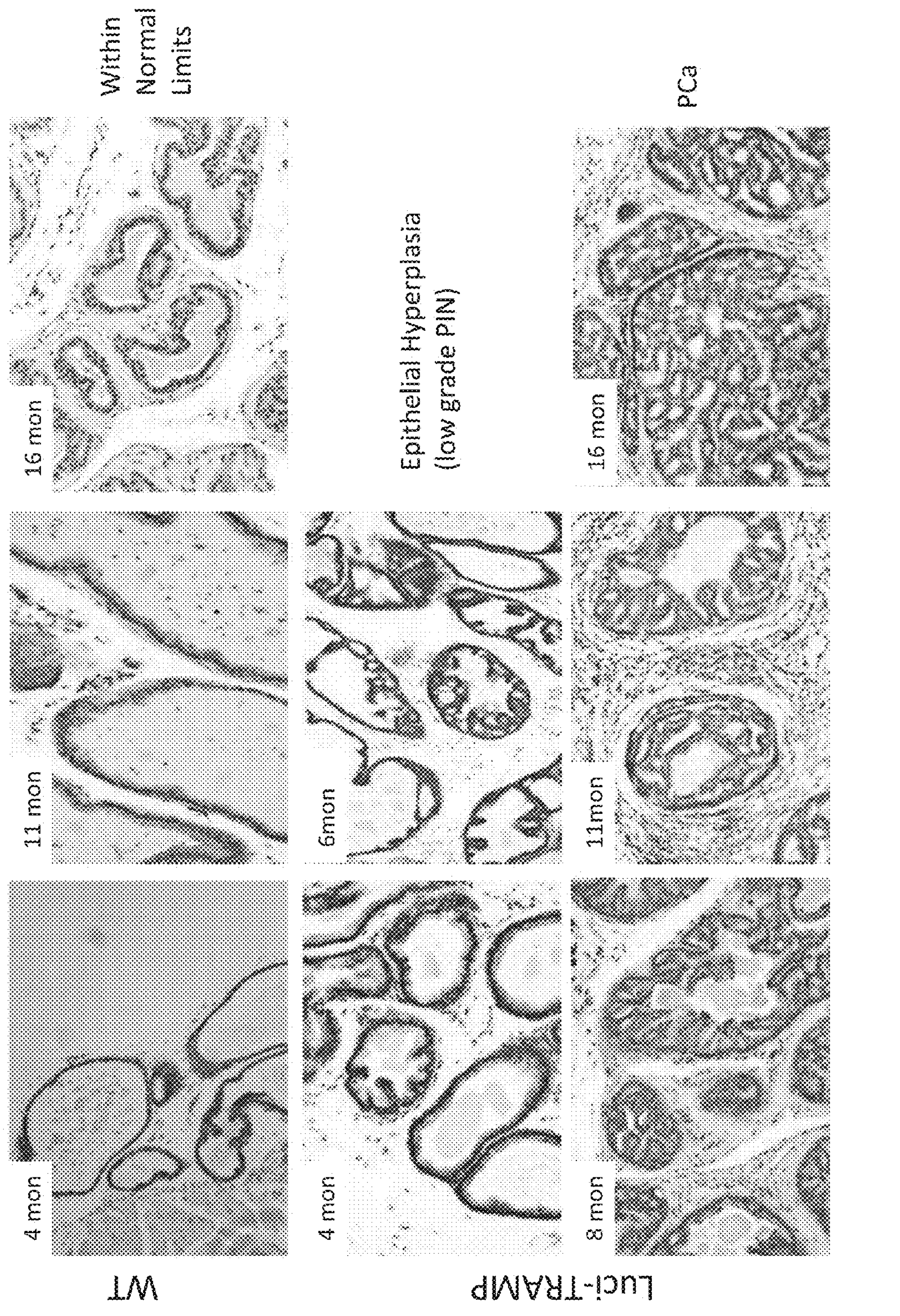
FIGS. 4A-4B are representative hematoxylin/eosin staining images of paraffin sections of dorsal lateral lobes of Luci-TRAMP and wild type mice.
Figure 4B:
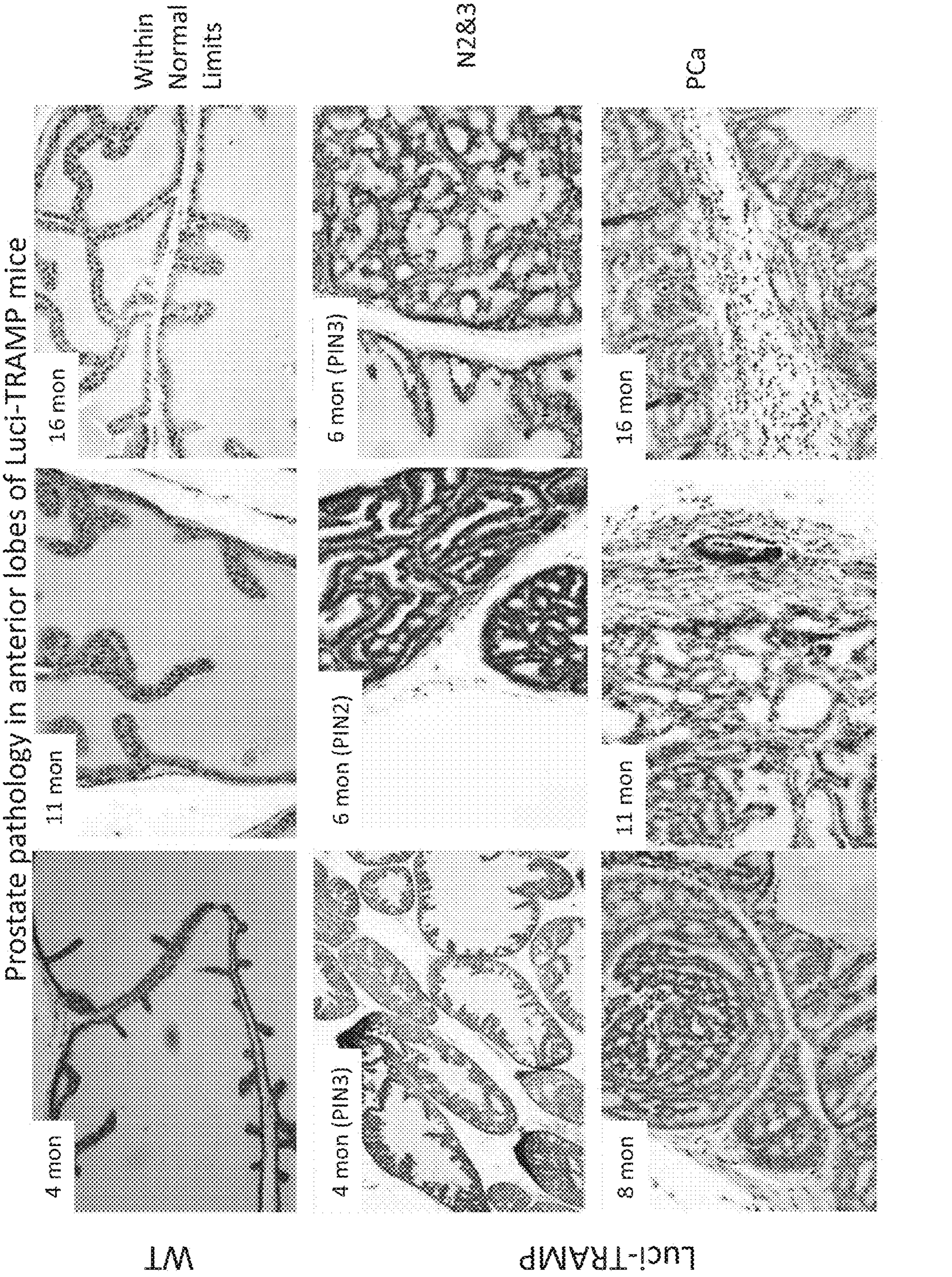
Figure 5A:
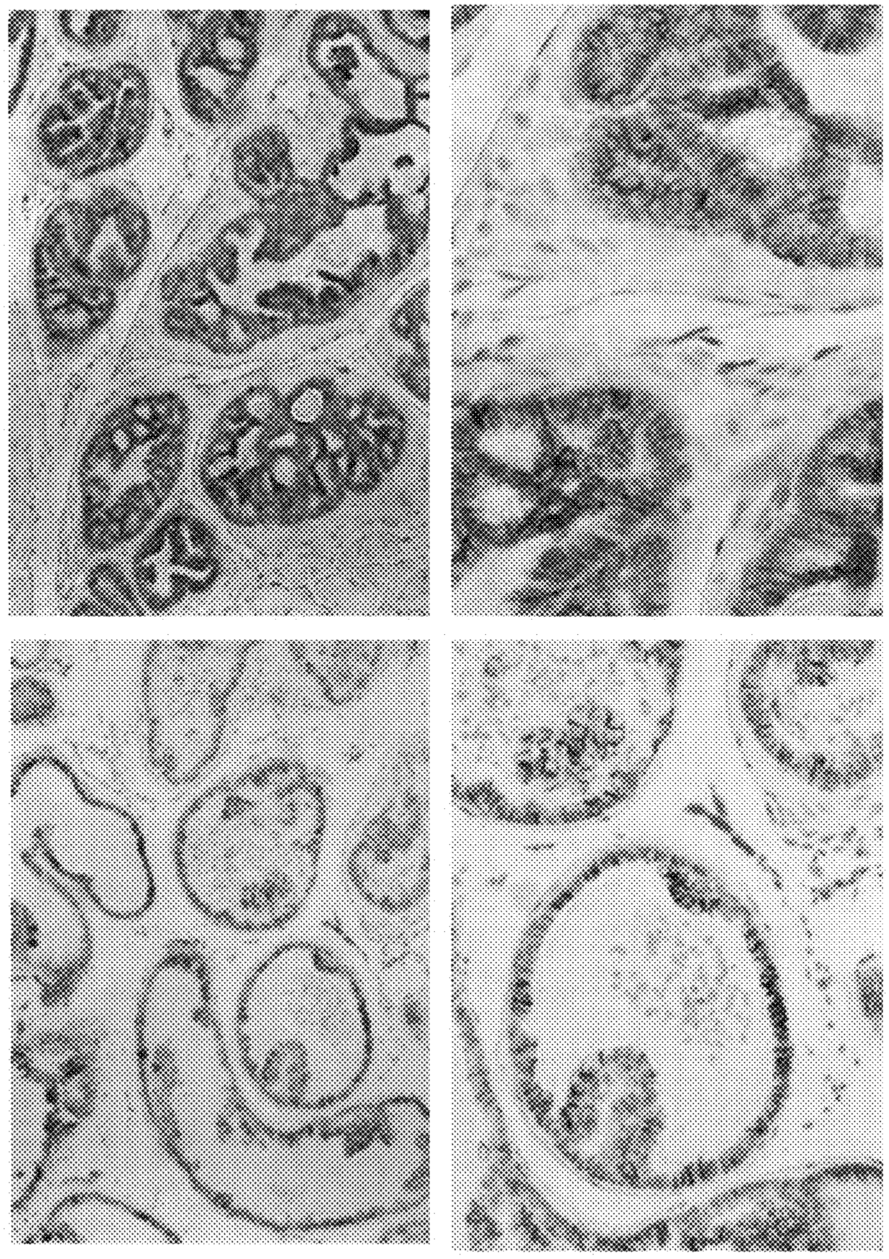
FIGS. 5A-5B demonstrate that the prostate tumors developed in Luci-TRAMP mice are epithelial tumors and not neuroendocrine tumors.
Figure 5B:
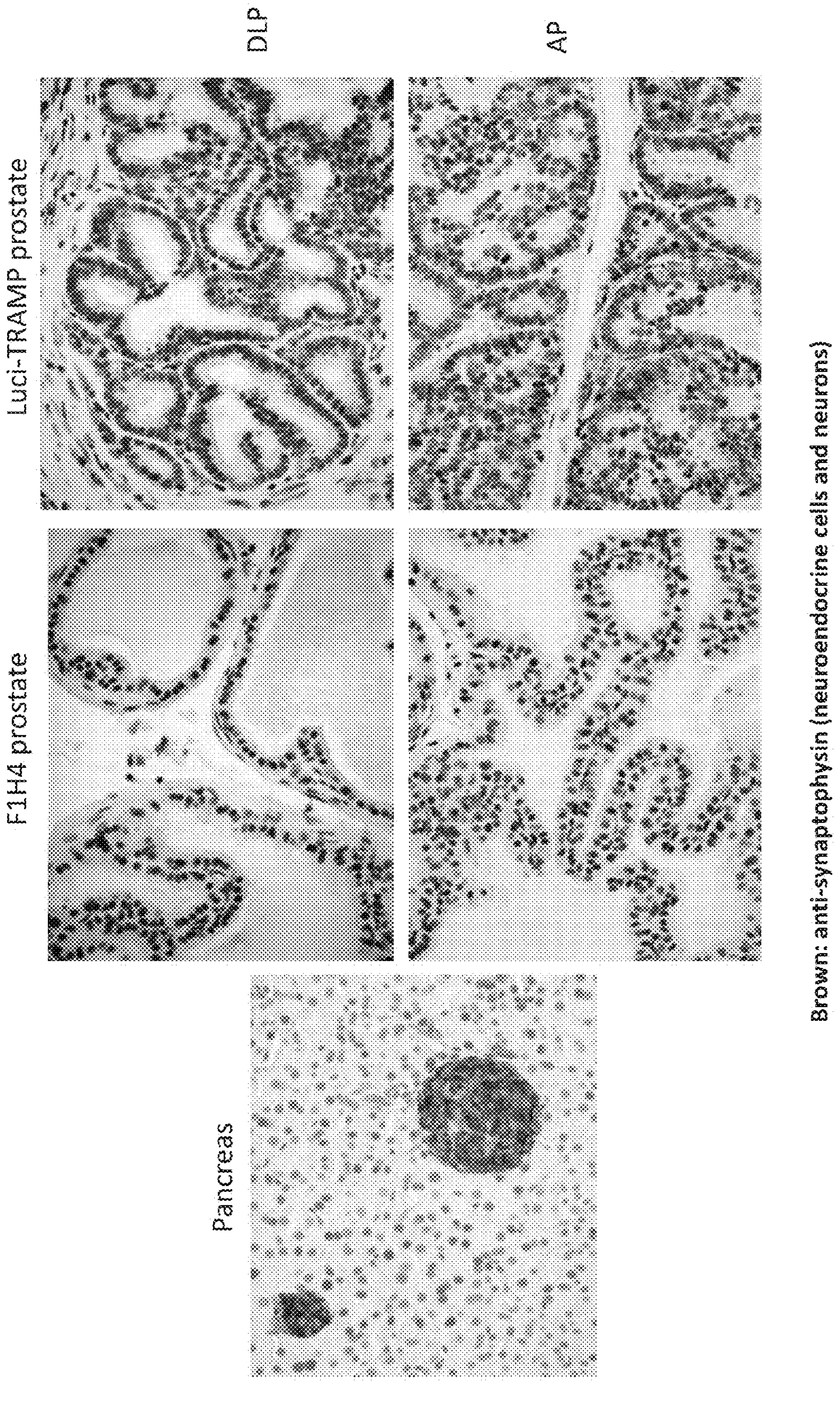

Representative pathology staining images are provided in FIGS. 4A-4B. Immunohistochemistry analysis of prostate tumor from Luci-TRAMP mice is shown in FIGS. 5A-5B. Tissues were fixed in freshly prepared 4% paraformaldehyde overnight, then paraffin embedded, sectioned, and stained with hematoxylin and eosin for staging. Some sections were assayed for neuroendocrine or epithelial antigens using antibodies against synaptophysin (Abcam #32127) or E-cadherin (Cell Signaling clone 64E10), respectively.

These studies have revealed the following.

Starting from 4 month of age, prostate tumor development was visible in all Luci-TRAMP prostates (5/5 mice each age group) under dissection microscope (solid whitish spots/areas within otherwise transparent prostatic glands), no abnormality detected in controls.

At 4 and 6 month, 3/3 Luci-TRAMP mice analyzed in each age demonstrated non-invasive prostate tumors in both dorsal lateral and anterior lobes. 4/4 control mice analyzed in each age group showed no abnormality in any lobes.

At 8 and 11 month, 3/3 Luci-TRAMP mice of each group demonstrated prostate adenocarcinoma in both dorsal lateral and anterior lobes. 3/3 control mice analyzed in each age group showed little abnormality in any lobes.

At 16 month, 5/5 Luci-TRAMP mice demonstrated prostate adenocarcinoma in anterior lobe and 4/4 detected for prostate adenocarcinoma in dorsal lateral lobes.

Ventral lobe showed minor changes (limited to epithelial hyperplasia) in Luci-TRAMP mice.

Although micro-invasion was observed starting 8 months of age, there was no evidence of vascular invasion by age of 16 month.

IHC analysis showed that Luci-TRAMP prostate tumor were stained positive for epithelial marker E-cadherin and negative for neuroendocrine marker Synaptophysin.

TABLE 1

Luci-TRAMP Mice Prostate Pathology Overview

| | LOBE | Mouse ID | Dorsolateral (DLP) | Anterior (CG) | Ventral |
|---|---|---|---|---|---|
| 4 Month | F1H4 | M6 | WNL | WNL | WNL |
| | | M8 | WNL | WNL | NI |
| | ROSA: 2319 | 1258782 | WNL | WNL | WNL |
| | | 1258784 | WNL | WNL | NI |
| | Luci-TRAMP | M6 | epithelial hyperplasia | mPIN-3, focal | epithelial hyperplasia |
| | | M8 | epithelial hyperplasia | mPIN-2, focal | epithelial hyperplasia |
| | | M10* | epithelial hyperplasia, focal | epithelial hyperplasia, focal | NI |
| 6 Month | F1H4 | M12 | WNL | epithelial hyperplasia, diffuse | WNL |
| | | M14 | WNL | WNL | WNL |
| | ROSA: 2314 | M12 | WNL | WNL | WNL (scant present) |
| | | M14 | WNL | WNL | NI |
| | Luci-TRAMP | M11 | epithelial hyperplasia | mPIN-3, focal | WNL |
| | | M13 | epithelial hyperplasia | mPIN-3, diffuse | EH; dilated gland lumens |
| | | M15 | epithelial hyperplasia | mPIN-3, diffuse | dilated glands, WNL |
| 8 Month | F1H4 | 16 | WNL | WNL | WNL |
| | | 18 | WNL | WNL | NI |
| | | 20 | WNL | WNL | WNL |
| | | M16 | adenocarcinoma | adenocarcinoma | epithelial hyperplasia (NI) |
| | Luci-TRAMP | M18 | adenocarcinoma | adenocarcinoma | epithelial hyperplasia |
| | | M20 | adenocarcinoma | adenocarcinoma | NI |
| 11 Month | F1H4 | 21 | WNL | epithelial hyperplasia, focal | NI |
| | | 22 | WNL | WNL | NI |
| | | 23 | WNL | WNL | WNL |
| | Luci-TRAMP | M21 | adenocarcinoma | adenocarcinoma | NI |
| | | M22 | adenocarcinoma | adenocarcinoma | NI |
| | | M23 | adenocaicinoma | adenocarcinoma | NI |
| 16 Month | F1H4 | 26 | WNL (dilated lateral) | epithelial hyperplasia, focal | WNL |
| | | 27 | WNL | WNL | NI |
| | | 28 | WNL | epithelial hyperplasia, focal | WNL (dilated) |
| | | 29 | WNL (dilated lateral) | WNL | WNL (dilated) |
| | | 30 | WNL (dilated) | epithelial hyperplasia, focal | NI |
| | Luci-TRAMP | M26 | adenocarcinoma | adenocarcinoma | NI |
| | | M27 | Very few specimen | adenocarcinoma | NI |
| | | M28 | adenocarcinoma | adenocarcinoma | NI |

TABLE 1-continued

| Luci-TRAMP Mice Prostate Pathology Overview | | | | |
|---|---|---|---|---|
| LOBE | Mouse ID | Dorsolateral (DLP) | Anterior (CG) | Ventral |
| | M29 | adenocarcinoma | adenocarcinoma | NI |
| | M30 | adenocarcinoma | adenocarcinoma | NI |

WNL = Within Normal Limits;
NI = Not IDENTIFIED

What is claimed is:

1. A mouse comprising in its genome a transgene comprising:

(a) a 5' regulatory region of a mouse probasin gene, wherein the 5' regulatory region comprises a nucleic acid sequence of at least 50 kb upstream of the transcription initiation site of the mouse probasin gene, (b) a nucleic acid comprising a first nucleotide sequence encoding an oncogenic protein wherein the oncogenic protein comprises an SV40 tumor antigen, and (c) a 3' regulatory region of the mouse probasin gene, wherein the 3' regulatory region comprises a nucleic acid sequence of at least 100 kb downstream of the transcription termination site of the mouse probasin gene, wherein the 5' regulatory region, the nucleic acid, and the 3' regulatory region are operably linked to each other, and wherein the oncogenic protein is expressed specifically in the prostate of the mouse, and the mouse is characterized by (i) displaying prostate intraepithelial neoplasia (PIN) in the prostate tissue after 2 months of age; (ii) displaying PIN in the dorsolateral lobes, or the dorsolateral and anterior lobes of the prostate; (iii) displaying PIN substantially in the dorsolateral lobes, the anterior lobes, or both the dorsolateral and anterior lobes of the prostate, but substantially not in the ventral lobes of the prostate; (iv) displaying adenocarcinoma after 6 months of age; (v) displaying adenocarcinoma in the dorsolateral lobes, the anterior lobes, or both the dorsolateral and anterior lobes of the prostate; (vi) displaying adenocarcinoma substantially in the dorsolateral lobes, the anterior lobes, or both the dorsolateral and anterior lobes of the prostate, but substantially not in the ventral lobes of the prostate; or (vii) a combination of one or more of (i)-(vi).

2. The mouse of claim 1, wherein the oncogenic protein comprises (i) an SV40 large T antigen or a functional active fragment thereof, (ii) an SV40 small t antigen or a functional active fragment thereof, or (iii) a combination of (i) and (ii).

3. The mouse of claim 1, wherein the first nucleotide sequence comprises the sequence as set forth in SEQ ID NO: 1.

4. The mouse of claim 1, wherein the nucleic acid further comprises a second nucleotide sequence encoding a reporter.

5. The mouse of claim 4, wherein the reporter is a luciferase.

6. The mouse of claim 1, wherein the transgene is integrated at an ectopic locus in the genome.

7. The mouse of claim 6, wherein at least one to ten copies of the transgene are integrated in tandem at the ectopic locus.

8. The mouse of claim 1, wherein the mouse displays PIN at about 4-6 months of age, and displays adenocarcinoma at about 7-9 months of age, wherein the adenocarcinoma is not neuroendocrine carcinoma.

9. An isolated cell or tissue of the mouse of claim 1.

10. A mouse embryonic stem (ES) cell comprising a transgene in the genome, wherein the transgene comprises:
   (a) a 5' regulatory region of a mouse probasin gene, wherein the 5' regulatory region comprises a nucleic acid sequence of at least 50 kb upstream of the transcription initiation site of the mouse probasin gene,
   (b) a nucleic acid comprising a first nucleotide sequence encoding an oncogenic protein, wherein the oncogenic protein comprises an SV40 tumor antigen, and
   (c) a 3' regulatory region of a mouse probasin gene, wherein the 3' regulatory region comprises a nucleic acid sequence of at least 100 kb downstream of the transcription termination site of the mouse probasin gene, wherein the 5' regulatory region, the nucleic acid, and the 3' regulatory region are operably linked to each other.

11. A method of making a mouse comprising a transgene, comprising
   (a) introducing into a mouse ES cell a transgene that comprises:
      (i) a 5' regulatory region of a mouse probasin gene, wherein the 5' regulatory region comprises a nucleic acid sequence of at least 50 kb upstream of the transcription initiation site of the mouse probasin gene,
      (ii) a nucleic acid comprising a first nucleotide sequence which codes for an oncogenic protein, wherein the oncogenic protein comprises an SV40 tumor antigen, and
      (iii) a 3' regulatory region of the mouse probasin gene, wherein the 3' regulatory region comprises a nucleic acid sequence of at least 100 kb downstream of the transcription termination site of the mouse probasin gene, wherein the 5' regulatory region, the nucleic acid, and the 3' regulatory region are operably linked;
   (b) selecting a modified mouse ES cell comprising the transgene in the genome;
   (c) introducing the modified mouse ES cell into a host embryo of the mouse at a premorula stage;
   (d) implanting the host embryo into a surrogate female mouse; and,
   (e) obtaining the mouse comprising the transgene, wherein the oncogenic protein is expressed specifically in the prostate of the mouse, and the mouse is characterized by (i) displaying prostate intraepithelial neoplasia (PIN) in the prostate tissue after 2 months of age; (ii) displaying PIN in the dorsolateral lobes, or the dorsolateral and anterior lobes of the prostate; (iii) displaying PIN substantially in the dorsolateral lobes, the anterior lobes, or both the dorsolateral and anterior lobes of the prostate, but substantially not in the ventral lobes of the prostate; (iv) displaying adenocarcinoma after 6 months of age; (v) displaying adenocarcinoma in the dorsolateral lobes, the anterior lobes, or both the dorsolateral and anterior lobes of the prostate; (vi) displaying adenocarcinoma substantially in the dorsolateral lobes, the anterior lobes, or both the dorsolateral and anterior lobes of the prostate, but substantially not in the ventral lobes of the prostate; or (vii) a combination of one or more of (i)-(vi).

12. The method of claim 11, wherein the transgene is integrated into an ectopic locus.

* * * * *

SEQUENCE LISTING

<160> NUMBER OF SEQ ID NOS: 17

<210> SEQ ID NO 1
<211> LENGTH: 2470
<212> TYPE: DNA
<213> ORGANISM: Artificial Sequence
<220> FEATURE:
<223> OTHER INFORMATION: Synthetic polynucleotide: SV-40 T antigen
coding sequence (encoding large T and small t antigens)

<400> SEQUENCE: 1
atggataaag ttttaaacag agaggaatct ttgcagctaa tggaccttct aggtcttgaa 60
aggagtgcct gggggaatat tcctctgatg agaaaggcat atttaaaaaa atgcaaggag 120
tttcatcctg ataaaggagg agatgaagaa aaaatgaaga aaatgaatac tctgtacaag 180
aaaatggaag atggagtaaa atatgctcat caacctgact ttggaggctt ctgggatgca 240
actgaggtat ttgcttcttc cttaaatcct ggtgttgatg caatgtactg caaacaatgg 300
cctgagtgtg caaagaaaat gtctgctaac tgcatatgct tgctgtgctt actgaggatg 360
aagcatgaaa atagaaaatt atacaggaaa gatccacttg tgtgggttga ttgctactgc 420
ttcgattgct ttagaatgtg gtttggactt gatctttgtg aaggaacctt acttctgtgg 480
tgtgacataa ttggacaaac tacctacaga gatttaaagc tctaaggtaa atataaaatt 540
tttaagtgta taatgtgtta aactactgat tctaattgtt tgtgtatttt agattccaac 600
ctatggaact gatgaatggg agcagtggtg gaatgccttt aatgaggaaa acctgttttg 660
ctcagaagaa atgccatcta gtgatgatga ggctactgct gactctcaac attctactcc 720
tccaaaaaag aagagaaagg tagaagaccc caaggacttt ccttcagaat tgctaagttt 780
tttgagtcat gctgtgttta gtaatagaac tcttgcttgc tttgctattt acaccacaaa 840
ggaaaaagct gcactgctat acaagaaaat tatggaaaaa tattctgtaa cctttataag 900
taggcataac agttataatc ataacatact gtttttcttt actccacaca ggcatagagt 960
gtctgctatt aataactatg ctcaaaaatt gtgtaccttt agctttttaa tttgtaaagg 1020
ggttaataag gaatatttga tgtatagtgc cttgactaga gatccatttt ctgttattga 1080
ggaaagtttg ccaggtgggt taaaggagca tgattttaat ccagaagaag cagaggaaac 1140
taaacaagtg tcctggaagc ttgtaacaga gtatgcaatg gaaacaaaat gtgatgatgt 1200
gttgttattg cttgggatgt acttggaatt tcagtacagt tttgaaatgt gtttaaaatg 1260
tattaaaaaa gaacagccca gccactataa gtaccatgaa aagcattatg caaatgctgc 1320
tatatttgct gacagcaaaa accaaaaaac catatgccaa caggctgttg atactgtttt 1380
agctaaaaag cgggttgata gcctacaatt aactagagaa caaatgttaa caaacagatt 1440
taatgatctt ttggatagga tggatataat gtttggttct acaggctctg ctgacataga 1500
agaatggatg gctggagttg cttggctaca ctgtttgttg cccaaaatgg attcagtggt 1560

```
gtatgacttt ttaaaatgca tggtgtacaa cattcctaaa aaaagatact ggctgtttaa   1620

aggaccaatt gatagtggta aaactacatt agcagctgct ttgcttgaat tatgtggggg   1680

gaaagcttta aatgttaatt tgcccttgga caggctgaac tttgagctag gagtagctat   1740

tgaccagttt ttagtagttt ttgaggatgt aaagggcact ggaggggagt ccagagattt   1800

gccttcaggt cagggaatta ataacctgga caatttaagg gattatttgg atggcagtgt   1860

taaggtaaac ttagaaaaga aacacctaaa taaaagaact caaatatttc cccctggaat   1920

agtcaccatg aatgagtaca gtgtgcctaa aacactgcag gccagatttg taaaacaaat   1980

agattttagg cccaaagatt atttaaagca ttgcctggaa cgcagtgagt ttttgttaga   2040

aaagagaata attcaaagtg gcattgcttt gcttcttatg ttaatttggt acagacctgt   2100

ggctgagttt gctcaaagta ttcagagcag aattgtggag tggaaagaga gattggacaa   2160

agagtttagt ttgtcagtgt atcaaaaaat gaagtttaat gtggctatgg gaattggagt   2220

tttagattgg ctaagaaaca gtgatgatga tgatgaagac agccaggaaa atgctgataa   2280

aaatgaagat ggtggggaga agaacatgga agactcaggg catgaaacag gcattgattc   2340

acagtcccaa ggctcatttc aggcccctca gtcctcacag tctgttcatg atcataatca   2400

gccataccac atttgtagag gttttacttg ctttaaaaaa cctcccacac ctccccctga   2460

acctgaaaca                                                          2470
```

<210> SEQ ID NO 2
<211> LENGTH: 54
<212> TYPE: DNA
<213> ORGANISM: Artificial Sequence
<220> FEATURE:
<223> OTHER INFORMATION: Synthetic oligonucleotide: T2A coding sequence

<400> SEQUENCE: 2

```
gagggcagag gaagtctgct aacatgcggt gacgtcgagg agaatcctgg cccc           54
```

<210> SEQ ID NO 3
<211> LENGTH: 1653
<212> TYPE: DNA
<213> ORGANISM: Artificial Sequence
<220> FEATURE:
<223> OTHER INFORMATION: Synthetic polynucleotide: Luciferase coding sequence (Luc2)

<400> SEQUENCE: 3

```
atggaagatg ccaaaaacat taagaagggc ccagcgccat tctacccact cgaagacggg     60

accgccggcg agcagctgca caaagccatg aagcgctacg ccctggtgcc cggcaccatc    120

gcctttaccg acgcacatat cgaggtggac attacctacg ccgagtactt cgagatgagc    180

gttcggctgg cagaagctat gaagcgctat gggctgaata caaaccatcg gatcgtggtg    240

tgcagcgaga atagcttgca gttcttcatg cccgtgttgg gtgccctgtt catcggtgtg    300

gctgtggccc cagctaacga catctacaac gagcgcgagc tgctgaacag catgggcatc    360

agccagccca ccgtcgtatt cgtgagcaag aaagggctgc aaaagatcct caacgtgcaa    420

aagaagctac cgatcataca aaagatcatc atcatggata gcaagaccga ctaccagggc    480

ttccaaagca tgtacacctt cgtgacttcc catttgccac ccggcttcaa cgagtacgac    540

ttcgtgcccg agagcttcga ccgggacaaa accatcgccc tgatcatgaa cagtagtggc    600

agtaccggat tgcccaaggg cgtagcccta ccgcaccgca ccgcttgtgt ccgattcagt    660

catgcccgcg accccatctt cggcaaccag atcatccccg acaccgctat cctcagcgtg    720
```

```
gtgccatttc accacggctt cggcatgttc accacgctgg gctacttgat ctgcggcttt    780

cgggtcgtgc tcatgtaccg cttcgaggag gagctattct tgcgcagctt gcaagactat    840

aagattcaat ctgccctgct ggtgcccaca ctatttagct tcttcgctaa gagcactctc    900

atcgacaagt acgacctaag caacttgcac gagatcgcca gcggcggggc gccgctcagc    960

aaggaggtag gtgaggccgt ggccaaacgc ttccacctac caggcatccg ccagggctac   1020

ggcctgacag aaacaaccag cgccattctg atcacccccg aaggggacga caagcctggc   1080

gcagtaggca aggtggtgcc cttcttcgag gctaaggtgg tggacttgga caccggtaag   1140

acactgggtg tgaaccagcg cggcgagctg tgcgtccgtg gccccatgat catgagcggc   1200

tacgttaaca accccgaggc tacaaacgct ctcatcgaca aggacggctg gctgcacagc   1260

ggcgacatcg cctactggga cgaggacgag cacttcttca tcgtggaccg gctgaagagc   1320

ctgatcaaat acaagggcta ccaggtagcc ccagccgaac tggagagcat cctgctgcaa   1380

caccccaaca tcttcgacgc cggggtcgcc ggcctgcccg acgacgatgc cggcgagctg   1440

cccgccgcag tcgtcgtgct ggaacacggt aaaaccatga ccgagaagga gatcgtggac   1500

tatgtggcca gccaggttac aaccgccaag aagctgcgcg gtggtgttgt gttcgtggac   1560

gaggtgccta aaggactgac cggcaagttg gacgcccgca agatccgcga gattctcatt   1620

aaggccaaga agggcggcaa gatcgccgtg taa                                1653
```

```
<210> SEQ ID NO 4
<211> LENGTH: 222
<212> TYPE: DNA
<213> ORGANISM: Artificial Sequence
<220> FEATURE:
<223> OTHER INFORMATION: Synthetic polynucleotide: SV-40 late poly (A)
      sequence

<400> SEQUENCE: 4

cagacatgat aagatacatt gatgagtttg gacaaaccac aactagaatg cagtgaaaaa     60

aatgctttat ttgtgaaatt tgtgatgcta ttgctttatt tgtaaccatt ataagctgca    120

ataaacaagt taacaacaac aattgcattc attttatgtt tcaggttcag ggggaggtgt    180

gggaggtttt ttaaagcaag taaaacctct acaaatgtgg ta                       222
```

```
<210> SEQ ID NO 5
<211> LENGTH: 2654
<212> TYPE: DNA
<213> ORGANISM: Artificial Sequence
<220> FEATURE:
<223> OTHER INFORMATION: Synthetic polynucleotide: Neomycin selection
      cassette (LoxP (5') -TATA box-hUb (human ubiquitin promoter) - EM7
      promoter - neomycin - polyA - loxP(3'))

<400> SEQUENCE: 5

tcgagataac ttcgtataat gtatgctata cgaagttata tgcatggcct ccgcgccggg     60

ttttggcgcc tcccgcgggc gcccccctcc tcacggcgag cgctgccacg tcagacgaag    120

ggcgcagcga gcgtcctgat ccttccgccc ggacgctcag gacagcggcc cgctgctcat    180

aagactcggc cttagaaccc cagtatcagc agaaggacat tttaggacgg gacttgggtg    240

actctagggc actggttttc tttccagaga gcggaacagg cgaggaaaag tagtcccttc    300

tcggcgattc tgcggaggga tctccgtggg gcggtgaacg ccgatgatta tataaggacg    360

cgccgggtgt ggcacagcta gttccgtcgc agccgggatt tgggtcgcgg ttcttgtttg    420

tggatcgctg tgatcgtcac ttggtgagta gcgggctgct gggctggccg gggctttcgt    480
```

-continued

```
ggccgccggg ccgctcggtg ggacggaagc gtgtggagag accgccaagg gctgtagtct    540
gggtccgcga gcaaggttgc cctgaactgg gggttggggg gagcgcagca aaatggcggc    600
tgttcccgag tcttgaatgg aagacgcttg tgaggcgggc tgtgaggtcg ttgaaacaag    660
gtgggggca tggtgggcgg caagaaccca aggtcttgag gccttcgcta atgcgggaaa     720
gctcttattc gggtgagatg ggctggggca ccatctgggg accctgacgt gaagtttgtc    780
actgactgga gaactcggtt tgtcgtctgt tgcgggggcg gcagttatgg cggtgccgtt    840
gggcagtgca cccgtacctt tgggagcgcg cgccctcgtc gtgtcgtgac gtcacccgtt    900
ctgttggctt ataatgcagg gtggggccac ctgccggtag gtgtgcggta ggcttttctc    960
cgtcgcagga cgcagggttc gggcctaggg taggctctcc tgaatcgaca ggcgccggac   1020
ctctggtgag gggagggata agtgaggcgt cagtttcttt ggtcggtttt atgtacctat   1080
cttcttaagt agctgaagct ccggttttga actatgcgct cggggttggc gagtgtgttt   1140
tgtgaagttt tttaggcacc ttttgaaatg taatcatttg ggtcaatatg taattttcag   1200
tgttagacta gtaaattgtc cgctaaattc tggccgtttt tggctttttt gttagacgtg   1260
ttgacaatta atcatcggca tagtatatcg gcatagtata atacgacaag gtgaggaact   1320
aaaccatggg atcggccatt gaacaagatg gattgcacgc aggttctccg gccgcttggg   1380
tggagaggct attcggctat gactgggcac aacagacaat cggctgctct gatgccgccg   1440
tgttccggct gtcagcgcag gggcgcccgg ttctttttgt caagaccgac ctgtccggtg   1500
ccctgaatga actgcaggac gaggcagcgc ggctatcgtg gctggccacg acgggcgttc   1560
cttgcgcagc tgtgctcgac gttgtcactg aagcgggaag ggactggctg ctattgggcg   1620
aagtgccggg gcaggatctc ctgtcatctc accttgctcc tgccgagaaa gtatccatca   1680
tggctgatgc aatgcggcgg ctgcatacgc ttgatccggc tacctgccca ttcgaccacc   1740
aagcgaaaca tcgcatcgag cgagcacgta ctcggatgga agccggtctt gtcgatcagg   1800
atgatctgga cgaagagcat caggggctcg cgccagccga actgttcgcc aggctcaagg   1860
cgcgcatgcc cgacggcgat gatctcgtcg tgacccatgg cgatgcctgc ttgccgaata   1920
tcatggtgga aaatggccgc ttttctggat tcatcgactg tggccggctg ggtgtggcgg   1980
accgctatca ggacatagcg ttggctaccc gtgatattgc tgaagagctt ggcggcgaat   2040
gggctgaccg cttcctcgtg ctttacggta tcgccgctcc cgattcgcag cgcatcgcct   2100
tctatcgcct tcttgacgag ttcttctgag ggatccgct gtaagtctgc agaaattgat    2160
gatctattaa acaataaaga tgtccactaa aatggaagtt tttcctgtca tactttgtta   2220
agaagggtga gaacagagta cctacatttt gaatggaagg attggagcta cgggggtggg   2280
ggtggggtgg gattagataa atgcctgctc tttactgaag gctctttact attgctttat   2340
gataatgttt catagttgga tatcataatt taaacaagca aaaccaaatt aagggccagc   2400
tcattcctcc cactcatgat ctatagatct atagatctct cgtgggatca ttgtttttct   2460
cttgattccc actttgtggt tctaagtact gtggtttcca aatgtgtcag tttcatagcc   2520
tgaagaacga gatcagcagc ctctgttcca catacacttc attctcagta ttgttttgcc   2580
aagttctaat tccatcagac ctcgacctgc agcccctaga taacttcgta taatgtatgc   2640
tatacgaagt tatg                                                     2654
```

<210> SEQ ID NO 6
<211> LENGTH: 51565
<212> TYPE: DNA

```
<213> ORGANISM: Artificial Sequence
<220> FEATURE:
<223> OTHER INFORMATION: Synthetic polynucleotide: 51kb 5' arm sequence
      (1-51565)

<400> SEQUENCE: 6

tcaacatcct taatcatcag gaaaatgcaa atcaaaacaa ccctgagatt ccacctcaca     60

ccagtcagaa tggctaagat caaaaattca ggtgacagca gatgctgccg aggatgtgga    120

gaaagaggaa cactcctcca ttgttggtgg gattgcaagc ttgtacaacc actctggaaa    180

tcagtctggc agttcctcag aaaattggac atagtactac tggaggatcc cgcaatacct    240

cttctgggca tatatccaga agatgtttca accagtaaga aaaacacatg ctccactatg    300

ttcatagcag ccttatttat aatagccaga agctggaaag tatccagatg cccctcaaca    360

gaggaatgga tacagaaaat gtgatacatt tacacaatgg agtactactc agctacgaaa    420

aagaatgaat ttatgaaatt cctaggcaaa tggatggacc tggagggcat catcctgagt    480

gaggtaaccc aatcacaaaa gaactcacac aatatgtact ccctgataag tggatattag    540

cccagaaact tagaataccc aagatataag atacaatttg ctaaacgcat gaaactcaag    600

aagaacaaag accaaagtgt ggacactttg ccccgtctta gaattgggaa caaaacaccc    660

atggaaggag ttacagagac aaaggttgga gctgagacaa aaggatgggc catctagaga    720

ctaacatatc aggggatcca tcccataatc agcttccaaa tgctgacacc actgtgtaca    780

ctagcaagat tttgctgaaa ggacccagat atggctgtct cttctgagac tatgctgggg    840

cctagcaaac acagaagtgg atgctcacag tcagctattg gatggatgac agagctccca    900

atagaggagc tagagaaagt acccaagtag atgaagggat ctgcaatcct ataggtggat    960

caaaaatatg aactaagcaa tacccctctg gagctcgtgt ctctagctgc atatgaatca   1020

gaaaatggcc tagtcggcaa tcaatggaaa gagaggccca ttggttgtcc aaactttata   1080

tgcctcaata caggggaacg ccagggccaa gaagtgggag tgggtgggta ggtgagtgct   1140

tctggaagcc tgttggggac tttctggata acattggaaa tgtaaatgaa ataaataccc   1200

aataataaaa aaagaacatt caaaaaaaaa aaaaaagatc ctaacccaaa acatccatga   1260

tatccaggac ataatgagaa agcaaggtta ttccattata aaaacatttt tttttttagt   1320

atagaataga gtttatatag ggtataggta ggggagttaa gagagtagta gagacagaga   1380

aaggcagaga gaagaagaga atagagaagt agaggccggt catgaccaca tggaaagagg   1440

gggaagggaa tgcagagaaa ggggacacat ggggcaggag agaggcaaga gtgtaagagt   1500

acaaaaccaa atttacacaa tgtttttcca taaatttagc cctacaaagg ataataggtg   1560

gaaaacacca caacaaggag ggaaactaca ccctcaaaaa agcaagaaag taatcttaca   1620

tcaaacccaa aagaaaatag ctacatgaac agaatttcaa ctctaataac aaaaataaca   1680

ggaagcaaaa atggctttta cttaaaatct cttaacatcc acggactcaa ctctccaata   1740

aaaacacata tattaataga ctggatatgt aaacaggacc cagcattttg ctgcatacag   1800

gaaacgcgcc tcagtgacaa agacagatac tacctcagag taaaaggcta gaaaacaatt   1860

ttccaagcaa gtggtcccaa gaaacaagct gtaataacca ttctaatatc aaataaaatt   1920

aacttaatag aaacagattt gtaaaagtgg attaaggaac tccacataaa accagagaca   1980

ctgaaactta tagaggagaa agtagggaaa agcctcgaag atatgggtac aggggaaaaa   2040

ttcctgaata gaacagcaat ggcttgtgct gtaagatcga gagtcaacga atgggacctc   2100

ataaaattgc aaagcttctg caaggaaaaa gacaccatca gtaagacaaa aaggctacca   2160
```

-continued

```
acagagtggg aaaggatctt tacctattct aaatcagata ggggactaat atccaatata   2220
tataaagaac tcaagaaggt ggactccaga aaattaaata agcccattaa aaatggggct   2280
cagagataaa caaagaattc tcacctgagg aataccgaat ggctgagaag cacttgaaaa   2340
aatgttcaac atccttaatc atcaggaaaa tgcaaatcaa aacaaccctg agattccacc   2400
tcacaccagt cagaatggct aagatcaaaa attcaggtga cagcagatgc tgccgaggat   2460
gtggagaaag aggaacactc ctccattgtt ggtgggattg caagcttgta caaccactct   2520
ggaaatcagt ctggcagttc ctcagaaaat tggacatagt actactggag gatcccgcaa   2580
tacctctcct gggcatatat ccagaagatg tttcaaccag taagaaaaat acatgctcca   2640
ctatgttcat agcagcctta tttataatag ccagaagctg gaaagtatcc agatggccct   2700
caacagagga atggatacag aaaatgtgat acatttacac aatggagtac tactcagcta   2760
ttaaaaagaa tgaatttatg aaattcctag ccaaatggat ggacgtggag ggcatcatcc   2820
tgagtgaggt aacccaatca caaaagaact cacacagtat gtactcactg ataagtggat   2880
attagctcag aaacttagaa tacccaagat ataggataca atttccaaaa cacatgaaac   2940
tcaagaagac caaagaccaa aatatggaca ttttgccctg tcttagaatt gggaacaaaa   3000
cacccatgga aggagctaca gagacaaagt ttggagctga gacgaaaggt tggaccctct   3060
agagactgcc atatccgggg atccatccca taatcagctt ccaatcgctg acaccattgc   3120
atacactagc aagatcttgc tgaaaggacc cagatatagc tgtctcttgt gagactatgc   3180
tggggcctag caaacacaga agtggatgct cacagtcagc tattggatgg atcacagggc   3240
ccccaatgga ggacctagag aaagtaacca aggagctaaa gggatttgca accctataag   3300
tggaacaaca atatgaacta agcattaccc cccagagctc gtgtctctag ctgcatatgt   3360
ataagaagat ggcctagtcg gccatcagtg gaaagagagg cccattggtc gtgcaaactt   3420
tatatgcctc agtacagggg aacagcaggg ccaagaagtc atagtgagag ggttggggag   3480
tgggtggggg agcgtgtggg ggacttttgg gatagcattg gaaatgtaac tgaaataaat   3540
acctaattaa aaaattagaa aatcaaaaaa agaaggtctt ttttttcac aatattaatt   3600
ctactaggct gtacacttac gagatcttca aattctagta tgtttctttt ttctttcttt   3660
tttttaaaga tatatttatt tattttatgt atgtgagtac actgtagctg tcttcagatg   3720
caccagaaga gcgcatcaga tctcattaca gatggtcatg agccaccatg tggttgctgg   3780
gaattgaact caggacctct ggaagagcag ttggttctct taaccgctga gccatctctc   3840
cagcccctct agtatgtttc ttaatctctt tctttacaca tttaaagttt tcattgtaga   3900
gggtttttta accactttg ttatgtatat tctaaatatt ttattttatt tgagaaactg   3960
gtaagaggag tgtgtccatg atctctttct cagaatgctt gttactcata tgtattaaga   4020
cttatgaatt tgacaagtcc cttccgcttg actcgagccc cgggctacct tgccagcaga   4080
gtcttgccca acacccgcaa gggcccacac gggactcccc acgggatcct aagacctctg   4140
gtgagtggaa cacagcgcct gccccaatcc aatcgcgcgg aacctgagac tgcagtacat   4200
agggaagcag gctacccggg cctgatctgg ggcacaagcc ccttcagctc cactcgagcc   4260
ccgggctacc ttgccagcag agtcttgccc aacacccgca agggcccaca cgggactccc   4320
cacgggatcc taagacctct ggtgagtgga acacaacttc tgccaggagt ctggttcgaa   4380
caccagatat ctgggtacct gccctgcaag aagagagctt gcctgcagag aatactctgc   4440
ccactgaaac taagaagagt gctaccctcc aggtctgctt atagaggcta acagagtcac   4500
ctgaagtaca agctcttaac agagacaact ataacagcta gcttcagaga ttaccagatg   4560
```

-continued

```
gcgaaaggca aacgtaagaa tcctactaac agaaatcaag accactcacc aacatcagaa   4620
cgcagcactc ccaccccacc tagtcctggg caccccaaca caaccgaaaa tctagaccca   4680
gatttaaaaa catttctcat gatgatgata gaggacatca agaaggactt tcataagtca   4740
cttaaagaat tacaggagag cactgctaaa gagttacagg cccttaaaga aaagcaggaa   4800
aacacagcca aacaggtaga aatcattaaa gaaaaacagg aaaacacatc caaacaggtg   4860
atggaaatga acaaaaccat actagaacta aaagggtaag tagacacaat aaagaaaacc   4920
caaagcgagg caacgctaga gatagaaacc ctaggaaaga gatctggaac catagatgtg   4980
agcatcagca acagaataca agaaatggaa gagagaatct caggagcaga agattccata   5040
gagaacatcg acacaacagt caaagaaaat acaaaatgca aaaggatcct aactcaaaac   5100
atccaggtaa tccaggacac aatgagaaga ccaaacctac ggataatagg aataaatgag   5160
aatgaagatt ttcaacttaa agggccagct aatatcttca acaaaataat agaagaaaat   5220
ttcccaaaca taaaaaaaga catgcccatg atcatacaag aagcctacag aactccaaat   5280
agactggacc agaaaagaaa ttcctcccga cacataataa ttagaacaac aaatgcaata   5340
aataaagata gaatattaaa agcagtaagg gagaaaggtc aagtaacata taaaggaagg   5400
actatcagaa ttacaccaga cttttcacca gagactatga aagccagaag agcctggaca   5460
gatgttatac agacactaag agaacacaaa tgccagccca ggctactata cccggccaaa   5520
ctctcaatta ccatagatgg agaaaccaaa gtattccacg acaaaaacaa attcacacaa   5580
tatctttcca tgaatccagc ccttcaaagg ataataacag aaaagaagca atacaaggac   5640
ggaaatcacg ccctagaaca accaagaaag taatcattca acaaaccaaa aagaagacag   5700
ccacaagaac agaatgccaa ctctaacaac aaaaataaaa ggaagcaaca attacttttc   5760
cttaatatct cttaatatca atggactcaa ttccccaata aaaagacata gactaacaga   5820
ctggctacac aaacaggacc caacattctg ctgcttacag gaaacccatc tcagggaaaa   5880
agacagacac tacctcagag tgaaaggctg gaaaacaatt ttccaagcaa atggactgaa   5940
gaaacaagct ggagtagcca ttttaatatc ggataaaatc gacttccaac ccaaagttat   6000
caaaaaagac agggagggac acttcatact catcaaaggt aaaatcctcc aagaggaact   6060
ctcaattctg aatatctacg caccaaatgc aagggcagcc acattcatta gagacacttt   6120
agtaaaactc aaacatacat tgcacctcac acaataatag tgggagactt caacacacca   6180
ctttcttcaa aggacagatc gtggaaacag aaactaaaca gggacacagt gaaactaaca   6240
gaagttatga aacaaatgga cctgacagat atctacagaa cattttatcc taaaacaaaa   6300
ggatatacct tcttctcagc acctcacggg accttctcca aaattgatca tataattggt   6360
cacaaaacag gcctcaatag atacaaaaat attgaaattg tcccatgtat cctatcagac   6420
caccatggcc taagactgat cttcaataac aacataaata atggaaagcc aacattcacg   6480
tggaaactga acaacactct tctcaatgat accttggtca aggaaggaaa aaagaaagaa   6540
attaaagact ttttagagtt taatgaaaat gaagccacaa cgtacccaaa cctttgggac   6600
acaatgaaag catttctaag agggaaactc atagctctga gtgcctccaa gaagaaacgg   6660
gggacagcac atactagcag cttgacaaca catctaaaag ccctagaaaa aaaggaagca   6720
aattcaccca agaggagtag acggcaggaa ataatcaaac tcaggggtga aatcaaccaa   6780
gtggaaacaa gaagaaatat tcaaagaatt aaccaaacga ggagttggtt ctttgagaaa   6840
atcaacaaga tagataaacc cttagctaga ctcactaaag ggcacaggga caaaatccta   6900
```

-continued

```
attaacaaaa tcagaaatga aaagggagac ataacaacag atcctgaaga aatccaaaac   6960
accatcagat ccttctacaa aaggctatac tcaacaaaac tggaaaacct ggacgaaatg   7020
gacaaatttc tggacagata ccaggtacca aagttgaatc aggatcaagt tgatcatcta   7080
aacagtccca tatcacctaa agaaatagaa gcagttatta atagtctccc aaccaaaaaa   7140
agcccaggac cagatgggtt tagtgcagag ttctatcaga ccttcaaaga agatctaatt   7200
ccagttctgc acaaactatt tcacaaaata gaagtagaag gtactctacc caactcattt   7260
tatgaagcca ctattactct aatacctaaa ccacagaaag acccaacaaa gagagaactt   7320
cagaccaatt tctcttatga atatcgatgc aaaaatcctc aataaaattc tcgctaacca   7380
aatccaagaa cacattaaag caatcatcca tcctgaccaa gtaggtttta ttccagggat   7440
gcagggatgg tttaatatac gaaaatccat caatgtaatc cattatataa acaaactcaa   7500
agacaaaaac cacatgatca tctcgttaga tgcagaaaac gcatttgaca agatccaaca   7560
cccattcatg ataaaagttt tggaaagatc aggaattcaa ggcccatacc taaacatgat   7620
aaaagcaatc tacagcaaac cagtagccaa catcaaagta aatggagaga agctggaagc   7680
aatcccacta aaatcaggga ctagacaagg ctgcccactt tctccctacc tgcccacttt   7740
ctccctacct tttcaacata gtacttgaag tattagccag agcaattcga caacaaaagg   7800
agatcaaggg gatacaaatt ggaaaagagg aagtcaaaat atcacttttt gcagatgata   7860
tgatagtata tataagtgac cctaaaaatt ctaccagaga acacctaaac ctgataaaca   7920
gcttcggtga agtagctgga tataaaatta actcaaacaa gtcaatggcc tttctctaca   7980
caaagaataa acaggctgag aaagaaatta gggaaacaac acccttctca atagtcacaa   8040
ataatataaa atatcttggc gtgactctaa ctaaggaagt gaaagatctg tatgataaaa   8100
acttcaaatc tctgaagaaa gaaattaagg aagatctcag aagatggaaa gatctcccat   8160
gctcatggat tggcaggatc aacattgtaa aaatggctat cttgccaaaa gcaatctaca   8220
gattcaatgc aatccccatc aaaattccaa ctcaattctc aaacgaattg gaaggagcaa   8280
tttgcaaatt tgtctggaat aacaaaaaac ctaggatagc aaaaagtctt ctcaaggata   8340
aaagaacttc tggcggaatc accatgccag acctaacgct ttactgcaga gcaattgtga   8400
taaaaactgc atggtactgg tatagagaca gacaagtaga ccaatggaat agaattgaag   8460
acccagaaat gaacccacac acctatggtc acttgatctt cgacaaggga gctaaaacca   8520
tccagtggaa gaaagacagc tttttcaaca attagtgctg gcacaactgg ttgatatcgt   8580
gtagaagaat gcgaatcgat ccatacttat ctccttgtac taaggtcaaa tctaagtgga   8640
ttaaggaact tcacataaaa ccagagacac tgaaacttat agaggagaaa gtggggaaaa   8700
gccttgaaga tatgggcaca ggggaaaaat tcctgaacag aacagcaatg gcttgtgctg   8760
taagatcaag aattgacaca tgggacctaa tgaaactcca aagtttctgc aaggcaaaag   8820
acaccgtcaa taagacaaaa agaccaccaa cagattggga aaggatcttt acctatccta   8880
aatcagatag gggactaata tccaacatat ataaagaact caagaaggtg gacttcagaa   8940
aatcaaataa ccccattaaa aaatggggct cagaactgaa caaagaattc tcacctgagg   9000
aataccgaat ggcagagaag cacctgaaaa aatgttcaac atccttaatc atcagggaaa   9060
tgcaaatcaa aacaaccctg agattccacc tcacaccagt cagaatggct aagatcaaaa   9120
atttaggtga aagcagatgt tggcgtggat gtggagaaag aggaacactc ctccattgtt   9180
ggtgggagtg caggcttgta caaccactct ggaaatcagt ctggcggttc ctcagaaaat   9240
tggacatagt actaccggag gatccagcaa tacctctcct gggcatatat ccagaagaag   9300
```

-continued

```
ccccaactgg taagaaggac acatgctcca ctatgttcat agcagcctta tttataatag   9360
ccagaaactg gaaagaaccc agatgcccct caacagagga atggatacag aaaatgtggt   9420
acatctacac aatggagtac tactcagcta ttaaaaagaa tgaatttatg aaattcctag   9480
ccaaatggat ggacctggag ggcatcatcc tgagtgaggt aacacattca caaagaaact   9540
cacacaatat gtactcactg ataagtggat actagcccca aacctaggat acccaagata   9600
taagatataa tttgctaaac acataaaact caagaagaat gaagactgaa gtgtggacac   9660
tctgcccctc cttagatttg ggaacaaaac acccatggaa ggagttacag agacaaagtt   9720
tggagctgag atgaaaggat ggaccatgta gagactgcca tatccaggga tccaccccat   9780
aatcagcatc caaacgctga caccattgca tacactagca agattttatc gaaaggaccc   9840
agatgtagct gtctcttgtg agactatgcc ggggcctagc aaacacagaa gtggatgctc   9900
acagtcagct aatggatgga tcatagggct cccaatggag gagctagaga aagtagccaa   9960
ggagctaaag ggatctgcaa ccctataggt ggaacaacat tatgaactaa ccagtacccc  10020
ggagctcttg actctagctg catatatatc aaaagatggc ctagtcggcc atcactggaa  10080
agagaggccc attggacttg caaactttat atgccccagt acaggggaac accagggcca  10140
aaaaggggga gtgggtgggt aggggagtgg gggtgggtgg atatggggga cttttggtat  10200
agcattggaa atgtaaatga gctaaatacc taataaaaaa tgggaaaaaa agacttatga  10260
attttataag tcaattatgt atcacaatag ttctctgaaa ttattgataa tttctataat  10320
ttttctagtc aaattttggg aacattgggt aaaaggtaat atgatcttca attgaaaata  10380
attttactta ttatttttct atttgtatcc cttctcttgc cttattgctc cagctaatgc  10440
ttcaatcaca ttatggataa gcagtaggga tagtgagcat tcctttccca ttttgatttt  10500
aatggtgctt attaatgttt tttattaatt taggaagata ttggccatag ttttgacata  10560
cataaccttt attatgttgg aatatatttc ctacagtcct acttgttctt tggcttttat  10620
taaaaagaca tgttgaggcc atcatgggcg cgaactcagt gggccctagc acacccagga  10680
tcttggaatc actggtgagt ggaacgcaac atctgttcca aaaaacccag agggtcttgt  10740
gccagcagga acaaggacaa aggaaacctg ctcaaccagc tgctggggtt tgttcccatt  10800
ggcgccagcc ccatctgatc ttggacgcat actcagcagg ccatagcaca cccagtatct  10860
tgggattact aacaccagtc tgctcaggag agcacataag cagcagaagc aacagagctt  10920
cttggacagg gtcccttcgg gccttcatcc tcagccagga ggcagagctg agacccagac  10980
ccctgggtac cttccccatc agaggagagt tggcctacgg ggagtactct gacctcagaa  11040
ttcaggaggt gaatctgggc tgcagaattc tgtgcacctt tcctgcaaga ggaaagcttg  11100
cctgcagaga gtgctctgac cactgggatt caggaaagtt agtctctcag gagtgctgac  11160
agaggctaaa gaatcacagg aggaacaagc tccagacaga gatagctaca acatctaaca  11220
caagagatta ccagttggtg aaagaaaaac ctaagaatct taataacagg agccaagacc  11280
actcagcatc atcagaaccc agtacaccca ccacagtgtg ttttggatat cccaacacac  11340
ctgaaaagca agactctcat ttaaaatcat atctcatgat ggtggtagaa aattttaaga  11400
atggcattaa taactcactt aaagaaatat aggagaacac tgctaaacag gtaaaaaccc  11460
ttaaagagga aggacaaaaa cccctcaagg aattacagga gaacactgct aaacaggtag  11520
aagcccttaa agaggaaaca caaaaatccc tcaaggaatt acaggagaac atggctaaac  11580
aggtagaagt ccttaaagaa ctacaggcaa acactgctaa acaggtagaa gtccttaaag  11640
```

aagaaacaca aaaatccctt aaagaattac aggaaaacac aaccaaagag gggatggaat 11700
tgaacaaagc catccaagat ataaaaatgg aagtagaagc aatgaagaaa acccaaaggg 11760
aaacaactct ggagatagaa accctaggaa agaaatcagg aagcatagat gtgaacatca 11820
gcaacagaat acaagagatg gaagagagaa tctcaggtgc agaagattcc atacggaaga 11880
tggacacaac aatcaaagaa aatgcaaaat gcaaaaagat cttaactcaa aacatccagg 11940
aaatccagga caaaatgaga agaccacacc tatggataag aggagtagat gagaatgaag 12000
attttcaact taaagggcca gcaaatatct tcaacaaaat tatagaagaa aacttcccaa 12060
acctaaagaa tgacatgccc atgaacatac aagaagccta cagaactcca aatagactga 12120
accagaaaat aaattcctcc caacacataa taattagaac aacaaatgca ctaaataaag 12180
agagaatatt aaaagcagta agggaaaaag gacaagtaac atataattgc aggcctatta 12240
gaattactcc agacttctta caagagacta tgaaggctag aagatcctgg acagatgtta 12300
cacagacacc aagagaacac aaatgccagc caaggctaat ataaccagca aaactctcaa 12360
ttaccataca tagagaaaca aaggattcca tgacaaaacc aaattcacac aataccttttt 12420
cgtgaatcca gtccttcaaa ggataataaa gggaaaacac caaaacaatg atggaaatta 12480
tgccctagaa aaagcaagaa aataaccctt caacaaaact aaaagaagac agccacaaaa 12540
acagaatgcc aactctaaca acaaaaatga caggaagcaa caattacttt tccttaatat 12600
ctcttaatat caatggattc aattccccaa taaaaagaca tagactaaca gactggctac 12660
ataaacagga ccaacatttt gctgcttaca ggaaacccac ctcatggaaa aagacagaca 12720
ctacctcaga gtgaaaggct ggaaaacaat tttccaagca aatggtccaa agaaacaagc 12780
tggagtatcc attttaatat ctaaaaaaaa tcaacttcca acccaaagtt atcaaaaaag 12840
tcaaggaggg gcacttcata tgcattaaag gtaaaatctt ccaagatgaa ctctcaattt 12900
tgaatatcta tgctccaaat gcaagggcat ccacattcat taaacaatag tatagtaaag 12960
ctcaaaacac atattgcacc tcatacaata atattgggag acttcaacac ccaactgtca 13020
tcaatggaca gatcctggaa acagaatcta aacagagaca cattgaacct agcagaagtt 13080
aggaaacaaa aggatttaac agatatctac agaatatttt atcttaaaac aaaagtatat 13140
accttcttct cagcacctca tggtaccttc tccaaaactg accatataat tggtcacaaa 13200
acaggcctca acagatgtaa aactattgag attatcccat gcatcctatc agatcaccag 13260
ggactaaggc tgatcttcaa taaaaataat aataaatatt agaaagtcaa cattcacgtg 13320
gaagctgaac aacactctac tcaatgatat cttgatcagg gaagaaataa agaaagaaat 13380
taaagacttt ttagagttta atgaaaatga agccacaaca tacccaaact tatgtgacac 13440
aatgaaagca ttcgtaagag gaaaactcat agccctgagt gcctccaaaa agaaactaga 13500
gagaatcata cactaacagc ttgacaacac acctaaaagt tctagaacaa aaggaagcaa 13560
attcacccaa gaggagtaga cagcaagaaa taatcacact cagggttgaa atcaaccaag 13620
tggaaacaaa aagaactgtt cagagaatca accaaaccag gagctggttc tttgagaata 13680
tcaacaagat agataaaccc ttagccagac taactaacgg tcacagggac agtatcctaa 13740
tgaacaaaat cagaaatgaa aagtacccaa ggagctaaga ggttcggcaa ctctatagga 13800
ggatcaacaa tatgaagtaa ccactacccc cacagaactg agtctctagg tgtatatgta 13860
gcagaggatg gcctagtcgg caatcaacag gaggagaggc ccttgggaag attatatgct 13920
ccagtatagg gggtggttaa catgtagaga ttccacctca gaccagtcag aatggctaag 13980
atcaaaaact caggtgacag cagatgctgg catggatgtg gagaaagagg aacactcttc 14040

```
cattgctggt gggattgcaa gcttgtacaa acactttgga aatcagttta gcggttcatc  14100
agttaattgc acatagtact accggaggat tcagcaatac ctttcctgtg cattggagaa  14160
aacagaaaac tctgagatgg aagctctgct gctggctctt gtgtttgctt ggatttgttc  14220
tagaagtggg tcgaatggac agctcaatga aacccaggta tcatgaaata ataagtataa  14280
tatataaaaa attcttattt cattattcat ttatctcaaa tgctgagcaa cacctcaata  14340
tcatttacta aatatttatg tactagagaa atcactcatt cagggagcaa gtcaggggaa  14400
atgcaacact ctaaatagaa tatgatttaa tatttagttt catatgactt aatatttaat  14460
atttttattt tagacatttt acatttagac tttcacacac acatatatat gtatgtatgc  14520
atatatatat atgtatatgt atataaacag catgcaaact gcaattacaa acattaaaat  14580
ataccagata aaatgttagc cttattatat gcccattgta gtattatgat ttcaaaataa  14640
aataggatat aattacatgt cttcatatta atcactcatg taaaaataat attaaatgtc  14700
agcatctcgt cacctgtgtc tatttatccc tctgttttcc tcaaagagat ttatataaat  14760
gtcagattct gtaaaccgtt ggttcacact catgtctgca ttgaaaacaa atattattta  14820
ctgtcaattt tatattttct catttctatt tagagcagat tttaggtgat aaaacccaga  14880
gaccaaatga aatattttgt tttctgtgat atttgttaac tcagtcttaa atatgtcaaa  14940
agtctttcac cgttatgctt taaatgtaga tttggacaat tgtgtcacct tttgtttgta  15000
cacttcaggg aacagaaaat ttactctgta tttaggaatt gtattattga ttgtatgtca  15060
cactatacaa taaatggaat atgttcaatt gcatttagta atttttattt tttttcctgc  15120
aatacatttt gattgtattc attcctctca actctcagat cttcccccac ctccctacct  15180
acacaaattc atgttctttc tctaacaaaa atatggaata taagtttttt ttgtttttta  15240
tttttttttt tttttgagac agggtttctc tgtgtagccc tagctgtcct ggaactcaat  15300
ctatagacca gactggcctc gaactcagaa attcacctgc ctctgcctgc caagtgctgg  15360
gattaaaggc atgtgccacc actgcccagc tagaatataa gttttttttt aaagattttt  15420
ttatttatta tatgtaagta cactgtagct gtcttcagac actccagaag agggagccag  15480
atcttgttac agatggttgt gagccaccat gtggttgctg ggatttgaac tccggacctt  15540
cggaagagca gtcgggtgct cttacccact gagccatctc accagcccta gaatataagt  15600
tttaaggagc agaattgtat acttctcatt aaaaatcaaa aatttcccct ctcaagctaa  15660
agtatttgtt ggagatgaaa gaaaacatcc atttattttc ctaatggcat cttcattctc  15720
agatctcagg tgattggtac accattgcca tagcagccac agatcttgat gtgatcaccg  15780
atgatggatt gttgaaactg tttttccgtc atcttgagtg tactgaacaa tgcaaagaaa  15840
tcatcctgac attctatggt gagtaagcta accttgctgc aatctaaagg ttcagacatt  15900
ttgatatgat aggaggtatt gacacatttc ccagactgac agtttcatga cactgtcact  15960
taccacaata tatacataat tccaaaatag aaaataatgc tgaggtattg ttccacattt  16020
caaataaaat acatttaata tgaatattta tgaatggtaa tataaacaat attaatatta  16080
ctaaaatatt taatatttat aatgtatgtt tcctatacat ttaaattatt taaaacagca  16140
tgcatattat aatgacaaat gatattcggt atactggata gaatgtatgt catattgtat  16200
atatgattac aatataaatt atgacttaca tttatatatg attacaatat aaaatgagtt  16260
gtatactaca tgtatattaa aatgaacatg ttatgtgtgt acttacaata ttgtatttta  16320
tataatatca tatttcacat taatatcaaa ttttgtggct ctatactaca gaaaatatca  16380
```

-continued

```
ggctagaaaa aattgctcag tgaataaagt acttttaaat ttatttataa cattgtgtta  16440
ttttatgata acatacacat gtcactatgt aaaaattatt atatttatat gtcatatatc  16500
atactttata ttttaattat acctatatat tattgtttgt tgttaaagat ttgtgtttta  16560
tggtattcct gtttgtgtga aagtgtggat ctctgcatct atatgtgttt cttgtgcttt  16620
ttctttgtct cttgtgtttt tttttttct gtttctttgc tttgccctca tctggtttgc  16680
ttttatttat ttatttcttg tctttagtat gcattctcat tttctaatga aagaaagtgt  16740
gagaatttgg atgggtggaa aggttgggag gatatggaga tataggaagg gaaaccataa  16800
tcagaacata gtatatggaa atattctttt aattaataaa acgatgggtt ttagttatat  16860
caagtgtctg gaaattagtt ttaaatagtt tttcatagtt ttaattgtta attccagtca  16920
tagaagtggg aagtatttca gatggaaaaa tagcatttgt atcactaagc agcttgtgac  16980
caagaccatt tcagatcttg tgggtaagac tgtcaatcac ccatagctgg aatggttgac  17040
aattaatggc tcctggggga ggaataatta tattacttta agaatatagt cacttgtggg  17100
tttacattca tgcacatatg ttcaatgata actggacata attggttact tctttaaaat  17160
gaaaggagga aagggagaga gaatctggga tttggaagga ctggactaga tgaaggtgga  17220
tccaagtatg ctcttgcatg tatggaattc tcatatgtac agcagtgact ggaagtatat  17280
aaacttcaat agcaataaat tcaggacata tagagaaata ggaaagcaga aacagggggc  17340
tatataagat cacattttat tttatgtgtg tatgggattc tacaaagaaa agttaaagtg  17400
aaatataaaa gtacttaaaa taaattcata gatcagcata caattaggac tagggtaaat  17460
aaagatccca tatcccctaa agaaatagaa gcagttatta atagtctccc agccaaaaaa  17520
agcccaggac cagatgggtt tagtgcagag ttctatcaga ccttcaaaga agatctaatt  17580
ccagttctgc acaaactatt tcacaagata gaagtagaag gtactctacc caactcattt  17640
tatgaagcca ctattactct gatacctaaa ccacagaaag atccaacaaa gatagagaac  17700
ttcagaccaa tttctcttat gaatatcgat gcaaaaatcc ttaataaaat tctcgctaac  17760
cgaatccaag aacacattaa agaaatcatc catcctgacc aagtaggttt tattccaggg  17820
atgcagggat ggtttaatat acgaaaatcc atcaatgtaa tccattatat aaacaaactc  17880
aaagacaaaa accacatgat catctcgtta gatgcagaaa aagcatttga caagatccaa  17940
cacccattca tgataaaagt tttggaaaga tcaggaattc aaggcccata cctaaacata  18000
ataaaagcaa tctacagcaa accagtagcc aacatcaaag taaatggaga gaagctggaa  18060
gcaatcccac taaaatcagg gactagacaa ggttgcccac tttctcccta ccttttcaac  18120
atagtacttg aagtattagc cagagcaatt cgacaacaaa aggagatcaa ggggatacaa  18180
attggaaaag aggaagtcaa aataacactt tttgcagatg atatgatagt atatataagt  18240
gaccctaaaa attccaccag agaactccta aacctgataa acagcttcgg tgaagtagct  18300
ggatataaaa ttaactcaaa caagtcaatg gcctttctct acacaaagaa taaacaggct  18360
gagaaagaaa ttagggaaac aacacccttc tcaatagtca caaataatat aaaatatctc  18420
ggcgtgactc taactaagga agtaaaagat ctgtatgata aaaacttcaa gtctctgaag  18480
aaagaaatta aagaagatct cagaagatgg aaagatctcc catgctcatg gattggcagg  18540
atcaacattg taaaaatggc tatcttgcca aaagcaatct acagattcaa tgcaatcccc  18600
atcaaaattc caactcaatt cttcaacgaa ttagaaggag caatttgcaa attcatctgg  18660
aataacaaaa aacctaggat agcaaaaact cttctcaagg ataaaagaac ctctggtgga  18720
atcaccatgc ctgacctaaa gctttactac agggcaattg tgataaaaac tgcatggtac  18780
```

tggtatagag acagacaagt agaccaatgg aatagaattg aagacccaga aatgaaccca 18840
cacacctatg gtcacttgat cttcgacaag ggagctaaaa ccatccagtg gaagaaagac 18900
agcattttca acaattggtg ctggcacaac tggttgttat catgtagaag aatgcgaatc 18960
gatccatact tatctccttg tactaaggtc aaatctaagt ggatcaagga acttcacata 19020
aaaccagaga cactgaaact tatagaggag aaagtgggga aaagccttga agatatgggt 19080
acaggggaaa aattcctgaa cagaacagca atggcttgct ctgtaagatc gagaattgac 19140
aaatgggacc taatgaaact ccaaagtttc tgcaaggcaa aagacaccgt caataagaca 19200
aaaagaccac caacagattg ggaaaggatc tttacctatc ctaaatcaga taggggacta 19260
atatccaaca tatataaaga actcaagaag gtggacttca gaaaatcaaa taaccccatt 19320
aaaaaatggg gctcagaact gaacaaagaa ttctcacctg aggaataccg aatggcagag 19380
aagcacctga aaaaatgctc aacatcctta atcatcaggg aaatgcaaat caaaacaacc 19440
ctgagattcc acctcacacc agtcagaatg gctaagatca aaaattcagg tgacagcaga 19500
tgctggcgtg gatgtggaga aagaggaaca ctcctccatt gttggtggga ttgcaggctt 19560
gtacaaccac tatggaaatc agtctggcgg ttcctcagaa aactggatat agtactaccg 19620
gaggatccag caatacctct cctgggcata tatccagaag atgccccaac tggtaagaag 19680
gacacatgct ccactatgtt catagcagcc ttatttataa tagccagaag ctggaaggaa 19740
cccagatgcc cctcaacaga ggaatggata cagaaaatgt ggtacatcta cacaatggag 19800
tactactcag ctattaaaaa taatgaattt atgaaattcc tagccaaatg gatggacctg 19860
gagggcatca tcctgagtga ggtaacacat tcacaaagga actcacacaa tatgtactca 19920
ctgataagtg gatattagcc caaaacctaa gatacccaag atataagata caatttccta 19980
aacacatgaa actcaagaaa aatgaagact gaagtgtgaa cactatgccc ctccttagaa 20040
gtgggaacaa aacacccttg gaaggagtta cagagacaaa gtttggagct gagatgaaag 20100
gatggaccat gtagacacta gcatatccgg ggatccatcc cataatcagc ttccaaatgc 20160
tgacaccatt gcatacacta gcaagattat gctgaaagga ccctgatata gctgtctctt 20220
gtcagagtat gcctgggcct agcaaacata gaagtggatg ctcacagtcg gctattggat 20280
ggatcacatg gcccccaatg aaggagctag agaaagtacc aaagaagcta aagggatctg 20340
caaccctata tgtggaacaa cattatgaac taaccagtac cccggagctc ttgactctag 20400
ctgcatatgc atcaaaagat ggcctagtcg gccatcactg gaaagagagg cccattggac 20460
acgcaaactt tatatgcccc agtacagggg aacgccaggg ccataaaagg ggagtgggtg 20520
ggtaggggag agggggtggg tggctatggg ggacttttgg tatagcattg caaatgtaaa 20580
tgagcgaaat atctaataaa aaatggaaaa aaaaaaagaa agataagatt gcactaaaga 20640
tcattgtgac ttcaatgaat gttggccacc atgtgcaaaa tgggtttaga tgattttaac 20700
taacctaact ggaagtataa atcaaaaaag ttaatgctga aaaaatttac tcataataaa 20760
cgttatttga ggtttagcag cagggaagtt agcatggatt ctgtgtgaag agaaaagaat 20820
gatattgttt attttctgta caataacttg ttctcagtta ataataaatt agagattata 20880
catcaagaag aattctagaa acatgtcatt gaataataca tgtgaaaatg aatctgtttc 20940
ccattttata aatataatta gaatctatat gaaggcttta atatcccatt ccttgcttct 21000
ttcaaagtgt tcattattta agatggcact attgaaatct gagtagaaaa aaatggcata 21060
aaatatatca ttacaaccca gtaacaacaa agacacatat gaattataga tttcatatat 21120

-continued

```
aactgatttt gtattcctca gatctatatc tgatatgtaa atacaattat ctgcttgtac  21180
atttactgtg caggtctata tgcccatccc cacctagaat cactgatgtc tatataaatt  21240
tttgctgaat aaatataagt tgaattaaca gaagtcaaat tatgcattag acaatggtag  21300
attcagtggg gtatagtagc acatgccttt aatctcagca cacatgaggc agaggctggt  21360
gtctctgtgt ttgaagccgg cttggtctac agagttccag gatagccagg tctgttaaac  21420
agataaacca tgtcatagaa aaaaagaaag aatgaaagag caaaggaagg aaggagagaa  21480
ggaaggaagg aaggaaggaa ggaaggaagg aaggaaggaa ggaaggaagg aaggaaggaa  21540
ggaaggagaa gaaggaagga aggaaggaag gaaggaagga aggaaggaag gaaggaagga  21600
aggaaggaag gagaaaaaca aacaaataat gatgaattca gtgacctaga aacagaagtg  21660
tttatagaag atagttagat agatagatag atagatagat agatagatag atagatagat  21720
agatagatag atatagatgc tttaaaaaaa agactacaca tatcaaagta atctgcagct  21780
actaccaggt aaagtatatt gatatcgttg cttgaaccat tgcacataaa caatcctcag  21840
tgacaaagtc aactgttgtg gtttctatgg cacagtgagt cagtgtccag tgatctgaga  21900
aggaagatgt tcgttatgcc catcattaca ctattcaggt cacacaggac catgataagg  21960
gatatacata tctgtctctt tttgttttag ggtagatgaa gaatgtgaaa agtttgaagc  22020
taacgcacag acctaccaat cagatgggtt tacttttacc tgtgagtata tgtgatcttt  22080
ctggaatatt taaattcctt gttactggta tcatcccata gcctgagcct ggaagaattt  22140
cttcttgcag ctttccacca ggccttacac ctctcactgg gtctgtgaag aagtcaggat  22200
ctcatcacac atgttacatt aaattgccaa aataaatgaa caaaactctc aggtcttatt  22260
gtgagatgtt cacatataaa acaactgaga atatatttta tgtagagtaa tttaagtctc  22320
acttacataa taattattgc gactattcaa taaatagtca agttggtcaa taaaaaaataa  22380
atatgtaggg caagagtgat ggtcagcagt taagggaggt tgctgctctt ccaaaatttc  22440
cctattctgg tcacagtagt cacatttgat ggtgcacaac attctgtaac tctggttttt  22500
ggagatccaa tgttttctac tggactcgaa gaacaccctg gtcacatgca aaagaaaaac  22560
aaaaacaaga caaaaaacac cacaagtgca cctttacaca tagatgaaaa taaaatcaat  22620
ttttaaaaaa gataaaatat tcaagtgttt ggaaagacat ttgataaaaa gagtttggca  22680
agtacattat aattagcaga catcagaagt taataatggc agtgattaaa atgacagatt  22740
gaaatattca taccaaagtg tacttaattt aaaattcaat cccaatgaga agaaaactgt  22800
ataggttttt gtttgtaata attggcaata atttgcagta atcagttttc taaaatggaa  22860
tgaccaagtg cttaagtaac ttactttgta gaaaagtgta caatatatta ttctcatctc  22920
agtttgaaaa atatctattt ttaacttaaa tgcaactgag gggattatta atgaatcagt  22980
gacactgaag aaggaagggg acgcatttct ggggtccttg aattgagcct gctaaaatga  23040
aatggaatag tgttaaaatg tttgaattct gacatctacc tttttacact acagatccag  23100
gtgagtgtta ctttaggatt tcatatatat caagtgcaag tatgatactt attagttact  23160
gtttgaagga tggtttgcat tggaaatccg cactcatttt gcttggtaag tatcatgact  23220
ccttcttatt atgatgacga ttattattat tactctttct tatgcctgca tatgggtctg  23280
cataccacat gtgtgcttgg tgtacacaga caccagaaga gagcatcaga taccctgcaa  23340
ctggaatgac aaatggttgt gagccaccac gtgagtgatg ggaattgagc ccagtttccc  23400
tgaagagcag ccagtgctct taacctcagg accatttttc cagccccacc tagatctttt  23460
tctataatac agaacatggc tacattatgt ctgcttttga tttaaaagaa aaatttatgc  23520
```

-continued

```
ataggttgtt tatataaaat gtatttattc atagatgtgt ctacatagga gattcaatat  23580
tccccttgac tgaatcaagg atgcaaaaac attttatcaa aaataaagat ttatgtccac  23640
cagggacttc catcagaaag atttccttaa attggacaca tacaacgtgg tgatacaaga  23700
cattccatgg tgcccttatt gaagtatcag agttcactca ttggtagatg gcttagggaa  23760
cctcataatc caaaaataaa aattttagtt tagatgcttt aaaggaaaat catgttaggt  23820
ataagaaata tgaaggggga ggattttttt attgtcttgt ttctggaaag ttgacattat  23880
ttactccccc ctcattccat caggggtctg gagtaggcag gaatggatat gatgataata  23940
atataggttg agtaggaaga aaaagtcatt attttggaaa ccttctgaaa tcttaaatgc  24000
aactaacttg aattccaaag tggttatgtt tagagaatac tactacccag ggagctatta  24060
gaggaggaca gggaatgtgc tcaagtcaca ggagcatatc ctatgtgctt agaatgtatt  24120
caattgtgaa ctcaataggt ttacaactgt gaatgatgtt tttgtgaact caataggttt  24180
acaactgtga atgatgaaat gatgttccat gtttttagtc cttgtcaagt caccatgaaa  24240
gacagaggtg ggagtgagga gaggattgga cacacagtaa gataacatgg aggatacatt  24300
ctactctgaa gaacattcca catgattctc ttcatttttt ccacacaatg aagggaaagg  24360
aaatggtgtg agtgaaattt acagatgagt gtactaggag gatacttcca aaggagaatg  24420
taagatatgt gcttgagaaa ggtaataagg caatgaccat agaggatacc ctagatgtcc  24480
cctgagactt tatatgaaat aaaaaattta aaaccatatt atatttgatt caaatttact  24540
actcaacaat ttttgaagtt ataatcctta aaacaatgtt gtttcccacc ctgttttgca  24600
gatatttgtc ctaaataagg acatgcatac cttgggtgag tagaaacata atgacagatc  24660
ccattcttac taaaaatcaa tgcttttta tttttatcgc ttcttggcct tttggctgag  24720
atcaagtgta tttttttattt gttactttta tgaaaaaaaa aatcgatggg tggatgtgat  24780
gtgggtgcag tgctgttgga aaacagaaga tggcaccaga tcccacagac tcacatggag  24840
ctgagacata agtcttgtgc aagatcagag atgactcttt ttttttcttt tccatttttt  24900
attaggtatt tagctcattt acatttccaa tgctatacca aaagtccccc atacccaccc  24960
acccccactc ccctacccgc ccactccccc tttttggccc tggcgttccc ctgttctggg  25020
gcatataaag tttgtgtgtc caatgggcat ctctttccag tgatggccga ctaggccatc  25080
ttttgataca tatgcagcta gagtcaagag ctccggggta ctggttagtt cataatgttg  25140
atccacctat agggttgcag atccctttag ctccttgggt actttctcta gctcctccat  25200
tgggagccct gtgatccatc cattagctga ctgtgggcat ccacttctgt gtttgctagg  25260
ccccggcata gtctcacaag agacagctac atctgggtcc tttcgataaa atcttgctag  25320
tgtatgcaat ggtgtcagcg tttggatgct gattatgggg tggatccctg gataaggcag  25380
tctctacatg gtccatcctt tcatctcagc tccaaacttt gtctctgtaa ctccttccaa  25440
gggtgttttg ttcccatttc taaggagggg catagtgtcc acacttcagt cttcattctt  25500
cttgagtttc atgtgtttag gaaattgtat cttatatctt gggtatccta ggttttgggc  25560
taatatccac ttatcagtga gtacatattg tgtgagttcc tttgtgaatg tgttacctca  25620
ctcaggatga tgccctccag gtccatccat ttggctagga atttcataaa ttcattcttt  25680
ttaatagctg agtagtactc cattgtgtag atgtaccaca ttttctgtat ccattcctct  25740
gttgaggggc atctgggttc tttccagctt ctggctatta taaataaggc tgctatgaac  25800
atagtggagc atgtgtcctt cttaccggtt gggacatctt ctggatatat gcccaggaga  25860
```

-continued ggtattgctg gatcctccag tagtactatg tccaattttc tgaggaatcg ccagacggat 25920
ttccagagtg gttgtacaag cctgcaatcc caccaacaat ggaggagtgt tcctctttct 25980
ccacatcctc gccagcatct gctgtcacct gaatttttga tcttagacat tctgactggt 26040
gtgaggtgga atctcagggt tgttttgatt tgcatttccc tgatgattaa ggatgttgaa 26100 catttttca ggtgcttctc tgccattcgg tattcctcag gtgagaattc tttgttcagt 26160
tctgagcccc atttttaat ggggttattt gattttctga agtctacctt cttgagttct 26220
ttatatatgt tggatattag tcccctatct gatttaggat aggtaaagat cctttcccaa 26280
tctgttggtg gtctctttgt cttattgacg gtgtcttttg ccttgcagaa actttggagt 26340
ttcattaggt cccatttgtc aattctcgat cttacagcac aagccattgc tgttctgttc 26400
aggaattttt cccctgtgcc catatcttca aggcttttcc ccactttctc ctctataagt 26460
ttcagtgtct ctggttttat gtgaagttct ttgatccatt tagatttgac cttagtacaa 26520
ggagataagt atggatcgat tcgcattctt cgactcttat ccattgagtc tatcagccat 26580
catactatcc ttctctactt aatttgctcc cttgagatct caagataaag agtcaatatt 26640
ttaattttgg aaacaaagaa atccgtgaga tatgaaataa tgaagtttag cgtgaattct 26700
gggcagccaa atagtttgca gcttttggtg atgcacatat ttatgcattt ttctctgtgg 26760
tataaatctc agtatttacc ttggatatat gaaatctcag gatttgttca gaggtttaca 26820
aaattaatat aattttatga aattcttcaa aataatatcc atacatggca tccatgtaca 26880
cagatggaat cccatgaagc aactttgtca tggacaaagg tccactttgt aatggatagg 26940
gtctactaag atccaacaca actcagacac tgaatcaata cagaaaacaa aaatttattg 27000
taatcaaact gctactgatc aatcagcaac attgaacaga cttgggagct gaactatagt 27060
ccccagccaa aatgtttaca gggctttagg cctgaaagac acaaatatct atgtcaagtc 27120
acagttaaat ttttccatca attgagattc aggtataggg gacttttcta gaaacatttc 27180
tttgtggtac atttatcctg tcctcattgg ttagtttact taactgtggc agagtgactt 27240
gcccagcatt catgtctcaa cttgtcaacc aaggtgtcgg tcaccctggg agatcttaga 27300
aacttaaact ttgtttgaac cctattcaaa atggaagatt tattcaaaat ggctctttat 27360
tacaaatttc cctctgatac attgctcatc aaaggaatca attataaagt tatttaatgg 27420
catataatat ttatatatag aactgagttt cataatgaca ttctttatac atgtatatca 27480
tacattttaa tcatatttcc cccctttatc tacctcttat tctaacctgt tgctttcctc 27540
atcccaacag ccgagtcttc attctacttt cacacacaca cacacacaca cacacacaca 27600
catatatgtg tgtgtatgtg tgtatgcata tatgtattgt atataaattt tattatagag 27660
tatagagcat attatatatt acattcacta tattatacat tgtcttgtgc attatattat 27720
atatatatga actttctggt gacacaatca atttaattag gactgcttgc ataagcatgt 27780
gtacagactt atttacagga gcatggacac aacatcagca tctagatcac taaaaatcat 27840
ctcaggctcc ccctaacaac catgacttgc ctgtaaagtc tcagaaatgt ttggggcctt 27900
gtgagtgagt ctcctgaacc acccagcaac ttttattatc tataatccct cagaagaagg 27960
gggaccacat gaaccctgcc aattccacca atttggttca ggtcttcctt cattgaaaac 28020
ttaaggacat tatgctacta agaagaactc aactaaatta aacattttca ttctcatctc 28080
cacagatatt ataaagaata tttgaaattg taacttctca atggcaattg attcatctct 28140
gtgaagtcta attattctgc tccccatcct atgaagacct aagtcccaat ttattgcttc 28200
ttttctttcc tgcatttatc ccttgtatga cgttactaac ttactgatta aattgatact 28260

-continued

```
gtatgcatac acacatatca gaagcatgct cttaaagttt ccaatgctta aaaatgtttc  28320
actatgcaca actcttaaaa aatatactca tctattatca agcaggataa atgtacttaa  28380
aagaatagtt aaagagttgt acagatgtct tagtcggtgc tcactaaaac ctgtctattg  28440
cctctagctt ctggggtagg atgtgtctca tgagcactcc cctacctagc tataattgca  28500
tggtcaggcc tcgcacacat aaccacatct gctttgagtt catgagcaca catcaccaca  28560
tctgctttga attcatatca atgggcactg cagaaattaa aaaaaaaaaa ccattaggtc  28620
ttacttcaaa agcctgtact tcacaaaatt ggaaaatcta aatgaaatgg atgattttct  28680
atatacatac cacttaccaa agttaaatca aggtcaggta aacaacttaa aaagtcctat  28740
aactcctaag taaatagaca aagtcattaa aatattccca accaaaaaaa caaaaagccc  28800
agggccagat tgttttagtg cagaattcta ccagactttc aaacaagagc taataccaat  28860
atgcctcaaa ctattccaca aaaataggaa cataaggaac actacctaat tcattgtatg  28920
aggccaaaat caccctgata cctaaaccac acaaagactc aacaaacaaa agactctcag  28980
accaatttcc cttatgaaca ttgatgcaaa aacactcaat aaaatattag caaactgaat  29040
cagagaaagc atcaaaaaca tcattcaaca tgatcaagta acattcattc aaagggttgt  29100
agggattttt caatgtatga aaataaatca acataattca caatataaac aaactaaaaa  29160
aaaaaactaa tcatctcatt atgtactaaa aaaggctttg acaaaatcca atctctttca  29220
tgttaaaagc cttggagaga tcaggatacg agcacatatc taaatacaat aaaagcaatg  29280
tacagcaagc caatagtcaa agtcaaatag agaaaaactt aaagcaattt tactaaaatc  29340
agggacaaga cacagctgac cactctctcc acatatattc aacattgtac ttgaacttct  29400
agctagagaa ataggaaaat taaaacagat caaggggata caaattggaa aggaagaagt  29460
caaagtatca ctctttacag atggtgtgat agtactcata agtgaaccca agaattatac  29520
cagagaactc ctacatctga taaacacttt cagcaaagcg gctggataca aaattaactc  29580
aaagaaatcg gtagccctct tttatacaaa ttataagtgg gtcgagaaag aagttaggaa  29640
gaaaatacct ttcacaatag ccacaaataa tataaaatag ctaatagtaa ttctaaccaa  29700
gcaggtgaaa gatctgtatg acaagaattt caagtatctg aaaaagaaat taaagaagat  29760
atcagaagct agatcccaca tgcttatgga tcaattgaac taacaatgtg aaaattgcat  29820
ctctccctgc ccttatggat catcagacaa tactggtcca tgtggtcaaa gggaacagag  29880
atgagagacg agaggttaac atgccctgtg agtacataca gtaaataaga tacatcagaa  29940
ccagatgcag ggaggcagac aaactttacc tggggtgatt caagaactat ataatttggg  30000
gatgctagaa aaatccaaga tggccagagg tcattgactg aagacttagg gtactgaaat  30060
aattcactag catgggaaag tatttcacga atctcagatg ctagctgaat gagttcttat  30120
caagagaaat aaagggatat ggactccaca ggaaaaccaa cagagtcaac tgacacagac  30180
ccttgagggc tcccagagac tgaactacca accaaagagt aagcatgagc tgtacctatg  30240
accctacaca catatgtagc agatgttcaa catggtcttt atgtaggtct cccaacaact  30300
agagtgggga ttgtccttga ttctgttgcc tgcttgtgga tcctgtttcc ctgagtaggc  30360
caccttgtct gtcctcagtg ggagaggatc cacctagtcc tgcagtaact tgatgtacca  30420
gagtaaggtg atacccaaag aacacacacc ccttctcaga ggagaaacgg aaggggaggg  30480
gagctgtgtg agggtgagac taggaagaga gagaggctga gattgggata taaagtgaat  30540
aaataaatta acagaaaaat aaattggaga ggaaaaagtc aaagtattgc tagatggttg  30600
```

-continued

```
gatagtatgc ataatctcta caaaaattct accagggaac tcctacagtt gataaacatc  30660
cttcagcaat gtagctggat acaaaattaa ctaaaaaaaa tcagtatctt ttctttatac  30720
aaatttgaaa tgggctgaga aagaattggg gagacaatac actttacaat agccacaact  30780
aatataagat aacttggtgt aattctaacc aagcaagtgg aagaccccta tgacaagaac  30840
ttcaagtctc tgaagaaggg aaatgtggta catttattaa atgggatact cctccagaag  30900
gggaaataac atagacttgg gaaatgtttt ggaatagtag gacataggac tgagtgagcc  30960
agaggggtca aggacaccac aataagactc acacggtcaa ctaactcggg cctatggtag  31020
ctcacagaga ctaaatcacc aaccaaagag catgcatatg ctggaagtag gcccccctac  31080
acatttggag cagatgtata gcttggtctt catgtaggtc ccctaggaat tggagcaagg  31140
attgtctttg actctgttgc ctgcctttga aaccgctcct cttggctggc cttccttgaa  31200
gggctacact gggaatggat gcactaagta cttctgcaac ttgaagcacc aggactggtt  31260
gaggagaaag gatgaggtaa tgggggaagg ggtttgtgag ggtagtacta ggagaagggg  31320
aggttgtaat tggggtgtaa agtaaataaa tagatagata gatgatagat agatgataga  31380
tagatagata gatagataga tagatgatag ataggtagat agatagatag atagatagat  31440
agatagatag atagatagat agatataaga aagaaaattc aaatactaga atccatattg  31500
tgatctaacc atgtaaaatt ctttcttcct acttgatatt ataaggtatt ctttacccaa  31560
agaaaaatat tatttcaagt ctggtttcta ataccatgaa atataaaatg tgattgcagc  31620
attgggaagg taaatcaaat ttcatacagg agaagacatt tttcctgtct gatacttgaa  31680
atagtgtttt catgatattt ttcatgaatt tcactgctgc aaagatatat ttactcttgt  31740
gtttttaaac attatcataa tgaataaagg accttggttt tcaaggcata tacacctcct  31800
tcatggagta tataccactg caatccttag gcatttcaca caatgtaaca aatacaatat  31860
tggcccttaa ttaactacac aagcatgaag catcagggat gaattaatct caaatacaca  31920
cccagtatcc catcaaaatt atttggacaa taacacatca aacttatttc cctaaaggtt  31980
tacttttttt ctaactccat aagctcatcc atcagtcatt gttttaatat acccgatatt  32040
aagtcaatat cttaaatgta atgagatata aatttttttt ctgacaaaca agaagggaag  32100
gattatggat ttctattttg ttgctcataa ggaaacatgg gtgacataat gtgctagttg  32160
agccattcaa acaacatgga cttcagattt tgattttcgc actgagtgga tgatacaaca  32220
agaggtaaaa ttggaagatg cactacctaa aacaaagaga tacaaaccaa atctttaatg  32280
gtttttagac acatctttga ccatgaaaat atggcaaagg aaagttgtct ttaaatgtct  32340
tcattattat ctgaactcaa aaattaattc acatcacagt gttcacactg tgaacactaa  32400
gtcacacata gtctcatctt gtcttcagga gacttttctg ggaattatca ttattttgat  32460
aggggaattt agaagagata gttgggtttt acaaagtgac agacaactga ccaacagatt  32520
ctctatgctg ggttccaaat gacacttctt ccatttcttg ccatcaaatg cagtaagtga  32580
aactaatccc actaaagaaa tgtaaagact atgtaaattg aacaagaaat aaaaaactcc  32640
cataaaatta ttataaatat ctataaagta agtaatagca ttctttttgt ataaaataag  32700
ctgagaccag agaggtttat agattcttga ttccaacacc tgatttacaa aaaactgcat  32760
atatatatgt gtgtgtgtgt gtgtgtgtgt gtgtgtgtgt gtgtatacat atatatatat  32820
atacatatac atatatatat acatatatat ataaaacaaa atcccttaaa gcattgatga  32880
acttcaataa ccttttctct atttgtacat tttaattttt ctcttatttt ttaaaagtag  32940
aacataattt ctttttcttt tagttttaag aatggtgaca ataaattaca taataataaa  33000
```

-continued

```
gagataagaa agaaaacaca tcagtcagca caatttgagt ttgcttacta agactgtttc  33060
tctcaacaga tgcagagtcc catagcaaaa ccttaggcag agcttgggga gtcctgcaga  33120
ggatggggag gaaggatcac ctaaccagag gagtcaggga caccaaaagg acaaggctca  33180
cagaatgaac tgacatggag gctgtcagag atcagggagc cagtaggggt ctaataggcc  33240
ttgggtgtat atgttatggc tgagtgtagc ttatgttctt ctagggttcc taacaatgga  33300
agtaggacct atctctgact cttttgcctt cttatgggat cctttcactc cttttgggtt  33360
gcctagcaga gccttgacgt gatggtatat gcctgatctt attgtaactt gttataccgt  33420
gtttggttta aattgctggg aggcctgctg tttttggaga ggacatggaa gggatggata  33480
tatgaaagag gggaggtaag agagacacag agggaagggg aggaaggaga aactgcagct  33540
aggatgtaat atataacaga agagttaatt aattaattaa attttaaaaa agcctgtggt  33600
ggttttaata agctcagccc aggcagtggc actattagga ggtgtggcct tgttggtgta  33660
ggtgaggctt ccttggaagt agtgtgtcac tgtgggggtg agctttgaga ctcttctcct  33720
agctgcttga aaacagtctg ctcctggatt cctttcaatg aggatttagg gctctcagct  33780
cctccagcac catgtcttcc tggatgctgc catgcttccc acctggatga taatggactg  33840
aatctctgaa cctgtaagcc agccccaaat aaatattgtg cttcctaaaa tttgacttgg  33900
tcatcatgtc tcttcatagc aatggaaacc ctaactaaaa cagagcctct ctggctctta  33960
agccatgctg gctataaagc ctcacatatt acatgacata ttattataga aactttgtat  34020
cacaccctga atatcatatt tacaatattg taggtaatat tttcctctct aattatgaca  34080
tgtaaatgaa ttacgtaatt atactcaaaa gaatttcttc tgacattatt gactacctta  34140
ggttttgttg catttttatg tgtttattat tttatttgtt ttgttttgaa acacattcaa  34200
actatgttag caacggttat cctcaaactc aatatataga tcagggggc ctcaaactca  34260
cagaaaacaa tatgactctg cttcccaaga cacagaatta acagtatgga tcaccatgct  34320
caattaatca caggttaatg tattttagtt tttaattatg tagatattca ggtatctgca  34380
tatgagcaat gttaccaggt gagttcagta cctgacgagg gcagaagagg gagcagattc  34440
ctctggacct aaaattacac atgattgtgc attgcaatat agttgctagg aactgaaccc  34500
aggtcgaaag gaaagctagg actctgaccc agtgagtcat cctaagccag attatttttt  34560
aataggtaca gtgcacattt tctttgttgt gtatgatggc tagaatatgc ttgccctatg  34620
gaaattggca gtatgaggag gtgtgtcaat gttggggtag gtgtgacctt gttggaacat  34680
gtgtgacact gtgtgagtgg gttttgaggc tcctatgccc aagctctgcc aaatgaggaa  34740
gagagcctcc tgctggctgc ctgcagaaga aagactctcc tggctgcctt tggatcatga  34800
tgtagaactc tcagctcctt ccccagcacc atgtctgcct gcagactgct atgcttcctg  34860
ccatgatgat aatcatgaac ctctgaacct gtaaggtggc cacaatgaaa tgtttgcctt  34920
taatagagtt gccttggtca tggtgtctct tcacaaatat ataccccccta attcagacat  34980
tgtgtattac atcacattga ttgaagacag aatgtgtaca tgaaaaatca atttatttta  35040
tcaacaaaag aatcagtacc atggtaggag tatgggaaac aaatccatga agcagagatt  35100
ctggcttcat aggaaagatg aaaagaaaaa ctaagaaaag gatgagctct cttcattgtc  35160
atgattctga tttcatgaaa gaggtgatgt gggaaatact tctgatcttg ctgtcatctg  35220
tgaagcttca aaagtaaaaa acaagacaaa caaatgaaac agtaagatgt gcatgagctg  35280
gtgcttctga catgagcttt ctgagattgt aaatgaaaaa caaaaattaa tcgacacgga  35340
```

-continued atatggtgaa aggtttgatt ttaaaaatga cacatgtcac agggttagac ctaggtttgt 35400
tcttggttga cttccataac tctcttccgg catttaaact gagagttttt ggtctaaatg 35460
taatctacca taacacctat gtgcaaggtt gtgtctaagg agactttaca aagttcatgt 35520
acatttacag tatttccaca ttcatgctac actcttggct gtcacaaata tcacttattt 35580
tcaatagtca agtttcatta aattcttacc tattaccttt aagataaaag aaatcaacac 35640
tttggtatag gagagttgct tattcccatg ttataaatat taacagcaac ataaacgata 35700
gctttgccac cttggattat atatgtaatt agaattataa agagatttcc tctactaaag 35760
gcataactaa tagactaaag aatgaatttt tagcagatta aaatattaac aggctctgct 35820
gccctgttgt actcacccat attgtgtctt tattggttac aagtgtctgt gagagacaga 35880
aaggaaggaa ataaccacaa acaaaagaca tagttagagc tccttaatat ctccagtgac 35940
tttaaataat tttaaaaatc tgatttagac gactgaaatg atgattatcc tggatatctt 36000
caggtgcatt agtttgctgt gtgaagcaca atgttgttac ctgtgggcgc caagtgctgg 36060
atattctcct ttggaatatt gtattccttg accagcttcc caagctcctg cttctgtgct 36120
ttgctcaggg tctctccttt tcctacatca cataaagcag aaaggaagaa aaagtgtagc 36180
ttacagtact gggtggctca gaacagatgg agttataatg ggttgtgtga tattgatgca 36240
tggaaacatc ttactttgtg ggccctccct caccccatca gtctcattct gatcaaccta 36300
agatctctaa agtaaaaaga acacatttaa tgaagctgaa ctatgatagt ccacacccta 36360
atgaataata tcgttatttg tggtggaatt gttattgttg ttattgccat catcactatt 36420
aatactccta ctactactat tataattatt cgtactttcc atatgaccgt atatttattt 36480
ccaaaaaggc ctgtacataa tcctggtgtt tgaaatactt gaactaaatg tttgtccatg 36540
ctgacttcta ccttacttct gtgtagattc tggagtccgt gccttggata attgataatt 36600
atcaaaataa gcagtgaaat caggctgaac aggctcatga acctgaatca attacgactc 36660
caacaccacc ccacctcacc acttacccaa cctcactacc agattccagt acccagtacc 36720
cagcctccag tcccctgcct ccaggcccaa gcccccaaat tgcctctgct tcctccattg 36780
cccctcacaa ctttggtaaa caaagcaaga ttgttgggtt tatatatata tatatatata 36840
tatatatata tatatatata tatattatca tgacacaaag caaggtcatc tggaaagagg 36900
taacctcaat taagaaagtg ctaccctcag actgctctgt gagaaacctt gtagactcat 36960
tttctagatt gacagttgat atggaagtgt ccaccccact gtaggaaact cagcagcaca 37020
gttttctttg ttagtgtttg atggtagggt gcctagacta tgggtagtgc cacctctggg 37080
gagatggtcc tgggtgctaa gagaaagcat gctgaacaag acctggggag caagccagta 37140
agcagcactc ctccatgccc tgtgcatcag ttcctgcctt caagttcttg gctgtttggt 37200
acagagacag atgggtcaat aattggaata ggattgaaga ccccaaaata cccccaacac 37260
acacacacat ggacacttga ttgttgacta agaagacact accatatagt agaaaaaaga 37320
gagcatcttc agcaaatcgt gctggcctac ctggtggtct gtatgaagaa gaatacaaat 37380
tgatacatat ttctcaccct gtacaaagca caagtccagg tggatcaaaa tcctccacat 37440
aaaatcatat atactgaatc taatagaaga aaaagtagga aatagcttgg aaggtattgg 37500
cacaggaaaa aattttctga accaatggct cagctctaag atcaacaatt gacaagtgga 37560
acctcataaa actgaaaagt gtcttcaaga caaaggacac tgttagtagg aaaaacagca 37620
acctacagat tgggaaagaa tcttcacaaa ccacacatcc aatagagggc taatatccaa 37680
aacatacaaa gaactcatat attagactcc agaaaaccag acaacctagc caaaaactgg 37740
ggtacaaact aagcaaataa ttcttaacta cggagacttg aatggctgag aagcaatgac 37800
ttctttttga aaatgaactg tgttatagga gcttaagcca aatcaaccct ttcttcccca 37860
agttgctttt ggtcatggtg cttatcatat cgatagaaac cctacaagag ggaccactct 37920
caccagcaac taaaatcaca tttgtctcct gtccgctctc atccacatta acgttgtgaa 37980
agaaaagggc gccatcttcc ttcattacaa cttcgaagta atttctacca gagtctgcaa 38040
ttaaaagaga atcagcttag aaatcagtag aatcattgga ggtttcacta ttattttaca 38100
tatgaaatct atgatatttt tatttctttt tcaattattt gacaaatgtc atttacaatg 38160
gtttaaaatt gtaaatgaga attactaagt ggtagagaca ctcttgcatt aattaaaata 38220 ttttttgaa tttaaaaaga atgtccataa ttagacggga atgctggcac acgcctttga 38280
tcccagcact tgggaggcag aggcaggtag atttctgagt tcaaggccag cctggtctac 38340
aaagtgggtt ttaggacagc cagggttata tagagaaacc ctgtctcaaa aaatgaaaaa 38400
aaaagttcat aattacctta tgtctccaca gcctatttaa aaagtgaaca caacgctaat 38460
attaaaatac cacactgaag cagggatggt gactcaaaca tcaaatccca gcaatcagga 38520
ggatctctgg ggctagcctt gtcgcagaac tagttatagg acagccaggg ctatgcagag 38580
taactctgta tcaaaaaaaa ttttaaaaac aaccacaaat gtgtctatgt atgtctgtgt 38640
gtgtgtgtgt gtgtgtgtgt gtgtagcaaa tgtatagttt tccatatatt aaacccttaa 38700
gaaatcagtc ctgtagcttt atgggactgc cttctaaatg tcatttatac ttaaataata 38760
ggcacaaaaa tgtctctaat aatacttttg tatgaatgtg tataatacac cttaactgat 38820
aacataaatg tctggaagtt tagttaggat tttggaagtt gcatcaaaaa ttatcagatg 38880
aaattgttca aggatcctgg ccctttagtt gtgcggcctt gtcaaacctt gcaaaatttc 38940
tctctgtctc tctgtctttc tgtccctccc cccctctctc aattagatta tgcatcccat 39000
taattgatta catactcaca gtcagtagtg taccgcccat cttcttgttt ttctcccaca 39060
acagtgtgtg tctgacactt gccattcatc cttcagaaat aaaaatcaaa aacttgcttc 39120
tgaatttact ctttcaggtt gctcatattt ccttattgtg tggtagtatt aactgtcttt 39180
gggaagtgtt taatttgttt aaataaaccc acatctgaag actgacacca acactctggg 39240
gttatgattg acatggaaag taaatccagg cttccagggg aagacactgt cctcattttc 39300
tacccacatt tcctgttcat gactagtttc aaccagaatt acccaaccct gtaaaactgt 39360
agaacacatt gcattcagtg ttccttaaat caaggacaca actcagaata aatatgccca 39420
ggagatcaat tccatttttt cacatggccc aagtgtcagt gaaaatttca cagacattca 39480
tgtgcccagt ttctcagtcc tgtccatgtg catcaggtga atgtcactta ctggacatgg 39540
aatttgattt tgagtgtccc acagtcgtca ttgcactcca tatgctcaaa gtacgctctc 39600
aggtctccat tcatctttac tttctccacc ttgtccgcag ctatgtaaag ggtgcgccag 39660
tccccattaa cctaaatagg acagacacca ttgcaaaagt tggttagtca atctgttccc 39720
ttttattcag caacatttgt cctaattact acatgacaac aattccataa gtcaacaaat 39780
gaacttggac caagtaaaat gcagatgtct ctctgctaga gagtagatta ggagattgtg 39840
tcatcactca ttcacactag aatatggaac acaggataca gttcacactt tgtcaatcaa 39900
taacaatgca aagtccaatc tgtaattttc tcttcttaac cttctttcat actagacaga 39960
agtcattgaa aacatgcaaa gagttgaaaa tacactagga ctgcattaca gataggattc 40020
agataatgta tatatgctat atataccaca tataatatgt aatgccatac catttatagt 40080

-continued

```
atatgatata tatgctcaaa ccaactacag agtgtacata aacaccccag accctttatc  40140
cccaaatgca cacacctctg agggactgat atcaagagat tcatgatgtg cacaggatac  40200
acctaatgca agcgcaatta gcaggaactt caccatggta gagcctggat tctctccttc  40260
cgaaggagtt cagagaccaa gggcaggtga tggggagacc cagaaccatc tccaccttat  40320
atagtattga ttattggcct gagattggca tggattgcct gtggtaaaat tccagcatat  40380
cctggtggtg gaaacatctg tgatgacaat tctgtttttc tgctactttt gaaataagat  40440
taacttgagt aaagccatga aattgacctt ttagacttct gtggacttgg gctagctgtc  40500
agaaaacaca aatatccatg tccctaaagt ccaagtttct catttggaac actttaaaga  40560
aatgaactta tttgactcag gctattttaa tgatgacaaa ttttccatca atcagaccct  40620
ttgatcacag gttaccatat ggatattaac aattttttat acaattgaat atcaatggac  40680
atatatttct agaacattct agagtgttct agaatgttct acaacattct ggggcattct  40740
tgtaaaaacc tttgtgaaga agtgtactgt tttcctttct gggcaggaat ttgcaattta  40800
gattcatgat tttaaatatt tttataattt gatattttca tcaagatgtg aagattttta  40860
atgatgtaaa attcccattg ttttgtgggt acatttgttg atactatgtc ctggtaatca  40920
gcattgcttt tgctaacatt actttatata ttcaataaata tatacacaca cctttgtttc  40980
tgattgctat aagtgtattt tttgacaact gtgtctctaa atcatttatg caatgaaaag  41040
tcagctgcta attttctcat gtttgtgtct gagaaattct caacgttttc tccattgaga  41100
actttgacct gtggatggat ttgcaaatat tcaccgaaat gcatgactca aaactagttg  41160
tcaatgttcc aaggctttaa ataagaaata ttcacccatc ccatgttcag aaaggttctt  41220
gatgtatgtt cttcttttt agtataccccc atacaaatgt gatccttatt atatttttac  41280
atatttttct tgattcattc cttcttctct gtgtttgatt attcaagaga taactcagtt  41340
ccactggaac aagattgggc tgacctacaa acatatttat tttcatccat tcatttcttg  41400
tgaaatctct actttccttc agaattctaa tgtgatttgg aatacagata atgttgggaa  41460
aatgtaatga aaatcaacca gaaaaagctg tcatttaata cttccaaagt ggataattac  41520
ttaagactgt atgtgcactc attaaagtcc ttctcatttc tcctccagac ccagtaacaa  41580
caacacatta atcctattta ttgagtatcc ttctggaaaa ttacctacaa ttttgcacaa  41640
actcaggttc attcttccac atttccaaca gttttattaa aatataagct ttccttcctt  41700
atttattaag tgaagtgagt ttctctccct tctacctgat tacagagaaa ggtgatacaa  41760
cacagcctaa actggagtct tggaaagata aaaacaaatt ctgcctcatg tcaaaacata  41820
catttattcc taaggaactt aaagattatc tctgtctgtt tgaactttaa tattgaagca  41880
tgtacacaaa cacacacaca catgcacaca cacatacata cacacacata cacacatgtt  41940
tcttatgttc ttgtgtattt attcataaat attttatata tggatatggg tttttatata  42000
ttttctatct gtggatatat atttatgtgt aatgtaagta tagctatatt ttacattcag  42060
atttatatat tccaatttat acatgtatga tacatatata catgtgtgat acatacatat  42120
ttgtttccat tttcagtaat ttaccaatta aattcctaat ccacacattt tgtctacctc  42180
agaaaagtga agaaagaatg gaaaatgtag gtgcttcaaa ggacagagtt aaaacataca  42240
aaatactgac acaacggatg ctgttattga agtcatggcc aagcttagaa ctctttgatg  42300
tctgaccttt gagtagaact tggctaaaag tctgtctcct ttcttcttct tttttaattg  42360
gatattttat ttatttacat ttcaaatgtt atcccctttc ctggcttcac ctctggaaaa  42420
cccctatccc atcttcctcc atctctttct gagggtgctc ctacccaccc attcccacct  42480
```

-continued

```
caccacactg acattccctg acactggagc attgagtcat ttacaactca aatgctatcc  42540
taaatgtccc ttatatcctc cccccaccca gtagccttat ttataatagc cagaacctgg  42600
aaagtgccct gatgtccaag ggcctccctg ccattgatgc caaacaaagc catcctctgc  42660
tacatatgct gctggagcca tggatccctc tatgtgtact ctgtggttgg tggtttagtc  42720
cctgggagct ctggggttac tggttatctc atattgttgt tcctcctatg ggctgttca   42780
tcccttcaac tccttcaagt accttctcta actgctgtat tgtggtcccc atgctcaatc  42840
caatggttgg ctgcaaacgt gtgcctctga atttgtaagg ctctgtcaga gcccctcagg  42900
agacaaccat atcaggctcc tgtaagcaag cacttcttgg catccccaat agggtctggg  42960
tttggtgtct gtatgtgatg gatccccagg tcgggcagtc tatggatggt ctttccttca  43020
gactctgatc cacactttgt tcccatactt cttttagaca ggttcaattc tgggttaaaa  43080
atttggatat gagtgggtga ctacgtcccc caacctgggg tcttgcttaa cttctggata  43140
tggtctctac atgttcatcc tcccctttt  tgggcatttc agctaatggc atccaagttg  43200
ggacctggga gcctcttaat ttactggcat ctgggacttc ctgatggcta tccctgtttc  43260
ccatcattca ttgctacaca cctctgttca aattcctgac cctctgtaaa atcgtccctg  43320
tctcctagca cacttgttct tacaccccag tccctctcct tctcctctct tccttccaag  43380
tccctcctat cctctacctt ccaagaatat tttgttctcc cttctaagat ggtctgaagc  43440
atccatactt tagtcttctt cttgagcttc atatggtctg tgaattgtat cttgggtatt  43500
ccgagatttt gggttaatat ccacttacca ttgagtgcat actatatgtt ttcttttgtg  43560
actgggttac ctcaataagg atgatacttt tttgttccat tcatttgcct aagaatttca  43620
tgaagtcttt gtttttaata gctgagtagt tctccattgt gtaaatggac catattttct  43680
ctatttgtct gtagaaggac atcagggcac tttccaggtt ctgcctatta taaataaggc  43740
tacttggtgg ggggaggata taagggactt ttaggatagc atttgagttg taaatgaaga  43800
aaatatctaa taaaaattat tataaataaa taaataaatc tattataaat atagtggagt  43860
atgtgtcctt gttatatgtt ggagcatctt ttgggtgtat gttcaggagt ggtatagcta  43920
gatcctcatg tccaatttg  tgaagaacca ccagaccagt tataccacca gattagttat  43980
acctccttat aattccacca acaacagatg agtgttcctc tttctccaca tctttgccag  44040
catctgctgc cacctgagtt cttgatctta gtcattctga ctggtctgta gtggaatctc  44100
agggttgttt tgatttgcat tttcctgata actaaagatg gtgaacattt gtttaggtgc  44160
ttcttgtcca ttcaatattc cttagttgag aattctctct tcatgtctgt actccattta  44220
aaatagggtt atttggtcct ctggagtcta actttagaat tatttgtata tttcggatat  44280
tagcactcta tcgaatgtag gattggtaaa gaacttttcc cagtctgttg gtttctattt  44340
tgtcccattg acagtctcct ttcccttaca aaagctttgt aattttagga ggtctcattt  44400
attgattgtt gtttttagat cataagccat tgctgttctg ctcaggaaat tttcccctgt  44460
gcacatgtgt ttgaggctct tacccacttt ctcttctatt agttgcatta tatatggttc  44520
tatgtggagg tccttggtcc acttggagtt gatctttgta caaggatata agaatggatg  44580
gatttgcatt cttctacata ctgactgcca gttgaaccag caccatttgt tgaaaatgct  44640
gtctttttc  cactggatgg ttttagctca ttgtcaaaga ccaggggaat ataggtgtgt  44700
tggttcactt ctgggtcttc aattctattc tattgatcta cctgccttag tctgtaccaa  44760
taacatgcag tttttatctc tattgctttg tagtacaact tgaggtcagg gatgatgatt  44820
```

tccactgaag ttcttttatt gttgagaata ttttttgcta tcctgggttt ttgcttattc 44880
caaataaatt tgaaaattgc tctttttaag tctatgaaga agtgtctcct tttcagtagc 44940
ctgctgacat tccctactca agaaacaaca aatgtttatt gtttttteta ttctttgatt 45000
ttgtcccccca ttatatttta cacaatgttt gggtttattt gcttccctct ttgttttctt 45060
tcctttctat tgatttaata atctatggat tcttctgtgc attcagtttc gaggaaaaac 45120
agtgaggaaa tgaggcacta gaaattctga ggctttcata gtagtgaggg atggatctgc 45180
taattgtccc atttattggt ggaagatttc tgtcattctc agaatcaggg tttctgtgtt 45240
agaaatttca tggccttggg agaggtgtgg tgactaatgt aaaaactcaa ataaaatttc 45300
agttaaaacg ttaaaaagaa aagaaactat acaaccttgc ctttttcaga tcatagaggg 45360
aaaatgttca actttttctc atttaatatg tttaaggttg aaatagcata tgttaattgt 45420
attaattata catcattata gatttcattg tgataaataa taatcgggtt tatttcaaag 45480
tgcagcccta ttcactgaca cttaaacgat ttttaatatt ttagatttta atgagctaac 45540
aaattagcag tattcttgat caattttcaa acacttaatt ttgattaaca ctctcatatc 45600
ttcttgtgtg ccctccaact ccactcccca acccagctaa accattcact gtccaacact 45660
ggcatttctt tattacatca tgtttacata gtactgatac tcctttatgc tctattttat 45720
tttaagactt ttgaagatat tttattttag ttttgcaaac atatccacac actttcttcc 45780
tcctatatat gcacatatat gttgcaagct aggttttgtc tactggttgg taattttcat 45840
gattagctga tttcttaaaa ttaataatat gaactttatg tatcagttga gataattacc 45900
atgggtattg cccatagtcc tactgctttt gcacctggtt ttgtcatcaa gtggtgtgga 45960
gctgacctca accaaatcag tttagtagaa tttcttcatc tttggaatct taaaataagt 46020
taagaaaaag tatgcttgct tctttttcaa atgattgcta gggttcggta tcaaaataac 46080
ttggtcttaa atctgctttt ggaggaaaat attttattac tgactcaata aatagttaac 46140
tgaaaaatag ttaatgttgt cctgtgtaat tttatcttaa ggtgtctact gctaggatga 46200
aacaccacga ccaaatgcaa cttggggagc aaagggttta tttggcttaa aaatccacat 46260
catagcccat caattaagga agtcaggaca ggaactcaaa cagggcagga atccagaggc 46320
aggcactatt gcaaaggcca tggaggggtg ctgcttactg agtagctcag cctgttttct 46380
tatacaactc aggaccacca gcatgcggtg gctccatgaa caacaggctt tgctctcctt 46440
catttatatc taatctttaa aatgtcctat aagcttgtct acagcctaat cttatggagg 46500
cattttctca attgagatcc tttctctcag atgactttag tttgcgtcaa gtggcataaa 46560
actcaccagc acacttcatt taattcagtc ttagtgaaat gcatgttagt agcaataaat 46620
ccattttctg cagactctcg gacctgtgtc actgaagttt tcttaataaa acaaatttgt 46680
gtcagtttct gtgttgttaa tgtatgttta tctgatttcc tttcttgatt ttattaattt 46740
atttatcttt ccttctctca ggcactttct cttctctccc ttctctttac ctcatcaaac 46800
aatttcttgc tttgatcttt aaatgtgtgt gtgtgtgtgt gtgtgtgtgt gtgtgtgctc 46860
tttggactgt gtttttgtta tgcctgtact gaaaagaggc gtggagctca aacacgtggt 46920
taaaaataac gtggatctca atgtcagtga caggaaaaaa aaacccatat gattccaaaa 46980
accttcagtc ctcatatgtt tcatgcaaca aatttggaaa aagggtgatt tagtgacaga 47040
attcatacca actcttcaag tgagtaactg tccaaaatta gatcttgtca agtgtcaaat 47100
ttaaatattg agtcatcttt gggaaatatt gagaagtgga gtaataaagg ttttaagaaa 47160
ataagagtga acctatctgc atttcaatat gatagctact cacttctggc agagtgagaa 47220

-continued

```
taaattttaa agggtatggc ctttagtagg tcacacacct gtaagtatgt actgtacaca  47280
aatacaactc caagcataat ttaaaatttt tttttaaaaa aatgagaaag tggaggaata  47340
aaaaaacagc tggaaggaat tagcgggaga aatggggatc aatattatca aaattcattt  47400
tgtatatgta tgaaattttc aaacacttaa taagattatt atatgcatta aaataacttt  47460
aagcatgttc agtgtggata agtcaatatg taaatgaggg actgaaaaag taacagaaaa  47520
caaaaattct gcatagaaat acttaatatc tggaaagaac acagatgtcc ctcaacagag  47580
gaatggatac agaaaatgta gtacatttac acaatggagt agtactcagc tattaaaaac  47640
aatgaattta tgaaattctt aggcaaatag atgtatctga aggatatcat cctgagtgag  47700
gtaacccaat cacaaaagaa gtcacttgat atgcactcac tgataagtgg atattagccc  47760
agaaacctag aatacccaag atgcaacttc caaaacacaa gaaaatctag aaggaagacc  47820
aactcatgga tacttcattc ctccctagaa tagggaataa aatatccatg aaaggacttg  47880
cagagacaaa gtttgaagct gagacaaaag gatggaccat ccagagactg ccccacccgg  47940
ggattaatcc cataatcagc caccaaatgc agacactatt gcatatgcca gcaagatttt  48000
gctgaaagga ccctgatata gctgtctcct gtgaggattt gccagtgcct ggcaaataca  48060
gaagtggatg ttcacagtca tttatagcac ggaacacagg gctcccaatg gaggagctac  48120
agaaagtacc caaggagcta aagggatctg caaccctata ggtggaacaa cattatgaac  48180
taaccagtac cccggagctc ttgtgtctag ctgcatatgt agcagaagat ggtctaattg  48240
gccatcactg ggaagagagg ccccttggtc tagcaaactt tatatgcccc agtacagggg  48300
aaagccaggg ccaagaagtg ggagtgagtg ggtagaggag cagggcgggg ggagggtata  48360
ggggactttt gggagagcat ttgaaatgta aatgaagaaa atatctaatt aaaatttttt  48420
taaaagaaag gcttcatata gactctgctc ttctatttac taaatactca aatagcccac  48480
tttacataag ctttatttaa aaccaaaacc agtcatcaaa cacaagatca aacacactct  48540
atccttgtct gtggaaaatg aagattgtca cctgagtttg acatcggaca ttcttcacac  48600
atttgctagg gcatgtgcat gccttcgctc acaggaacat atacacatat gcgcgcacac  48660
aggaattttt ttaaaacaca catttttctg gagaataatt tattcgtttg tttgttattt  48720
ggttggtttt ctggaggcaa gatgtcacta agtagctctg gctgtcctgg cactcactat  48780
gtagaacaga ctagacttga actcacacag atcaacctcc ctctgcttct acagtgccag  48840
gattaaaatg tatgcatccc catgcctgat taagaccatt gtattttcaa aacaaacttc  48900
acattcctgt gggaaatgct cacaagtata gctataaatg cagataaata gagtcattat  48960
ttttctgtat caacattggc tctggaacaa atgtttaaag agctgatcca aaaattagat  49020
ctcaggagga ggagtattgt tattttctaa aatgttcaga tttctgcttt acttttcaac  49080
tgtatgctga agtatctttt tttcacagca ttaaaatacc tttatttgta attagatttt  49140
aaaatactgt caaaaattat gccaggaaac aggaaggaca cagcttaccc tagagggaaa  49200
aacaataaat ccaagacaga tgatttcctc tacaagggtt tttcttggca aacagatata  49260
taagcagaac cagggcactc acagtagata gcaactgcac agacaggttg ggagtttaca  49320
aaaccaaaac ttgcattgtt gaggaaaggg aaatgacaca gaggagcata ttgactggag  49380
aatacccatt gtctgaattt tttttctctc ttttctgttg tgacatttac tacttagtaa  49440
cacagtaagc taaacaacca gtgccatggt aggcttgagt cagctctttc aggttcatgt  49500
ccatcaaaga tctacatctc tcccctggta gcttaagaga agccatggtg gttggtattt  49560
```

-continued

```
cctactgcca gacagctggt tgttaagtga atattttgaa gtcctaaaaa ttgtgttgaa  49620
ttttatagca ttatccatca ctttgcatta tttacttttt tcaaaaaaat tgacaatctc  49680
atgactgcac ataatatatt ttgatcaatt ccactacatc ctctttaata ggacaatagg  49740
aggtgctgtt tgggttccta tagaggactg atctcacagg aggaagtatg ccactttgag  49800
gaattggatt tgaggtctca atgcaatgct tgtctacttt tctctgttta ccacttttgg  49860
atcaagatgt aatctcttag cttctggatc gagacagtgc catgataaag atggaaactc  49920
atacctccga aacagtgacc ttgaagaaaa acttccttct gtatgttgca ttttctactc  49980
taacaaattt acttttgtag tgctccaatg agtaactgac atatcaatta aaagtggggt  50040
taggggagac atactgactt gaataatttt tgcactatag tgtaggtttt gacaatttct  50100
acagtgtttt atatttcaga actgtgttcc tgagatgtgc gatatctcag gggtaatga  50160
tgactgagtt ttgtgaccta cttagtagga gaagaaagaa ccagtatcca ccagctatct  50220
tctgacctcc acacacatgc caaggtatgg gcatacccag tcccatgtac aaaataaatg  50280
ataaagtttt aacatgtatt atgcacaaat ccaaaattaa taaggacact tactacgtgt  50340
ataactgaaa cccaaagtaa ttgtaaaatc aagtatttca tatttctctt tcatgtgcag  50400
atggataaca gaagtcaaaa ctgtctttct ggctgtttta atataacata taattctatg  50460
caaaaaatac tgatactatc ttttaaaaag aaaaaaactg tatatgcata cattatttca  50520
tattaaacac tattaagaag aaatgagtgc aaacattgta tttcaaattt cagattaatg  50580
gattctgaca tgtggaaggg ttacatttcc caaatgtctc atcagcacag gttcctgaaa  50640
actggggaaa cccaggacta atgagatgga ttttcacata gaggtggata ctgccaagcc  50700
tgggtacctg agcccacaca cccatgaact caaaataatt tttaaaaaga agaaatttaa  50760
aatttaacta tatatattat gattatccaa taagctttct agatgtttct ttggttatat  50820
gtcataattg tcgtgattga caagctgtta aatttgagtg atgtttgtaa agaaataaca  50880
ataaattata tctatagaag caagacttca tctttaggat caagactgta tgctccatgt  50940
tatcacagct gtttaaccag acaaaggcta gaacctccag ttccacaaac aaatgtgaat  51000
tctactgtgt ccagtttact gccatgtttt tggtcatgtg aacaatgtgg tttgtgccaa  51060
cattagagca gagttcacaa gtgcattttg cctccccagt attgctgatg aatccatggt  51120
tcaggttcaa gggtgttgaa aacttgattg aaaatggtca gacttgatat tcttccagta  51180
tatctgattg gaggaactga taatagatat cagatttaaa cctctaccat tccagttaag  51240
ataaatatgat agcatcttgt tcttcatctt cctttttctt aatagggaca taaaaccaat  51300
gaataaaaat atacctgaaa catgggatag gcactgggca ttggaaatga caataaaagt  51360
aaattttcca tccctagtaa agttctccag gaacctattt gtatactaaa tgacacaatg  51420
tcaatgtcag tgcacaactg ccaactggga tgcagaacac tgctcacgcc aaccatcctg  51480
aaagccaact ataaaaagca gagagatact ctgcaccttt tcagtgaggt ccagataccc  51540
acagagcaga gacagtcgct cacac                                        51565
```

<210> SEQ ID NO 7
<211> LENGTH: 107376
<212> TYPE: DNA
<213> ORGANISM: Artificial Sequence
<220> FEATURE:
<223> OTHER INFORMATION: Synthetic polynucleotide: 107 kb 3' arm
sequence (58665-166040)

<400> SEQUENCE: 7

-continued ctcaacaaga tcaggattag gtgagtcaaa gcacattaat tttatatctt gaagttttaa 60
ttttaatttt attttaatat ttaagttatt aatatttaat atttaaagta aataatattt 120
tatttgttct ttatcctttt catatattta tataatgtat atttatcttt catacttcca 180
cacacctcat ccaagcaaca catctccctc tatacttcat ggcttttaaa ttttattatt 240
atttattatt attattacct caatgaatcc aattggtgct atttctgaat agggtatgtc 300
aattcctgga ggcatgagta atgtaatata ccagggctat tatgtaatat aaaaaaatgg 360
actgcaggga gctggtggca catgcattta acctagcgct caagaggcag aagcaagcat 420
atgtctgcgt tttagataac cctagtctac agagtgagtt ccaggacagc aagggctact 480
cagagaaacc ctgtctcata aaaccaaaaa gtatattttt taaaggcaga agaggaaagg 540
agggagggag ggagggaaag aggcagacag acagacaggc aggcaggcag gcaaaaagaa 600
ggaaaaagaa aaatatggac cctccctctc ccagaaacta tcaactggca atagctcttt 660
ggtggggggg gggggtcctg aatccctctc tgctcaattc tagaatgtta attagcttga 720
tctgaccagg gtcttgtgca gaacaccaca gttgctgtga gttcatgatt gtaacagatc 780
tgtcatgttc agaaaacaga attttatggc tctactcccc atccagatga taattgatgg 840
ctaagcatcc acagtcactt gtcctcatcc tttgaccagc tacaaatttc tgcacaaacc 900
actccccact gtaaaaagtt gagcagaagt caaacatgga ggcacacacc cttaatccca 960
acacttggga ggcacgggta gatgaatctc tgtgagtatc aagccagcct gatctacata 1020
ctgagctcca gaagatccag gtacatagtc tctatctaaa caaacaaaca caaagttaaa 1080
aagttgattt gaccaaaatt gagagaagca taaatctatg agtattttta agaccgtggc 1140
ttggaaacat gacagttcat caccactggt ctccttcata ggctccatga gctccattgt 1200
cacaggcttt tgactcgaat tacaatagaa acccaccctt acccctgttc ttccatagat 1260
atgaagttcc ttccatggag ctggcatgaa atttaatcag agagtgcttg gctccccaat 1320
acagccttta ttgcaccagt ggacgcaagg atgattttat agtgtgttgg ggaagcatgg 1380
tgacatcact gacatcttat cccacataca cagcctatta agtacatcta agcactgtga 1440
acgagtttcc tagtccattt gacatcgatt tcttgatgcc ctacagccac agcatttggt 1500
gtcttcagca atagtgccct accatttaga tatggtgtat agtcaagaga tatggcaata 1560
gccaagttat tttggttatt ccaaggcttc cttccattaa taaatatcat ggtggtaccc 1620
ccatgactaa aaattagatt ttcactgaat aaaccatgtc ttctgggaac agcattatac 1680
cattgcaggg atcctctgct gaaacttttt taatactata tttttactta gcttacaaac 1740
tagtggattt ctgtaagact tcatttacct tcagtttcag ttgaccctcc cctaccctgt 1800
tcttccctat gcccaaacac atccacacct actcctctag cccacagctc tcactttcta 1860
atcttccctg tcaccagtgc ccaattatat cgcctgtatt attatatttt aatcacacaa 1920
ccataggttt ccatatgagg ttttaataac ccttcattct ggttaaacct tccaccacac 1980
cctgatttcc ccattccaca accaactcca tgattaagcc ttcctgcccc aagtattctt 2040
ctttatactt cattttaatg gcattacatt tgatggaccc acttccttga tggacccaat 2100
tcaaaccagt ttctaattac ctggattcct tacatactcc atattatgca tacaaaataa 2160
aagattcaag tctaatgtcc acatgtgaga tagaatgtgc agtttgtctt tctgagcctg 2220
agtggcctca ttaagtataa taatttccag ttccttctat ttacttggaa atttcatatt 2280
ttcattgttc tctatggctg agtaatattc catcttatac attacatttt ccttatccat 2340
tcattagttg atgaacagtt gggtcaactt cgtttcttag ctattatgaa cttaacctca 2400
gtgagcatgg acattcaaag gtctctgtaa cagaatataa accccttttgt gtacatatct 2460 agaaatggag gaactagaga aagcacccaa ggaactaaag ggaactgcaa ccctataggt 2520
ggaacaacaa tatgaactaa gcagtacccc ggagctcttg tctctagctg catatctatc 2580
aaaagatggc ctagtcggcc atcactgcaa agagaggccc attggacttg caaactttat 2640
atgccccagt acaggggaat gccagggcca aaaagggggg atgggtgggt aggggagtgg 2700
gggggggttg gggacttttt gtatagcatt ggaaatgtaa atgagctaaa tacctaataa 2760
aaaatggaaa aaaaaagaaa tggtgtaact gagtcacatg ggaagtcttt ttctaatctt 2820
tggatttgtt tatttgatgt tcatagtttt tgggttttgg ttggttttgt tctaagttct 2880
ttgtatattg tagacactaa tcctccatca catgtgtagt tggcaaagat ctccattccc 2940
cgagatacct gtgcatttaa ttgacagctt cctttgccgt agtttttaat tccatgatat 3000
ctgacaagtg tttgtcttac tttcttgcta caagaatcct attcaaagaa tccatacctg 3060
tgtctatggt taacacacac tccatgcttt cttctctatc agcttcaggt taccatgtct 3120
tatgacacgg tctttgaatc atttggagtt gaggtttttt tcaaggtgac agggaagagc 3180
ccaggttcat ttctctgtat cctgatgtcc actttttcct attcggtcta tttatggaat 3240
tatatatttt tatgttaggt catttttcag tggaggcatt aacaatatcc agaaggggac 3300
tatttcttac tagtgttgag atggtattct cctatatggg gctggtactg aaggcagcaa 3360
gttctacccc tagtcttcct gtgagattca actactatct gggacctcga gtgagactct 3420
gtctgtagga tacatggggc ttggtaaact ccaatgtgaa acaaaaaaata tataatttta 3480 gtttagattc atagaaacta catcctcaaa taaacacata agttctaaaa agtaccaatt 3540
taggtcttga tataagatca tttgtcatat aaaaatttc catataagga aaatttccat 3600
acaaagttca tgtatatttc caaatataca aaattctgta aaatgttttt gcatgataca 3660
tcttgtcatt gtttgcctct ttaatggctt gtatttgttt cattttctac tctcatcaaa 3720
tatcatgtat tactatccta aatatatgaa ataattctgt tccagcatta cagatgacat 3780
caggaatttt ccagtatatt tttcctggaa cctgaaacat caatatgaag atgaagcaat 3840
cttgtctctc agatcatatt ttcctattta ttgcaaatta caattcctgt ctctgtactt 3900
tctctttcac tcattgtttc ccatgttcta atcggtatta gtgcatcttt gaatgtttaa 3960
ataaatttat tttacttgca tacgtgttgt taaaagggga agctaaagta caatgcacat 4020
aaatacctat ttgacttttt ttaaaggaga ggagggttgg aggggtggca tgtgattgct 4080
cacgcctgta atttcagcac cggggaaaga ggtagagaca gttgaatcct ctgatgtcac 4140
cagtagccag cctagactac atgaaatatt gcaggccagt gagagatcat cccagaaaac 4200
aaggcaggga catgacaggc agctcagtgg tcaagagcac tagctgctct tccacaggac 4260
ctgggttata ttcctaacac tcacatgaca actcacaact ttctgtaatt ccagttccca 4320
gggatttgac atatatatgg acaaccatgc aagcaaaaca ccaatgcaca taaaatttta 4380
aaaaactaat tcaattaagg cagatgtgaa tgaaggatgc cacctgacat aatcctgtgg 4440
cactcaacat ttacatgcac acacttgtgt ccatgaacac aagtgcaaaa atacagagag 4500
agagagagag agagagagag agagagagag agagagagag agaacataca ccaaagagtc 4560
tcatcattcc tacatgttac aaactccaat attgtaattt tgactttaga aaggaaggta 4620
aaatattata ttggttgttt aaagtaaaca tttaaaaact ttgtagcaga aaatggccta 4680
gttggccatc attggtagga gaggcccttt gtcttgcaaa gattatatgc cccagtacag 4740

-continued

```
gggaatgcca gggccaataa gcagaagtgg gtgggttggg aagcagggtg gggaagtgta   4800
tagggaactt tcaggatagc atttgaaatg taaatgaaca aaatatctaa taaaaaaaaa   4860
gctttgtgtg ctagtagttt gtcaacctga cacaggccat agtcatttgg gaaaggagac   4920
actcaagaaa atacctccac caggttcaac tgtggagcat ttcttgactg gtagtcaatg   4980
tgagggcagg tcctactcac tgtggaaaac actgccaagc aaaccatgag gaaccagaca   5040
gtaagcagaa ctcttccata gcctctgtat cagtttctgc ctccaagtct ctgccttgac   5100
ttccccaagg tgataagcta caagtggtca gatgaaataa acccttttct ccctaagatg   5160
cttttggcca tggagttcac aaaagcaata gaaaccctaa gacacagagt aatgttgaag   5220
agcttagatc acaaatcata tcttaaagtt gaaagaaacc accccacaca cttgtatgca   5280
tatatacaaa ttcacatgtg gacaaacata catatatact caaaccatac atgtatgtat   5340
atttaaaaat ttgaaatgtc acaggaagaa ttattttgta gtctttgaac tactttgatt   5400
tatttacttt aaccacttgc ctgctattgt tgggttcaat ggtcatgctt tcataatgcc   5460
ttctaaatat taatttgcat ctctggacca ggatcatgct caacttttgt cagagaagct   5520
tgtttttgtg gtgagatgaa tgttatgaca ctgaagtttt tgcatcacgt tctgacatat   5580
gtctatccac ctaccatttg atcacccact acgtgtgtgt gtgtgtgtgt gtgtgtgtgt   5640
gtgtgtgtgt gtgtgtgtgt gtgtgatttg aatgagaaca gcccccgtag gctcatagat   5700
ttgattgctt gatcactaag gagtagcact atttgaaagg ataaggagat gtggacttgg   5760
aggaagtgag tcactgagga tgagctttgt ggtttcaaga gcccaagcca gaccctgctt   5820
cctcatccta cttgctatgg actcagatgt aaaaatctcc actccttcag caccatgtct   5880
gcctgtgtgc taccatgcca aaaaatggaa taaatctctg acactgtgtg accctccctg   5940
ccccgagaat tgttgaccta tattggtcca tgaggagcag agacaatggg gaaagagcag   6000
gggcttagaa accctgtatg tatggtaata acgatacaca gggaccagct tcagagagac   6060
aggtcaagtt tacttgtggt gattcaaggg tgatatagtt gtcttagtta gggtttctat   6120
tgctgtgggg agaaaccatg gccaaaaaca caaatgagga ggaaaaggtt tattgggctt   6180
acacttccac agcactaatt atcattgaag aaagtcaagg cagaaactca aaccagacaa   6240
gaacccagag gcaatagctg atgcagaaac catggaaggg taatgcttac atattactca   6300
tggcttattc agcttgcatt agctttttat tattattaat cattccatta gtttacatct   6360
caaatgatat ctcactttca ggttaacccc tccaccaatc cccatgaata ataacccaat   6420
tcctggatac ccctccattg acccccatcc cacatccacc ctccaccttc ccctttgctt   6480
gtatgagatt tctcccccat ccactcacat tctctgaacc cactgctcca gcatccacct   6540
acactggtgc atcacccctc ccattgctgt caggcaaggc catcctctgc tacatatgta   6600
tctggagcca tggatccatc caggcacact ccttggttgg ttgtctagat tctggaaaaa   6660
ctaggtgatc aggccagcct aagttgttat tccattgggg tagcaattcc cttctgttcc   6720
tccagttctt ctgccagctc ccccaccagg ttccctgagc tcagtctgat ggttggctct   6780
aagcatccac atctgcattg gtcagttgct agccagactt cccaaggaac tgccacacca   6840
ggttcctgtc agcaagcacc tcttgaccat ggcaacagtg ttaggtttgg tgtctgcaga   6900
cagggtggat ctccaggtgg agctttcccc aaatggcact tccttcagtc tctgttcaat   6960
tttttgtccc tgttcttctt ttggatagga acatttatgg gttgaaaatt tgagatgggt   7020
gggtagcttc atcccttgac ctggagctgt gcctatctat tggaggtggt ctcttcaggt   7080
tctgtctccc ccttctctgt gcatttctgc taatgtcatc tcctttgggt cctggtagcc   7140
```

-continued tcatgtttcc ctggtgtctg tgaccctcca gtgactgtcc ccagttcctc atttcttact 7200
gctacatatt ttttgttcga tatcttgacc ttctgtatct ctttgacatc tcctccagtt 7260
cctgatactt ccctccttat ttcctcaccc tcctctctcc ctcccaggtc ttcctctaat 7320
agaacaaaaa atggggaaga gactcaaata cttgggcaca gaagaaaact ccctgaagat 7380
aacaccaatg tgttatgctt taagatcaat tgacaaatgg gacctcagaa aatgaaaaag 7440
cttctgtaag gcaaaggaca ctgtcaatag gacaaaacag tcacccacag attgggaaaa 7500
aatctttacc aaccctacat ctgatagagg gctaatatcc aatatataca aagaacttag 7560
gagttaaact ccagagaatc aaataactct actaaaaaat gagataaaca gagaattcat 7620
gactaaagaa acttgagtgg ccaagaagct cctaaagaaa tgttcaccat ttgtagtcat 7680
caggtaaatg caaatgaaaa caaccctgag ttcctacccc acaccagtca gaatggctaa 7740
gatcaaaaac tcaaatgaca gcagatgctg gtgaggatgt ggaataagat gaacactcct 7800
ccattgatgg tggggttgca agctggtaca accactctgg aaatcagact ggtggtttct 7860
cagaaaattg gacatagtac tacctgagga cctagctata ccactccagg aagtataccc 7920
agaaaatgct ccaacatgta ataaagacac atgctccact atgttcatag cagtcatatt 7980
tataatagcc agaagctgga aacaacctag atgtccctca acagaggaat agatacagaa 8040
aatgtgatat atttacacaa tggagtacta tgcatagatt taaaacaatg acttcatgga 8100
attcacaggc aaatggatag aactagaaaa tatcattctg agtgaggtaa tcaagacaca 8160
agggaacaca catggtatgt actcactaat aagtggatat taacgcaaaa gctcacaatt 8220
gccataatac aatccataga ccatatggag catagaaaga aagaccagga tgtggatgct 8280
tcagtcttgc attgaggggg gatcagcttg cattcttaag aaacccaaga ctatcagccc 8340
aagggtaaca ccactcagaa tggctggtc cctcacccat caatcactaa ttaaaaaatt 8400
gccctacagg cctattgagg cactttcatt tttttctttt tttattagat attttcttca 8460
tttacatttc aaatgctatc cactataccc tccccccaac cctgctcccc aacctaccca 8520
ctcctgcttc ctggtcctgg cattcccctg tactggggca tatgatcccc gcaagaccaa 8580
gggttgaggc actttcttaa ttgggcttcc tttctctcat atgactacca cttgtgtcaa 8640
gatgacataa aactatgcaa cacagacagt atatacatat gtattatcta tcatctagaa 8700
attcatcatc tatgcattca tcatatatct atccatcatc tatcaataca tcatttgttt 8760
atccatcatt tatctatgta tcatctattg tcgctctgtt caccctctac ccatctatct 8820
attaaaaaat taacttgatc agggccatag tgacacaaac ttttaatccc agaatttggg 8880
aggcagaata cggctagcct gatctacata cagagtaagc tccaggatag ccagagctac 8940
acaggaaaag gttgtctcaa aacaacaaaa aataaattaa tgtgtataat gatcaaggaa 9000
gacacttaac ataaatttca tcatctatgg gaatccatga acctgcacac ataaaaacgt 9060
atgtttactg aatatacata cacctggagt atttaatttc tgaagtacac tagtgaaatg 9120
tcccatctat ccacacaact ctagggatct gggttaaatt cctgggacac aagtaaatga 9180
gggagggggg agaacagagt ctccaaaagt gtcccctgaa gtccatacat gtgctggcta 9240
tggtgtatac acccactcct agacatgcac aataataaat aactttccta aatacagaag 9300
aatctaatta cctcaaaaag agatctttat tacagatttg ttcaaatgct agactataaa 9360
agtttactca gatagcatgt aactttttga tatcctgttg ttcttttctc aacataccag 9420
agatgaacat aaaaaagagg tatgttttcc tcttttttga atatatattt aattggttgt 9480

-continued

```
attgatgaca caagattcca atacacctga tcatgtatga catattagtt tcttttggcc   9540
aactacttgg cataaacagt ttgagaaagg aagtgctgat tcactcatga tttaagatag   9600
tgtacagccc atcatagtgg gacagaaact ggggcatgta ggcctactct gtgacacacc   9660
attaagaaat atcactgact gtccctactg caaaagccat tactcctcca tagtgcctca   9720
gttaggagta gacctataag tgacatccat aactatgcat atatattaat catctcttta   9780
ttgattattt catctatgca tgcatccaac catgcatcta tctatctatc taatctatta   9840
cctatctatc tatcaatcta tcaatctacc catcatctat tatcaattga tctatcttat   9900
agtgatatat catttcattc tctataatct acccacttat aatctatcac atattcttcc   9960
atcatctata tcaatccatc atctgtctat catctaatca gtcttttttt cacctgtcat  10020
ctaccaatat gtttccttta ctactatcat gttctatatt gtgacacagc ctcactaaga  10080
agcccagaaa cttactttac aacactagct ggacttgagt tccatgatcc cacattctca  10140
gacttacaag tatatgtgat tacatagata aatagatagg tttataggta ggtaggtagg  10200
taggtaggta ggtaggtagg taggtagata gatagataga tagatagata gatagataga  10260
tagatagata gatagataaa tagaaagaaa tatatgtgat agattcataa ttgatagatg  10320
attgatagat caattgagag acagataagt acatatataa gaagatagat ggatagagag  10380
atatcaatac agaatgtata gatagaaata gatacatata gatgatatag atagattaat  10440
tagattgata aacacagaat atacatagat gcttatatag atggtagtag atgtatagat  10500
aacaggtgga gagttagatg atagatttta tgttagacaa gcatatgata tctataaaca  10560
tatgtgtcta tgttatgtag ataggtaata gattaatgat acacaaataa atggttgata  10620
tatggatgag tgaatggata gatatatcca taagtatatt tcagtatata ttaaactgaa  10680
atatttctat tgatatatga acatatatac tttttataag tatactaata tgtttgtaaa  10740
tatttagata tctgatgtat atacatgtct atcttatata tagatgtcat cttcctatct  10800
atacctcata tatcaataat ctgtcatcta cctatgttat aactcattaa cccagttaat  10860
catacacaaa ttcaactaaa ataaattctt cctcttttta ttggatattt tatttattta  10920
catttcaaaa gttatccctc ttcctggttt tgcctctgaa aacccctatc ccatctgccc  10980
tccccctgca tctatgaggg tactccccaa cccacccacc ctcccactcc cacctcacca  11040
ccttggcatt ctcctacact ggtgcaccta gccttcacag gaccaagggc ctctcctccc  11100
atgatgccag ataaggccat cctctcctac atatgcagct ggagccttgc aaaccccttc  11160
aattccttca gtcctttccc taattcctcc attggggtcc ctgtgctcag tctaatcaat  11220
gattggctgc tagaatccat atctgtattt gtcagactct gtcagagcct ctcaggagac  11280
agccatacca gggtcctgtg agcaagcact tcttggcata ggctgggttt ggtgtctata  11340
tatgggatgg atacccatct ctagatggtc tttacttcag cctctgctcc acactttgtc  11400
cccatattcc ctttagacag gagaaattct gggttaaaat tttagagata agtgggtggc  11460
catatccccc aactaggggc cttgcctatc ctctggttat ggcctctaca ggtcctccct  11520
ccactttgtt gggcatttta gctactcatc tccactgggt cctgggagtc tcttgctttc  11580
ctggcatctg agacattaag gtagctattc ccagttcgcc atcccccatt gctagacacc  11640
tctcttcaat ttcctgaccc tctgtgtatc atacccatct ccttccatac ctgatcctgt  11700
ccccctttat tgtgtctcct ttctctcttc ctcctaagtc ctttgcaccc tctacctcct  11760
gtattttgtt ccccattcta aagaggacta aagtatccac acttgctctt ccttcttctt  11820
gagcctcata tggtctgtga gttgtagcat gggtattctg agctttttac ctaatatcca  11880
```

-continued

```
cctatcagtg agtacatatc atgtgaccat gtatgttctt ttgtgactga gttacctcac  11940
tcaggatgat attttctact tccatccatt tacttacgaa tttcataaag tcgttgtttt  12000
aatagctgag tagtactcca ttgtgtaaat gtcccacatt ttctgtatcc attcctttgt  12060
tgaagggcat ctgggttatt tccagcttct ggctgttata aatatgtctg ctatgaacat  12120
agtgaagcac gtgtccatat aatatgttgg agcatctttt gggtatatgc acaggagtgg  12180
tatagctggg tcagcaggta gcactatctc cagttttctg aggaatagcc agactgattt  12240
ccagagtagt tgtaccagtt tgtaattcca ccagcgttgg gagagtattc ctctttatcc  12300
atatccacac cagcatctgc tgtgacctga ggttttgttc ttagccattc tgcctggtgt  12360
gaggtggaat ctcaaggtca ttttgatttg catttcccag atgattaatg atgttcaata  12420
tttcttaagg tgtttcttgg ccattcgaga ctactcagtt gataattttc tctttatctc  12480
actacccaat tttaataggg ttatttgatt ctcaggactc taacttcttg aatctttgta  12540
tatattggat attattcctc tattggatgt aggattggta aagatctttc ccaatctgtt  12600
ggttgccatt ttgacctatt gacagtgccc tttaccttat gctttgcaat tttatgagga  12660
gtgtaaaata ttatggagtg taaaaatgtg aattaaaaat aaaatttaaa aaagtctaaa  12720
ttttttagtc tctttctcta tttcttccct gcccatgtta tcattgagta gagagttgtt  12780
cagcttccat tcctatgtga gctttctgtt gattttgttg ttattgaaga ccagccttag  12840
tcggtggtga tctgatagga tgcataggat tatttcaatc ttcttgtatc tattgacacc  12900
tgttttgtga cctattatgt ggtcaatttt ggggaaggta ctatgaggtg ctgagaagaa  12960
ggtatattct tttgttttag gatgaaatgt tctatagata tctgttaaat ccatttggtt  13020
cataacttct gttagtttca ctatgtctct gtttggtttc tgttttcatg atctgtcaat  13080
tgctaaaagt ggggtgttga agtctcccag tattattgtg tgagtttcaa tgtgtgcttt  13140
gagctttagc aaagtttctt ttatgaatgt gggtgccctt gcatttggaa catagatgtt  13200
cagaattgag ggttcatttt ggtagatttt ttcctttgat gtgtatgaat gttatctttt  13260
ttgataactc ttggttgaaa gtcgatttta tttgctatta gcttgtttct ttggaccatt  13320
ttcttggaaa attgttttcc agccttttac tctgagatag tgtttgtctt tgtcactgaa  13380
gtgcatttcc agtatactgc aaaatgctgg gtcttgttta catatccagt ctgttagtct  13440
atgtcttgtt attggagaaa tgagccaatt gatgttaaga gatattaagg aagagtggct  13500
gttgcttatt gttgttttc ttgttggagg tggaattatg tttgtgtgtc tatcttcttt  13560
tgggtttgtt gaaagaagat tactttcttg cttttcctag ttataatttc cctacatgtg  13620
ttggtgtttt ccacaaatta tcctttgtag gactgaactt gtggaaagat gttgtgtaaa  13680
tttggttttg tcatggaata cttgggtttc tccatctacc gtaattgaga gttttgctgg  13740
gtatagtagc ctgggctggc atttgcattc tctttgggtc tgtataacat ctgtccatga  13800
tcttctgact ttcatagtat ctggtgagaa gtctggtgta attctgatag gtctgttttt  13860
atatgttact tgaccttttt gccttactgc ttttaatatt ctttctttgt tttgtgcatt  13920
tggtgttttg actataatgt aagagaagga atttcttttc tggtccagtc tatttggagt  13980
tctgtggtct tcttgtatgt tcatggacat ctctttcttt aggataggga agtttccttg  14040
tataattttg ttgaagatat ttactggcac atttagttag gaatcttcag tctcttctat  14100
acctattatc cttaggtgtg gtcttctctt tgtgtcctgg atttcctgga tgttttggat  14160
taggagcttt ttacattttg cattttgcat tttctttgac tgttgcataa atgttttcta  14220
```

-continued tgctatcttc tgcccctgag attctatctc ttgtattttc ttggtgatgc ttgcatctat 14280
gactcctgat ttatttccta ggttttctat ctccagagtt gtctcccttt gtgatttctt 14340
tattgtttct atttccattt ttagatcctg ggtggttttg ttcaatccct tcacctcttt 14400
ggttatgttt tcctgcaatt ctttaaggga tttttgtgtt tcttcttaaa gggcttttac 14460
ctgattacct ctgttctcct gtatttcttt aagtgagtta tttatgtcct tcttaaagtc 14520
ctctatcatc atcctgagat gtgattttaa atcataatct tgcttttctg atgtgttggg 14580
gtatccaggg tttctgatga ctccaagtag ccttggtttc tgttgcttat gttcttatgc 14640
ttacctcttg ccatctggtt gtctctggtg ttagctgaac ttgttctctc tgaatggatc 14700
ttatccctcc tatgagcttg tgagcctgtg atcttaggtc tatcagcact cctcagagac 14760
cagttctttc tgggtggggt ttgggtaagg agaactgtag cacagggtta tctcaggggc 14820
acagatggaa accagaagct aagttcttcc tcttatatct gcgcctcaac atacccacat 14880
caccttgaac ctttcctaaa tataccatca tgatttatcc cattccagta gttgctttac 14940
actatatatt tatttcaatt ttatcctgga gctatgtata gcaataaagt caatttggca 15000
agagagttca ctgacatctt ttatttaaaa tgtgcataga accctctaaa attggctgct 15060
taatatggtt tttgatttgg tttgattttg attttttttt ttttttttt ggagacaggg 15120 tttctctgtg tagccctggc cttcctgaac caggctgggc ttggactcag aaatctgcct 15180
gcctctgcct ctgttggaat taaatgtatg tgctacgacc acctggcaag ataatatgta 15240
tttaactcag tctgaaactt cttataatct actgttcctg tattacctgg aaccaacctc 15300
cctaggcacc attgaccatg tgttgtgagg attaattctt cactaaacat taatttagta 15360
tcacaagtat gttttacatt tttttctaaa agtgtcaaat cactttacac cactttccaa 15420
actgcttcat aatttagttt gtttttattt aattctgtgc acacttgcaa acaaaagctt 15480
tcaaggattt cgtcagagtt gaaaaatctg tatttgtaga tttttatttg catttttgca 15540
aaactgcata aattaatatt tgcattttat gactacaagc gagcctgata aattttgcta 15600
ctaacacaca ttctgatatg tttctgtgtt aagtaaatgt tttaattctc aaatcttaat 15660
ctcatacatc tggaagagga ggtgaagagg atctcaaaga agttgtggag gggaaccata 15720
atcagattat attgcatgaa aaagagtata ttttcaatta aaaaaatgta aagctcatct 15780
atctgccata aaagtcaatt cgcttataaa ataacatttt taaatttttt atttgatatt 15840
ttctttattt acatttaaat gttatcccct ttcccagttt ctcctctgaa aaccccctat 15900
ctctttcccc ctccccctgc tccccaaccc accgactcct gcttcctagc cctgacattc 15960
tgctatactg gggcatagaa ccttcacaag accattgatg accaactagg acatcctcta 16020
ctacatatgc aactagagcc acaagtccca ccatgtgttt tctttgattg gtggtttagt 16080
acctgggagc tctgagggta tgaattggtt catattgttc ttcctaggag gctacaaacc 16140
ccttcagctc tttgggtcct ttctctagct ccttcattcg gggccctgtg ttcagtccaa 16200
tggatgactg taagcatctg cttctgtatt tgtcaggcac tggcagaccc tctcaggaga 16260
cagctatatc atgctcttgt catcaagctc ttgttggcat ccataacagt gtccgggttt 16320
ggtggttgtt tatgggatgg atcctcaggt ggggcagact ctggatggtc attccttcag 16380
tctctgctcc gaattttgtc tctgtacctc cttccatggg tattttgttc ccccttctaa 16440
gaatgatcga agtatccaca ctctggtctt ccttcttctt gagtttcata tgctttgaga 16500
aatgaatctt aggtattctg agcttctagg ctaatatcca cttatcagtg agtacatatt 16560
gtgtgagttc ctttgtgatt gtgttacctc actcaggatg atgccctcca ggtccatccg 16620

-continued tttgcctaag aatttcatga attcattgtt tttaattgca gagtagtact ccattgtgta 16680
aatgtaccac attttctgta tccattcctc tgttgaggga catataggtt ctttccagct 16740
cctagctatt ataaataata ctgctatgaa cgtagtggaa catgtgtcct tattacatgt 16800
tggtgcatct tctgggtata tgcccaggag tggtatttct ggaccctccg ctagtactat 16860
gtccaatttt ctgagtaacc gtcaaatgga tttccagagt ggttgtacca gcttgcaatc 16920
ccacggatac tgtcaataag acaaaaaggc aaccagcaga ttgggaaact atctttatca 16980
atcctacatc agaaagaggg gacatatcca atatatacaa agaactccag acatccacat 17040
aaccctattt aaaaatgggg tacagagctt aacaaagaat tctcaactga ggaataccga 17100
atggctgaga agcaactaaa aaatgttcaa tatccttaat catcagggaa gtgcaaatca 17160
aaacaaccct gagattccaa tacctcacac cagtcagaat ggctaagatc aaaaactcag 17220
ttgacatcag atgatggcaa ggatgtggaa aagaataaaa tgacaatatt aactgtgtct 17280
gttttacaag agtttctcta taatggcact ttctttccac agctcaatga gaatttgata 17340
tattgatttt taatgtgtat tatcatgtac agttggcata tgtgctgata tgtggtgtga 17400
cagaaaatac agtgaaaaat attcacaggc ctactatttt gaaaattctg gttttatgtg 17460
cataatttgg aatagattct cagacccctt ctgtggggaa atattggccg ctctatggtt 17520
ctggttatat accccagagc ctttggggac aaatacttct aaatattaat ttttcagcta 17580
tatttttata ataaaatttg agtgtgttca caggcatatt tcctttctgt ctgccatctt 17640
cataatatga gcatgcctag tggtgttgct atgctttcaa acaaatgatg cataatttta 17700
caggaatcat gaccaaacat gcatcatgct attttgtttc tgaaacaaag aactttaaac 17760
tgagcatggt catgaatgtg catcttcact gtgcattttc agaaatgtgt ctgctcacaa 17820
atcatttttc tatatgaata tgcaaaggtc ccctgattaa atgtcactct ttaattgttg 17880
aaggaattgt cattactttg gaaataacct catgtgtcat ctattacaca aaataaatat 17940
ttttgtacta tgttcactct gtaaacacca aaatgtgaat tcacagacca aaagaacaat 18000
tcttatcaaa tatgtattac acacataaca gattcaaata cttttagggt gtattgtgtt 18060
attattattc tcttatacca tcataggctt ctcagtgttc tccattgttt acttcatagc 18120
ttcgtgctac atcctggtta gcatgaaatt ggaattttct gtgctgggca tatttttgtt 18180
tttctgaaca gaaaattccc cattcaggct cctgaaaaac tttctgcatt tgagtagaac 18240
agatacattt ttaaaactta catttaaatg ttctttcttt tcctatctaa agaatgttgt 18300
tagctttctg gaaacttcta aacaaaaacc tggtccaaat caataaactt tttataaaata 18360 actccctatg gtttagccaa tgcacagtaa tttatatatt tcaccaaact aagtgatgat 18420
acacagacat tttttatatt atgctgactg aaacttatta tcagatgatt gagaattttg 18480
agcactagtt tgaatggaaa attaataata acaataataa taaataaaat ttattataat 18540
tttctaagga tatctttgtt aacattttgt gtcaggacac tattgctcta atatgaaaat 18600
ttgaggtttc ttttctcctt ttgagacatt tgaaagagtt tgtgaagcag gaatgatgtg 18660
ttggctcagt ggacaatgaa gcttgtcacc aatcctcatg acttgagtta tagcacaagg 18720
aaccatgttg tagaaggagg ggatcaacac ccaaaagtga tcttctgggc tctgtggcat 18780
agacatacat atacacacag taaatatttt ttaattaaat taaattaaaa ggtcataaag 18840
tcaaggtatt aactaccact gattatccaa tccctgactt tgctttgagg atgaaaaatt 18900
ttttctaaga gaggttttta attaatttat ttatttgttt gtttgtttat tatgtacaat 18960

-continued

```
gttctgtctg catgtatgcc tccatgccag aagagggtaa aagatctcct tatagatggt  19020
tgtgagccac catgtggttg ctgggaattg aactcaggac ctctggaaga gcagtcagtg  19080
ctctcaacct ctgaaccatc tctccagcct tgttatagat ctatttggtt acctgtctat  19140
ctatacatgt atctatctct ctatctgata ctttctgcct tgcaggagtg tgttcatttt  19200
aactgtgcgg cctagacacc accaaaagat tagttatcac cattcttaca gtttagattt  19260
cagcaaattc aaactaatgt agctttgatt tctcattgta tttgctactc tgtcaatatg  19320
acttattttt ttcctcatgt tgatctctac ataatatcag cctttgactt tgttgacttt  19380
ctccctactt ctttattttt ccttaatttt actataaatat gacatatgca gcttcctcta  19440
atacgtggtt taatttggtg ttaatgatgg accatattga gatgagtgtt tagattgtta  19500
gccatgcaat attacagtcc tgacataaag acgttgacaa ctgtacattg tccatttgct  19560
accatgagtc ctagataaaa tgtacaaaat cctacaaatt tggccagatt ccattttctt  19620
ggaaacattg aaatcaaatg ttattctttt ctcctttgac agtggatttt gtgtgaccag  19680
gctgttttat ttacacatat ttgcaaattt caaaattttc cttttattca cgacttccag  19740
tttagtctct atgctggtgt ttgtcaactt gttacaaatc tatgcatacc tacaaagttg  19800
gattctcaat tgaaaaaatg cttccatcac atgggcctgt aggaaatcct gtagggcatt  19860
ttattgattg gtggttgatg ttgaaggccc aaaatcaatg tgggtgatac cacccctaag  19920
ctggtggtcc tggaatacat aagaaagcaa gctgaaaaag ttatggggag caagtaagta  19980
agaagcaccc ctccatggcc tgtgcatcag ttctgcctcc aagatcctat tttgagttcc  20040
tgtcctgact tccctcagtg atggactgtg atttgaaagt ggaagacaaa tgtaccctgg  20100
gttataattg tgtccttcat ccagcccaaa cccattgctt cctgattcac caagatatca  20160
gaaaaaaatg tagcaatctc ttcccaacac acacacacaa aattagtttg ctttctattg  20220
ctgtgacaaa cccctataac taaaacctaa cttagaaaag gaaagggtta acccatctta  20280
cacaggtcac catctaccat tgagggaagt tagggcagaa tcttcaatca aaaaccatgt  20340
atgctatgta ttggcttgtt ttttaactca tgcttaacca acttcctagt acagcccaca  20400
aagcctgact agggaatgat gagcccacac tgagatgagt catccatatc aatcatcaat  20460
caagacattc cccaacagac aatcccacag aaaaaaacat gagctgggca atccctcaat  20520
tgagacttcc ttcctaaatg attctaaact gtgtcaaatt gaccattaaa gttgactacg  20580
aaaaaaaaaa tagagactct tcatctgcgc catgtttccc accatgatag gccacacctt  20640
caaactaggg accaaaataa ggccttccct caattgacta ctgtcaggta ttaaatcaaa  20700
gtaccaaaaa gatatttata tgggtctcta agtcccctct ctagtattaa caacaaacta  20760
tatcaacaac tgtctaaact atcagttgta gtaagaaagt gaaataactc tggattaaaa  20820
gtctctacag ttaacaagca ctaaatactt ccagaacaac tgctgtaatt actgttgaat  20880
atcaacctga caggatatag gatcatctat aacataaacc ctttggtata tctgtgagaa  20940
tgcttttaga ttggtataac tgaggtggga aatccctccc taagtgtggg cactactatt  21000
taatggcatt tgattttgta taccctttcc tgcttgtatc agaggagtta ggggaaaaac  21060
aaaggggtaa gtgacaaggg gaagaagggg tgtccttccc cacttgggta ccacagaact  21120
taatatccat caaagcctac ctgatcagtg gctttgagga tcttctttaa tgaatttgaa  21180
gaatattatt tgaggacccc agagggtgga ttatttgtct tgaattgggt acttgggtga  21240
ccagtgggtg ggcactttag agtgagaaag agacatagca gagctgggca aggtcagggc  21300
tttgggtgat aacattatga tctgaaggga ttttgacagg atttatggta attctgaggt  21360
```

-continued

```
gcttcatagt agtgaatgag agggattaaa actcaggctg acatccaatt tcaggtacaa  21420
caggactgaa tgggacatca tcgcagtatt attttaacaa accacccacc atgaatggca  21480
tggaaaaaag gctggcaagt gaattcttta tggttgccac cctctggctt ggagtattgc  21540
ccatgctgac ctctaattcc tggaaaaaca aaaacttaag aaaacaaaac tagtttccta  21600
ttttcaaata aaaattgaat gacttactta caagaaaatt ctccccattc taatatttta  21660
tgtgagagtt tgaaaagcgt ttttttcccc atttttttatt aggtatttag ctcatttaca  21720
aaatttgtat attctttttt ttcttttttt tgtttttttt ccatttttta ttaggtattt  21780
atttcattta catttccaat gctataccaa aagtccccca tacccaccca cccactcccc  21840
ctttttggcc ctggcgttcc cctgtactgg ggcatataaa gtttgcaagt ccaatcggcc  21900
tctctttgca gtgatggccg actaggccat cttttgatac atatgcagct agagacaaga  21960
actccggggt actggttagt tcatattgtt gttccaccta tagggttgca gttcccttta  22020
gctccttggg tgctttctct agctcctcca ttgggggccc tgtggtccat tcaatagctg  22080
actgtgagca tccacttctg tgtttgctag gccctggcat agtctcacaa gagacaggta  22140
tatctgggtc ctttcagcaa aatcttgcta gtgtatgcaa tggtgtcagc gtttggaagc  22200
tgatcgtgag atggatctct ggatatggca atcactagat ggtccatcct tttgtcacac  22260
ttccaaattt tgtctctgta actccttcca tgggtgtttt gtttcctatt ctaagaaggg  22320
gcaaagtgtc cacactttgg tcttcgttct cttgagttta atgtgtttag caaattgtat  22380
cttatatctt gggtatccta aatttctggg ctaatatcca cttatcagtg agtacatatt  22440
gtgagagttc ctttgtgatt gggttagaaa agcgtttttt ttccctaggt ttattcatat  22500
taaatctttg gctgtaaatt ctcagcattt ttgccagtgg atttgaacaa ctttgtgtgc  22560
tgaactgttg aactgtgaat gaatgaatat gaatatgcag gaaacagatt tttgcctgac  22620
atcttaatca tttctcagcc acttaacaag gccaaattca tactgaaaaa caaaggctta  22680
ttggattatc tacattggga agatgaacaa agagatccag taacctaccc tcactcaccc  22740
ccttacacca ccccacccaa ccctaacgct accccaccct cattccctta ccactgctac  22800
cacatcacca cgccaccatt acccctatcc tcacccctgg taacaaaccc attgtcaggg  22860
tcctgacata aggttaaagt agcagttctg gtgaagctgt ggtcccaccc atacctgacc  22920
ccgcagagag tctattatcc taaaatgtga acttaaaagc tgtcaaactc tctcagggaa  22980
aaatttacct tctacctagt ctgggtttct ggatttgtct tctctcggga tgatatccct  23040
gaggaaattt cagacttttg agtcccatta tttggatatt ccagaaacta gagggaatgg  23100
tacaaagtcc ttacccctac ccccaaggct ggttaaagca tctctctata gaaaactatc  23160
atgggaggct taactctgtg tagaaactcg cagcaaaaaa caatgttttg tctaccctca  23220
aattatttcc atttaaatat ttattacagt attctcatta ttgttttaaa aataaaactg  23280
tggttatgta gtggaaacac tgccttaaca actattttaa gatttattgt atatgttagg  23340
tctcaaaact gacctggctg tcaggttctc tcaccatctc taagtcgtta cctgttacag  23400
ggtatggcca actccctaca caaaatttct ctagctgggc tgctcttccc tatataatgc  23460
atccattttg atcattcagc ccctttttgt ctagcctttt tccctcttga gctcttgatc  23520
tcctggcttt ccacttccca ctctcccctc tccctctgtt tacatgcccc tgctcaggga  23580
cctgttgact ctggactctc ccagatgtgc ctgcctctgc ttatgctctc ctgatatcta  23640
caataaacct atcatctata tctacaataa acctatctat catacctagg agtagtcacg  23700
```

-continued tcctgatttt tattttttca ttcaatatat gcatataaaa tttatttcag tgcctcaaaa 23760
gacgatggag taaacatggc tttgtgactg gttttacatt tatatttagg aatatgtatg 23820
tatatacata tatgcatgca atataattca tttgaaatgg ggcatggact tgaaagagag 23880
caaggagggg tatatggaag ggtttagaga gaggaaatgg aggggcaatg atataattat 23940
attattatta tctcaaaaaa ataaaaagga gattttaaaa gtaatacaat attggaggtg 24000
gagtgaagaa ccctgttcat tccccagcac cctggtgggc agcacacaac cacctgcaaa 24060
tccaatgcct atggatccta caccctcttt cagacttcac acacacctgc aaaaagaaat 24120
aaatggccca cacataaaaa agaaattcaa ctttgaaaaa gtagtcccac attagaaaca 24180
tttttaaaca caccttcttc ctggaatcac tatgtcacct tttatctggt tttactgaag 24240
aactttcatc aatgcatcaa taacatttta ttaatgtcat aaaatgaata aacgccttga 24300
actctaggaa ggaaggaagg aaggaaggaa ggaaggaagg aaggaaagga gggagggagg 24360
gagggaggga gggagggaga gagagagaga gagagagaaa gagagagaga gagaaagaaa 24420
gagagagaga gaaagagaga gagagaaaga aagagagaga gagaaagaaa gaaagagaga 24480
gaaagagaga gagagaaaga aagagagaga gagaaagaaa gaaagaaaga aagaaagaaa 24540
gaaagaaaga aagaaagaaa gaaagaaaga aagacagaca gaccaaagca tatatttcag 24600
gaaggggaat gcaagtgcca attcagaggt cacagaggga aaaaagatca ttggtaataa 24660
atgaaaatga atgagttgtt atctggcctg gctgtatcca ttccactggt tagaaacaaa 24720
actgaatgtc accatagact gtaattgtaa caacccttca cttttggcat caatctcact 24780
gtaagaaatc cacattggga ataaatcaat tcaggaagtg tgagtccttg aagggaatac 24840
taggacccca gtatcatttt tcctctctct ctctctctct ctctctctct ctccctctct 24900
ctctctctct ctctctctct cctacacaca cacacacaca cacacacaca cacacacaca 24960
ctttcagtca tttatttatt gctagaacct cctgtagttc cctgtggcct ccactatgta 25020
actgagcatg accttgaagt cctgaattcc tgaccccttc ccctgcctat gcctctcata 25080
tactgagaag atggatgaga cacacacacc agaccttgac atttattatt attgttattg 25140
ttgttcaaag tctgactttt atgtaattta catgatttct ccttcaatag ttaaatagga 25200
aattactgat tccaattctc tatcattaat tcaattactt ggaagctaat gctaaacagc 25260
acatgatagg aatatatatt ttgtgcactt gtcagcatgc acctaacaaa aattgattac 25320
cctgtgtagt gatagctttt gtactggctg gttttgtggg tcaactggac acaagctgga 25380
gttatcacag agaaaggagc ttcagttgag gaaatgcctc catgagatcc agctgtggag 25440
cattttctca attagtgatc aagggggaag ggtcgcttgt gggtggtacc atccctgggc 25500
tggtagtctt gggttctata agagagcagg ctgagcaagc caggagaagc aagccaataa 25560
agaacatccc tccagggcct ctgcatcagc tcctgcttcc tgacctgctt gagttccagt 25620
cctgacttcc tttggtgatg aacagcagta tggaagtgta aactgaataa accctttcct 25680
ccccaacttg cttcttggtc atgatgactg tgcaggaata gaaaccctga ctaagacagc 25740
tttatagaga tcttggcata gaaactggaa ttttagaaga aaaaataagt ggaatgggtt 25800
aaagtttgac cttcaagtgt ggatttctgc ttcactctta tctcagcaaa gcaaacacct 25860
ggcagaacct tccagaagga gtgatgggca cagctacctg aaaagattct gtttgcttag 25920
aaaggaattg ttcctttatt gttccctgcc agcccagtcc tggaagcctt gataacaaat 25980
atttgtacat ttttattgtt ccccgcaaaa tcatcctctc ataactgcag atcctgtcaa 26040
catgcctgcc agatggcaga aatcacctat catgtgacct ataaaagctg tgagaaatta 26100

-continued

```
tggggtgttt gggaactttt caaagcatca gcccagtcat agctacaaaa tttcttgtgt  26160
ctcccagggc ctgctgggtt gattcgtggt tggagttttc catagcagca cacaagtgga  26220
aaatacattt tggtagaatc acctcattgg tgtcaattga tttcataaga aaaattaaca  26280
gtcacaataa gattgggtac tttcaaagtt ccctatgtcc aaatagtatc ccattgtact  26340
ctcagaacaa gtgaacattg caacctttat ttcaaaagat taatattcta attatgttta  26400
tatctattat atattgtatt atacacacac gtatgtacta tgagctttat ttttacactt  26460
ttattttagt attaattgtg tatatgtgtg tatatgcaat acatattata ttacacatat  26520
atatgtacat tacaattttt attttaaaat ttttcatttc agttatatgt atatgtggag  26580
tggggcaggg tgggcacatg tgagtatagt accatgagag gccagtagag ggtggtgagc  26640
ccccaggatc aggaacaaca ggtgtttgtg ggcttcctgt gtaggtgttg gaagctgaac  26700
ttggtcccta tttgttggcc ttgcttgtgg gggattacat gctacacttt gctggaggaa  26760
ttacatcagt gggggagagc tatttgagat tctgaaacat tcagcaagtt ctgtttggtt  26820
ggagatggga gctctcagct ccttgttggt gccaccttgc cagccccttc ctgctgtact  26880
tgtcccttat gtgtgcttct gtcacagcca tgcccacccc tcaccactat gcttccctgt  26940
gccaacgaac tcatcaccct ttggatctta aatgcataag tcaaaatatt tcttgcatac  27000
actcattttg tttgtgatat cttgtcacag caacagaaaa ctcttattgc ttaacactaa  27060
gctacctctc cagcccctag aggtttttgg tttggtttgg cttttaatat catttttttt  27120
ttatttatgt gtaggggtgt gtgcctgtgt gagttttccc catttaattt atttatttat  27180
tcattttaca tgccccccctc cttgtcccca ctcacatcgt ctcttcccca ttccccctcc  27240
ccttctcttc tgaggcccct ctgggtattc cccgatcctg gcacatcaag tctcttcaga  27300
gctaggtgca tccactccct ctgaggcaag acaagcagct cagttagggg aacaggttcc  27360
acgaagattt gagagaagga atgaaggccc taaaggggat agaactccac aagaagacca  27420
acagagtcaa ataatctgga ccccgagagg ctctcagaga ctgaaccacc aaccaaagat  27480
cctacatgag ctggacctag ccctccccac ccccaccccc cacatatgta gtagatattc  27540
aattcggact tccaatagga gctgtcccta aagctgttgc ctgtctgtgg aatctgagag  27600
attagttttt tgtttttttgt ttgtttggtt ggttggttgg ttgttttggg tttttttggga  27660
ggattggggg gctgtttgtt tttgtttttg taccctgaaa gttcttcaat ggaatagttc  27720
tcagtgttgc ttctatttca ttcatgctac ccacaggctt gcttttgaaa ttacatgtat  27780
ttttcccatt ttcttctctc taaatttgag tcaatttctg gtatcagcat gtttgaaaca  27840
ccaagcagaa taatgtgtct gctttatttt atattttgtc gtacttatgc acatggaaac  27900
acacacacat gttatgtgct caattattgg aacaaatgtt ttcctttttt atctactctc  27960
actatgtgac cctttatttg tttcaagtaa ataaaataac aaactgataa tcaaactaat  28020
aaaactgtaa catttacaga tgatgtcatt atttgcatca tctaattctc atggaaaagg  28080
tgcccttttt cttactaatg ctacttacag gtagacactc ttagccaaaa ataatccgga  28140
agtgaaactg cctgccaaca caaaccactg atgactgata agattcctga ggattaggaa  28200
aaccacacgg ttcttacagg gaacaactga ttcttcagag actgcctaag aaaacactga  28260
cacatttgca gaaaagctat tgagttggat aaaagtttta caaaatgccc acaatgaatt  28320
ttaatactaa acctgcaaaa gaaatatgct aaggaaatca cacacacaca cacacacaca  28380
cacacacact accaccacca ccaccaccac caccaccacc accaccacca ccacacaaat  28440
```

-continued aaatgcataa gccaagtcct gagggcctgg gatatcagcc ccaaattcag taggctgggt 28500
aagaaggaag ccaggactct gttttaagat gaatttcttt caaaatccac aggaacacat 28560
catgcatatc acatcatgtg ctatatcctg gccctggggt tgtggagtgt ccaagaagga 28620
tgcggaggca caggttatga ttaattatct gagcatatca agcagcaaac tcagacactc 28680
cttcctcttc tgtcttccaa aggatgtttg tttcgggaca ttttctagaa agacaggtac 28740
caatgtatat tgacagatga ggcacaccaa tgatagtcaa aggaaatttt tcacatgagt 28800
ctttctgggt tgacttacag gagggtgttt tccaccatca catatggaat gtttcacttt 28860
ctgccatttc acatcagtaa atataaatat tgatgagtgg gcgtccttcc ttcaagacat 28920
gcatttaatt gggttttgat caaatgttca ggcactggga ggaagccagt ggcatcaaag 28980
ttgtccacaa acccaacatc acactagggg actagtgtga aaactcagta aaagttgccc 29040
aagtcatgta tctgttgttg ttgttgttgt tgttgttgtt gttgttgttg tcatcgtcat 29100
ctttggaggt ggtggtttgg tttggtttgg gagtgtttgt ttattttgtt tgagacagag 29160
tctcacttca tagctctgac tgatctggaa ctcactatgt agaccacact gaccctgaat 29220
ttggagagat cctgcctgcc tctgcctcct gagagctggg attaaaggca tgcaccactg 29280
tgacatgcaa gttaattttt tttaattata ttttttctac aactaacatt catcagtgtt 29340
tcagcctgga aggaagaaaa cttgcatgca atcaatgttt taattgaaca agaacatatg 29400
caaatggcac aggcatttct atcatttgga tttagaagaa aatcccaaga tgatgttgca 29460
gttttcccac ctcagctgtg aacacttact attcgtgatt gagtctgcag gcagttggcg 29520
ggcaaaagcc tgtcaggggt attattagcc ttcataccag atcataaaga aggatttgcc 29580
aaaaatccta gtttccagaa gagctctgtt gtaccaaggc agtggagcat cgccacctta 29640
cgactgtacc ttgcaatgca actagctcgc acaaattaca aatgctattt attgattggg 29700
gcagggaggg gaaaaaaggg gagggcagag gcagactgtt ggttggtttg gttgggttgg 29760
ttggttggtt tgttggttgg tgatttttca agacaggatt tctctaacag tcttcgctga 29820
cctgaactcc ttctgtacag cagtctagcc tcaaattcac agagatccac ctgcctctga 29880
ttctccagtg ctgggctcaa aggcaagcgc cactactgcc tagcctgtgt tgtttttttgg 29940 ttaagcaaaa catctttaaa tgtctagatt agatatccag attaaatgtc tagactaaga 30000
tctctaaaca ttttctaata taaattttat cagttgaaac ttgtccactt ttatgggatg 30060
ctaaggatgt atggaactca ggactttgtg cattcagtcc cactgtctgg tagacactgt 30120
tatgctgtat attcctaatg gggagcagcc aaaaacaaaa acaaaacaaa caaaaaaatcc 30180 aaacctcaat tccttaatta attaattaat taattttta gaactaagat ttaatcagga 30240
aagttgcatt atatgcatac ccctggttat tcaggtaagc atagtaagaa tataattaaa 30300
agttgtctgc acatttgaat ttagatggat atgaaagtgt ttcagatttc ctacttaagt 30360
aaagtgaaac aatattgaaa tttttcgaag gttgttactg tgggatcccg ggtccacaga 30420
cacataaaat aaatctttga aaaaaataata ttaatattta gtaatgtgac atgaaattaa 30480
attaaaccaa tgtttttcct ctggcaagaa acgcagaaag taaaaatgat acattgtatt 30540
cgtggtaaaa atcctaatct catttaatcg atacacattg catccattat gagttgcagt 30600
cattaataat aaaataatat tattaagcag caagcaaata gtcttaaagc agcacgtagt 30660
gagacctcag agctgttaat ttcctaataa aagaatacac ttcccaggaa actttacggc 30720
caggccaagc acttccggaa ggagggacta cgggacggca ataggaccct tctgtaagaa 30780
aagggagaaa tgtggcttca aaagaaacca tacttattca tgtgagtggc gatttgtcac 30840

-continued

```
atgtgtgtga cgatagccaa tatgtctgaa gagaaagacc ggttgtggcg ctaactgggg  30900
ggacctactg cctccctgta agccttcctt acaaggctat ctcggcgcaa ggaatgctgg  30960
aaagtgtagt gatttggctg gaaactacca gctattaagt aaaatcgcgt catcaccccg  31020
accagttctg ttcccaagcc tgctgatcta gaccttatcc cacctccgtt cctgctccat  31080
tctgagccct gactgtgaag gtttcactct cttcacttac aggagcttta gggaagaagt  31140
ctcccacagg agctgagggt ggggggcggg cggtctccct cttctggcct ctatcggtac  31200
tgcaaggagg ggccaccaat tacatgcaat ttttatgcca cactaagatg cacaaataaa  31260
taaggccaga gattccccag agtcaggatt tgaggctttg gggaccaatg agagttgttg  31320
gattgaatgc aaaatgtaca cacttggaaa caagactggg caaggctgca ttttctagtc  31380
tgcagggaga cctgaaaagt tagtagaagt acatgtgtgt gtcagttcta aatgaaacga  31440
cgggggacaa atgcctgagg tgcctgttag cataccaaag cacatgatgg cctctagact  31500
cacttgggac cgctgactat gctctactct tctgatctgg ccccataact taatccaagc  31560
cagaccttct cctagcatct tttacctata taaccagcca tttaggccat gctcccactt  31620
ggtcctctca gtctcctctg ttccctctct tttcttcttc tcttattctc ctcacccttt  31680
ccacctctgt cctctcatgg ctgggttcag tctactgtcc aggtttagtc cactactttc  31740
tctgctctgg actcttccag aagcctctgg ctgttcttat ccgtacctgg gagtggccat  31800
accctcattt gtacagtatc ttcctccagc gtctccctgt ggctgaccct ggaggccttt  31860
atgctttctc cctggaaaaa ttctaattgg gggggggggg ggaatccagt ttgttgcaat  31920
gaccagacag ctgaaggggt ggctcaaggg ccggggcata ggtcattgaa atatactcag  31980
ggctactagg agtggcagtc agtgttcaag tacacaggaa gcaactttct ctgcaaaggt  32040
ataaagaaaa gtaaaaagtt ttgaaaaagc taaaaattta aattaaatta aagacaatca  32100
tctgggcagt gatggtgcat gccttaaaaa ccagcagatt agggctggag agatggctca  32160
gcgattgaga gcactgactg ctcttccaga ggtcctgagt tcaattccca gcaaccacaa  32220
gatggctcac aaccatctgt aatgggatcc agtgccctct tctagtgtgt ctaaggacgg  32280
ctacagtgta ctcacataca ttaagtaaat aaatagattt aaaaaaaaaa ccagcagatt  32340
atacatggga gacagaggca ggtgaatctc tgagttcgag gccagcctgg cctacagaga  32400
aagttccagg acagcaaagg ctatacagag aaaccctgtc ttgaaaaact aataaattaa  32460
attaagagga caacaaaggt gagctgagtg ctttctgggc cagtgagtcc aggtcctctt  32520
accctctgaa ccacatctcc agtcccaaat taacctttag tttctactcc ccaggaacat  32580
aaaacaagcc ctggacctta taaaaggtgt caggagataa gagcagccta aggcttcttt  32640
atttctttcc tctacactcc tggaaaagaa agggtagcag gaaagccagt ggtcagataa  32700
aatacaaatt gtcagattaa aatcttaatt ctggttgtat ttattttaca ctctctgagg  32760
actcattgcc ctacagtatg tttggggact agaaaggaaa tgaaatctca gtgtcagtag  32820
cccacaaaga gacagaagca aaagtagttt gcaaaggaca gtgagaaagt cctctgatgt  32880
tctctccctc tccctttcct tctaccctct tctttctgca tttttttttg acccagctcc  32940
tgtgaccccc atctccaacc ctttgatcca gtaggacttt caagttttct gaacagtgct  33000
caaagaaaac actttacttg tggttttcca tatcctctga ggtctggact ttctgtcccc  33060
agccagcagg tggtgctgtt actacagctg gaagcaaagt tcccaaaacg tagctgaaca  33120
cctgggaggc tgattgactg gtagtgtgtg gagatgtgca gagttggaat cctgagagtc  33180
```

-continued

```
cagagcctaa ttatgatttc tcttggacaa ttttcagctc tctagataga tgtccctaag  33240
ccacctatgt cagacctgac gtcctgtgac taacagattt aaaaaacaaa caaaaataaa  33300
acattttttt ttgtctgtct aatttgatca aattgttctt tcacagcaaa gggcctagta  33360
aaagcaagga cttctggctc tgcttcatcc acctggctta atattcccac tcatgtattt  33420
tgaaaagaac cttgattgat gttcctataa aaacttcatg aaactgtgtc tatgtccctc  33480
catgggattt ggggatgcag tttaccatgc cttaccgcaa cctgatgtgt ggaaccttca  33540
aactgtggct taaaacaaac tcttctttcc tttaaagtgc ttgactcaag tattttgtcg  33600
aagcaatgtg tagggtaact aatacccttg gatagattaa atcagtggaa atacactctc  33660
tgtcactgga tgagaacgtg cttttagcaa ggctcaatgg catctttcat cctacccagc  33720
acttaggaag cagaggcaag ggaatctctg agctcctggc ctgcctgatc tacataaagg  33780
atttcagtcc ctgtgacact tactcaataa cagtgacagg agagaatttg gttcccagga  33840
acttggagat gggggcggga tattggagag gttgggggag gatgttggac agctggctac  33900
catgtgagtt ccaaatttag gtggacagtg atagaggggg gtattccatg ccccctctac  33960
atttccatat gtgcacatat gtgcttatct aaatgagtca ttttattact ctttgattcc  34020
catttcccaa tttccttcta tcaagagagt aaagacaaaa aacaaatcca ttattttttt  34080
tgtgtgtaaa ttcttctgct catgaatatt ctatgtattt tagttcccta aaaacaaaac  34140
ttcattaaaa attttgaaag ctgcccataa ttttttgac atagaggaat tcaagttata  34200
cattcaattt tacattttga ttgcatttta aagcatggga ctactgcagc tcaaagcagc  34260
tgcaaatctc aaaccttcct gcctccactt cccaggcact gtttacaggc atggagctcc  34320
attattggat atagaaacac acaaagagaa acatacacac agacatacat acacacatat  34380
aaaataggct ttgctggaag aaaataaaca agaacaaaac agtgattatt cagtttggtc  34440
aggcccaagt tccaaggcta tacacatctg tgacaagaat ttcagatata aacatgtgaa  34500
ggaaatttta taggtgcacc ttttttattt atttttgtta gatattttct ttatatacat  34560
ttcaaaagct atcccgaaag ttccctatac cctccctcca ccctgctccc ctactcaccc  34620
actcccactt cttggccctg gcatttccct gtactgggac atataaagtt tgcaatacca  34680
aggggcctct ctttccagtg atgaccaact aggccatctt ctgctacata tgcagctaga  34740
gatatgagct ctggggacac tggttagctc atattgttgt tccacctata gggttgcaga  34800
ccccttcagc tccttgggtg ttttctctag cttctccttt gggggccctg tgttccatct  34860
tatgactgtg agcatccact tctgtatttg ccaggcactg gcatagcctc gtacaagaca  34920
gctataacag ggctcttca gcaaaacttt cctggcatat gcaatagtgt ctgggtttgg  34980
tggctgatta tgggatggat ccctgagtgg ggtagtcact ggatcctttc gtcttagctc  35040
caaactttgt ctctgtaact cctttcatgg gtattttgtt ccctattcta aggaggaatg  35100
aagtatcttc cctcttcttg attttcttgt gttttgcaaa ttgtatcttg ggtgttctat  35160
gtttctggac taatatccac ttatcagtga gtgcatatca aatgacttct tttgtgattg  35220
ggttacctca ctgtcttagt cagggtttct attcctgcac aataatcatg accaagaagc  35280
acctggggag gaaagggttt attcagctta cacttccaca ttgctgttta tcaccaaagg  35340
aagtcaggac tggaactcaa acaggtcaga aagcaggagc tgatgcagag gccatggagg  35400
gatgttcttt actggcttgc ttcccctggc ttgctcagcc tgctctctta tagaaccaag  35460
actaccagcc cagagacggt cctactcaca aggggccttt cccccttgat cattaattga  35520
gaaaatgcag aaaatcaaga atttcacaca caactatgac aggcatttca tacacataca  35580
```

-continued

```
catatgacaa gaatttctct ctctctctct ctctctctct ctctctctct ctctctctct  35640
cacacacaca cacacacaca cacacacaca cacacacact cctgtgacaa gaataccata  35700
cataaaactc tggtaggaat ttcacataca aacctgtgac aggaatttca catacacaca  35760
tacccacaga catctgttaa atgaatttta aacacacatg tgaccagaat ttcacacaca  35820
cacacacaca cacaatcacc tgatacagga gtttcactca tacaactgtg acatgaattt  35880
tatatacaca cgtatctgtg aaatgaattt tacacaggta catgtgacag gaatttcaca  35940
cacacacctg atataaaagt ttcacacata tacatgtgac atgaatttca catacacgca  36000
tatcagtgaa attaattttg cacacacaca tgtgacagga atttcacaca tacacatacc  36060
tatgacaaga gtttcacaca caacactgca ataggaaatt taacacccat acaaaacagt  36120
gatatggatt ttatacacac acacacacac atacacatgt aacaaaaaat tcacacacaa  36180
aactgcaaca ggactttcac acacacacaa agctgtgacc agggttcaca cacacacaca  36240
cacacacaca cacacacaca cacacacatc tgtgaaatga atgctacaca catgcctgtt  36300
accagaaatt cacatgcaca cacatacaca catacctgtg atgggaattt cacacacact  36360
gtgacaggaa tttcacacat atgcacaaac tcctatttca ggagtttcac acacacacct  36420
gtgacacaaa tttcacacac atacacacac acacacacac acacacacac acacacacac  36480
acacactgtg atagggttgt taataagtag ctagctagat ggatagttga atgatgggtg  36540
ggtgggtgtc tgtactgatg gaaagatacc cagaggtgat gaattgacat ccagaggtgg  36600
acatatggat ggaaagagga aggcatgaat actgaacaaa tggaagcatt ggtgaatgga  36660
tgggtgtatg aatggatttg tcgtgcatgt actggtagag ggtctaatga gtgtatatat  36720
gagtgggtgg ctggctggct ggctgaatga gtgagtggat ggatgggtgt ttgggaggat  36780
tgttaaagtt ccttttgttc tcctgatata actattgttt taaaggctta ttgcctccat  36840
ctgctaacct aagcctagtc ttggaagctt ctagcctcca tacaatctta tctaggccta  36900
gaatcttttc aacatttgag acttgctgct gaatatgctc accttttcta gttatttctg  36960
aactcctgct agctggtcaa ttcagcagtt ctggctcaga actcttttcc atgctaactg  37020
attcaatctt gcttctcttg gcttctcttg aatttctcta cttggcctca taataacttt  37080
ggcaatatgt tctatacaga agtatatggc tccttctcat tctctgactc attctgtctt  37140
ctcctgtgtc ttgcttggtc tctctctctc tctctgcaat ctgcctctgt acaactgtcc  37200
cagtaaaact gcctccttcc tccccccctcc actctctgca ctgctctctt aagtagcttc  37260
cctttcttct ctcttcttat aggatatgtt acttcctcct acaaactaac tttaccttca  37320
ttgtttggga ttaagggtgt ataccaaggg catgtctata ttccagcaag ggggattaag  37380
ggtgtgtgct aagggtgagc cacaccacaa ctagaaacag gtttttccag taaataattc  37440
aatcttgggt ttcccagtgt gatcaaatat cctacaacag tgaatggata gtaagatggg  37500
tggatggatt ggtggattgt gagtagatag atgaataggt gaatggatgg ataggtggtt  37560
ggataggtgg gtgggtgaat gaacaggtca tgtattgtgg atgtgtggat atatgagagg  37620
gtggatagat agatggatgg atgggtgggt ggatggatgg atggatggat aggtggatat  37680
atgtgtgagt aaatgaatgg gtgggtggat gaatggatag gtggatatat tggtggatgt  37740
gtggattagt ggtagatggg tatgtggaca catggataaa tggatggatg gatggatgga  37800
tggatggatg gatatgtaga tggatgtata aatggatgga taggtggatg gattgatgga  37860
tgtgtaggtg tcagtaaatg gatggataaa tgtataggat gatgaatgaa gggtaaacgg  37920
```

-continued

```
atgtgtgggt gggtggataa ataggtgtgt gtgtgtgtgt gtatgtgtgt gtgtgtgtgt  37980
gtgtgtaggt gtttggatgg atggtggatg gatggtttag tggattggtt gattgtgaat  38040
atgtgagtga attgatgact agatgggaat attgaagttt gaataaatgg atggatgggt  38100
ttatggatga atggatggat aagtatatgt atggatatat atatgtgtga gtgggtggat  38160
ggatgaatgg atgagtgaat gggtgagtgg atggatggat ggatggatgg atggatggat  38220
ggatggatag gtggatgagt tggtagatat gtggatgtgt gagtggatgg atgaatagat  38280
ggatagtgaa tggatggtgt agtggctatt cctggttgtc aacttgacaa tatttggaat  38340
gaactacaat ccggaattgg aaggctcacc agtgaccctt atctggaggc ttggagatcc  38400
ttatctggat cttggtttga agatcttgag ccatagtggc tatggattcc agaagattga  38460
atctccgagt ttaaggaaca cacccttaat ctgggctacg cctttcatct gggattaaag  38520
gtgtggtgga acacaccttt aatctgggct ccaccttctg ctggagacaa tataaggaca  38580
ttggaagaag ggagtctagc tcttgctctt gctcctttgc ctgcttgctg cgtgagactg  38640
agtaactgct agatccttgg acttccattc acagctgcga ctgaacaatt gttgggaatt  38700
cggctgccga ctgtaagtca tcaataaatt cctttactat ttagagatta tccataagtt  38760
ctgtgactct agagaaccct gactaataca gatggataag tagatggatt gatggatgga  38820
tgtttgagtg ggtgggtgta tgtatgggtg ggtgggtgga tggatagaag aatgggtgta  38880
ctgatggaga atatgttcat caatgttgct ttgtaacaac ccaattgtaa gcttctattc  38940
aacaatgtac tgctttcttt gttcccaagg tcatgcctta tctgtgatgt tcaaaatgaa  39000
ttcacagcca gatcttaact tcccatggcc gactgtgagc accaaggatc ttaaatcact  39060
gacaccacat tccttgaacc ttgaccctga aacatcctgg tatggatgtg acatcagctc  39120
agctgcaatc aggactatat gagagggaac tgagaatgtt catttgtaga gcagagagac  39180
aatctctaca cagcccacat gaagaagaaa gtggagaaag gggaggcaga aaggaaaagg  39240
gaagagggat ggactgaatg aagggaaggg aaaagatcag tagggagact acctccagag  39300
gtggttcaac tacagaagca cagcacagaa gtctctgctt caaaaataga attgtttgca  39360
aactcgttcc tctttctcat ttctccaaaa gaagggaggg gctggaatca cacccatggt  39420
ttaatgctaa ccaggaacaa tggagtagat gctgctaaaa gtgaaggacc tgctacaact  39480
tctgagaaac tacaaagtca caatcaagta ccctaagctt ggcctggatc acagggtgct  39540
tctagaagtg tgactcttct aaaagattct acttcataca aggccgtgac ttttcaaatt  39600
cacctttaat ttgaagggct ggttttatgt atttatcatt gtcagttctt tatccattta  39660
cttaattttt tgttgtgttt atttctggtt tttcaagaca gggtttctct ttgtgtagcc  39720
ctgcctatct tggaacacac tctgtagaac aggctggcct cccactgaaa gatcagcctc  39780
ccaagttctt gtcttacagg attaaaggca tgcaccacca ctgactggtt atttaaatat  39840
ttttaagatt ttttaaaatt gtatatagtt ttttcccata atcactgtgg gaggtacatg  39900
gggttcagat tttggataac acattacaaa atctaccaca ggaggatact ccctttgagg  39960
aggcagatgt tttctaaaga aaagtattta tttctgtcgc ccactgtcca gtcagactca  40020
tttaaagagg aatcaattga caagaaaact aactgtgcag gggtctggcc agaagagggt  40080
cacttggaag gttctgtgaa aggctgagtc aacaacagga agttgatctg tgtggtttga  40140
gatagcatct ggcctggcct catagcagtg acaaacattt cctcaaaaaa gatactgtga  40200
gaatgagtta ggttgagtga gaaagctaat accaaaactc acctattatg atttattctg  40260
taagagtaaa catgttttta ataaggaaaa aataaaaaag ttgtggagaa caaaaaacaa  40320
```

cccagcacta actaaacata tttcctgatt ttaacattca caattttggg gccagctagg 40380
tggcttagga ggtaagagtg tttgtgacca agcctgggaa tcagagttca attctgttgt 40440
cccatccaga agctgacttt gatttttact tttatgtatt gttatggcat gactgtcaga 40500
ggacagcttc attgccatca gctctgtctg tccagctttc catggcttct gaaaattgaa 40560
ttcatgtttc caggcttgag tatagtctta ggatatctaa tattgaaact ttttcttttt 40620 tttttcact aaaaaagtga atttagcttg tgactatgtc ctcgcacttt cgagtgtgtt 40680
gagtgtgtgt gtgtgtgtgt gtgtgtgtgt gtgtgtgtgt gtacaccttt tctcgctgta 40740
tcaagaatct aaataatttt ggcattttct gccacccact gtaaggatca caccaaggtg 40800
aggaatttct cctcttccaa tccaagcaca catttctgca attttatcaa aactgtttat 40860
cattattgga ctgaagttca tcaaacttca cctcctattc ccctcatctg agcagaagca 40920
atgtgcattt ttccttattg tgtttgtttg tttgtttgtt tatattttgg atttcgaga 40980 cagggtttct ctgtgtagca ctggatagtc tcaaacttgt agaccaggct agccttgaac 41040
tcacagagat ctacatgtct ctgcctcctg ggtgttattt tctttagatt ctgcaatatt 41100
attgtaaaca cttcccaggt agggaactca aacttaaaaa ttcgtttaca atttcctcat 41160
aatacacacc tataccctca gtagaatttc atgtagtgtt ctttggggat ttgggtggtt 41220
tgctttgttt tatttttctg tcaagagaca aggtctcacc atgcagcctt ggctggccta 41280
gaatttacag aaatccctct gtctcagttt ccttagtgct ggcctcacag gcatgcaata 41340
tgcacctttt agcaagtttt taagtgaggg tctgtaaagt ttcccaagtt tacttagttt 41400
atagtccttg accctggcct gcagccacca agtagtcacc tgaaagaaaa gaaaatagaa 41460
tttgcagcta tttttcatga gaaaccaagg tggtatctgc agagatggag actgagtcat 41520
gaaaaggaga tagagttgcc acagagaagg ttgctgccca agggaaactt actctgctga 41580
gctccatgct gtgaccctga aaactagagt ttcacagatg atctgagact aggggatatg 41640
ttcgagtgtc ttcaaggatt gtcccaagtg aatccatagt aaagcaggga taatccatgg 41700
atctaaaagg aaacaacagg tgcccatcca gtcatgaaat agttaatatc cagacttgta 41760
aaagcaggaa gttcctagac actaaacgaa tgaatgaatg aatgaatgaa tataataaaa 41820
gtatgtatgg ggctagagag acagcttggc aattacaagt acaacctacc tttgcagcca 41880
acccaaattc agttcccagc acccacaagg aggcttataa attccacaac ttcagcatcc 41940
agatctccat ggtcaatgac ttctgacttt tagaaaacag atccaacttc cagtgacata 42000
aactctgaag ctttaacctt cctggctgtt ttgttttcca ctagaacctg tgactgaagc 42060
cctactacaa cacaaccccc accatacata catacacaca cacacacaca cacacacaca 42120
cacacacaca cacacgtaac ttgatccctg actgaaagca agttcttact ttcaccagag 42180
tacttgagct ccacccacct cctcgtcaat cacttaactg accacaagaa aatccaaatg 42240
ctttgttgac aagatgcatc tatggacact acaacaaacc cacaaaccct tcttaaacat 42300
agtttttaag tctacagaag attcgtatct cacctttccg aggctatttg gagctaggct 42360
atactcacta ggtagtgctt acagctcagt ggcaaaaatg cttatagcta ctaggataag 42420
gtgttcaata gctcagtgga tagggtgctt gaagattagt gagtaatgtg cttgtagctc 42480
agtgtcttag ttagtgttct attgctgcag taaaacacca agaagcaagt tgtggaggaa 42540
agggcttatt cgtcttacac tttcacactg ctgctcatca ccaaaagaag tcagcactgg 42600
aacacacagg gcaggagcct agaggcagga actgatgcag aggccaaaga aagatgctgt 42660
gcactggatt gcttcctctg gtttgcttag catgctttct tatagaaccc aaggctacct 42720
gggccctccc cctcttgatc actaattgag aaaatgcctt acagctggat ctcatggagg 42780
cattgcctca actgaagctc ctttctctgt gatatctcta gcttgtgtca agttgacaca 42840
caaaaccagc tagtatgctc agtttgtagg gtgcatacct agcatgcagg gagtcatcag 42900
ttcagttctc ttagctttgt gggtccaagg actgaactca ggccattagg catgatgcaa 42960
gtgcctttac agacccagcc atcagacccg atgtttttaa tgctttcaga tagcacccag 43020
gtgggtgtac tagcacacat ctggaatctt aagaatcttc agcctcactt aagaagctga 43080
ggctgaagaa ctcctgcatt tgacatcagc ctcactgatg tagcttgtgt ttcgatttct 43140
tgcctgttgc tgtgacaaac tccctgacca acagcaaaag aacatgactt ttatttgaaa 43200
acaagaaccc tctgaagctc acttgcaatg tcactgccaa atatagaaac tgaacaaagg 43260
gtagaaagca gcagcatttt cccgaaaatc actgataggg aagagaaacc catccaccca 43320
tgaggagaaa aggggccact catgagtcac tcagaatctg gaagggactg aaagaaccct 43380
ccctggggcc tgacaaggaa gcctcataca ttgtgtgcta cctaagagtg cctgcaccat 43440
cttgtagcac acctgctctg tgccattttg gatcccaccc ttagattcaa cccaacctgc 43500
accatcttag atctgatcca ccctgggtca tcttggatgt cattcactct gggccatcct 43560
gggtctaata ctctaccaaa caagctccca gtgctctacc ctctgagcta gaagaactct 43620
actcaatgag tcacaaatac tcaactacaa gcactctacc tactgagccc catccctagc 43680
cccatatcca acctttgact gcccatgttt cctttcattt atttttctgt atttctacct 43740
gttaggagca gattccttgc caccatgaat cctttgtgct gtgtctgagg cagtttcact 43800
tcagttatca gtgacagttg gtttttaaca aaccagctct gcctgtcaga gtttgaggtg 43860
ccaataaata atgcacaggg tcatgacctt ttttcaggcc aaagcacatg ctgctttcag 43920
gtgcatgtgc aagtgctgtg accccccccca gctccaccct ctgaggccct gaagccatgt 43980
gatcagcaat catcaagccc atgatgtcag cagagcaccc aattcaagag gcctgagtcc 44040
acaagattgt ggggactaag tgatggctat gtgggaacaa aacaagactg cagagagcaa 44100
agcatgaaaa aagagaccca ctatgtgatg agggggagga gaaatcacag tcacagtgga 44160
gcagccctag atactgagtc tgcagcactc cctgggtgct ctgcctgaca tcaccctggg 44220
tttctggagg atgatacctg ttagggcaat ggcagaccct agggtgagtg gtaatgtgca 44280
catgcagaag aaggtgggca gaggagcaca ctggaacaat tctggccatc ctcctgcctt 44340
aggcacatgt atatatgctt catgtgggct tagagattcg aactcagatc ctaattgcta 44400
gagcacccat tctcatagag tatctgtctc atcagaagat caatgtttgc agagttgaat 44460
aaatgctttt tgttgttgag atgtttacca aagactgcat ggacatgggt ttgaggcaat 44520
agaaattctt tattagccag ccagagacta catttgggta cttgggttcc aagtgtaccc 44580
taagcctttc tcagggtgag cttttaaaac agaaactatg ttctaggttg acatgtttta 44640
acaagaacaa ttagccagaa gtggaactac agaaaccaaa atgcaagctt agtagattta 44700
gaaactttcc cagaactaag ggctttgatg gactagtctt ttagttttgg taggtggcgc 44760
tgtcttcatt ttgagtgtta taacctgaat gatacttcca tcatggagtc agctgtataa 44820
agtctggggg tctactaagg tctgggatca ggctacagtt ttgtcatagt gtaaccaaac 44880
tcaaaataat agcaggctct gtgcattctg actagtggag tatcaggtcc tagcatgtgt 44940
ttattgaatg agaaaatgtt ctcaatgtga aacaataaaa aaaaataata ataaataaag 45000
cagccagcag actttcttgt tgccaaggtc agtgtacttg ccacctacgg gcatcatcgg 45060

-continued

```
ggcaactggt tccgaatgga tggtccccac ttcattcctg acttggggcc ctattggccc  45120
tgtgtcttct aggacccagt gcctcaaagc taggagcggt gcagtgcagt gagcatgcac  45180
tgagcagccg ggagaccaca ttctttgcat tccaggctca gggaaacacc gccctcacct  45240
tgcaggtggt ggctgcggtc tgtgaagcac ccagttctca gcactgccta cgagcccagg  45300
cctgtttgaa gccgcataac aagtccctgg aaacccggtc tactcaggag ccccagggct  45360
caggatcagc aggtgctgca gggccactga gagcccgggc tttcgggagg gcggcactcg  45420
gggactacag aacaccagga gttcaatccc ctgagattaa ggagaaaccg agaaaccctg  45480
cccaacccgg actccttctg gtgcctttac ccactgctaa ggctctgctg gtaaatatcc  45540
aagcagcagc cggaagttcc tgcacctctt ccttcccgct tcctgccaag ggggaggaac  45600
caggcatgcg gtgtgtgtgt gtgtgtgtgt gtgtgtgtgt gtgtgtgtgt gtgtgtgtgt  45660
gagagagaga gagagagaga gagagagaga cccatggtgt gcgtgcgtgt gtgtgtgtca  45720
agctggaccc cgtggcccca gtgcagcccc ctccattact tttactttgg tgcaggtaca  45780
tcccatgggc gtgggccccg cgggtgagta acaataggca gggttgggcc aacgccgggc  45840
tcctccccgt cggttacgca acaaggcgga gcgagatgaa ggctcttccc cctcgcgtca  45900
tccagacacc ccactccccc gccgtcacaa gccggtcgcc gcccagccgg cttccgccgg  45960
gaatgaagag ggttgcggtt ggctccggtc ccgcggaccc cacgcgcgtc cgtggagccc  46020
tcgggcgact tccatgagcc cctcccatcg ctctgagacc cgctgagttt gcttccattg  46080
tcctctcggc cgcgggctcc ggaacacccg tgcgagccca ctgctgatgc acagactgcc  46140
attgcgccgc tgtcacaccg tgcgtccccc gccccatgga gccgcccgct ggtgccgcgg  46200
cgaccgtaaa agatccagac catgaccccg tgaagaccaa ggtctcggcg cccgccgcgg  46260
accccaaacc caggacatcg tcacagaagg cggggcactc gttacaagat tgggacacca  46320
tagccaccgt gggtgagtga gaactgagta agaacttatg tgtggggacg cggcttggga  46380
gcgaccctca gatttctgtc tcccacactc tcattactgg gcctccggaa acggggcagc  46440
cccacgtcac agagctttca ggagggtgac ttcaccttag ggactcggag gctccctact  46500
ggggtgctag ccacccttgg gacaccacgc ccggcctccc tggcgcttgc gcacccgctc  46560
atgcccagga tttctcggga tcgcatccag cctccgcact gtagacccct ggcgggactc  46620
gaagggacgc gtgaccccca agggaccctt cggggacgtt ttcccagcat ctattgtgtg  46680
cctgggtctc gttttttctt tagtggctca aacttggtac cctcgtgacc ccgaaagttg  46740
ctagggaagc cggtagatcc ccaaacgtgc cggagtactg gggagggagg ctaggatctt  46800
gcgaatcatg ggcgccagct tctcaagtct gaagcccagg agtcccgggc ttctcagcaa  46860
acttggtcac taggacagtt gtgcctggtg tgttgatgat taggaaagtg ttccgggagg  46920
atggaggaag gacagaggga gggattggcg tcctccgatc agctgtgagc agagattcta  46980
gaggcttctg tgttcaccct ggtgtggaag tcaagtcagg gttcaggacc aggatgaggg  47040
gcaataaaca ctttctcagc tgagcaggtg agatgttaaa aaaaaaatgt gtgtgggtaa  47100
aagggcttgc aagtttgatc ctggttccct cttggaggct ggctgacact cgctgcatct  47160
tggcttttga ttgacttttg agggaaactg agctgcttga atgaatgtcg tttatttatg  47220
tatcatgttg tattctaggc tggcctttcc atcactgtgt agccaggatg accttaaact  47280
acacattctc cgcctccccc tctttctgag tgctgggaac cgagccccac tccaccacag  47340
attggttatg ggtgctgggg aatggggact gccctctata tgtttgagac attgacctga  47400
```

```
aagtcactgc atagcctaag ctgactggag atgccagaca atcctcctgt cttagctttc  47460
ccagtgctga gacttcaggg actcattcac aggcacttgg cacctcaact ggttctccac  47520
ccttttcttt ctgtctgtct tccttgccct ctccctccac gccccatctc ggcaccttag  47580
ctggttcttc tctccttcct tcctttttc tttccttctt cttcgtcctt ttttgtgttt  47640
gtttgtttgt ttgtctgttt gtttgttttt gaaaacaagg actctctcca tagctctggg  47700
tcactaactc ctagagatgt gcctgcctct gcctcccaaa atgttaggat taaatatctg  47760
tgccaccaca cctggctctt ttgttaattt taaaatttac ttatttactg tgtgaacgag  47820
gggagggggc agcacaagtg tggggtcaag gttcaacttt tagaagtctg ttgttttgcc  47880
aagtaagtcc atggtatcaa actgaagtcc ttagacttgg caacaagcct attggtctgc  47940
tgagccctct tactgcccca ctgtgtccct agaatagacc tcatgggaca tcttgggagc  48000
gtccttgtcc tgaagtcctc caacttcttc accttttcct taccatgacc ctgttccctc  48060
ggaatctttt agaaggacct gggcacacac atcagcctcc cctctcccct actcatcctt  48120
tcatatatat acacacataa ctgagctata agcgctctct tcactgagcc ctcacataaa  48180
tttagatggt gtctatgacc aacggagttt tgtgggtgtt tgagacaggg cctccatgtg  48240
tagctctggc tgtccaggta cttgctgtgt agaccaggtc ttgaactgca ggtgcctaac  48300
aagtacatac cacccaaatt aacatggagc acctccgtac tctctctctc tctctctctc  48360
tctctctctc tctcacacac acacacacac acatacacat actcacacac aaagacaact  48420
cctgcgtccc tagtccccag cacacactgc gttctccagg aaataagtgt tgatgctttt  48480
gtctctgacc taaagctcat ttctccattc attaggagac tcaagtagag aacatttcag  48540
gctggggatg tgattcagtg gatacagtgt ttatagctta gttgagataa tgtttatagc  48600
ttagttggga tggggagact gcttgtgatt acagtacatg tgactcagta gacagagtat  48660
ttatagctca gtgggtagag tgcttgtagc tcagtacaat gcttgcattc agtgggtaga  48720
attaagtggg tagagtgcct gtagctcagt ggacagagtg cttgtaattc agtgaatctc  48780
atatctaaat ttgctgaaca ggccccctct gtccagcagg tctaatgtag tcttgtttcc  48840
ctgtactcag ctgtgatctc ttgagtcctg tgcctcagtt tacttttcag tgcttccatg  48900
gcctgctgcc ttatggaaag ccagtactaa atcttcagtc ttacaagggc agaagatctc  48960
cagtctgtct ggatgggaac atcctcctta gatgaagagt cacatgagca gctgtcagat  49020
gctctgacag atcactacag gctagtgtct tttacactag agaggaatta ctgagggtcc  49080
tgtgggggat gggggagttg gcatctgaga tacattgagg ccatctggta gtccatagtg  49140
acattaatac aaatttagaa ctatctagga gacacttgaa gtccagatca ttgaggaaga  49200
agaatcctgt gcatgggtgg ggacccagag tgcttaaaag ggaaatcaat tacccattaa  49260
tattgccaag tcaccagcgt tcatccctat tgatgtaagg agagcaacta tgtcctgctt  49320
ttgcctccat gaagtcatct cccctggaag gcccactctc accaccatac aaccctagtc  49380
attagtaatg gtgtaggctg tgggagttgc attaacattc atgaatatgc agatatacac  49440
tctgtatata cacacccaca ttgtacaagg ccagcctctg cctctttcta gaccagtccc  49500
attgtgcaga ggagagattg taatcaccca tagtacactt ggctgttctt ttgcaaagtc  49560
cctaaaggtg gaatgctgtg cacaatgcct cccaccatgt catcacttcc ctgagtgcta  49620
ccttctaatt cattgtggtt tatgagatgg ggcttcactg tcattcaaac caggcatcca  49680
ctccaaccga aactaaagga tcatgggttg gagggatatg accacaggat gtctggaaca  49740
cccagaagca ggacatggtt gggagggtct tctttgaggc ctgcaggaga tggggagtag  49800
```

ggggctgatg gacctgtacc tcatatttcc acccttggac aaaggataac aggtgagcct 49860
acccactttg tgccaccttg gatgtcttct gttctatgtc atcctgactg aacctatctg 49920
ggccatcttg aaccccaccc accctgagcc atcttaaatt ccacctaacc tgtgccattt 49980
tgccttgaag ctatgtatgc tatcttgaat agcacgtaac ctttgccatt tgaatgccac 50040
ccaccctgga ccttcttaac taaaccatct agaaacccat ccaaggcagc catcttgaat 50100
tgctcactgt cttgatatat tctttcaggt ttcttttctt gactgttttc tcctgatagt 50160
ataaagaacc tgtcctgtcc tccttctcaa cccctaaacc ttgtctgtgt atctgtccat 50220
ttcctgctca gcccttagca tcctcatcct gaatcaccaa gggtgataaa tcacactctc 50280
tctctctctc tctctctctc tctctctctc tctctctccc tccctccctc cctccctccc 50340
tccctccccc atgcccccctg ccccctgcccc ctctcccctc tcccctctcc ctctccctct 50400
ccctctccct ctccctctct ctctccctct gaaaggcact tgtcctgagc cactggtggt 50460
cctagagtga gtttcaggat gattttccta caaggacatc acccaaaagg agagcaggaa 50520
gtcacagctt cagtcacgca ggccaaagct tcttgcttca atctcgttta gagcctggat 50580
gctctagtct tagtctaacc acacactaag gacagcacct tcattctctt gaggacttat 50640
gcatccttag gcgttctctg tattgacatt ttcatttaat tttatttttg aagtgctggg 50700
tgttgaatat agagcctcac tcacattaag aaaatctcct agtctctctt aagtctcctc 50760
tgtcctccct ttttctttcc agagtctccc agagtagctc aagctttcct ggaactcact 50820
gtgtattcca ggctgccctc aaaccgctgt taatccttct gccttacttt agaagtgcta 50880
ggattaaagc ctaccctact aggctgaatt tatgcaaagc ttgggattgt gtcctgggct 50940
tcatgcatac tacacttaaa tatcctactt ttagttttat ttcctatctg aaataaccac 51000
catgccatca cacttccttt attttaaaaa gatttctccc tgaggctgag ggtggaactc 51060
agtgatacag agcttgtaat tctgttgata gggtgcttat ggcttagtag attggctctt 51120
cctgtgggag gccatccaag ctaatgacac actgctgtac ctgatacttg gctccttcag 51180
gaattatctg ggttgtgttt ccagtccact cttctgttta tattttcctt tccaaggcta 51240
gggttagaat gtgaggggaa tagtaataat aatagccaca gtaataaccc acttattatt 51300
attatatcta ttatttgggg ggttggactg gaacccagtg cctcatgcat gctaggtaac 51360
cagccactga gctgctacac acagagccca agagcaaact tgttagtagt agtatcatca 51420
cttttttttt gtttcttaca tttattttat tgcatattgt tagtaaatat tccatttaat 51480
acaattatgt tgtcaaaata aagcaagaaa tagtgctatg actcattgtt gacatatacc 51540
acaaatgata acataaaact ccagtataag agaaacacac acacaatata tatatatata 51600
tatatatata tgtatatcca gtgttctaat tttatgtaca gttttaagtg ggggtaaatt 51660
ttaaacattt ctatttttc caattttttt attggattgt tattgctctt attgttgctg 51720
tgtgaggtgc tgggaatgca accaaggaac tcatttatgc cagtcctgag ttccagcgct 51780
gagttgcatc cctagcccat ccttcctgcc tctatatcaa atgctgtatt gaccttggac 51840
aaaaatcaca atttcccaat atgatgggga aaaggaaagg acctgcatct atcttcacag 51900
cctgctgcaa ttgttcctgc ttgtgcatgt tggattttga aacccagttc tgggtatctg 51960
ggcgacttcc atgtaacatc ttcctcagct accccaggag ccttgttacc cacataaaag 52020
tttacatttc ctcctcacca tgtcagacac agaaaattat gtctgaaagg ttacaggtgt 52080
tcatgtatgg aacacttgac taccatttgt agagcatgtg tgtagattag atcttcctct 52140

-continued

```
gaggtagtca tttggggttt ttgttgttgt tgtttgtttg tcttattggc aaaggcattc  52200
atccttgtgg aaggcaacct tggaatctat aagggctgta aagtaatttg caatgaattt  52260
aggtggtgtt gtttgttacc ttgatgacct gtgacctctg agtcacctta taggtcaagg  52320
gactctgctg tagtgactgt tgtaaatggc tggggtatga gcatcaaaga tggagtgatt  52380
ttgtatcaca tagggatgct gggacattga ctgggatagg catatacaac atacatttga  52440
gtgaatgtag gttgtgttga tggcttacaa ccaagggatt gggggtggag gaggaggaga  52500
gacaagcaac ttaggtttgg gtccaatgac aacacaattc tttcttacag actttgaata  52560
ttggtgtgga atgtgtatta gctagcttcc cattgcagtg acaagatctc tgacattata  52620
aaattataaa gaagaatgat ttgtggtggc ttgtgctgtc aggcatccat ccatggctct  52680
gttggtttgg acctgtggag atttagagca tcatgggagc ttgtagtaga acagagctgc  52740
ttaccacgta gtggccagta cacatagaaa agagaagatg agtcccagtg tctccttcaa  52800
tgtcatgccc ccaatgagct aagtttctcc cactaggcag taaatagcac cttaccctga  52860
gactttctgg tccttttgct tgactttgtt ctgacagctt ctggcagttg gcactctgct  52920
gtactgttct tttccacagt gttaggtttc tctctcagcc tgtgctctgc tctgtgtaat  52980
caacaccacc agctgtttct gcacccacaa gtctcaggca caagtgtgaa ggaaacaagt  53040
cggtagccat ctgatacaga agtcatcctg tggactgcgc atcgcagtac agctgtcaca  53100
ggctctcttc acctactgta ctttgaacac aaaggtgaca tgtgatccac caatcagaag  53160
cacaggcaag ggttccagtg tcaagaccct tgcttttctc attttgctgt gacaaaatgc  53220
ctgataatag gaatttaagg ggagagggga ttattctgac tcagactgct gctggtccat  53280
catggaggca ggagcaaaga gaaggaatgc tggggctcag cttactttct ggatccagga  53340
ccccagcaaa gggatggtga tgcccatatt cagggtagga tttcctacat cagtgaacta  53400
gatgttctgg ggtagcttgg agcaaactga ggttatttta agcattttca gcttgattat  53460
cccgttcctc attgaaatgt ctataaattc tcacccacac tttctatcca tctgatccac  53520
tgtaggccag tcttggcttc cactcaggct atgactctgt gtccctcctc cattcctatg  53580
tattctgtgg caggtgtctc ctgactgata gacatcacct tttctttaaa gaacaaaaca  53640
aaacaaaaaa ccaacaaacc ccaaaaatcc ctaagcaccc aagaccaatt ttatatccca  53700
attaattcat tgtaagctta gatagcagaa gtaaaagaat gtttttgag gctgggcatg  53760
acagaggatg cctgttgtcc cttttaaata actttagtac taaacatggt ttttttgtgg  53820
ttattgggct gttcggcctg ctgtctagct gtgggtgtgt ccttcttgat cctgcatctg  53880
gatctagctt gctgtgggga gcattctgta ttttttcccc tttttattgg atattttctt  53940
tatgtatgtt tcaaacgtta tccccttcc tggtcccccc tcctgcaaaa cccctgtccc  54000
atttccccct tcctctgatt ctgtgagggt gttcctccac ccaaacaccc accttaccgc  54060
cttcacactc cctatactgg ggcacctagc cttcacagga ccaaggacct ctcctcccat  54120
tgatatctga caaggccatc ctctgctaca tatgcagcta gagccatgag tccctccatg  54180
catactcttt ggttggtagt ttagtccctg ggagctcagg cagtggaggc ttctggttgg  54240
ttgatattgt tgttcttcct gtgaggttgc aaaccccttt agctccttca gtcctttctc  54300
taactcctcc attggagacc ctttgctcag tctaatggtt ggttttgagc atccgcctct  54360
gtatttgtca ggttctggca gggcctctca ggagacagct atatcaagct cctttcagca  54420
agcacttctt gtcatcctca atagtatctg ggtttggtga ctgtatatgg gatggatccc  54480
caggtggggc agtctgctcc acactttgtc tccatatttg ttctgtgagt attttgtttc  54540
```

cccttctaag aaggaccgaa gcatccacac tttggtcttc cttcttcttg agcttcatgt 54600
gctctgtgaa ctataacttg ggtattccga gcttttgggc taatattcac ttatcagtga 54660
gtgcatattt tttaatggtg agaaaagaat gaaattgtat gaggtttgca ttttttttgg 54720
agtacatcat aagatgtcct tttctacatc ataagacaga aagcaactgt gtttaaaggc 54780
tgggatgggg agagaggtgg gggatggatg aaggaatggg ggaatggatg ttggtgcgtg 54840
agggtggatg agttagtata tagattgaaa tggaagagaa agagtaagag gaaaagagga 54900
caagatggat atggagctag aagagaaaag gaacacaggg ggcataggga gagatacaga 54960
tggaggaaga tgaagaataa ttaggaggaa aatagggaag agatgatgaa agggcagatg 55020
aggcagaaag ttcagtggag gaaaaaaagg aggaggagca gagagattca gaaagagaag 55080
aagcaggaag tcttggaaga agaggagggg agggggtagg agacaataga ggcagataga 55140
ggtggaagag gaaggcagac agagagagca aggattcaaa gttccccacc aggagtcacc 55200
aagtccagca tttcagctct tcccatggct gtgtttcaat ctccaatgca catagcaggc 55260
aattatttgt tttaggtttt agtcattatt attactgtgc atatttgtgg ttgtaggcaa 55320
tagcatgctt gtggacagac atcacaggaa actttgttga gtgactgtcc attcattccc 55380
caaagcaagc tctttaccct cagagccatc tccctggccc cttgattgac agttgtgtgt 55440
gaaaaaatat ctatacagag ctcaagtgct catctaagtt tcttttcttg tatttatctt 55500
taaggcccca gattggcatg atgtccattc ctcaggtatg tttccttttc ctgatccttg 55560
actgaatgca ttgtcttcct caggcactgg gacctttggc cgtgtaaacc tggtgaagga 55620
gaagacaggc aggcaatact gtgccttgaa gattatgagt atcccagatg tcatccgcct 55680
gaaacaggaa cagcatgtgc agaatgagaa agcagtcctg aaggaaataa accatccctt 55740
cctcattaaa ctgtgagttc ctggctcctt cctttccacc tcctcacctc cctaacgtta 55800
ttctcccaag agtgcgatgt aggggtgctg ccagggctgt agctcagtgg atagagtgct 55860
tttagctcag tggatagagt gtttgcagct caattggtag agtgcttgca actcagctaa 55920
tacagtgctt gtagcttaga gggaagagta cttatatata gctcacctta tggaacgctt 55980
gcagctcaat tgttagagtg cttatagctc agtgggtaaa gtgcttgcag ctcagctaat 56040
acagtgtgtg agtagcttag tgggaagagt gcttgcagag cagtgataag agagtatgta 56100
gctcagtgga tagagtgctt gtagctcagt ggtgtgaggt gggagatact atccagattt 56160
tgtcttgatt tattattgtg tgtgaccatg cacatgggca cagtaccaca caaaggccac 56220
aggagagcac tatatttcct tggaacttta gttacaggtg gttgtgcact gctcaattgg 56280
gtgcttggaa tccaatttac atctttaaga gcagcaagtg ttcttaaatt ctggtccata 56340
cctcaaccct taacttagga gtttttataa caactacttt ttgtgtgacc tgaccaggag 56400
ccatgattct aacagtctct tcaatgttta tgcccaaaca ttgcttatgt tatgtaaaag 56460
tccaagacct gggtctttta ttacggcttc tagtcaaggt gacagagtaa gctaattatt 56520
catttgatat tcatataaag caactggtga tttttttaac aatattaaat ccctctttga 56580
atttgagaaa tatagatgta tataaaaata cttatataca tatatagtat gtgaaggtcc 56640
atatgggcgt atgcatgtgg agatctgaga acatctgctg tcattcctta atttaaagtg 56700
tttgagacaa ggcttcctga tagcccagga cacagaaagt ccagggagct tcagggaggg 56760
taaattaccc agcatgtcgt tattgaaaca ccactgcaca attgtcatgc tattctagag 56820
tattctatgt tgtcagaaca ttacataagt gcactatagt caaaattcat tagatagtgt 56880

-continued agaaactaga gcatcgggct gaaggagaag gatcaggttg agtacttgtt ccttttgcag 56940
agcacctggg tttggttccc agcactcaca gcgcacagtc atctgtaatt ctaatttggg 57000
gacacataca cacaaataaa tatgtaaata agatacaaat aaatatgtat ttttaatatt 57060
tgaaacacag ggcatttaaa ttctacacag acttcaatat tagccaaaat atgttcctgt 57120
tagccacagc accaactgag gctcatcgct ctgtgagtgt ttgtgtccca gtctcctctc 57180
cttatgagga cccagtcctg ttaggtcatg tctaccccaa agacctcatt ctaccccagt 57240
ttccccattt aaagatccat ctccacacag ctctgtccca aggtcctagg tatgcagaca 57300
tttaatacag gaattctggc agaaagaatc ctgagtgctt agctaagtca gactggacaa 57360
ttctacccac cactgtgtaa ttacacatgc cttaaaggaa tcttttcttt tttgctttct 57420
ttatcttgca tttacaggat tcagcaggtg ggttaaaaac tatgtcaaag tgacttagtg 57480
ctatagagat ttgcacttgg cctgcatgct gtattcacag catggcagag cacactgtat 57540
atctgtccag ctgtaggaac acaacttagc aggtctttga acttcaaagg atgatatgca 57600
tgctacttaa ggcctttaaa gtcttatact ctgtccttta actgtgaaca cttgtgaggt 57660
catccatcca acttgtgcat gttgcctatg aacatggagt agtctgtctt gaggaaacat 57720
gggatgccca gcatagtggg aaaggcttca aacggctgat gaaaatcaca gcttacattg 57780
ctgcagaaat ctggacttat ttacaaatgg ttttaacaag agtcagtatt aggctcagcc 57840
tactgtacat ggcactattc ccaggacagg gaaaaatgtg tgataagctt caactatcaa 57900
ttggcacaac ccaaaatccc ctgggaatgg tttcactgag ggatttccca catcagtcca 57960
gcttgtgaat atgtctgtga gagtgttcta attgatgatt gacataggac tccacccacc 58020
atggacaaga tgagggtgta gtgtcaattt gacacagaaa gtttgtgctc tacatgcata 58080
ccatgaccct tcatctgtgc tttcattcct ttatgtcaga ggtatttgca catagaggta 58140
taacaagaaa tgaagtcttg actgggctgc actgtgcact cttgaaaggt ccagtgcctt 58200
tgggtgccct actgtgggtg ctgagagaag aaacctctca tcctaggggc ttataatcag 58260
agtgctcttt agacattgct ttgtacccct ggagagcaat gatgtttctg gatgaaaacc 58320
ttgtggtagt tgggtgggaa ttacttgcat gatatatgat agatagatag atagatagat 58380
tagatagata gatagataga tagatagata gatagatgga tggatggatg gatggatgga 58440
tggatggata gatagtatat gtagatgata gcagatagat gtacgtagat aacatagatg 58500
atagatcatg aatggaagga caatagatgg tagaaaggtg atagatggtt ggatagatag 58560
gttaaatagc tagataatag atgactgact gatagataat gataacatac atacatacat 58620
acatagtatt gacggtaata ttgaaggtct cacctagggc accatctctt agcatatact 58680
ctccttgtga attccaccct caggttgtca ccacagtttt agcatcctct gatattctaa 58740
tatcaacctg catctacagt ccagctaagc acaaccttat gatctgggtt gactgacatc 58800
agatatctta tcaaacatct tgattacttg ctggtgagct ttgattctgt tgtgattaaa 58860
caatgactaa gagggactga gggtaggaaa ggcttaactt ggctacttgg ctttcacttt 58920
gctgtcacag gccatctgag aggaaagtca gagcaggaac cagaagcata aagctttcat 58980
ccagcccaag aacccagtcc atgatgggtg gggcttccta tgtcaattat caaacaggac 59040
actccccaca gacacccaca ggccaatcta atgtgagaaa tgactcactg agaccctacc 59100
taggtgactt caagctgtgt tagagctgac agcacatctt ccccctgcta gggactggcg 59160
ccaccctcca tggagatgat cgtcatactt caatcaacta atcagctgaa taaagacatc 59220
cccccataga catgcccaca ggctaggatg atatgggaaa ttcttcactg agtaccttcc 59280
caagtgactc tgggtcataa aggtgatggt taaagctaac caggacacat tcacatgttt 59340
gcatctgttt atgtgtttat cttgatatct gtatttatat tttgatattt gcatatatgc 59400
acctgttagt gtctgtgtat accagtatat taatgggaac atctacctct gtatatctgg 59460
agtctgtaca catatcttgt catcagtgtc tgtcaatcac caacatacat ccatccatga 59520
gtatccactt ctgagcaccc aacttattac ccatcgtgca ctctgttgtg tctcgcaggc 59580
tttggacagg ccatgacaac cgcttcctat acatgttgat ggagttcgtg cctggtggtg 59640
agctcttcac ctacctgcgt aatcgtggcc gattctcctc agttgcttca gtcttctacg 59700
ccacagagat tgtgtgtgcc atagaatatc tacactcaaa ggaaatcgta tacagggacc 59760
tgaagcctga aaacatcctt ctagacaggg aaggacatat taaactgaca gacttcggct 59820
tcgccaagaa actggtggat aggtgagtgg gaacagccat tggctcatca gaggttaatt 59880
aaaaaataaa ggtttgattt aaatgggtgg acagaaaggg gcagaagatg tatggtgggc 59940
tctggtgtga tgcacttctc cctccatcta tttagatggg tctcccattt ttcccccatt 60000
ggtatagtaa taaaaccatc tttaaaaagc agattaagga agaacaggga taaaggtgcc 60060
aacaggagca tgtgtagagg acagctgttt acattgtagc cacatatagg aagagcaagc 60120
aggaagtaga gcagggttat tgtcttagtt agggttttac tgatatgaac agataccatg 60180
aacaaggcaa gtcttataag gacaacattt aattggggct ggcttactgg ttcagaggtt 60240
cagtccatta tcatcagggc aggagcatgg cagcatacat gcaggcatgg tgcaggagga 60300
actgaaaagt tctacatgtt tggctgaagg cttctggaag actggcttta ggacatctag 60360
gatgagagtc tcaaagccca ataccagagt ggcacaccta ctccagtagt gcccctccct 60420
gggccaagca tatacaaacc atcacattct actccctggc ccccataggc ttgttcaaac 60480
atgagtcatc cacgggggcc atgcctaaac atagcatatt aaaaaaatac atttagtcca 60540
acttccaagt ccccacagtc tatagcagtc tcaataatgc taaaagtcca aagttcaaag 60600
tctcatctga gattcaccca atcaattaac tgtaatcccc aaatcaaggc aggaaaccag 60660
ctgggcaaac tcaaactctg aattcccatg tctgatgtca aaggagtctt cagatctcca 60720
gctccttttt catcattgtt gactgtaaca aatttctttg cctgggctgg ttccactccc 60780
ttttagcaac tttcctcaac atgtatccca tgaccctggc atctttaaca tcttggggtc 60840
tccaagtcaa cttcagcttc acagcttctt gttccagtgt ctgggatcta cacatgatct 60900
tctgggctcc tccaaaggac ttgcattgcc acaggtcctt cattcccgct gcaacaggaa 60960
cttcatggac accaagtcgg gttcacacaa tgacttcttt acttgtggct ttttccttta 61020
cagctctctt ccccagcagc ttcttcttag ggcaagggct aaactacaac tcctattaca 61080
atagcttctc ttactcctac ttctactcac agcaagggct aaactatatt caaaccgact 61140
cacctccttc tagctccacc ccacctcatc caatcagaat tcacacacgc tctaggcatg 61200
agctcagatc gttcacagat aggctgacag gtcctgatca caaggatag tctagcctgg 61260
caggcagccc acgcatgcag cctcactgca catgctcggg caaggcagta aacaacttgg 61320
cccatgcagc cacatctgct tcccgcgtcg catcacttct tcaactctgc cctctatagc 61380
actatagtct ctggttgact ccactccact gctgctgcca ttcttggtac tgacatctta 61440
aatatgctgg catcttccac agcaactagg cttcaccaat agcctctcat aggctctctt 61500
catggtgcca ggcctcaact ttgcatggcc ccctcagtcc caggccatca actataactg 61560
agactgcacc ttcaccaatg gctccccatg gcctctcaca gtgctaagcc tcagctgctc 61620
tccatggccc cttcatacct tcaaaaccag taccacttgg gtgattctta tgcattatca 61680
agtccagctg caacatgaca tacaacctcg gctatctctg gaacacagct tctttgtgct 61740
ttcagaaaat acttctcaga agatttcact tcaatgatgc tggtcttaat cactgctaat 61800
atcttagctc cagctaacca gcaacaattg ttcctgtagt cccttttatt cttgactctg 61860
aagctagagc cacatggttg aaactgccaa attctgcagc ttgctagtgc cggaacattc 61920
tgcccactta ttctattagc agctttctat tttccaactc cctcaaggct tggctgtcct 61980
tgaacttgca ctgtagattg accttgaact cagagatctg catggctctg tctcctgaat 62040
gcccctccag attgtgagca gaagagaaaa ttgttctgcc atcaagatgg ttgaatatgt 62100
tccagaaaat tccaatattg tatgtgtgaa tgttttcata attgcatata gatagatata 62160
tagattactt atatcatcat ataatttata tatctatata atcctaccat tcctgtactt 62220
aagcttttct tcacctagaa cttgctctgt accaggctgg ccttgaactt agaactgctt 62280
gactttttct cctgggatta aaagtatgta ccagcatgcc tgggcctaag cttttcatag 62340
ccactgtttc tcaagatcca gatcaaaagc ctgtgtcttc tagcctcaag atctggatca 62400
caagtgtacc cttcatttct agattgtagt ttattccaga ttaaaagtcc acactattcc 62460
ttgtttaact gcaaacacaa gcagtaggtt tagctaggtg ggttcttgca gtgagattac 62520
cactccctga atgtctttat ctccttgaac accggattca gctccatttc acttcctgga 62580
gtccctttat aacttggacc atacatttta tatttttcct ttctcagctt gtttctcttg 62640
ttcaaaacac ccttcctgag acttaatcag agaacaaagt ttctgttggg ctttttgaga 62700
cttcctttgt caatgcaatt aatataaatc tctttacgtt aacctcaggt agacgcttca 62760
ggcaagggca aaaagcagcc ccattcttca ccaaaatatc acaagtctct cagccacata 62820
ttaaaattgt tctcctctga aatctctata accaggcttc cacagttcaa atcactcaca 62880
gcaataacat cttccatatt cctaccagga tggcccattg agccccacat aaagcattcc 62940
agtgctttcc aaatacaaag tccccaaatc cacattcttc caaacgaagg catggtcaga 63000
cctatcacag taatatgcca gtccctgata ccaacttctg tcttattact gctataaaca 63060
gaccaaggca actcttttaa aaacatttat tggggctggc ttacacgatc agaggttcag 63120
tacattatca aggtggaagc atgacagcat ctaggcaggc atggtgcagg cagagctgaa 63180
agttctacct cttcatctga aggctgctag aagactggct ttcggacatc caggatgagg 63240
gtctcaaagc ctatgtccac agtgacacac ctactcaaac aagggcacaa atactccagc 63300
atttccactc cctgggccaa gcacatatag accatcacat ttaaaaaaaa aaaccttgag 63360
ccccactgct actgacatac tttctcctgt gaggctccac tttacctaaa gcttatccag 63420
aactttccca aacagagctg cctgctggac caagtgttaa aatacctgag cctgtggggg 63480
acagcccaca cctagtgtac agctatggga gtggagaggc ccctccagat tgtgagcaga 63540
agagaaaatt gttctgccat caagatggtt gaatatgttc cagaaaattc caatattgtg 63600
tgtgtgaatg ttttcataat tgcatataga tagatatata gattacttat atcatcatat 63660
aatttatata tctatataca tttatatata actatattat atatatttgt atattttaca 63720
cacagtaata tgctcaggga tactatagct ggatcacatg gcagttcaat ttttttagtg 63780
ttgtattttt ccccataaga tacatttatt ttatgtctct atggtgtgcc tatatgcatg 63840
tcatacccac agaggccata agagggcatc agatacccta gacctggagt tacaggtgaa 63900
tgtgtgcagt cttatgggta ctaggtgttg aacccaggtt ctctgcaagg gcagccagca 63960
atcttaaagc taacatgcct ctccagcctc tgtcttagag ttttctattt atagaactca 64020
gtccttaggg tcctttgccc agggctcctt cccctattca tagctatgga agttctttac 64080
tgataatgaa gaagatggtg tcatgttcct gttaacccat agccggggta ggggggggaaa 64140
ggctcaatat tgagggaatc agatactttc cagcctcaaa gggtgtccat gctgtgtaca 64200
gattctctat gatcccagta ttgctgtggt gtgctaagta cccttaacca gccagccagc 64260
cattggtgca ttttgtaaaa aaaaaaaaaa aaaaaaaaaa aaaaaaagaa tgtgtgcaga 64320
aaggttcaaa gctataggaa caagccagaa ctagaaaatt ccacagcctg aggcatgcag 64380
gcctccagcc tggggcagac acaaaaagac tcagctttca gtggggtaag cagagctgcc 64440
tccggtagag ttacctgtga cctcatcagc tcattagctc tatctgccct gatcttgttc 64500
tgagacaagg ctacaaggat caaaatctga gttattgggc ccaggggcaa atggaatgtt 64560
gggagcctgt gatggactga cttctagttg atttccatta cggagagaag agaggaggca 64620
gagggtgtat gtgcagccca ggctgtcata gcactcacta gggagccaag gatgaccttg 64680
aactgatccc tcctatctgg acctctggcg tgctagtatg acaagtaagc atctccacat 64740
cttgtttatg ctggggttgg gatctgggct cagtgcctac aaggcaagca ctctgcccat 64800
tgagctacaa gcattctgtt cctggtccta ccctatagtt ctatcccttc tgagttggat 64860
cagttcttta caggttcttg actcgaatcc ccttctatct gttccctgtg ctgtactgct 64920
cagaagctct tgagttttgg gccctcatct ctgtcagttc cttcctgagc cctagaatcc 64980
ttattaggaa gtcttcctga tatgtccgtc tgtgggtatc agggttggag caaaatggat 65040
ggaactgagc aatggataaa ttcaaggaaa catgtaggct tgaaattgtc ttaatagaat 65100
cagttatttc ttctttctct tctaattcat atctttgccc cttttctttt taattgcaca 65160
gtcttgccat acagcccagg cacccccaaa tgtcattatc cctttgcctg agtcttctgc 65220
atagttagat tgccagtggg agccccagac tgagcataga attttccttt taaaaacatt 65280
actttattat tttatgtgtg tgactcttgt ctgcatgtct attatgtctg taagtctatg 65340
taacacatgc attcctggtg cccccagagg tcacaagagg ccatcaggtc ctcctgaaac 65400
tggagttaga ggtgatttta tcaccactat gtggatgctt agaatcaaac tcaggttccc 65460
acaagaacaa gtgctcttat tcactgagcc atctcttgat cccactttaa aaaataatta 65520
catttattta tcttggatgg gggagagtac agttcagagg tcaactttca gaagtcagtg 65580
ttctgttacc atgagggtcc caggaattga actcgggttg tcaagcttga cacaattgtt 65640
tgacctgctg agaatctctg cttcaagcat gcttaggcct ctctcaactt taccatggtc 65700
ctagcttcag gacattttga tcatatgtaa acatctctcc tcatttgtgc ctcatgaccc 65760
tgtggtatgc ctctctggat cttcctagcc tacatacttt acacacacag catcattaca 65820
atattttttt tttatttttt gttccagctt atgtaatggc attgtctatc tatgaggtac 65880
cactgtcaaa cttactgtcc ttttcatggc tgaataatat tcctttttat agttggacca 65940
catggtgttt attaaccttg tataacttaa tttacttttt atttgaatct ttcttttgaa 66000
gaaagaaaca atcatttttt cctattttat ctttctttaa aagaaacaaa tcaacttttc 66060
attttgtata ctctgcagct tgcagctgct tgccacacca attggctctt ttaaatataa 66120
attaaagcag gacaaggtag cacttgcctt tgataccaga tagcattcaa tgggcagaag 66180
aaggtagatc tctgtacgtt tgaggctagc ctggtctata agacagccaa ggctacacag 66240
agaaaccctg tctcaaaaaa aaaaaaaaaa atagagcttt ttgttctttc aaatgggttc 66300
tttctttaaa attattcttt tctcctgtga ggacacagta gaaagcctga agctatagtt 66360

-continued ttgtggtaga gcagtttacc aaggatagag cttcatggta aaccagttag gtaatgtata 66420
aggccctggg ttccatcccc aggactgtag gatctgctgg tggaagagta ggatgtagtc 66480
tccatcccag cagggagaga tggggagaat ttttttaaa aagaaacaaa caaaaatcct 66540
agatttgtcc aaacatccta ctgtccttca tctttcttgt ctgtgggtgg caccaaaagc 66600
taaactcaac ctccaatcct gccaactgtc ctaatttctt ttgacaaaaa tgtttcttga 66660
tgagggattg gagagagaaa ttatcaacat tctggaaatt tttctcttca gaaaggagct 66720
tgttgccaca caagcaggaa gtgctggcac agcagagttg atgaggagag gagaggggtc 66780
atattatttt ttatttcttt gatttttgac acaagcccct gatcccacca cttgggaggc 66840
agaggcaggt ggatctctgt gagtttgagg ccagtttgag atctatagag caagttgcag 66900
gacagcataa gtacatagag agaccttgtc tcaaaataca caaaaactct gaagtcctga 66960
tcctcgtgcc tctacctcca tgctatgctg gaaattgaac ccagagtcta aacaccagcc 67020
atgctggtac caacgatgct gtaccaactg agttatatcc ctagccccta tcactaatgt 67080
taaaaattat taatactgca tattgattta cccacccatg atggtttgta tattcttgga 67140
ccagggagtg gcacctttg aaggtgtgac cttgttggaa ttggtgtgac ctggttggag 67200
taggtttgtc actgtgggtg tgggcataag atcctcaccc taggaaagag aggcccatta 67260
gtcttgcaaa ctttatatgc ctcagtacag gggaacgaca gggccaagaa gtgcgagtgg 67320
gtgggtagag gagtgggggg gggtatggag gacttttggg atagcattgg aaatgtaaat 67380
gaagaaaata cctaataaaa gtaaataaat aaataaaata aaagcaaaaa aaaaaaagcc 67440
tcaccctagt tgcctggaag tcagtcttcc actagcagcc tttgaatgaa gacatagaac 67500
tctcagctcc tcctgcacca tgcctgccta gatgctgcca tgttcccacc ttgatggtaa 67560
tgaactgaac ctctgaatct gtaagccaga cccaattaag tgttgttttt tataagactt 67620
gccttggtca tggtgtctgt tgagttttgt ttacttttta agtgttttta ttttaagttg 67680
tgtatctctg tgtgtatgtg tatgccagtg cagtactagc tgaggacaag aaatgatcat 67740
gggatcatct attaactaaa ttaaattgaa gttaatgctt gtaagtaaag aacattcagc 67800
aaggaacttg ccattacagg gtcagtttat gtgataaata tagatggagc aactagaggt 67860
gatggtctat gcatataatc caaggagtgg gcaagtttga ggccagccag gcctaaaaac 67920
aaggaaaaga gtatagaatc aggagtgttg ttgtatatat gctgagtgtt tggacacatg 67980
gtacaagtgt aggagtcaca gcatgaacaa aagcattttg cactctgttc tttcctacct 68040
ctcacccgcc ccagacagga tttttctgtg ttcccctggc tgtcctggaa ctcactctgt 68100
agaccaggct gacctcaaac tcagagatcc acctgtctct gcctcctgag tgctgggatt 68160
gaaggcgtgt atcaccacca ctcagcttct tctacctctt ctgtagatct atcttatact 68220
tgtacaataa tctaccagct aagccatgtt catgtaccta ggcacatgta acaggttcat 68280
gtacctaggc ccataggcca atctgatgtg ggaagtcctc cactgagacc cttcccagga 68340
aattctggat tgtgtccgct gacagttaaa gctcacagca cagcttcgtg tgcctgggga 68400
atgggtctac ccatggtgac tatgacttgt gcctctttca aatcatggaa tcttatactt 68460
gtcacatcat tgatgcttag aaagttttag atttaggagc attttgtttt agttagaagt 68520
gttcaaccta taaggccata tgttaatttt ttgcacagtg gccacacttg tagtgtgatc 68580
tttatcgctg tatcttttag caccttccaa gtttcatgga ttcatgcttt tgttaccccc 68640
acaggacatg gactctctgt gggacaccag aatatctcgc cccagaagtc attcagagca 68700
aaggtcatgg aagggctgtg gactggtggg cactgggcat tcttatattc gagatgctgt 68760

-continued ctgggtgagt gaccctcctg acagacatgg ctgcatacac ggcctatgaa gaaccttagc 68820
atccccttttt tcctaagtct gcagatacat ggcatatgga tgcactcaca taatgtactg 68880
tcaagattga agggtgattg ggtgtttagt ttacttaaac aagactttaa cgtttcatag 68940
acatccatag ttacttatgt ataacatcca tcttctttat gtgatggaca cccaaggcta 69000
atcagtaccc aaggtgaaca aatgacacta atcagaaaca gctttgtaag tagtgatgga 69060
agagcagatg aggaaggcaa gctcagttgt tttattcacc ctaatttccc tctcttggca 69120
atgcacaaga tacaggagtg tgggctctgt ctctgtctcc cagttgatgg gaaggttggt 69180
tgttcctgat ggtcactggt agctgtggag gcaagtatac acctgataaa aattgtgtaa 69240
acattgaaag caagattccc aagatctagg tgtagccgag ggaattgtag gccaatacca 69300
tgggagagtt attcctctgg ggaggtgaca gttttcccag tcccaggggc ttttctctgg 69360
tactgagata aaggaaaatt catcctttgg tagatcaacc caggtaggaa aaaagcttga 69420
aggaggattt tactaaaata gtgtgagatc tgtcaagaga aagaaagcat ctccttaccc 69480
acccaccagt catctatcta cccactcatc tatccacatg tctattcacc tacctaaggc 69540
attaatccac ccacccatcc atccatctat ccactctttc agctcctgga ggtgccaggt 69600
gtgcttggct tttgtagccc catcaccccc atctctgcag ggcttctgtg agtctgcatc 69660
tcttttttttg tctgtcatga ggtcactgtc attgcattta aggtcatctg cagccagggt 69720
gtgctcatgt caagatctgt cactcattct ctaggcagag accctatatg caaatgatgt 69780
cacagtcatg tgttctgaaa aatgtacaca tattgtatgt gtttgtaatc catgaagctt 69840
atttcttaa aaatttacaa atataaaacc acatttattt atatacacat aatttataat 69900
atagaacata atttattata tatatatata aaatctatgg agtctaccac atttatttat 69960
atacacataa tttataatat agaacataat ttattatata tatatataaa atctatggag 70020
tctagtatat acctgataaa attgtataat catacacaca cacacacaca cacatatata 70080
tatatatatg tgcatacata tacacacaag agaatgattt agaatcaaca aaaaatgatt 70140
ttttcacatt gaagtgattg tgaagagcct ggggtcccag tgtctttgaa gagggcatct 70200
ccagcaatct aacttcttcc cactaaacct ggcttcttga aggtttataa tgatcacttc 70260
cacccccctgc tgggaaggaa gctatcaact gaagctcttt gggagccctc aggaccctcc 70320
atgctgtctc tctcctcctg tggctatacc atctcctaag atcatctgtt tcccatctgt 70380
cttcagatgg tcatgttaac agttatcaag cagtggatcc atttgacaaa aaaaaaaaaa 70440
tgtttgcatc cattaagaaa aaataatagt taacacaaaa tagatataat tctgtattta 70500
actctctact aaatatccat gcttctctct gtgacaggtt tcccccattt ttcgatgaca 70560
acccgtttgg gatttaccag aaaatccttg catgcaaaat agatttcccc agacaattgg 70620
atttcacctc taagtaagtg cactcccggc ccggtttcct gccctgcccc catgtctact 70680
ttcaaagttg tgtgaaatca cactgcaagc atacactcct ggcaaactgg atcagtacaa 70740
ttctgtcagt catttgtttc caccaggaaa gaaaaacgtt tcagttattc tcattttact 70800
gaaatttaat attcaaaaga cctgctacat atctcatttc ttttgagatg gacagtgttg 70860
aaattaacgc agatttggga caagttgtgt aagcgatcag tttgtccatc catccatcct 70920
tccctctatc caactatctg gttttttttt catttattag ttattaacta acttattgaa 70980
acagggtctc aatttatagc cctagctagc ctggctagtc ttgaactcat agatatctga 71040
cccctgagtg ctgagataaa aggtatgcac caccatacac agcttcttta ttaacttttt 71100

-continued

```
aacttgtcta aatttttaac ttttctttga actgttaaga agggcttaga ggaaaagtta  71160
gtttatggga agtatgacct tgaaggagac aatggaccct aggctcttct tcatgatcat  71220
ttccatgtgt aaatatagta ttttttatta attttttgag atacttccac acatatggtg  71280
tgttttaatg gcattggttt atttactgag ctaggagaat ctttgtgaat gaatctctgt  71340
gccaccacaa aagttaactt taattcattt ttttcttttt actgaaattg tacatatcat  71400
aaagaattcc tttttattaa tcattttgtt tacatttcaa atgttatccc ccttcctggt  71460
ctcccctcca cgaatctctc accccctccc cctcctcttt gcctctaata aggtgctccc  71520
cctacccact cctgcctcaa ccctctagca tccccctttct ctgggtcatt gagcctccac  71580
agaaccaagg gctgcccctc ccactgctgc cagatgaggc aatcctctgc tacatatgta  71640
gtgggagcca tggaccaacc catgtatact ctttggttgg tagtttagtc cctgggagct  71700
ctgtgtggtc cagttagttg atgttgatct tcctgtaggg ttgcaatccc cttcaccttt  71760
tcagcctttc ccctaactct tccattgggg accccgggct caatccaatg gttggctatg  71820
agtatctcca tctcttgtag tcaggctctg gcagaacctc tcagaggatg gccataccag  71880
gctcctgtct gcaagcacat cttggcatca gcaatagtgt cagggtttgg tgtctgcaga  71940
tgaaatggat cacatggtgg gacagtctcc agatggcctt tccttcagcc tctgctccat  72000
tttttgttgc tgtatttcct ttagacaggg agaattctgg gtaaaaattt ttagataggt  72060
ggatagcccc atccctccaa aggaggccat gcctatctac tggaggtagt ctcttcaggt  72120
tctgtttccc tgctgttgtg tatttcagct aatgccatcc ctattgggtc ctgagagcct  72180
gtttcatccc tggtgtcttg gacgtttgag tggttcccca agttccccac ctaccactgc  72240
tatttctgtc tattcattct ccttggccct ctggagttct ctcctgtctc ttctcatacc  72300
tggtcctgtt ctcctttctt tttcctccct ttcctccctc ccacccaggt ctttccttcc  72360
ctttgcctcc tgtgattatt ttgttccccc ttctatgtgg gagtgaagca tccacaagtt  72420
ggccttcctt cttgttaagg ttctatggtt tattatttat atgggggtat tctgagcttt  72480
tgggctaata tccacttatc agtgagtaca taccatgaat atccttttgg gtctgggtta  72540
cctcactcag gagtttattt gcctacaaaa ctcatgaagt tatcattctg tagagctcag  72600
tagtattcca ttgtgtaaat gtaccacatt ttctgtatcc attcttcagt tgagagacat  72660
ctaggttatt tacagcttct ggctattata aataaggctg ctatgaacat agtggagcat  72720
gtatccttgt tatatgttgg agcatctttt gagtatatgc ccaagagtgg tatagctggc  72780
tcttcaggta gatctatttc aaattttctg aggaaccaca gattgatttc cagagtggtt  72840
gtaccagttt gcaatcccac caacaatgga gaagtgttcc tctttctcca catccttgcc  72900
agcatctgct gtcacctgag tatctcagcc attctgactg gtgtgagatg gaatctcagg  72960
gttgttttga tttgcatttc catgatgact aaggatgttg aacatttctc taggtgcttc  73020
tcagccattc ggtattcctc tgttgaaaat tctctcttta tctctgtgcc ccatttttaa  73080
attgggttat ttggttctct ggagtctttc tttcttgagt tctttgtata tattggatat  73140
tagccctcta ttggatgtag ggttggtaaa aatcttttcc aaattaccag gttgctgttt  73200
tattctgttg tcctttgcct tacagaagtt tttcagtttt caaaatgaga tcccattttg  73260
tcaattgttg atcttagagc ctgagccagt ggtattctgt tcaggaaaat tttccctgtg  73320
ccaatgtatt caaagttctt tcccactttc tcttgtatta gattgaacat atctggtttt  73380
atatgcaagt ccttgatcca tttggactgg aactttgcac aaggagataa aaacggatca  73440
ttttgcattc ttctacatgc agaccaccag ttgaaccagc accatttgtt gaaaatgctg  73500
```

tttttttcac tgggtggttt tagctccttt gtcaaagatc aagtaaccat aagtgtgtgg 73560
gttcatttct gggtcttcaa ttctattcca ttgatcttcc tgcctgactc tgtaccagta 73620
ccatgtagtt tttatcacta ttgctctgta gtacagcttg aggtcaggga tgatgagtcc 73680
cctagaagtt cttttattgt tgagaattgt tttcgctatc ctgaattttt ggttattcca 73740
gaggaagttg agaattgatt gctctttcta tctctgtgaa gaattgagtt ggaattttta 73800
tggggattgc attgaatcca tagattgctt ttggtaagat ggccattttt actatattaa 73860
ttctacccat ccatgagcat gggagatttt tccatctcct gaggtcgtct tcgatttctt 73920
tcttcagaga cttgaagttc ttgtcttata ggtcttttac ttgcccagtt agagttaagt 73980
caacatattt tatattattt gtgactattg tgaagggtgt tttcttgatt tctttcttag 74040
cccatttacc cttagtgtag aggaaggcca ctgatctgtt taacttaatt ttatatccag 74100
ctactttact gaagtagttt atcaagtgta agagttctct gctagaattt ttggggttgc 74160
ttatgtatac tatcatattg cctgcaaata gggatatttt gacttcttcc tttccaattt 74220
gtatcgcttt gacctaattt tgttgtttaa ttgctagcta gaacttcaag tactatattg 74280
cataaataga gagagagtga gcagccttgg cttgaccctg attttactga gattgcttca 74340
agtttctctc catttagttt gatattggct actggtttgc tctatattgc ttttaatgtg 74400
tttaggtatg taccttgaat tcctgatctt tccaagactt ttagcatgaa ggggagttgt 74460
attttattgg aggctttttt cagcatttaa tgagatgatc atgtggttat tttttcattt 74520
gagtttgttt atatagtgga ttatgttaat ggatttgcat atattgaaca tccctgcatc 74580
cctgggatga agcctgcttg attgtggtga atgatggttt tgatgtgttc tttgcaagaa 74640
ttttattgag tatttttgta acaatattca taagcaaaat tggtctgaag ttctctttct 74700
ttgttgggtc tttgtgttgc ataaatatca gtgtaactgt ggcttcatag aacgaattgc 74760
gtagagtacc ttctctttct attttgtgga atcgtttgag aaatattggt atttggtctt 74820
ctttgaaggt ctgatagaat tctgcactaa aactatctgg cccagggctg tttttttttt 74880
tggggggggg tgggactttt aacgactgct tctatttcct taggggtttg gggactgttt 74940
agacagttta tctggtcctg atttaacttt cgttcctaaa tctgtctaga aaatcattca 75000
tttcatctag attttccagt aggcttttgt agtaggaact gaagattttc taaatttttt 75060
cagtttctgt tgttatgtct cccttttcat ttctgatgta agatgtttag aggtcaacac 75120
actgcttcac aaacaattac tcagtattca tgttgaccat gcatttcatg aagattatgg 75180
caaaaatagt gaaaaagaaa aaacacagag catatttata tatttaaaaa acatataaat 75240
accttcaact ttctttgatt tgaatgtggt cagatttgag cattttctaa ccagaatgag 75300
ctttggtttc caattgtttc tttagttagt taggcagcag gatcccacat agcccagaac 75360
ttctgatccc ttttcctcag ccttctgaag gcagggtgac aaacagactt gtgcccccag 75420
tgatgcaaca gatgagatcc agggctaggt gaagactgta ctcactgagt ataagaactc 75480
agaaagcact ctgctcactg agctaagaac atccttttca ccgagctaca gtccctgctg 75540
gatattatca taggttctat ggattgcagg gtgtttgggt atatgagtgc tcagacatgt 75600
gcgcgctcac acacacatac acacacacag ccataaccca tggcattctg tctctaccct 75660
gctttaactt ctctaagtct ttgatttaat ccaccttacc atcctttgca ttctcttgtc 75720
ttttgtcgac aatagagaca caggagaata acagatattt gggaactcat tccataggtg 75780
tgtgcagcct gcaaactcag tttccctgta cagaactgtg taaatgaaca caggtgtggt 75840

-continued cttcaaaaca gcctcctcag ttagttacac aggaaggaac aatactggaa tggataaatg 75900
ctaaagggtt gcaggcgaaa cactggctta tagctcagtg ggtggagtgc acataactca 75960
gtggagagag tgcttgaggc agagtgggct gagtacttgt agctcagtgg gtagagtgcc 76020
tgtggctcag tatctagaat gcatatagct tagtgggcag agtgcttgta actcagtggg 76080
gagaatgttt atacctcagt tggtagagag tttgtaactc actgtgtaga ctgtctatag 76140
ctcacatggc atagtactta actcagtggg tagagtgctg gtggccgagt tggcactaac 76200
atgccccaag ggctgggctc catttcttac catgtaaatg gaaagccagt ctgcatccgt 76260
ggcatatagg agattgaggc tggaagacag gggtttaagg tcattgttag ggttggagc 76320 ccagagtgca agctgcctac ctgcttgctc tcacaaatcc tggtaagtct ttttcccaca 76380
atagagatac catgtggtgg tgtgggtgga atgagcacct cagttgattc tggcattttc 76440
tggatccaag tggagtcttc tctgctaaca cagggacctc atcaagaagc tgctggtggt 76500
ggacaggacc cgacgcctag gcaacatgaa ggtgagtcat gctagagcat tccagtttgc 76560
acactgacgg tgatgtcatc cactaagagg atcccagacc atgctcaatg ttaaattagt 76620
ttttggcttg tttgtttgtt gctggtttgt ttttattaat tctgtgtatg tactactcag 76680
gtttattacc tgccacagtg gactcaggtc ccctgcagct gcagttacag gagattgtct 76740
acttccatat agatgctgtg aatctaacct gggtcctctg aaagagcagc catctctctg 76800
gcccctattt gctgttttcc tgtagcccag actacaatca aaatcactat gttgtagcta 76860
aggataacct tgaacttgtg acccactcaa cctcccacct cccaggactg ggatgacatg 76920
catatgcctc cactcatggt tgacttattc tttattttg agtatttatt tatttataag 76980
acagggtctc agtatatact tctgagtgtc ctagaaatct cttttgtaga ctaggctggc 77040
atcaaagtta tcatctgcct ccttctccag agtgctagaa ttaaaggcat gtgccaccaa 77100
acctggccac ttaatttatt tttaaattgc tttattggag attttagaaa tgatacacat 77160
gcacacgcac atacacacac actttttttt tcaaatgctt tttactgagt gtttatgttt 77220
cctctcaaga atggggcaga agacatcaag cggcaccggt ggttccgagg tgtggagtgg 77280
gaatctgtgc cacaaagaaa actgaaggtg ggagtattat acacccttga attaaatgaa 77340
cagcttcata tatggtccta accacccagt gagctcccac tactgtgtct cagtcttcca 77400
aattaattta ctagaggttt attgtcattt attttgcgct tgatgtatgt gtattgtttc 77460
tgtgttcatg cgcaccatgt gacttcagta ctggagtacc ttcagcctct cataaaattt 77520
gtattccaag tgacaggcat tacatgtccc cactgggcta cccagtgtca cctcattcac 77580
ttattttatt tctttgttgc tttgtttatt ttgaatgact ctcagccacc cattgtgccc 77640
aagttatcgg gtgatggtga catctccaac tttgagactt atccagagag tgaattggac 77700
aagacacctt ctgtatctga caaagacctg gaaacattca aaaatttctg aggatgagaa 77760
ctcatgtctg aaaggtaaaa cttttttttt ttctgaattt ctaagtaggg tgtcatgtag 77820
ccaaagatag cttttaattt accatgtagt tgagaaaata tacattcagt gcaactgaga 77880
atgatgaatt aaccagtctg cagggtttct tactatgtat gattgtcagg taactcagta 77940
gtaaatgttg ataatctctg aaccctcccc cttccttttc tttgccagat gtatgtgaag 78000
acatcgatac cacaccatac cacaccacag cacaacatac cacaccaatg gccagaacct 78060
tttttgtcgt acgtttccat ttcctactat gaaactagaa ggtttggtgt gtgtattcca 78120
gttcctgaaa gatcaataca atcatcaccc ttggaaccca gcctcatttc aacaactgga 78180
aacctgccca atgagaattc gcaaaacctg ttaaattgta ggttttctcc ttcttcatga 78240
gtcttgtgtt tgtgctgtga attttgtttc tttttttgtt tgtttgtctt tctactgaac 78300
tttttaagtt tgaatttgac ccatttggtt ttatggctgt cagtgtatat gtgcacagaa 78360
attgtgcaaa ctggaaattt tggcactttg tgcttgtgac atgttcattt tttaaagctt 78420
tctgaaaaat ctttcaccct acaggcaaaa aaaaaaaggg tgagatatat gctttttaaa 78480
aatgcctttc tatgcatttt gcaatcattt gtgtacattg tttatttagt tactgtttgt 78540
ttatttagtt cctttctggt cactttaaac ttggaagtca ggaagccaca tgccctgcag 78600
acccttattc agatatagca caaatgtgtg gctttcctcc aatcttccag tttagatgtt 78660
ttcagtaaaa tatcccttcc taaagttaag ccagaactct gcatacagca tggcacctgg 78720
gtgcaaagat tgccttttta tgataataca aatgtaccca catccccaca agggaacttt 78780
aaggatccac cccttaagcc cctccctcct ctgttgtaaa tggcattttc ttctcaccat 78840
cttaactttg ttctcccagc catgtccgtc cgtgaaaact caggttccag gccgggaact 78900
tctatgaaag tttgtacaga gctgtatttt tggtgagctt tctcagtgct ttccaatatg 78960
caaactaact gggttatgta cctcaaacaa acaaacacat acaggagata gaatgcagga 79020
ttataatcaa gtcctgtcag tagatgtttg ctattaagta ggaaataaca tgaaattagc 79080
ataggaaata ttgccttaat tctaaacaca catggggaga tcacacatgc gcacatgcac 79140
cctctgtgtg ctcctaaagc accttgcaat ctgactccaa tcctaaaaat caaataaaaa 79200
acccttaatc aggctgtaaa tcaaatgaca ctatgcgatg tcactacagt gacatcagac 79260
atcatatagg aatcataatt ttctatttta agatttttaa ttctgtgtgt acatgtgact 79320
gcagtacaca cagccaacaa gtgcaccaga gaccctacag ctggacttat aggcagttct 79380
atgccgccct gcggatgctg agaaccaacc caacctcgat cctctgcagt ccatgtagtt 79440
aacatgcaag aaggggtggt aaggcaaaag cagccatgaa aaagggtgag ggaaatatgt 79500
cctgttctta actctgagtc cagggagagt tgtgcaccca acaccttctc atgaaacaat 79560
ggaatagtta ataaatttca aatttctctg gtggtagctt gattcgaacc aaagtataaa 79620
agataatcac tagcaaataa aaatttaaaa acaaatttct gggctggaga gatggctcag 79680
cggttaagag cagtgactgc tcttccggag gtcctgagtt caaatcccag catcaacctg 79740
gtggctcaca actatctgta atgggatccg atgccctttt ctgatgtgtc taaagacagc 79800
tacaatgtac ttacatataa taaataaata aatcttaaaa agcaaaaaaa aaaaaaagga 79860
aatcccctct tttaaaaaaa aaaaaaacaa atctctatgc tcttcaacta agactgactt 79920
taatgtttag tacagataaa gtactacgtg ctgtggattg gtgcttgtct cactaaacta 79980
gctgttacat gttacactgt agaatgtgat ttgatggctt aatactgttc acaggaccct 80040
ctggctgtgc aaatatccca acattggacc aaaacatacc aatcaccact gtgttgctag 80100
gtgaacccta gtgaaaattt agcattgtgt gggtcttgat gttgaggtga aaatcacaga 80160
aagggtctca cttctgactg tagatttgaa atatgttgat ttcctgggat ttgtttgttt 80220
gtttttgtta ttgttttgga tgaagctccg taggaagcat ttgatgaaca ttcaacacct 80280
gtcattctta tttgtcagaa cactgtaaac cacctgaaac ttataatgca aagtcaaggt 80340
ttatgtgtga gttggtgccc ccattaggtt gtgtttgttc ccatcagttt agggggagga 80400
tctgcttccc aactgttaaa tgttactatc aaatctgcct ttgagtctca cacccttgca 80460
tctggcctca cagttatttg ggagagggag gttgctccag ttggttatgt aatagacatc 80520
atgacatcat tatctgtgtg acttagagaa agtgagcacc ccagcgctcc tggtcctcac 80580

-continued atgtcagact aaaacccctt gtcacctccg ttcttctcag agtgtggggc tcatcacttg 80640
acctgctata acacaggtcc cacgtgcact gttcaggtgc accccccccc ctgctgccga 80700
gcaaccgtca gcttgcctga aattatgcag aatgaaaaag cctgtttctt tttccttttt 80760
tatcctgatg catattaaaa aaaatcactg tgatttgtgt gtatatctct ctatatattt 80820
gccccaggaa aactttctgc tgtctaattt ataaaatact attactgagt ccaggtttgt 80880
ttaataaaag tttgtatgtt ttaagaaatc tgtttcaggt cgtttcttga cttttcctgt 80940
aacacagggt aacaccataa aacacaagtc attgaccatg gttaatgacc tcagtgatcc 81000
agtcaccaac agtagttggt gcccatttct cagaggcaga actagtgaag ctgaaatgaa 81060
gttgggttaa tcaaggaaat tggtctgcac ccctgtaaca ggttgatgat tgttttgagg 81120
aatattagta cccaggatag tggaagtatt acaaacttca gacgtcatta acttggggga 81180
tgggggtagg gtggtgcata acctaagtca caagagtgtg ctatgtggga tttcttttct 81240
ggtccttata cgtttctgtg catctcttta tttttctttt actttttta atgaataata 81300
tctttattta cattacaaat gttatcctct ttcccagttc ccctccccag aagcccccta 81360
tcccatccct ctaccccctg cttctatgag ggtgttccct cacccaccca ccaactccta 81420
cctccctgcc ctcgattcac ctacactggg gtatcgagcc ttcacaggac caagggcctc 81480
tactcccact gatacctaac aaggccatcc tctactacat atgcggctgg agccatgggt 81540
ccctccatgt gtactccttg gttggtggtt tagtccctgg gagctttggg ggatctgggt 81600
ggttgatatt gttgttcttc ctatggggtt gcaaacccct tcagctcctt cagtcctttc 81660
tctaactcct ccattgggga ccctgtgctc agtccagtgg ttggctgtga gcatcgcctc 81720
tgtatttatc aggctctggc agggcctctc aagagatagc tatataaggc tcctgtcagc 81780
atgcacttct tggaatccac aatagtttct gcatttggtg actgtatatg ggatagatcc 81840
ccaggtgggg cagtctctgg atgacctttc cttcagtctc tgcttcatac tttatctcca 81900
tatttgctcc tgtgagtagt ttgttacttc atctaagaag gaccaaagca cccacacttc 81960
ggtcttcctt cttgagcatc atgtggtctg tgaattgtat cttgggtatt ccgagctttt 82020
gggctaatgt ccacttatca gtgagtacat accatgggtg ttcttttgta tcttggttac 82080
ctcactcagg atattttcta gttccatcca gttgcctaag aatttcatga aattattgtt 82140
cttaatagct gagtggtact ccattgtata aatgtaccac attttctgta tctattcctc 82200
tgttgaagga catctgggtt ctttccaact tctagctatt ataaataagg ctgttatgaa 82260
catagtggag catgtgacct tgttatgtgt tggagaatct ttggggtatg tgctcaggaa 82320
tggttctctt agttttaatc tattggtttc tgccctgact ttgatcattt cctgctatcg 82380
ctcctcctgt gtgtgtttgc ttcttttttc taaagtcgtc agatatactt ttaatatgtt 82440
agtatgagaa ctctccaatt tgtttatgga ggcatttggt gctataaact ttcctcttaa 82500
ccctgctttt agagtgtccc ataagtttgg atatgttgtg ccctcatttt cattgaattc 82560
tagaaagtta ttcattcctt tcttttctct gaccccagtg atcattgttg ttgttcagtt 82620
ttgatgagga gtatgtggac tttctgttgt ttctgttgtt gttgttgttg ttgttgttgt 82680
tgttgttgtt gttgttgaag ttcagattta atccatggtg atctgatagg atgggattat 82740
ttcaatcttc ttgtatctgt tgagacttgg tttgtgacag actatatggt cagtttcgga 82800
gaaggttccg tgaggtgctg agaaggtata ttcttttgta tttgggtgat agatatatgt 82860
taagtccatt taaatcataa cctctgttag ttttgttatt tctctgttta gtttctgtct 82920
caatgacctg tcaattggta agagtggaat ggtgaagtct cccactatta gcgtgtggga 82980
ttcatgtgtg attaatcttt agtaatgcat cttttacgaa tgtgggtgcc tttgcatttg 83040
aggcatagtt gttcagaact gagatgcctt cttggttgat tttcctttag tgagtatgaa 83100
gtattcttcc tggtcatttc tgattgcttt tggttgaaag tctgttttat tagatattaa 83160
aatggctagt ccatcttgtt tcttaggtgc atttgcttga aaaacctttt tttcagcctt 83220
tattaatatc tatctttttg ctgagatgtt tcttgtgtac agcagaatga tggattctat 83280
ttacacatcc attcagctag cctgcgtctt ttaactgggg aattgaatct atggatgtta 83340
agagatatta atgatcaatg attgttataa ctttctgtta ttttgatggt ggtagtggtg 83400
gtagtatgtg tgtgtgtttc tcttctattt taatggtgtg gatctattta tttatttatt 83460
tatttattca ttgtattttc tttagtgtag ttagcctcat tgggtttgac ttttccttct 83520
agtatcctct gaagggttgg gatagtggaa aggtagtttg aatttggctt tgtcatagaa 83580
tatcttagtt tcttcatcta tgttgactga aagttttgct ggggcagtga gccccgtctg 83640
ccagaccttc aaggttccac catgttctcg aaggtgagta ttgtcaggct gtcggcctgt 83700
gccacgcagc cgcaatggat ccaagtttga aacatggcaa ctctgaaaga tattaccagg 83760
agactgaagt ccatcaaaaa tatccagaaa attaccaagt ctatgaagat ggtggcagct 83820
ataaagtaca cccgggctga gcgggagctg aagcctactc aagcgtatgg aacagggacc 83880
tgaggacaat aagaagcacc tcattattgg tgtgtcctca gatagagggc tttgtggtgc 83940
tattcattcc tcagtggcta aacagatgaa gaatgaagtg gctgccctca cagcagctgg 84000
gaaaaaagtt atgattgttt gagttggtga aaaaatcaag gtcatacttt ataggactca 84060
ttctgatcag tttttggtgt cattcaaaga tgtgcgacag aagcccccta cttttggaga 84120
tgcaccagtc attgcccttg agtttttaaa ttctggatat gaatttgata acgactctat 84180
catttttaat cagttcaagc ttgttatctc ctacaagaca gaagagaaac ccatcttctc 84240
tctcaatacc attgcgactg ctgagaccat gagcatttat gatgacattg atgctgatgt 84300
gctgcagaat taccaggaat acaatctggc caacctcatc tactactccc tgaaggagtc 84360
caccaccagt gagcagagtg ccaggatgac tgccatggac aacaccagca agaatgcttc 84420
tgatatgatt gacaaattga cgttgacttt caaccacacc cgccaggatg tcatcacaaa 84480
ggagttggtt gaaatcatca tcatcatgct gctctgaatt aatgaaaatc aagttgtatc 84540
ctcagacaag aggtaaagaa gaagaatgtg caggctgatt ttaactgatt gctatctttg 84600
tcagaagaaa cttggtccac tgagttacaa agatagcagg atgtttgttg agaaattggg 84660
tgtaagtata atatatccat ctttatattt tacttggcct tttccccttg cagcttttaa 84720
tattctttct tctatatatt tagtgttatg attattatgt gacaggagga ctttcttttc 84780
tggtccaatc tgtttggtgt tctttaggct tcttatacat ttatatccat ctctttcttt 84840
aggttaggga taatttcttc tatgattttg ttgaagatgt ttctggacct ttgagctggc 84900
aatcttctcc ttcttctatt tctattattc ttaggtttgg cttgttcata gtgtcccaag 84960
tttcctggat gtttcgtgtc atgaactttt tagattttgc attttctttg acataaatat 85020
tgatatctac tactactact gactcatctc ttgtattctg ttgatgaggc ttgtatcttt 85080
agttcttgtt ctctttccta ggttttccat ctccaggatt tcctcagttt gtgttttctt 85140
tattgcttct atttctcttt taaagtcttg tacagtttta ttcatatcct tcacctgttt 85200
ggtcggattt tcctgtcttt ctttatattt atttgcttcc ttgtttaatg cttctaactg 85260
tttgaatgta cttttctgta gttgtttgtt tgtttgcttt tcaagacagg gtttctctgt 85320

-continued

```
gcagtcctgg ctgtcttgga actctgtaga ccaggctggc ctcgaactca gaaatctgcc  85380
tgccaccacc tcccaagtgc tgggattaaa ggtgtgcacc accactgccc ggcttctgta  85440
tttctttatg ggatttattc atgtcctctt taaaggcctc tatctttata agactggatt  85500
taagatcctc ttcttgtgtt tcagtttcct tagggtatac agggtttgtt gtggcagcac  85560
agctgagctc tggtggtgcc atactaccct aggtcttgtt ggttgtgttc ttaagctagc  85620
ttttaggcat ctgcttttcc ctggtgttgg ctgtatgatc ctgatgccag caggacttct  85680
ctggaagatg ggggagccat agtacagaca atggaggtca ggttacacaa ttctgggggc  85740
tgtgcctgag gtggacccca ctgataaggg attggtggag caatgctcca acctggaagt  85800
tcttggggtt tccacaggcc tccacataga aacaggatgc tcttgaggtc ccctaaggct  85860
cttcaggact gaagagcaag cccagaacta ggcagtagag ttcaggggac tgtgcacaac  85920
tctgcctgct gtatcccagg tggacccaac tgagaaggga ttggtggagc aggtttccaa  85980
gctggttagt tttggggtct ggaagtcttc cacaggaaag catgacagtc ttgggatcct  86040
ccaaggttct gtcaggactg aagagctaat tcagagttag ataatcaagt tccctttgat  86100
ttttcatgtg actttttgt ataacataca tttacattta ttaatgaata tctctaaaat  86160
cagcaaccat taaaaagtga ttgcattatg tggtcaagca gaactagcaa ctttcgtttt  86220
ttaaaaagca caaatcttaa aaatctcaat ttattcacat acataataca gcatactagt  86280
tatgttaaat gctacaaacc aatgtgagtc taatcggatg ggaaaaagca cacatttaag  86340
ctttaagaaa catttttccc tatatattag cattttctta aatacataca tgagataaat  86400
gaggtaacta taaaatatac agggaacaac catccatctt gtgtatatgt atatgtatat  86460
gtatatatat atatatatat ttatatttat atatatatat atatatatat atatatatat  86520
atatatacac acacacacat gcatacatac atctataaaa cctttctaac acagaaaaca  86580
gtgctgggcc cacattgtta ggaaaagata actactatta tgactaggcc agaagttggt  86640
aaataaagag taaacaatgc caagccccca ccacaggaaa ccattggtaa catggagtct  86700
atagcaaggt cagcaaatca caaacatcct aagtaattgt gttccaagat atttgatcac  86760
attgtgaacc ccaagattgt gaactggaaa aaaaaaaact ttcttgttgt tgtatggctt  86820
agccctagca cacaccttta acccaagagc tttctttttt tgttgttgtt tctttttttt  86880
tccatttttt attaggtatt tacctcattt acatttccaa tgctatacca aaagtccccc  86940
atacccaccc acccccactc ccctacccac ccactccccc tttttggccc tggcattccc  87000
ctgtactggg gcatataaag ttccaagagc tttctataaa taagagctaa ataaagtcaa  87060
ctgtaggtca agaggcagag caaacaacca attgagagag agtgaacata gaaagtagaa  87120
tggacggaca ttgagttgaa ggttatttaa gacagtataa agaaggaaaa ggaacttttt  87180
ccttctggga cactggtgga atagaaaggt caactgggtg ctttttttctg cctctctgaa  87240
ctagcaggct ctcatcataa tgtctggctt ttgagtcttc atttggcaaa tagaacattt  87300
gggattctgt ttttaaaaca acataactgt ttcataatta gtttttaaat aattttaaaa  87360
agtgtatacc cctcagacct gcttgttggt attactgtag ccaacacaat ccatgagcca  87420
attctgctgt cccagggttt caaatcacag ggtttgaatt tttttgttgt tgttggagtg  87480
aggaagagat agaggttgga gaaggtggtt ctctgtgtaa aacaggtaga taaatatagt  87540
gtaaccatca cctggttaca tacagtaaac tttaggttct tgtagggtgg gccaatgggc  87600
ccctggcagg ctgggtggga tgcaggaaac ctgggctgct gcatgagaat ggggtttgtt  87660
ggaacaggcc tgctatcagg tgctggcccc acaagtggtt tattcactta gggcaacaac  87720
```

-continued

```
cccagatggg gataggaaag gaaataaatg ggacttgaaa gtgtagggaa ctcagacttc  87780
tccagacctt gagggcagga gtcaggccag gaagggccat aagatagagg ttcatgccct  87840
ccttgtctct gtccttatgg gattcctagg agactcaccc aggcaggtga gagacaggcc  87900
ctgactggag aggaaatgcc ttgaaaatca aacagtcctg gtagtctcat gtgacttata  87960
aacactttta ttaaaacact cccttggttt ttcttttctt tttaagattt atttattatt  88020
atatctaagt acactgtttt agctgtactt cagatgcacc agaagagggt gtcagatctc  88080
atcatggatg gttgtgagcc accatgtagt tgctgggatt tgaactcaag accttcggaa  88140
gagcagtcag tgctcttaac cactgagcca tctctcatca caggtttttg tgtcttaaat  88200
gctgtcttgt tacataacca gagtggtctg aagctcagat tggcattaga cacactgttg  88260
tcttcctcct accaaggctt tgcagctgga gttagggatg gttgtaaact actatgtggg  88320
tactgggagt caaaccaggg gcctctacta gagtaaccag tgttctttaa aaatgattta  88380
tttatttgtt ttatataagt acactgtagc tgtcttcaaa tacaccagaa gagggcatgg  88440
atcccattac agatggttgt aagccatcat gtggttgctg gggattgaac tcaggacctc  88500
tggcagagca gtcaatgctc ttaaccactg agtcatctct ccagcaccta aatgctgaaa  88560
ttctaatttg taccttccct acaaaggtag aaacaaatgc taatgtatgc tttgtatgaa  88620
ttattgtgac tcagaatgag gtagttgact gtgtcttgca agcccgaggc cctacctttg  88680
atcttcagtg ccatacagaa acaaaacaaa cgtattaaag agtcctcaga ttttcagtag  88740
ctccccttc tgcctctata catgtggcca tagattggat tggacaaata ggcagatgga  88800
gaccctgtga ggggtgagat gagcaaaatt attctagaag tagtacaggg ggtacactaa  88860
ggctgactgg tctttggggt aaaatggttt gttataccac agaaagacag caaggcaaga  88920
agagctcttg aggggaactc tggtccatgt gggaaagtag gaatccctcc ttgtacgctt  88980
aggaggaggg gtaaaaatcc atgctacata cacaaaagat tttatgcttg taactgacat  89040
gattgcagta gttcccacag accaccttca ctgcaagaca gaagttctaa gcataggctg  89100
tgatctgcag aaaggaccct tgacaatgtc aaatgacagt tttgcttcca ctttggagaa  89160
ggcatttttc ccaacatgga gaggtatcca ttgcttctca gaattctaga gtgcttagaa  89220
tggccttgct acttgcaata tgcccaaggg tccttactct caactccaga aactctctgt  89280
atgactatta tcaacaataa tattaaataa tgcattacta ttatttattt gtctaaattt  89340
ttattgaatc tctatatagt atattccatc tatttacctg tcaatattta tctcattttt  89400
ttctcttgaa aatatttctg tgcatcaatg tttttcttgc aggtatgtat acctagtgcc  89460
gatatagact gtaaggatcc catggaattg aagttgcaga tggttgtaag aggccatgtg  89520
gaggctgtaa atcaagcctt ggtcccacag aagagcagca aatgcatttt aataggtgat  89580
ccatcagtcc aggactcatt cttccctttt ctatttgagg gagcatctgt aagcctaaag  89640
gggccttgaa gtcacaatcc tcctgtctca gcttccaggg gactgggagt gtagttgagt  89700
ctgctctaac taaacttaac aggcttttat ggtgcttagt gccaataagt aaaatgatgg  89760
agatgagaaa atgaaaagag cccagagcag aagatagatg cccaaggcca acccagattt  89820
aaatatggat taggctcagg aggccagggt acatttacca tgctagaggc tcatcagggg  89880
ctatagacac ctgttgtgta ctggatctga tcctggattg ggtccacaag tgctctggaa  89940
ttttttttaa ttaggtattt tcctcattta catttccaat gctatcccaa aagtccccca  90000
taccctcccc cccattctcc tacccaccca ctcccacttc ttggccctgg cgttcccctg  90060
```

-continued

```
tactgaggtg tactgaggca tataaagttt gcaagtacaa tgggcctctc ttcccaatga  90120
tggccgacta ggccatcttc tgatacatat gcagctagag acacgagctc cggggtactg  90180
gttagttcat attgttgttc tacctatagg actgcagatc cctttaggtc cttgggtact  90240
ttctctagct cctccattgg ggaccctgtg atccatccaa tagctgactg tgagcatcca  90300
cttctgtgtt tgctaggctc cagcatagtc tcacaagaga cagctatatc agagtccttt  90360
cagcaaaatc ttgctagtgt atgcaatggt gtcagcgttt ggaggctgat tatgggatgg  90420
atccccggat atggtagtct ctagatggtc catccttttg tctcagctcc aaactttgtc  90480
tctgtaactc cttccatggg tgtttagttc ccaattctaa gaaggggcaa agtgtccaca  90540
ctttggtttt cattcttctt cagtttcatg tactttgtat cttgtatctt gggtattcta  90600
agtttctggg ctaatatcca cttatcagtg agtacatgtc atgtgagttc ttttgtgatt  90660
gggttacctc actcagaatg atgccctcca ggtccatcca tttgcctagg aatttcataa  90720
attcattctt tttaatagct gagcagtact ccattgtgta aatgtaacac attttctgta  90780
tccattcctc tgttgagggg cttctgggtt ctttccagct tctagctatt ataaataggg  90840
ctgctataaa catagtggag catgtgtttt tcttaccggt tggaacatct tctggatata  90900
tgcccaggag aggtattgct ggatcctcca gtagtactat gtccaatttt ctgaggaacc  90960
accagactga tttccagagt tgtacaagtt tacaatccca ccagcaatga aggagtgttc  91020
ctctttctcc acatccttgc cagcacctga attcttgatc ttagccattt tgactggtgt  91080
aagatggaat ctcagggctg ttttggtttg catttccctg atggttaagg atgctgaaca  91140
tttttcagg tgcttctcag ccactcggta ttcctcaggt gagaattctt tgtttagctc  91200
tgagcctcat tttttaatgg ggttttctga ttttctggag tccaccttct tgagttcttt  91260
atatatgttg gatattcgtc ccctatctga tttaggatag gtaaagatcc tttcccagtc  91320
tgttggtggc ctttttgtct tattgacggt gtcctttgcc ttacagaagc tttgcagttt  91380
catgaggtcc catttgtcaa ttctcaatct tacagcacaa gacattgctg ttctattcag  91440
gaattttccc cctgtgcttt tccccacttt ctcctctata agtttcactg tctctggttt  91500
tatgtggagt tccttgatcc acttagattt gaccttaata caaggagata ggaatggatc  91560
aattcgcatt cttccacatg ttaactgcca gttgtgccag taccgtttgt tgaaaatgct  91620
gtcttttttc ccattgcatg gttttagctc ccttgtcaaa gatcaagtga tcataggtgt  91680
gtggattcat ttctgggtct tcaattcttt tccactggtc tacttgtctg tcagtatacc  91740
agtaccatgc agtttttatc acaattgctc tgtagtacat ctttaggtcc ggcatggtga  91800
ttccaccaga ggttctttta tccttgagaa gagtttttgc tatcctatgt tttttgttat  91860
tccagatgaa tttgcagatt cctctttctg attcgttgaa gaattgagtt ggaattttga  91920
tggggattgc attgaatctg tagattgctt ttggcaagat agccattttt actatatcga  91980
tcctgccaat ccatgagcat gggagatctt tccatcttct gagatcttct ataatttctt  92040
tcttcagaga cttgaagttc ttttcataca gatctttcac ttccttattt agagtcatgc  92100
caaggtattt tatattattt gtgactattg agaagggtgt tgtatccctg atttctttct  92160
cagcttgttt attctttgtg tagagaaagg gctctggaat ttttacatct tccagtgggt  92220
ttagcagagt ccataaacct aggctggtga ctagatccaa cattgggtta ggtcatcctg  92280
gtctacagaa tgagttccag gacagccaga gctacatagt aattccctgt ctcaaaaaaa  92340
aaaattaaaa agaaagaaac aaagaaagaa agaaagaaag aaaggaagga aggaaggaag  92400
gaaggaagga aggaaggaag gaagagagaa agaaagaaca acatgagtta gggaactgta  92460
```

```
gagctggctt tctaatgcaa acacttacac tagatctaaa gctctgacta tagtccccta  92520
aaccttaaca tgacaaagta tacactcata cacctagacc cagacctacc ttacatctca  92580
aagataattt acattcacaa gtattgtaat tgaatgctac aggaaaaaat ggacaaaata  92640
tgaaacctat cagattttgg tataaaaatc aattttaatg ctttcactaa ccctaagacc  92700
atgaccataa tcccctaatg ctaatcctaa ccttaacaca gcagaccaca aaacactcct  92760
tacttataaa aaaacaaaac taacataacc ttaccttgca tcatagacat aacttatatt  92820
aagagacatg gtaacttgat gttaggtcaa aaaaaatggg atagattatg aaacctattg  92880
gatttgggtg taaaactttc ccaaatatca agattagaaa ctcaggtttt gagaagcatg  92940
attgaatctt ttttgaggca ataaaaaatt taaacctgga ggatgatggt ggcatatgcc  93000
tagaatccca tcactccgga gacagaggca gatggaactc tatgagttcg aggacagcct  93060
ggtctataga atgagttcaa ggacagtcag agccacacaa agaaaaacct gtctcagtaa  93120
aatcaaaaaa caaaacacca aaaaacccac cactgccact accaacaata aataaataaa  93180
taaataaata aataaataaa taaataagtt taaacctgcg gttactagac taatgggtaa  93240
ctctatgatg ctttatagct ctatttcctt gagtcagaat gactggagaa gtgctctgca  93300
gattccagat ggaatgaaag ctattaacct agaaatggta cactgaggca aaggaaccca  93360
ggcagggtgg tagagtgaag aaattgcagc catagaagtc tctacaccaa aggtgaagac  93420
taaggagcag cactcaacat ctatagggtc ttgggggccc cttgagttcc tacaaaatgc  93480
ctctgcctca taaacaatat gtttgtctgg aagtcagcta ctttcagccc cctatcataa  93540
aacgataacg gaacctgcca tgtccaggtc tgtctgacat gcagaagtcc aagtaacaag  93600
atttggctat acacttctta aagattctct gtctcgctgt ctctctgtct ctgtctgtct  93660
ccttctgtct ctgtctttct gtgtgtattt atatacaagt gtgtgtgtgt gtgtgtgtgt  93720
gtgtgtgtgt gtgtgtgtgt gtgtgtgtgg tgagtaccta tttactgact cttgggcctt  93780
agtaaaatat attgcaatct gctctaaaac tagaaggcaa gtttttacaa tcagtagata  93840
tttgttctaa agaggcctgg atttttaaag caaaatctga tatcaaaata tctgtgaggg  93900
aggcatgaca ctagcaaaga tatagaagaa gccagacata ataataccat tatgatcaac  93960
tatccaagat aagtgccacc agatataaga ttaacaagga acaaatacct agaaccagaa  94020
tcaaagggga aaatgacaca tgggaataaa tactacctac cattaagcta cagaagatca  94080
cttgtgttta ttgccactat accaaaaact aggacatcaa ggaacacaag gactaaaaca  94140
ctgaatagac taatgcaata ttcaggaatc ctggcatgtt attaagaata ctattagcta  94200
gatggttgtg gaacacacct ttaatcccga cactcaggag gcagaggcaa gagactctct  94260
gagtttgaga tcaccctggt ctacagagtg agttccagga gagccagggc tacatggaga  94320
aactctgtct tgaaaaacaa acaaccaaat actattaaag gttgtgaaaa aagttctcac  94380
ggatactttt taactagata caactctatt ggtaaggcta cacactgtaa gatatatgta  94440
tttaactata caatacaaat acacttcgta ggaccattga tcaaatatag aagtaaatat  94500
acatgcacaa tggcaaacac ctttatagga ttaggcattg tagtgcgcat accctactca  94560
gcaagcctcc atgaacaatc tttggttctg gtacacagcc tttgattgtc ctaagtttat  94620
aatagactct gacaaaggct catacttcgc aggcaaaatg acacaagaaa cggcaaataa  94680
ttagatatct aatggaattt ctatatacca tatagcccta gaacatcagg aaacatgaga  94740
gatgcaatgc tttgatcaaa gaataattaa tgttgtctgg ttaaatttac ctgcaattgg  94800
```

-continued

```
cttttattaa taaagcagct tataccctga cccagctggg acttagcctg tctatattgg  94860
cttgttcttt tccaaaatct ggacttcagc aacatctcca ataaaacctg gagatattaa  94920
gcactgacta cactatttgc ttcagtggca cattggttga aagatgaaat gaaagataaa  94980
ggtggcattg ccaccttcaa atcaatgttc tcacaactta gtgggacata gtataagact  95040
aatttgcaca ggccctaatt ggtctaaagc agctctcatc actctttgtg actttactac  95100
cttaattaag ttttatcagt tccattcact ttatatgcaa attgtttttg agatttggcc  95160
tctcagacat atttaagtta ggagaagaac taccagatat accattattt gaaagcataa  95220
taacctttct agaacttata aacaaattta ctatacaacc tcatattggg agcagatttt  95280
gttttggtcc tggaagacaa agaatggaac tagatcttaa gacgtaatgg tagatacaca  95340
ccccttcact ctcttcacac tttatattgc cttaattgta gtcttactca gttttgaact  95400
ggctctatat caaatactat gaacacctct ctccaagcac cacgcaccta ctgggataca  95460
acacactaac atttagaaag aagtggatca aacctctctt tgtgttgatg ataggtagaa  95520
ggccctcttt gaagctacta ccactactgt cactgtagcc atctggacct agctcactat  95580
attcatttcc ccagaactcc ccaatattgt aggatggaag gacttaatgt aaccatcaga  95640
cttgataata acaatagccg cctattggaa tgttacagaa ttggcacata aacctgttgt  95700
cttaggatct ccattgctgt gaagagacac cacagcaact tttataaagg atatcattta  95760
attggggctg gcttacaggt tcagaggttc agactattat catcatgatg gaaaacatga  95820
caacatccag gaagaaatga tgctgaagtg gtaactgaga gttctatatc ttgatccaca  95880
gacagcagaa gactgatgtg acacactggt cagacttgag ctttttagac ttcaaagctc  95940
atacccagta gcctacttcc tccaacaagg ccacacttac tccaacatag ccacacatcc  96000
ttattgtgcc acttcctatg accaaacatt caaacacatg aatctatgtg ggccaccaca  96060
cctgttgaga tgcacatgat aataaatgca aacaggctat gcagaatagt aagcatttta  96120
actcacaact taagagcttt accaacctag acaaatgcaa taatcctact aaagcctcta  96180
gcaatactaa ttgttgaaaa taactggagg attacagaaa ggcacaaaaa agcaatttat  96240
gcagaccact ggatatactt agaacaaatg gagctcttgt ctctagctgc atatgtatca  96300
aaagatggcc taataggcca tcacttgaaa gagagatcca ttggacttgc aaactttata  96360
tgccccagta caggggaacg ccagggccaa aaagggggag tgggtgggta ggggagtggg  96420
ggtggggtgg gtatggggga cttttggtat agcattggaa atgtaaatga gctaaatacc  96480
taataaaaat ggaaaaaata aaaataaata aaagagtaaa aaaaacataa aaaatcaatg  96540
ttgatcaaca catttcgtct gctaagatgc cctacctaca agatgagttt ttaattattc  96600
caagctggta ctctgatgga actcttacaa gtaacacagc tatggaagtc agctttatac  96660
taattctggt acccatatgg gatggaaaag ataaggacta taaatatgta gaaactgagg  96720
tatccaacaa taaggatgac acagcaacaa taacaaccaa accatatttt aatcctctca  96780
agccatattt taatccatct aatgacagta tatccttcat atttagaata caagaaggaa  96840
cagatttaaa aagaaatgag caatgagagt atatattatg ttttaggctt cattaatttt  96900
ccatactttg gacatctctc tctctctgac cacccatgag gtgaaggagt tcacagaagt  96960
ctcatcttgg gacagctgat ctctaatacc tcttaatccc ccatcattat gggattctaa  97020
tacttttgga atatattggg acatatacca attcccactt gtgcctactg aacccaaatg  97080
tctgccctac tctttagaaa gattacaaca aaagtcttta agacagaacc aggcacttac  97140
tctcctaaat tcctatccca ttatttcata ttattagaaa ccaagctagt ggcacatgta  97200
```

aatttaattt tatcacagcc ccaaactata actctacatt gcctaacttt gaaatgattt 97260
gtgtatgttt agaattaaaa caaaaccttc cacttttacg gggtcacaat tggacaatat 97320
ttggggcaat caacttgtag aaaactggtt agcttaggca gaaaatcgca actctaaaat 97380
cactgtccaa cacagatgga acatgtctgg agaagtgtat ctcctagtgg tatggggtgg 97440
tactacaatg agatgagcac tcatactact ttggctcaat gtaacaatcc tggctgacaa 97500
acataatcca gcaatagtca aaacactatc aaaagcatct agtttgatac atcaggcatc 97560
aaatatacac agtgatcaaa tatatacagc tatcaccaac agttaatcag gaactcaaat 97620
ccatttaatt tgatgttggc tattggcttg ctgtatattg ctttgattct gtttatgtat 97680
gtgccctgta tccctgattt ctctaatacc tttaacatga aggggtattg gattttatca 97740
aagtcttttt cagtgtctaa tgagataatc atgtgatttt ctttgtttat atggtggatt 97800
atattgatga tattaatata ttgaatcatc tctgcatccc tgggatgaag cttacttgat 97860
catgttggat gatggtttta atgtgttctc tgattcagtt tgctaatatt ttattgagta 97920
tttttgcatc aatgttcata aaagaaatta gtctgagaat cttttgttga gtctttgtgt 97980
ggtttaggta tcagggtgac tgtagtcaca caaaatgagt ttggcagtat tctttctatt 98040
tccattttgt ggaatagttt gaggagtgtt ggtattaggt cttctttgaa agtctggtag 98100
aattctgcac taaaaccatc tggccctggg ctttgggtgg aggattggga gacttttaat 98160
gactgccccc ccacacttag gggttatagg gctgtttaaa tagtttacct gatcttgatt 98220
taactttggt aagtggtatc tgtctagaaa attgtccatt tcactgagat ttccccgttt 98280
tgtggagtat aggcttttga agtaagacat aaaaattctt ttaatttcat cagtgcctgt 98340
tgttatgtct cccttttcat ttctgatttt gtttacttgg atactgtctt tctgtctttt 98400
ggttagtctg gctaagggtt tgtctatctt gttgattttc tcaaagaacc ggctgctggt 98460
ttcattgatt atttgtactg ctttctttgt ttctaaatga atgattttag ccccaatttt 98520
gattatttcc tgccttctac tactcttagg tgtacttgct tcttttttct atagctttca 98580
ggtgtacttt tttaaactta attttatttt ttacttattc actttacatc ccactcactg 98640
ccccctccca cagtccttcc cccatccccc ttccccttct cctctgagca gttgggagcc 98700
ttcctggcta tctcccaatc ctggcacttc aagtctctgt gaagttaggt gcttctccca 98760
ctgaggccag tcaagggagc ccagctagaa gaagaacata taccacatac aggcaacagc 98820
tcttgggata gcccctgctc cagttgtttg ggacccacac aaagaccaag ctgcacatct 98880
gctgcacatg ttggggaggc ctaagtccag cctgtgtatg ttctctttga ttggtgttca 98940
gactctgaga gctccaagag tccaggttat ttgctctgtt ggtctttctg tggagttcct 99000
atccctttct gggccacaat ccttcctcct agtcttccaa aagagtcccc aagctccatc 99060
cactatttgg ttctgggtgt ttgtatctgt ctgagtcagc tgttgggtgg agcctcccag 99120
aggacaatat gcacctgtgt gcaagcataa cagagtacca ttaatagtgt tagggattgg 99180
tgcttgtcca taggatgggt ctcaagttgg gccagttatt ggatggccaa ttcctcaatc 99240
tctgctccat cccctgtccc tgcatttctt gtggaccgga cagattttgg gttgaaattt 99300
ttgtgggtga gttggtgtct ctgtcgctcc actggattct tgcctggctt caggaggcag 99360
gttccatatg cccaattttg tgagtcacag ctaaggtcac tcccattgat tcttgggtgc 99420
ctcccttatc ccaggtctct gtcttgtcct ggagatgccc ccccccatct cctcatcctt 99480
gtcagttgca aagtttttta tggtttaaaa tattactttt actaaaatta aagcatgcta 99540

```
tagaatacca ccataagata tttagaattg tgtgtgttgt ttgcttgctt tgtccttctc  99600
aatgtctttg gctatggcag gtatcaaatg aggaaatgaa aatgatttgt ataaaaatat  99660
gcttttgata agacttttta gatggaggag agttgctggg tattaaacca gtgcctcatg  99720
cagactattt cctctgcttt tgaaaaaaaa aaatcttaaa aacatctttc atcccttgta  99780
aagctcctaa aatgtagata tatcatatac ttatctgggc aatgatttca tctgatttgg  99840
aattctatca atagcaagtg atggttaatt catgtcccaa aatcaaagag gatcaggaat  99900
atatatgtgg ctagtaggag agatcttgcc cagagtgtga gcctagaata tcaccacaag  99960
cctcacagca aaagagaaaa tggcttcaaa ctgaatctta aatgactaaa tacttaacat 100020
ctgaaatgat tgagaatttg tgcctagggg aaacatagtt ctacataaat tataaaatta 100080
ttcatggaac ttgttagaaa aaaaatttca tgctacataa gacacaagcc atgaaaacca 100140
tatagcttta cagctaaaat gatttaaaac aatttttaaa atacttaaaa attataaagg 100200
gagagattgg ttaagagcac aaattgctct tccaggggat gcagtttcta atttcggcta 100260
ccagatggtg actcacacct gtctggccac ttcagtggat ctgctgccct cttctggcct 100320
tcttgagcac cagacatgcc catagtacac atggtaccaa acacccatac acttaatttt 100380
cttaataaat aaaaagaaaa cctagagtca taaatatgaa agaaaaatga ttgtaagatg 100440
aatttttgga tatttgattc catctcactt taatgtacat tcccagaaat cattttacac 100500
cctaaaaaaa gggagcatat actactagat agtaaaagct ttaagagttt ggaaatagat 100560
ctcactgtta aagcatttgc ttagcatgca tatgactttg gattcaattc tcagcactga 100620
aagaggctct acaagaaagg aaaatacaaa ctgcattaag atgagacatt aaagttcatt 100680
tctatcaaat tcattaatta tattagtctt ttttttcaat gctaaggatt gagcccaagg 100740
aagaattatt tcactcagat gagttttctt taaactttgc tactaaagat tcaaatactg 100800
ggctggaaat atggtctggt gacatagtgt ttacccagca tgtttggttc ctgaatttga 100860
tccttagtag cggcactttc cccttaagta accctccctt cgaggagagg cccttggtcc 100920
ggtgaaggtc ctctgccaca gtaaagggga atgccaggtc caggaagtgg gagtgggtgg 100980
gttggggagc acggggagga aggagcggat agggggtttt cagaggggaa gccaggaaag 101040
gggataacat ttgaaatgta agtaaagaaa atatctattt accctttctt agaaatggga 101100
acaaaacacc catggaagga gttacagaga caaaatttgg agctgtgacg aaaggatgga 101160
ccatctagtg attgccatat gcagggatcc atcccataat cagcttccaa acgctgacac 101220
cattgcatac actagcaaga ttttgctgaa aggacccaga tatagctgtc tcttgtgaga 101280
ctatgccgga gcctagcaaa cacagaagtg gataatcaca gtcagctatt ggatgggtca 101340
tacggcccct aatggaggag ctagagaaat tacccaagga gctaaaggga actgcaaccc 101400
taataggtgg aacaacaata tgaactaacc agtaccccgg agctcttgac tctagctgca 101460
tatgtatcaa aagatggcct agtcggccat cactgcaaag agaggcccat tggacttgca 101520
aactttatat gccccagtac agggaaatgc cagggccaaa aaggggcagt gggtgggtag 101580
gggattgggg gggggtgggt atgggggacc tttgggatag cattgaaaat ctaaacgagg 101640
aaaataccta ataaaaaaaa agaaaatatc taataaaaaa aaagagtaac cctcccttca 101700
aaaaactcag gaagacaaaa ccactaattt tctttctgaa gaaaacaaat cttcaaaacc 101760
ttagacaaac agtgcacacc tacactctct acctgctgaa aagcaagaac ttcactagag 101820
cctgggaaga gagcctgatc ctgcatgtac ttccaaattc tctgccatcc ctcccaagaa 101880
aatcattagt cctgggacca gcactaatag gcttttgaaa cttcataaca gtttatcaaa 101940
```

ctttggagac atgtttccac tggcattaag acgtgtttta ctgctgggca gtggtggcac 102000
atgcctttaa tcccagctct cgggaggcag aggcaggcgg atttctgaat ttgaggccag 102060
cctggtctac agagtgagtt ccaggacagc cagggctata cagagaaacc ctatctcgga 102120
aaaacaacaa caacaaaaaa gatgtgtttt actgtatgaa gccaggttct tcccactatg 102180
gaatgcctgg atctaacttg gcacactgcg taagcaatgc attttgagaa gcacaggaat 102240
caatgtgaca gacattagag gccaacttgt ctatctgtga agactaattg gcatcgctcc 102300
tggagataca gacagaggtt ccgcttctgt tgaatgacaa gtggtggcag tagtgatatc 102360
ctccaggaag cacgaagtcc tgctgaacac tgacaagcta gcagcaaatg ctgtctgtgc 102420
ttgctcagct agaacaccac cttcagcttc tttgccaatc tttgccaatc aaagattaaa 102480
gaaatagtat ggactcagga ggcagaggca ggtggatctc tgagtttgag tccagtctgg 102540
tctacagaga atttaaggac aacacagaga aaccctgtct tgaggagaaa aaaagcaaag 102600
aaaccaaaaa gtaatgtgta tttgcccttt gcaaaagcat cagtggaaaa tggaaaactt 102660
tagttttaaa agttctgaag gtaggtgtgg taatcgtgta cctcagcagt tgtctgagag 102720
aagacagtta tatcgtgagg gttatatgtt gagagacacc tacagctagg tagcaccagc 102780
cagaactaca tagtaaaaca ttgtttcaaa caaaagtttc tatacaattt ctgaaggatt 102840
ttcaaagttc ttacacacac acacacacac acacacacac attcttcttt cactgttgga 102900
ctcattctag acttggtggg ttcttacaat ttcctctgat attagagaat tctctaaaaa 102960
acaaattgaa agtaagtagt ggtaacaccc ctgtgttcat agcactcagg gggctgagac 103020
aaccggcgtg taagttaaag cccaacctgg ccttcttaac cagaccctat ctttaatggg 103080
ctgagagtgg gtctaaaatt tgaggttatt gaaaaatgtc tgaacactaa aactatttgc 103140
atagcatttt gagtttgata cttgccccag aataggcaaa ggcatataaa tacaagaagg 103200
gtaaaaacct tgacaaaact ttcccactga aaatgacttg ggatgggggt tgccaaagat 103260
gtacaacata tttatagttt tacttctcca gtaagggaac aactaataaa gtagcagttg 103320
ctacaaaaag aactaattct aggtctggga aggtggttca ttgattaaga gccctgattg 103380
ctcttcctga ggacctaagt tcaacttcca gctcacaacc atcggtaact ggcgttccag 103440
ggatccaatg ccttctggcc tttgtatgta ctgggacatg gatggtgcaa agacacacat 103500
gcagacaaaa gaacacatac atataaaata aaaaaaaatt taaatacaaa taattctgtt 103560
aggtttgttg aatgtccact tttcttcata atcaacgtat aacttataac atgtccattt 103620
atatgtccca tgtatctttc tctgcctgtg ccccatctaa gctatgatag aacatgagga 103680
atgagggaaa aggaaaggga ggagaaatag aaggaagaaa tttccaacac tctcgtcctt 103740
tctcttcccc actttcattt tattattttg tttccctttt tcatctccct gtccctttaa 103800
ggtgatgtcg attgtatctc aggcaggcct caaagttgat ttgtagccaa agatgccctt 103860
ggatttctga tccccctgct tccaatttcc agatgttaag attatgggct tgtgacatct 103920
catccctaga aaagcataag cttgtagaag tcaagggaca cttttattta ctgctgcctc 103980
tctagaaact tcctgccagt ttggcactta caaaatattt tttagaaaga agaggaaagt 104040
agataatcta tatactaaat aagtacttga taactgagtg gaacttaaaa ttaaaaaaaa 104100
aaagcagtgt ttgtgaacag gtttcagtac ctccccattt ttctcaaagc aaatggtcct 104160
ggcggctgtg tctcacacgt gggtaatgaa atctccctgc ctaaagatgt acaatgtgaa 104220
agtctgtttc cccttgtgat agaggttaac attgtaagcc ctgcagcacc acatggctca 104280

-continued

```
ggtagtgttg tggttaaaat tgtgtttggc caaaagaaac tccaacacat atatgccatc 104340
gctacttcta ttttttttct taaacataat aaaatttaaa gaaagaaaaa cctcacaatt 104400
gttaggattt agtggcagaa ggtccttgat gggttggggc agagatgtgc tgcaaagaga 104460
tcacaccatg caaacagatc tcaggagaga ggccatctca gagtggggac ataaaagaga 104520
gagttagagt cagagagcca gactgaaaga gacagactga gagactggaa gacaaagaga 104580
atgggggtgt gttggggggg gggttggtaa gggttttgta acttgtggaa acagtgtaaa 104640
gagtggcatt tggggaaggg aggtgatgat gtgccttttg gcgctgagtt cctgagggca 104700
ggcttgacaa gtgcctgctt tctaacatta atggccattg atactggaaa aaaaaactat 104760
tttattacta cattaattga aatttgcaac tatatttata aataatattt atacatttat 104820
ggagtcatgt taactttcag cccaaggaga gataacatta aaaatgaaat atattttata 104880
aagaaaatat tttcttaacc tcgtaaaagt atacacagta aactatggtt atctgtaaca 104940
tttaaagtaa ataattttag cttacaattt aattatgatg ctgatggggt atgttcagaa 105000
agttattcat gaaaagttcc aattccttac acatagattt tccaactact ttcttttgtt 105060
tattcagaaa ggatgggaaa ctacgagggc taacacccta cctccttgtt taagggactg 105120
actcaatctt ctactggaga tgccccattg cttttgactt actatgttca ttcagccttc 105180
tattttaggt ttgattagtt tgattctaca cttaactttc tcctgacata aagctctcaa 105240
taagaaagta tattcattaa cattggcctc agaaagagag aggttttagg ctgttcactg 105300
gatatatgat cagaataaaa gagatacaat acatacacat cagagagagc tgctgtgttg 105360
gtgccagaaa ttgaatccag gtcctctgaa agaagagcca gtgctcttaa gcacctagta 105420
ctgtcttcag ctccaacaag taggtttaaa tcttatttg caatgggacc tggtggctca 105480
tgcctttaat cctaggtgaa tgactgtgat cttgaaggta gcttggtcta cataatgaat 105540
tccaggacag ccagggttat gtaaaaaaaa aaaaaaatgt gtcaaaacaa aacaaaaaaa 105600
aaccttattt tgggagggaa aaattggggt ttctgtcctg acaaatccct agcctttctg 105660
ttgaattctt tataaaaaat gtatttgtgt aaaagctctt ttgttccttt tgcacccaac 105720
tctcctgcat gaaaggtcaa catgaaaata ttaaaaatca caaccaagat cggatgaaat 105780
ttaaattata attactaaat gggcacatcc aaattattat gacagagaaa acaaaagccc 105840
taggactagg gagatgtgga aaaatgaagc agtcatgaaa tactaaaacc attcttaact 105900
gtccttattc tggaagggga aaatcaacat ttccctgaaa gctgctgtaa tcatgtgaag 105960
ttcaaatggt ttgatgagcc ttcctccaat caaacagata tgatagcaac taaatttctc 106020
caactaaatt atttacaact gactgagaca gtccctctga agccaggtac tcagctaaac 106080
tattcagaat gaaataggaa cggagaagag ggtggaaggc tctgtaatga cagaccacac 106140
tggaatagta gcccactacc tgacttcgta gatgtcctga tatgatggga atgatagaca 106200
agcatgacag taaggttatg aggtgggaag aagtgagtgg aattacacaa aatctataaa 106260
gaggaagtga agcaaatgat gtagcaagcc accctcatag gattttgcat ctgatgattg 106320
agatggttac taggatctct agctatgaaa tctaaaacag ctttttttggg ggggggggaat 106380
caattacctg tagttttatt tcttgttcat ttttctttct ttgaatagca tgtttgtcct 106440
gagccatgaa agtctcccac atacaaacca aaagaaggaa aaacaaacat tcgataatcc 106500
agttcactga aggaaagtac agtggtttaa atatgcttac cccagggagt ggcactatta 106560
gaaggtgtgc cttgtagaag gaggtgtggc cttgttggag ggagcgtgtt actgtgggtg 106620
tgggctttga gaccctcctt ctagccatgt ggaagacagt cttctctttg ccttcaaaac 106680
```

```
aagatgtaca actcagcttt cccggcacca tgtcatgctt cccactgtga tgataatagc 106740

ctgaacctca gaacctgcaa gtcagcctca attaaacgtt gtcctttata aaagttgcct 106800

tggtcatggt ttttcttcac agcaatgaaa accctaagaa agaagtgata atgaaattta 106860

taaagagaaa taatatgtat tttatgaggt atcacatgct gtaatattca gtagcacatg 106920

aggattgaaa attcactaaa attcagtggc tacttctggt ggttctacct ggaatgcttt 106980

tatttttaaa agaacatcaa ctcagtgcaa agtggtttcc attgttttta tgtaactttt 107040

ctagatatga acctctgttt cggctttcct gtctcaccaa tttgtctcta gacacccatt 107100

ctactaagaa attccacaga gtgtcttata catatactgt tttatacaag gtctctattc 107160

ctctattcca tacaccccat aacttgtttc tctcctattt ccttacaaat gaaggataaa 107220

gttaaagcaa tttttggaaa agaattttat tctcacatga aagcacaggt tgcggcctat 107280

gtgggtgctg cctcccttcc tcttcctcct ccccactcct ctctggttgc catggagaat 107340

acagttgatg gaaacataca attacaagca acgata                          107376
```

<210> SEQ ID NO 8
<211> LENGTH: 708
<212> TYPE: PRT
<213> ORGANISM: Artificial Sequence
<220> FEATURE:
<223> OTHER INFORMATION: Synthetic amino acid sequence of SV40 Large T Antigen GenBank: AAB59924.1

<400> SEQUENCE: 8

```
Met Asp Lys Val Leu Asn Arg Glu Glu Ser Leu Gln Leu Met Asp Leu
1               5                   10                  15

Leu Gly Leu Glu Arg Ser Ala Trp Gly Asn Ile Pro Leu Met Arg Lys
            20                  25                  30

Ala Tyr Leu Lys Lys Cys Lys Glu Phe His Pro Asp Lys Gly Gly Asp
        35                  40                  45

Glu Glu Lys Met Lys Lys Met Asn Thr Leu Tyr Lys Lys Met Glu Asp
    50                  55                  60

Gly Val Lys Tyr Ala His Gln Pro Asp Phe Gly Gly Phe Trp Asp Ala
65                  70                  75                  80

Thr Glu Ile Pro Thr Tyr Gly Thr Asp Glu Trp Glu Gln Trp Trp Asn
                85                  90                  95

Ala Phe Asn Glu Glu Asn Leu Phe Cys Ser Glu Glu Met Pro Ser Ser
            100                 105                 110

Asp Asp Glu Ala Thr Ala Asp Ser Gln His Ser Thr Pro Pro Lys Lys
        115                 120                 125

Lys Arg Lys Val Glu Asp Pro Lys Asp Phe Pro Ser Glu Leu Leu Ser
    130                 135                 140

Phe Leu Ser His Ala Val Phe Ser Asn Arg Thr Leu Ala Cys Phe Ala
145                 150                 155                 160

Ile Tyr Thr Thr Lys Glu Lys Ala Ala Leu Leu Tyr Lys Lys Ile Met
                165                 170                 175

Glu Lys Tyr Ser Val Thr Phe Ile Ser Arg His Asn Ser Tyr Asn His
            180                 185                 190

Asn Ile Leu Phe Phe Leu Thr Pro His Arg His Arg Val Ser Ala Ile
        195                 200                 205

Asn Asn Tyr Ala Gln Lys Leu Cys Thr Phe Ser Phe Leu Ile Cys Lys
    210                 215                 220

Gly Val Asn Lys Glu Tyr Leu Met Tyr Ser Ala Leu Thr Arg Asp Pro
```

-continued

```
225                 230                 235                 240

Phe Ser Val Ile Glu Glu Ser Leu Pro Gly Gly Leu Lys Glu His Asp
                245                 250                 255

Phe Asn Pro Glu Glu Ala Glu Glu Thr Lys Gln Val Ser Trp Lys Leu
            260                 265                 270

Val Thr Glu Tyr Ala Met Glu Thr Lys Cys Asp Asp Val Leu Leu Leu
        275                 280                 285

Leu Gly Met Tyr Leu Glu Phe Gln Tyr Ser Phe Glu Met Cys Leu Lys
    290                 295                 300

Cys Ile Lys Lys Glu Gln Pro Ser His Tyr Lys Tyr His Glu Lys His
305                 310                 315                 320

Tyr Ala Asn Ala Ala Ile Phe Ala Asp Ser Lys Asn Gln Lys Thr Ile
                325                 330                 335

Cys Gln Gln Ala Val Asp Thr Val Leu Ala Lys Lys Arg Val Asp Ser
            340                 345                 350

Leu Gln Leu Thr Arg Glu Gln Met Leu Thr Asn Arg Phe Asn Asp Leu
        355                 360                 365

Leu Asp Arg Met Asp Ile Met Phe Gly Ser Thr Gly Ser Ala Asp Ile
    370                 375                 380

Glu Glu Trp Met Ala Gly Val Ala Trp Leu His Cys Leu Leu Pro Lys
385                 390                 395                 400

Met Asp Ser Val Val Tyr Asp Phe Leu Lys Cys Met Val Tyr Asn Ile
                405                 410                 415

Pro Lys Lys Arg Tyr Trp Leu Phe Lys Gly Pro Ile Asp Ser Gly Lys
            420                 425                 430

Thr Thr Leu Ala Ala Ala Leu Leu Glu Leu Cys Gly Gly Lys Ala Leu
        435                 440                 445

Asn Val Asn Leu Pro Leu Asp Arg Leu Asn Phe Glu Leu Gly Val Ala
    450                 455                 460

Ile Asp Gln Phe Leu Val Val Phe Glu Asp Val Lys Gly Thr Gly Gly
465                 470                 475                 480

Glu Ser Arg Asp Leu Pro Ser Gly Gln Gly Ile Asn Asn Leu Asp Asn
                485                 490                 495

Leu Arg Asp Tyr Leu Asp Gly Ser Val Lys Val Asn Leu Glu Lys Lys
            500                 505                 510

His Leu Asn Lys Arg Thr Gln Ile Phe Pro Pro Gly Ile Val Thr Met
        515                 520                 525

Asn Glu Tyr Ser Val Pro Lys Thr Leu Gln Ala Arg Phe Val Lys Gln
    530                 535                 540

Ile Asp Phe Arg Pro Lys Asp Tyr Leu Lys His Cys Leu Glu Arg Ser
545                 550                 555                 560

Glu Phe Leu Leu Glu Lys Arg Ile Ile Gln Ser Gly Ile Ala Leu Leu
                565                 570                 575

Leu Met Leu Ile Trp Tyr Arg Pro Val Ala Glu Phe Ala Gln Ser Ile
            580                 585                 590

Gln Ser Arg Ile Val Glu Trp Lys Glu Arg Leu Asp Lys Glu Phe Ser
        595                 600                 605

Leu Ser Val Tyr Gln Lys Met Lys Phe Asn Val Ala Met Gly Ile Gly
    610                 615                 620

Val Leu Asp Trp Leu Arg Asn Ser Asp Asp Asp Asp Glu Asp Ser Gln
625                 630                 635                 640

Glu Asn Ala Asp Lys Asn Glu Asp Gly Gly Glu Lys Asn Met Glu Asp
                645                 650                 655
```

```
Ser Gly His Glu Thr Gly Ile Asp Ser Gln Ser Gln Gly Ser Phe Gln
            660                 665                 670

Ala Pro Gln Ser Ser Gln Ser Val His Asp His Asn Gln Pro Tyr His
        675                 680                 685

Ile Cys Arg Gly Phe Thr Cys Phe Lys Lys Pro Pro Thr Pro Pro Pro
    690                 695                 700

Glu Pro Glu Thr
705


<210> SEQ ID NO 9
<211> LENGTH: 174
<212> TYPE: PRT
<213> ORGANISM: Artificial Sequence
<220> FEATURE:
<223> OTHER INFORMATION: Synthetic amino acid sequence of SV40 small t
      antigen GenBank:AAB59925.1

<400> SEQUENCE: 9

Met Asp Lys Val Leu Asn Arg Glu Glu Ser Leu Gln Leu Met Asp Leu
1               5                   10                  15

Leu Gly Leu Glu Arg Ser Ala Trp Gly Asn Ile Pro Leu Met Arg Lys
            20                  25                  30

Ala Tyr Leu Lys Lys Cys Lys Glu Phe His Pro Asp Lys Gly Gly Asp
        35                  40                  45

Glu Glu Lys Met Lys Lys Met Asn Thr Leu Tyr Lys Lys Met Glu Asp
    50                  55                  60

Gly Val Lys Tyr Ala His Gln Pro Asp Phe Gly Gly Phe Trp Asp Ala
65                  70                  75                  80

Thr Glu Val Phe Ala Ser Ser Leu Asn Pro Gly Val Asp Ala Met Tyr
                85                  90                  95

Cys Lys Gln Trp Pro Glu Cys Ala Lys Lys Met Ser Ala Asn Cys Ile
            100                 105                 110

Cys Leu Leu Cys Leu Leu Arg Met Lys His Glu Asn Arg Lys Leu Tyr
        115                 120                 125

Arg Lys Asp Pro Leu Val Trp Val Asp Cys Tyr Cys Phe Asp Cys Phe
    130                 135                 140

Arg Met Trp Phe Gly Leu Asp Leu Cys Glu Gly Thr Leu Leu Leu Trp
145                 150                 155                 160

Cys Asp Ile Ile Gly Gln Thr Thr Tyr Arg Asp Leu Lys Leu
                165                 170


<210> SEQ ID NO 10
<211> LENGTH: 22
<212> TYPE: PRT
<213> ORGANISM: Artificial Sequence
<220> FEATURE:
<223> OTHER INFORMATION: Synthetic amino acid sequence of peptide F2A

<400> SEQUENCE: 10

Val Lys Gln Thr Leu Asn Phe Asp Leu Leu Lys Leu Ala Gly Asp Val
1               5                   10                  15

Glu Ser Asn Pro Gly Pro
            20


<210> SEQ ID NO 11
<211> LENGTH: 20
<212> TYPE: PRT
<213> ORGANISM: Artificial Sequence
<220> FEATURE:
```

<223> OTHER INFORMATION: Synthetic amino acid sequence of peptide E2A

<400> SEQUENCE: 11

Gln Cys Thr Asn Tyr Ala Leu Leu Lys Leu Ala Gly Asp Val Glu Ser
1 5 10 15

Asn Pro Gly Pro
20

<210> SEQ ID NO 12
<211> LENGTH: 19
<212> TYPE: PRT
<213> ORGANISM: Artificial Sequence
<220> FEATURE:
<223> OTHER INFORMATION: Synthetic amino acid sequence of peptide P2A

<400> SEQUENCE: 12

Ala Thr Asn Phe Ser Leu Leu Lys Gln Ala Gly Asp Val Glu Glu Asn
1 5 10 15

Pro Gly Pro

<210> SEQ ID NO 13
<211> LENGTH: 18
<212> TYPE: PRT
<213> ORGANISM: Artificial Sequence
<220> FEATURE:
<223> OTHER INFORMATION: Synthetic amino acid sequence of peptide T2A

<400> SEQUENCE: 13

Glu Gly Arg Gly Ser Leu Leu Thr Cys Gly Asp Val Glu Glu Asn Pro
1 5 10 15

Gly Pro

<210> SEQ ID NO 14
<211> LENGTH: 5
<212> TYPE: PRT
<213> ORGANISM: Artificial Sequence
<220> FEATURE:
<223> OTHER INFORMATION: Synthetic Peptide (the LXCXE motif)
<220> FEATURE:
<221> NAME/KEY: MISC_FEATURE
<222> LOCATION: (2)..(2)
<223> OTHER INFORMATION: X is any amino acid
<220> FEATURE:
<221> NAME/KEY: MISC_FEATURE
<222> LOCATION: (4)..(4)
<223> OTHER INFORMATION: X is any amino acid

<400> SEQUENCE: 14

Leu Xaa Cys Xaa Glu
1 5

<210> SEQ ID NO 15
<211> LENGTH: 166040
<212> TYPE: DNA
<213> ORGANISM: Artificial Sequence
<220> FEATURE:
<223> OTHER INFORMATION: Synthetic Polynucleotide

<400> SEQUENCE: 15
tcaacatcct taatcatcag gaaaatgcaa atcaaaacaa ccctgagatt ccacctcaca 60
ccagtcagaa tggctaagat caaaaattca ggtgacagca gatgctgccg aggatgtgga 120
gaaagaggaa cactcctcca ttgttggtgg gattgcaagc ttgtacaacc actctggaaa 180
tcagtctggc agttcctcag aaaattggac atagtactac tggaggatcc cgcaatacct 240

-continued

```
cttctgggca tatatccaga agatgtttca accagtaaga aaaacacatg ctccactatg    300
ttcatagcag ccttatttat aatagccaga agctggaaag tatccagatg cccctcaaca    360
gaggaatgga tacagaaaat gtgatacatt tacacaatgg agtactactc agctacgaaa    420
aagaatgaat ttatgaaatt cctaggcaaa tggatggacc tggagggcat catcctgagt    480
gaggtaaccc aatcacaaaa gaactcacac aatatgtact ccctgataag tggatattag    540
cccagaaact tagaataccc aagatataag atacaatttg ctaaacgcat gaaactcaag    600
aagaacaaag accaaagtgt ggacactttg ccccgtctta gaattgggaa caaaacaccc    660
atggaaggag ttacagagac aaaggttgga gctgagacaa aggatgggc catctagaga    720
ctaacatatc aggggatcca tcccataatc agcttccaaa tgctgacacc actgtgtaca    780
ctagcaagat tttgctgaaa ggacccagat atggctgtct cttctgagac tatgctgggg    840
cctagcaaac acagaagtgg atgctcacag tcagctattg gatggatgac agagctccca    900
atagaggagc tagagaaagt acccaagtag atgaagggat ctgcaatcct ataggtggat    960
caaaaatatg aactaagcaa tacccctctg gagctcgtgt ctctagctgc atatgaatca   1020
gaaaatggcc tagtcggcaa tcaatggaaa gagaggccca ttggttgtcc aaactttata   1080
tgcctcaata caggggaacg ccagggccaa gaagtgggag tgggtgggta ggtgagtgct   1140
tctggaagcc tgttggggac tttctggata acattggaaa tgtaaatgaa ataaataccc   1200
aataataaaa aaagaacatt caaaaaaaaa aaaaaagatc ctaacccaaa acatccatga   1260
tatccaggac ataatgagaa agcaaggtta ttccattata aaaacatttt ttttttagt    1320
atagaataga gtttatatag ggtataggta ggggagttaa gagagtagta gagacagaga   1380
aaggcagaga gaagaagaga atagagaagt agaggccggt catgaccaca tggaaagagg   1440
gggaagggaa tgcagagaaa ggggacacat ggggcaggag agaggcaaga gtgtaagagt   1500
acaaaaccaa atttacacaa tgtttttcca taaatttagc cctacaaagg ataataggtg   1560
gaaaacacca caacaaggag ggaaactaca ccctcaaaaa agcaagaaag taatcttaca   1620
tcaaacccaa aagaaaatag ctacatgaac agaatttcaa ctctaataac aaaaataaca   1680
ggaagcaaaa atggctttta cttaaaatct cttaacatcc acggactcaa ctctccaata   1740
aaaacacata tattaataga ctggatatgt aaacaggacc cagcattttg ctgcatacag   1800
gaaacgcgcc tcagtgacaa agacagatac tacctcagag taaaaggcta gaaaacaatt   1860
ttccaagcaa gtggtcccaa gaaacaagct gtaataacca ttctaatatc aaataaaatt   1920
aacttaatag aaacagattt gtaaaagtgg attaaggaac tccacataaa accagagaca   1980
ctgaaactta tagaggagaa agtagggaaa agcctcgaag atatgggtac aggggaaaaa   2040
ttcctgaata gaacagcaat ggcttgtgct gtaagatcga gagtcaacga atgggacctc   2100
ataaaattgc aaagcttctg caaggaaaaa gacaccatca gtaagacaaa aaggctacca   2160
acagagtggg aaaggatctt tacctattct aaatcagata ggggactaat atccaatata   2220
tataaagaac tcaagaaggt ggactccaga aaattaaata agcccattaa aaatggggct   2280
cagagataaa caaagaattc tcacctgagg aataccgaat ggctgagaag cacttgaaaa   2340
aatgttcaac atccttaatc atcaggaaaa tgcaaatcaa aacaaccctg agattccacc   2400
tcacaccagt cagaatggct aagatcaaaa attcaggtga cagcagatgc tgccgaggat   2460
gtggagaaag aggaacactc ctccattgtt ggtgggattg caagcttgta caaccactct   2520
ggaaatcagt ctggcagttc ctcagaaaat tggacatagt actactggag gatcccgcaa   2580
tacctctcct gggcatatat ccagaagatg tttcaaccag taagaaaaat acatgctcca   2640
```

ctatgttcat agcagcctta tttataatag ccagaagctg gaaagtatcc agatggccct 2700
caacagagga atggatacag aaaatgtgat acatttacac aatggagtac tactcagcta 2760
ttaaaaagaa tgaatttatg aaattcctag ccaaatggat ggacgtggag ggcatcatcc 2820
tgagtgaggt aacccaatca caaaagaact cacacagtat gtactcactg ataagtggat 2880
attagctcag aaacttagaa tacccaagat ataggataca atttccaaaa cacatgaaac 2940
tcaagaagac caaagaccaa aatatggaca ttttgccctg tcttagaatt gggaacaaaa 3000
cacccatgga aggagctaca gagacaaagt ttggagctga gacgaaaggt tggaccctct 3060
agagactgcc atatccgggg atccatccca taatcagctt ccaatcgctg acaccattgc 3120
atacactagc aagatcttgc tgaaaggacc cagatatagc tgtctcttgt gagactatgc 3180
tggggcctag caaacacaga agtggatgct cacagtcagc tattggatgg atcacagggc 3240
ccccaatgga ggacctagag aaagtaacca aggagctaaa gggatttgca accctataag 3300
tggaacaaca atatgaacta agcattaccc cccagagctc gtgtctctag ctgcatatgt 3360
ataagaagat ggcctagtcg gccatcagtg gaaagagagg cccattggtc gtgcaaactt 3420
tatatgcctc agtacagggg aacagcaggg ccaagaagtc atagtgagag ggttggggag 3480
tgggtggggg agcgtgtggg ggacttttgg gatagcattg gaaatgtaac tgaaataaat 3540
acctaattaa aaaattagaa aatcaaaaaa agaaggtctt ttttttcac aatattaatt 3600 ctactaggct gtacacttac gagatcttca aattctagta tgtttctttt ttctttcttt 3660
tttttaaaga tatatttatt tattttatgt atgtgagtac actgtagctg tcttcagatg 3720
caccagaaga gcgcatcaga tctcattaca gatggtcatg agccaccatg tggttgctgg 3780
gaattgaact caggacctct ggaagagcag ttggttctct taaccgctga gccatctctc 3840
cagcccctct agtatgtttc ttaatctctt tctttacaca tttaaagttt tcattgtaga 3900
gggtttttta accactttttg ttatgtatat tctaaatatt ttattttatt tgagaaactg 3960
gtaagaggag tgtgtccatg atctctttct cagaatgctt gttactcata tgtattaaga 4020
cttatgaatt tgacaagtcc cttccgcttg actcgagccc cgggctacct tgccagcaga 4080
gtcttgccca acacccgcaa gggcccacac gggactcccc acgggatcct aagacctctg 4140
gtgagtggaa cacagcgcct gccccaatcc aatcgcgcgg aacctgagac tgcagtacat 4200
agggaagcag gctacccggg cctgatctgg ggcacaagcc ccttcagctc cactcgagcc 4260
ccgggctacc ttgccagcag agtcttgccc aacacccgca agggcccaca cgggactccc 4320
cacgggatcc taagacctct ggtgagtgga acacaacttc tgccaggagt ctggttcgaa 4380
caccagatat ctgggtacct gccctgcaag aagagagctt gcctgcagag aatactctgc 4440
ccactgaaac taagaagagt gctaccctcc aggtctgctt atagaggcta acagagtcac 4500
ctgaagtaca agctcttaac agagacaact ataacagcta gcttcagaga ttaccagatg 4560
gcgaaaggca aacgtaagaa tcctactaac agaaatcaag accactcacc aacatcagaa 4620
cgcagcactc ccaccccacc tagtcctggg caccccaaca caaccgaaaa tctagaccca 4680
gatttaaaaa catttctcat gatgatgata gaggacatca agaaggactt tcataagtca 4740
cttaaagaat tacaggagag cactgctaaa gagttacagg cccttaaaga aaagcaggaa 4800
aacacagcca aacaggtaga aatcattaaa gaaaaacagg aaaacacatc caaacaggtg 4860
atggaaatga acaaaaccat actagaacta aaagggtaag tagacacaat aaagaaaacc 4920
caaagcgagg caacgctaga gatagaaacc ctaggaaaga gatctggaac catagatgtg 4980

-continued

```
agcatcagca acagaataca agaaatggaa gagagaatct caggagcaga agattccata   5040
gagaacatcg acacaacagt caaagaaaat acaaaatgca aaaggatcct aactcaaaac   5100
atccaggtaa tccaggacac aatgagaaga ccaaacctac ggataatagg aataaatgag   5160
aatgaagatt ttcaacttaa agggccagct aatatcttca acaaaataat agaagaaaat   5220
ttcccaaaca taaaaaaaga catgcccatg atcatacaag aagcctacag aactccaaat   5280
agactggacc agaaaagaaa ttcctcccga cacataataa ttagaacaac aaatgcaata   5340
aataaagata gaatattaaa agcagtaagg gagaaaggtc aagtaacata taaaggaagg   5400
actatcagaa ttacaccaga cttttcacca gagactatga aagccagaag agcctggaca   5460
gatgttatac agacactaag agaacacaaa tgccagccca ggctactata cccggccaaa   5520
ctctcaatta ccatagatgg agaaaccaaa gtattccacg acaaaaacaa attcacacaa   5580
tatctttcca tgaatccagc ccttcaaagg ataataacag aaaagaagca atacaaggac   5640
ggaaatcacg ccctagaaca accaagaaag taatcattca acaaaccaaa aagaagacag   5700
ccacaagaac agaatgccaa ctctaacaac aaaaataaaa ggaagcaaca attacttttc   5760
cttaatatct cttaatatca atggactcaa ttccccaata aaaagacata gactaacaga   5820
ctggctacac aaacaggacc caacattctg ctgcttacag gaaacccatc tcagggaaaa   5880
agacagacac tacctcagag tgaaaggctg gaaaacaatt ttccaagcaa atggactgaa   5940
gaaacaagct ggagtagcca ttttaatatc ggataaaatc gacttccaac ccaaagttat   6000
caaaaaagac agggagggac acttcatact catcaaaggt aaaatcctcc aagaggaact   6060
ctcaattctg aatatctacg caccaaatgc aagggcagcc acattcatta gagacacttt   6120
agtaaaactc aaacatacat tgcacctcac acaataatag tgggagactt caacacacca   6180
ctttcttcaa aggacagatc gtggaaacag aaactaaaca gggacacagt gaaactaaca   6240
gaagttatga aacaaatgga cctgacagat atctacagaa cattttatcc taaaacaaaa   6300
ggatatacct tcttctcagc acctcacggg accttctcca aaattgatca tataattggt   6360
cacaaaacag gcctcaatag atacaaaaat attgaaattg tcccatgtat cctatcagac   6420
caccatggcc taagactgat cttcaataac aacataaata atggaaagcc aacattcacg   6480
tggaaactga acaacactct tctcaatgat accttggtca aggaaggaaa aaagaaagaa   6540
attaaagact ttttagagtt taatgaaaat gaagccacaa cgtacccaaa cctttgggac   6600
acaatgaaag catttctaag agggaaactc atagctctga gtgcctccaa gaagaaacgg   6660
gggacagcac atactagcag cttgacaaca catctaaaag ccctagaaaa aaaggaagca   6720
aattcaccca agaggagtag acggcaggaa ataatcaaac tcaggggtga aatcaaccaa   6780
gtggaaacaa gaagaaatat tcaaagaatt aaccaaacga ggagttggtt ctttgagaaa   6840
atcaacaaga tagataaacc cttagctaga ctcactaaag ggcacaggga caaaatccta   6900
attaacaaaa tcagaaatga aaagggagac ataacaacag atcctgaaga aatccaaaac   6960
accatcagat ccttctacaa aaggctatac tcaacaaaac tggaaaacct ggacgaaatg   7020
gacaaatttc tggacagata ccaggtacca aagttgaatc aggatcaagt tgatcatcta   7080
aacagtccca tatcacctaa agaaatagaa gcagttatta atagtctccc aaccaaaaaa   7140
agcccaggac cagatgggtt tagtgcagag ttctatcaga ccttcaaaga agatctaatt   7200
ccagttctgc acaaactatt tcacaaaata gaagtagaag gtactctacc caactcattt   7260
tatgaagcca ctattactct aatacctaaa ccacagaaag acccaacaaa gagagaactt   7320
cagaccaatt tctcttatga atatcgatgc aaaaatcctc aataaaattc tcgctaacca   7380
```

-continued

```
aatccaagaa cacattaaag caatcatcca tcctgaccaa gtaggtttta ttccagggat   7440
gcagggatgg tttaatatac gaaaatccat caatgtaatc cattatataa acaaactcaa   7500
agacaaaaac cacatgatca tctcgttaga tgcagaaaac gcatttgaca agatccaaca   7560
cccattcatg ataaaagttt tggaaagatc aggaattcaa ggcccatacc taaacatgat   7620
aaaagcaatc tacagcaaac cagtagccaa catcaaagta aatggagaga agctggaagc   7680
aatcccacta aaatcaggga ctagacaagg ctgcccactt tctccctacc tgcccacttt   7740
ctccctacct tttcaacata gtacttgaag tattagccag agcaattcga caacaaaagg   7800
agatcaaggg gatacaaatt ggaaaagagg aagtcaaaat atcacttttt gcagatgata   7860
tgatagtata tataagtgac cctaaaaatt ctaccagaga acacctaaac ctgataaaca   7920
gcttcggtga agtagctgga tataaaatta actcaaacaa gtcaatggcc tttctctaca   7980
caaagaataa acaggctgag aaagaaatta gggaaacaac acccttctca atagtcacaa   8040
ataatataaa atatcttggc gtgactctaa ctaaggaagt gaaagatctg tatgataaaa   8100
acttcaaatc tctgaagaaa gaaattaagg aagatctcag aagatggaaa gatctcccat   8160
gctcatggat tggcaggatc aacattgtaa aaatggctat cttgccaaaa gcaatctaca   8220
gattcaatgc aatccccatc aaaattccaa ctcaattctc aaacgaattg gaaggagcaa   8280
tttgcaaatt tgtctggaat aacaaaaaac ctaggatagc aaaaagtctt ctcaaggata   8340
aaagaacttc tggcggaatc accatgccag acctaacgct ttactgcaga gcaattgtga   8400
taaaaactgc atggtactgg tatagagaca gacaagtaga ccaatggaat agaattgaag   8460
acccagaaat gaacccacac acctatggtc acttgatctt cgacaaggga gctaaaacca   8520
tccagtggaa gaaagacagc tttttcaaca attagtgctg gcacaactgg ttgatatcgt   8580
gtagaagaat gcgaatcgat ccatacttat ctccttgtac taaggtcaaa tctaagtgga   8640
ttaaggaact tcacataaaa ccagagacac tgaaacttat agaggagaaa gtggggaaaa   8700
gccttgaaga tatgggcaca ggggaaaaat tcctgaacag aacagcaatg gcttgtgctg   8760
taagatcaag aattgacaca tgggacctaa tgaaactcca aagtttctgc aaggcaaaag   8820
acaccgtcaa taagacaaaa agaccaccaa cagattggga aaggatcttt acctatccta   8880
aatcagatag gggactaata tccaacatat ataaagaact caagaaggtg gacttcagaa   8940
aatcaaataa ccccattaaa aaatggggct cagaactgaa caaagaattc tcacctgagg   9000
aataccgaat ggcagagaag cacctgaaaa aatgttcaac atccttaatc atcagggaaa   9060
tgcaaatcaa aacaaccctg agattccacc tcacaccagt cagaatggct aagatcaaaa   9120
atttaggtga aagcagatgt tggcgtggat gtggagaaag aggaacactc ctccattgtt   9180
ggtgggagtg caggcttgta caaccactct ggaaatcagt ctggcggttc ctcagaaaat   9240
tggacatagt actaccggag gatccagcaa tacctctcct gggcatatat ccagaagaag   9300
ccccaactgg taagaaggac acatgctcca ctatgttcat agcagcctta tttataatag   9360
ccagaaactg gaaagaaccc agatgcccct caacagagga atggatacag aaaatgtggt   9420
acatctacac aatggagtac tactcagcta ttaaaaagaa tgaatttatg aaattcctag   9480
ccaaatggat ggacctggag ggcatcatcc tgagtgaggt aacacattca caaagaaact   9540
cacacaatat gtactcactg ataagtggat actagcccca aacctaggat acccaagata   9600
taagatataa tttgctaaac acataaaact caagaagaat gaagactgaa gtgtggacac   9660
tctgcccctc cttagatttg ggaacaaaac acccatggaa ggagttacag agacaaagtt   9720
```

-continued

```
tggagctgag atgaaaggat ggaccatgta gagactgcca tatccaggga tccaccccat   9780
aatcagcatc caaacgctga caccattgca tacactagca agattttatc gaaaggaccc   9840
agatgtagct gtctcttgtg agactatgcc ggggcctagc aaacacagaa gtggatgctc   9900
acagtcagct aatggatgga tcatagggct cccaatggag gagctagaga aagtagccaa   9960
ggagctaaag ggatctgcaa ccctataggt ggaacaacat tatgaactaa ccagtacccc  10020
ggagctcttg actctagctg catatatatc aaaagatggc ctagtcggcc atcactggaa  10080
agagaggccc attggacttg caaactttat atgccccagt acaggggaac accagggcca  10140
aaaaggggga gtgggtgggt aggggagtgg gggtgggtgg atatggggga cttttggtat  10200
agcattggaa atgtaaatga gctaaatacc taataaaaaa tgggaaaaaa agacttatga  10260
attttataag tcaattatgt atcacaatag ttctctgaaa ttattgataa tttctataat  10320
ttttctagtc aaattttggg aacattgggt aaaaggtaat atgatcttca attgaaaata  10380
attttactta ttatttttct atttgtatcc cttctcttgc cttattgctc cagctaatgc  10440
ttcaatcaca ttatggataa gcagtaggga tagtgagcat tcctttccca ttttgatttt  10500
aatggtgctt attaatgttt tttattaatt taggaagata ttggccatag ttttgacata  10560
cataaccttt attatgttgg aatatatttc ctacagtcct acttgttctt tggcttttat  10620
taaaaagaca tgttgaggcc atcatgggcg cgaactcagt gggccctagc acacccagga  10680
tcttggaatc actggtgagt ggaacgcaac atctgttcca aaaaacccag agggtcttgt  10740
gccagcagga acaaggacaa aggaaacctg ctcaaccagc tgctggggtt tgttcccatt  10800
ggcgccagcc ccatctgatc ttggacgcat actcagcagg ccatagcaca cccagtatct  10860
tgggattact aacaccagtc tgctcaggag agcacataag cagcagaagc aacagagctt  10920
cttggacagg gtcccttcgg gccttcatcc tcagccagga ggcagagctg agacccagac  10980
ccctgggtac cttccccatc agaggagagt tggcctacgg ggagtactct gacctcagaa  11040
ttcaggaggt gaatctgggc tgcagaattc tgtgcacctt tcctgcaaga ggaaagcttg  11100
cctgcagaga gtgctctgac cactgggatt caggaaagtt agtctctcag gagtgctgac  11160
agaggctaaa gaatcacagg aggaacaagc tccagacaga gatagctaca acatctaaca  11220
caagagatta ccagttggtg aaagaaaaac ctaagaatct taataacagg agccaagacc  11280
actcagcatc atcagaaccc agtacaccca ccacagtgtg ttttggatat cccaacacac  11340
ctgaaaagca agactctcat ttaaaatcat atctcatgat ggtggtagaa aattttaaga  11400
atggcattaa taactcactt aaagaaatat aggagaacac tgctaaacag gtaaaaaccc  11460
ttaaagagga aggacaaaaa cccctcaagg aattacagga gaacactgct aaacaggtag  11520
aagcccttaa agaggaaaca caaaaatccc tcaaggaatt acaggagaac atggctaaac  11580
aggtagaagt ccttaaagaa ctacaggcaa acactgctaa acaggtagaa gtccttaaag  11640
aagaaacaca aaaatccctt aaagaattac aggaaaacac aaccaaagag gggatggaat  11700
tgaacaaagc catccaagat ataaaaatgg aagtagaagc aatgaagaaa acccaaaggg  11760
aaacaactct ggagatagaa accctaggaa agaaatcagg aagcatagat gtgaacatca  11820
gcaacagaat acaagagatg gaagagagaa tctcaggtgc agaagattcc atacggaaga  11880
tggacacaac aatcaaagaa aatgcaaaat gcaaaaagat cttaactcaa aacatccagg  11940
aaatccagga caaaatgaga agaccacacc tatggataag aggagtagat gagaatgaag  12000
attttcaact taaagggcca gcaaatatct tcaacaaaat tatagaagaa aacttcccaa  12060
acctaaagaa tgacatgccc atgaacatac aagaagccta cagaactcca aatagactga  12120
```

-continued

```
accagaaaat aaattcctcc caacacataa taattagaac aacaaatgca ctaaataaag  12180
agagaatatt aaaagcagta agggaaaaag gacaagtaac atataattgc aggcctatta  12240
gaattactcc agacttctta caagagacta tgaaggctag aagatcctgg acagatgtta  12300
cacagacacc aagagaacac aaatgccagc caaggctaat ataaccagca aaactctcaa  12360
ttaccataca tagagaaaca aaggattcca tgacaaaacc aaattcacac aatacctttt  12420
cgtgaatcca gtccttcaaa ggataataaa gggaaaacac caaaacaatg atggaaatta  12480
tgccctagaa aaagcaagaa aataaccctt caacaaaact aaaagaagac agccacaaaa  12540
acagaatgcc aactctaaca acaaaaatga caggaagcaa caattacttt tccttaatat  12600
ctcttaatat caatggattc aattccccaa taaaaagaca tagactaaca gactggctac  12660
ataaacagga ccaacatttt gctgcttaca ggaaacccac ctcatggaaa aagacagaca  12720
ctacctcaga gtgaaaggct ggaaaacaat tttccaagca aatggtccaa agaaacaagc  12780
tggagtatcc attttaatat ctaaaaaaaa tcaacttcca acccaaagtt atcaaaaaag  12840
tcaaggaggg gcacttcata tgcattaaag gtaaaatctt ccaagatgaa ctctcaattt  12900
tgaatatcta tgctccaaat gcaagggcat ccacattcat taaacaatag tatagtaaag  12960
ctcaaaacac atattgcacc tcatacaata atattgggag acttcaacac ccaactgtca  13020
tcaatggaca gatcctggaa acagaatcta aacagagaca cattgaacct agcagaagtt  13080
aggaaacaaa aggatttaac agatatctac agaatatttt atcttaaaac aaaagtatat  13140
accttcttct cagcacctca tggtaccttc tccaaaactg accatataat tggtcacaaa  13200
acaggcctca acagatgtaa aactattgag attatcccat gcatcctatc agatcaccag  13260
ggactaaggc tgatcttcaa taaaaataat aataaatatt agaaagtcaa cattcacgtg  13320
gaagctgaac aacactctac tcaatgatat cttgatcagg gaagaaataa agaaagaaat  13380
taaagacttt ttagagttta atgaaaatga agccacaaca tacccaaact tatgtgacac  13440
aatgaaagca ttcgtaagag gaaaactcat agccctgagt gcctccaaaa agaaactaga  13500
gagaatcata cactaacagc ttgacaacac acctaaaagt tctagaacaa aaggaagcaa  13560
attcacccaa gaggagtaga cagcaagaaa taatcacact cagggttgaa atcaaccaag  13620
tggaaacaaa aagaactgtt cagagaatca accaaaccag gagctggttc tttgagaata  13680
tcaacaagat agataaaccc ttagccagac taactaacgg tcacagggac agtatcctaa  13740
tgaacaaaat cagaaatgaa aagtacccaa ggagctaaga ggttcggcaa ctctatagga  13800
ggatcaacaa tatgaagtaa ccactacccc cacagaactg agtctctagg tgtatatgta  13860
gcagaggatg gcctagtcgg caatcaacag gaggagaggc ccttgggaag attatatgct  13920
ccagtatagg gggtggttaa catgtagaga ttccacctca gaccagtcag aatggctaag  13980
atcaaaaact caggtgacag cagatgctgg catggatgtg gagaaagagg aacactcttc  14040
cattgctggt gggattgcaa gcttgtacaa acactttgga aatcagttta gcggttcatc  14100
agttaattgc acatagtact accggaggat tcagcaatac ctttcctgtg cattggagaa  14160
aacagaaaac tctgagatgg aagctctgct gctggctctt gtgtttgctt ggatttgttc  14220
tagaagtggg tcgaatggac agctcaatga aacccaggta tcatgaaata ataagtataa  14280
tatataaaaa attcttattt cattattcat ttatctcaaa tgctgagcaa cacctcaata  14340
tcatttacta aatatttatg tactagagaa atcactcatt cagggagcaa gtcaggggaa  14400
atgcaacact ctaaatagaa tatgatttaa tatttagttt catatgactt aatatttaat  14460
```

-continued

```
atttttattt tagacatttt acatttagac tttcacacac acatatatat gtatgtatgc  14520
atatatatat atgtatatgt atataaacag catgcaaact gcaattacaa acattaaaat  14580
ataccagata aaatgttagc cttattatat gcccattgta gtattatgat ttcaaaataa  14640
aataggatat aattacatgt cttcatatta atcactcatg taaaaataat attaaatgtc  14700
agcatctcgt cacctgtgtc tatttatccc tctgttttcc tcaaagagat ttatataaat  14760
gtcagattct gtaaaccgtt ggttcacact catgtctgca ttgaaaacaa atattattta  14820
ctgtcaattt tatattttct catttctatt tagagcagat tttaggtgat aaaacccaga  14880
gaccaaatga aatattttgt tttctgtgat atttgttaac tcagtcttaa atatgtcaaa  14940
agtctttcac cgttatgctt taaatgtaga tttggacaat tgtgtcacct tttgtttgta  15000
cacttcaggg aacagaaaat ttactctgta tttaggaatt gtattattga ttgtatgtca  15060
cactatacaa taaatggaat atgttcaatt gcatttagta atttttattt tttttcctgc  15120
aatacatttt gattgtattc attcctctca actctcagat cttcccccac ctccctacct  15180
acacaaattc atgttctttc tctaacaaaa atatggaata taagtttttt ttgtttttta  15240
tttttttttt tttttgagac agggtttctc tgtgtagccc tagctgtcct ggaactcaat  15300
ctatagacca gactggcctc gaactcagaa attcacctgc ctctgcctgc caagtgctgg  15360
gattaaaggc atgtgccacc actgcccagc tagaatataa gttttttttt aaagattttt  15420
ttatttatta tatgtaagta cactgtagct gtcttcagac actccagaag agggagccag  15480
atcttgttac agatggttgt gagccaccat gtggttgctg ggatttgaac tccggacctt  15540
cggaagagca gtcgggtgct cttacccact gagccatctc accagcccta gaatataagt  15600
tttaaggagc agaattgtat acttctcatt aaaaatcaaa aatttcccct ctcaagctaa  15660
agtatttgtt ggagatgaaa gaaaacatcc atttattttc ctaatggcat cttcattctc  15720
agatctcagg tgattggtac accattgcca tagcagccac agatcttgat gtgatcaccg  15780
atgatggatt gttgaaactg tttttccgtc atcttgagtg tactgaacaa tgcaaagaaa  15840
tcatcctgac attctatggt gagtaagcta accttgctgc aatctaaagg ttcagacatt  15900
ttgatatgat aggaggtatt gacacatttc ccagactgac agtttcatga cactgtcact  15960
taccacaata tatacataat tccaaaatag aaaataatgc tgaggtattg ttccacattt  16020
caaataaaat acatttaata tgaatattta tgaatggtaa tataaacaat attaatatta  16080
ctaaaatatt taatatttat aatgtatgtt tcctatacat ttaaattatt taaaacagca  16140
tgcatattat aatgacaaat gatattcggt atactggata gaatgtatgt catattgtat  16200
atatgattac aatataaatt atgacttaca tttatatatg attacaatat aaaatgagtt  16260
gtatactaca tgtatattaa aatgaacatg ttatgtgtgt acttacaata ttgtatttta  16320
tataatatca tatttcacat taatatcaaa ttttgtggct ctatactaca gaaaatatca  16380
ggctagaaaa aattgctcag tgaataaagt acttttaaat ttatttataa cattgtgtta  16440
ttttatgata acatacacat gtcactatgt aaaaaattatt atatttatat gtcatatatc  16500
atactttata ttttaattat acctatatat tattgtttgt tgttaaagat ttgtgtttta  16560
tggtattcct gtttgtgtga aagtgtggat ctctgcatct atatgtgttt cttgtgcttt  16620
ttctttgtct cttgtgtttt ttttttttct gtttctttgc tttgccctca tctggtttgc  16680
ttttatttat ttatttcttg tctttagtat gcattctcat tttctaatga aagaaagtgt  16740
gagaatttgg atgggtggaa aggttgggag gatatggaga tataggaagg gaaaccataa  16800
tcagaacata gtatatggaa atattctttt aattaataaa acgatgggtt ttagttatat  16860
```

caagtgtctg gaaattagtt ttaaatagtt tttcatagtt ttaattgtta attccagtca 16920
tagaagtggg aagtatttca gatggaaaaa tagcatttgt atcactaagc agcttgtgac 16980
caagaccatt tcagatcttg tgggtaagac tgtcaatcac ccatagctgg aatggttgac 17040
aattaatggc tcctgggggga ggaataatta tattacttta agaatatagt cacttgtggg 17100
tttacattca tgcacatatg ttcaatgata actggacata attggttact tctttaaaat 17160
gaaaggagga aagggagaga gaatctggga tttggaagga ctggactaga tgaaggtgga 17220
tccaagtatg ctcttgcatg tatggaattc tcatatgtac agcagtgact ggaagtatat 17280
aaacttcaat agcaataaat tcaggacata tagagaaata ggaaagcaga aacagggggc 17340
tatataagat cacattttat tttatgtgtg tatgggattc tacaaagaaa agttaaagtg 17400
aaatataaaa gtacttaaaa taaattcata gatcagcata caattaggac tagggtaaat 17460
aaagatccca tatcccctaa agaaatagaa gcagttatta atagtctccc agccaaaaaa 17520
agcccaggac cagatgggtt tagtgcagag ttctatcaga ccttcaaaga agatctaatt 17580
ccagttctgc acaaactatt tcacaagata gaagtagaag gtactctacc caactcattt 17640
tatgaagcca ctattactct gatacctaaa ccacagaaag atccaacaaa gatagagaac 17700
ttcagaccaa tttctcttat gaatatcgat gcaaaaatcc ttaataaaat tctcgctaac 17760
cgaatccaag aacacattaa agaaatcatc catcctgacc aagtaggttt tattccaggg 17820
atgcagggat ggtttaatat acgaaaatcc atcaatgtaa tccattatat aaacaaactc 17880
aaagacaaaa accacatgat catctcgtta gatgcagaaa aagcatttga caagatccaa 17940
cacccattca tgataaaagt tttggaaaga tcaggaattc aaggcccata cctaaacata 18000
ataaaagcaa tctacagcaa accagtagcc aacatcaaag taaatggaga gaagctggaa 18060
gcaatcccac taaaatcagg gactagacaa ggttgcccac tttctcccta ccttttcaac 18120
atagtacttg aagtattagc cagagcaatt cgacaacaaa aggagatcaa ggggatacaa 18180
attggaaaag aggaagtcaa aataacactt tttgcagatg atatgatagt atatataagt 18240
gaccctaaaa attccaccag agaactccta aacctgataa acagcttcgg tgaagtagct 18300
ggatataaaa ttaactcaaa caagtcaatg gcctttctct acacaaagaa taaacaggct 18360
gagaaagaaa ttagggaaac aacacccttc tcaatagtca caaataatat aaaatatctc 18420
ggcgtgactc taactaagga agtaaaagat ctgtatgata aaaacttcaa gtctctgaag 18480
aaagaaatta aagaagatct cagaagatgg aaagatctcc catgctcatg gattggcagg 18540
atcaacattg taaaaatggc tatcttgcca aaagcaatct acagattcaa tgcaatcccc 18600
atcaaaattc caactcaatt cttcaacgaa ttagaaggag caatttgcaa attcatctgg 18660
aataacaaaa aacctaggat agcaaaaact cttctcaagg ataaaagaac ctctggtgga 18720
atcaccatgc ctgacctaaa gctttactac agggcaattg tgataaaaac tgcatggtac 18780
tggtatagag acagacaagt agaccaatgg aatagaattg aagacccaga aatgaaccca 18840
cacacctatg gtcacttgat cttcgacaag ggagctaaaa ccatccagtg gaagaaagac 18900
agcattttca acaattggtg ctggcacaac tggttgttat catgtagaag aatgcgaatc 18960
gatccatact tatctccttg tactaaggtc aaatctaagt ggatcaagga acttcacata 19020
aaaccagaga cactgaaact tatagaggag aaagtgggga aaagccttga agatatgggt 19080
acaggggaaa aattcctgaa cagaacagca atggcttgct ctgtaagatc gagaattgac 19140
aaatgggacc taatgaaact ccaaagtttc tgcaaggcaa aagacaccgt caataagaca 19200

-continued aaaagaccac caacagattg ggaaaggatc tttacctatc ctaaatcaga taggggacta 19260
atatccaaca tatataaaga actcaagaag gtggacttca gaaaatcaaa taaccccatt 19320
aaaaaatggg gctcagaact gaacaaagaa ttctcacctg aggaataccg aatggcagag 19380
aagcacctga aaaaatgctc aacatcctta atcatcaggg aaatgcaaat caaaacaacc 19440
ctgagattcc acctcacacc agtcagaatg gctaagatca aaaattcagg tgacagcaga 19500
tgctggcgtg gatgtggaga aagaggaaca ctcctccatt gttggtggga ttgcaggctt 19560
gtacaaccac tatggaaatc agtctggcgg ttcctcagaa aactggatat agtactaccg 19620
gaggatccag caatacctct cctgggcata tatccagaag atgccccaac tggtaagaag 19680
gacacatgct ccactatgtt catagcagcc ttatttataa tagccagaag ctggaaggaa 19740
cccagatgcc cctcaacaga ggaatggata cagaaaatgt ggtacatcta cacaatggag 19800
tactactcag ctattaaaaa taatgaattt atgaaattcc tagccaaatg gatggacctg 19860
gagggcatca tcctgagtga ggtaacacat tcacaaagga actcacacaa tatgtactca 19920
ctgataagtg gatattagcc caaaacctaa gatacccaag atataagata caatttccta 19980
aacacatgaa actcaagaaa aatgaagact gaagtgtgaa cactatgccc ctccttagaa 20040
gtgggaacaa aacacccttg gaaggagtta cagagacaaa gtttggagct gagatgaaag 20100
gatggaccat gtagacacta gcatatccgg ggatccatcc cataatcagc ttccaaatgc 20160
tgacaccatt gcatacacta gcaagattat gctgaaagga ccctgatata gctgtctctt 20220
gtcagagtat gcctgggcct agcaaacata gaagtggatg ctcacagtcg gctattggat 20280
ggatcacatg gcccccaatg aaggagctag agaaagtacc aaagaagcta aagggatctg 20340
caaccctata tgtggaacaa cattatgaac taaccagtac cccggagctc ttgactctag 20400
ctgcatatgc atcaaaagat ggcctagtcg gccatcactg gaaagagagg cccattggac 20460
acgcaaactt tatatgcccc agtacagggg aacgccaggg ccataaaagg ggagtgggtg 20520
ggtaggggag agggggtggg tggctatggg ggacttttgg tatagcattg caaatgtaaa 20580
tgagcgaaat atctaataaa aatggaaaaa aaaaaaagaa agataagatt gcactaaaga 20640
tcattgtgac ttcaatgaat gttggccacc atgtgcaaaa tgggtttaga tgattttaac 20700
taacctaact ggaagtataa atcaaaaaag ttaatgctga aaaaatttac tcataataaa 20760
cgttatttga ggtttagcag cagggaagtt agcatggatt ctgtgtgaag agaaaagaat 20820
gatattgttt attttctgta caataacttg ttctcagtta ataataaatt agagattata 20880
catcaagaag aattctagaa acatgtcatt gaataataca tgtgaaaatg aatctgtttc 20940
ccattttata aatataatta gaatctatat gaaggcttta atatcccatt ccttgcttct 21000
ttcaaagtgt tcattattta agatggcact attgaaatct gagtagaaaa aaatggcata 21060
aaatatatca ttacaaccca gtaacaacaa agacacatat gaattataga tttcatatat 21120
aactgatttt gtattcctca gatctatatc tgatatgtaa atacaattat ctgcttgtac 21180
atttactgtg caggtctata tgcccatccc cacctagaat cactgatgtc tatataaatt 21240
tttgctgaat aaatataagt tgaattaaca gaagtcaaat tatgcattag acaatggtag 21300
attcagtggg gtatagtagc acatgccttt aatctcagca cacatgaggc agaggctggt 21360
gtctctgtgt ttgaagccgg cttggtctac agagttccag gatagccagg tctgttaaac 21420
agataaacca tgtcatagaa aaaaagaaag aatgaaagag caaaggaagg aaggagagaa 21480
ggaaggaagg aaggaaggaa ggaaggaagg aaggaaggaa ggaaggaagg aaggaaggaa 21540
ggaaggagaa gaaggaagga aggaaggaag gaaggaagga aggaaggaag gaaggaagga 21600
aggaaggaag gagaaaaaca aacaaataat gatgaattca gtgacctaga aacagaagtg 21660
tttatagaag atagttagat agatagatag atagatagat agatagatag atagatagat 21720
agatagatag atatagatgc tttaaaaaaa agactacaca tatcaaagta atctgcagct 21780
actaccaggt aaagtatatt gatatcgttg cttgaaccat tgcacataaa caatcctcag 21840
tgacaaagtc aactgttgtg gtttctatgg cacagtgagt cagtgtccag tgatctgaga 21900
aggaagatgt tcgttatgcc catcattaca ctattcaggt cacacaggac catgataagg 21960
gatatacata tctgtctctt tttgttttag ggtagatgaa gaatgtgaaa agtttgaagc 22020
taacgcacag acctaccaat cagatgggtt tacttttacc tgtgagtata tgtgatcttt 22080
ctggaatatt taaattcctt gttactggta tcatcccata gcctgagcct ggaagaattt 22140
cttcttgcag ctttccacca ggccttacac ctctcactgg gtctgtgaag aagtcaggat 22200
ctcatcacac atgttacatt aaattgccaa aataaatgaa caaaactctc aggtcttatt 22260
gtgagatgtt cacatataaa acaactgaga atatatttta tgtagagtaa tttaagtctc 22320
acttacataa taattattgc gactattcaa taaatagtca agttggtcaa taaaaaaataa 22380
atatgtaggg caagagtgat ggtcagcagt taagggaggt tgctgctctt ccaaaatttc 22440
cctattctgg tcacagtagt cacatttgat ggtgcacaac attctgtaac tctggttttt 22500
ggagatccaa tgttttctac tggactcgaa gaacaccctg gtcacatgca aaagaaaaac 22560
aaaaacaaga caaaaaacac cacaagtgca cctttacaca tagatgaaaa taaaatcaat 22620
ttttaaaaaa gataaaatat tcaagtgttt ggaaagacat ttgataaaaa gagtttggca 22680
agtacattat aattagcaga catcagaagt taataatggc agtgattaaa atgacagatt 22740
gaaatattca taccaaagtg tacttaattt aaaattcaat cccaatgaga agaaaactgt 22800
ataggttttt gtttgtaata attggcaata atttgcagta atcagttttc taaaatggaa 22860
tgaccaagtg cttaagtaac ttactttgta gaaaagtgta caatatatta ttctcatctc 22920
agtttgaaaa atatctattt ttaacttaaa tgcaactgag gggattatta atgaatcagt 22980
gacactgaag aaggaagggg acgcatttct ggggtccttg aattgagcct gctaaaatga 23040
aatggaatag tgttaaaatg tttgaattct gacatctacc tttttacact acagatccag 23100
gtgagtgtta ctttaggatt tcatatatat caagtgcaag tatgatactt attagttact 23160
gtttgaagga tggtttgcat tggaaatccg cactcatttt gcttggtaag tatcatgact 23220
ccttcttatt atgatgacga ttattattat tactctttct tatgcctgca tatgggtctg 23280
cataccacat gtgtgcttgg tgtacacaga caccagaaga gagcatcaga taccctgcaa 23340
ctggaatgac aaatggttgt gagccaccac gtgagtgatg ggaattgagc ccagtttccc 23400
tgaagagcag ccagtgctct taacctcagg accatttttc cagccccacc tagatctttt 23460
tctataatac agaacatggc tacattatgt ctgcttttga tttaaaagaa aaatttatgc 23520
ataggttgtt tatataaaat gtatttattc atagatgtgt ctacatagga gattcaatat 23580
tccccttgac tgaatcaagg atgcaaaaac attttatcaa aaataaagat ttatgtccac 23640
cagggacttc catcagaaag atttccttaa attggacaca tacaacgtgg tgatacaaga 23700
cattccatgg tgcccttatt gaagtatcag agttcactca ttggtagatg gcttagggaa 23760
cctcataatc caaaaataaa aattttagtt tagatgcttt aaaggaaaat catgttaggt 23820
ataagaaata tgaaggggga ggattttttt attgtcttgt ttctggaaag ttgacattat 23880
ttactccccc ctcattccat caggggtctg gagtaggcag gaatggatat gatgataata 23940

-continued

```
atataggttg agtaggaaga aaaagtcatt attttggaaa ccttctgaaa tcttaaatgc  24000
aactaacttg aattccaaag tggttatgtt tagagaatac tactacccag ggagctatta  24060
gaggaggaca gggaatgtgc tcaagtcaca ggagcatatc ctatgtgctt agaatgtatt  24120
caattgtgaa ctcaataggt ttacaactgt gaatgatgtt tttgtgaact caataggttt  24180
acaactgtga atgatgaaat gatgttccat gtttttagtc cttgtcaagt caccatgaaa  24240
gacagaggtg ggagtgagga gaggattgga cacacagtaa gataacatgg aggatacatt  24300
ctactctgaa gaacattcca catgattctc ttcatttttt ccacacaatg aagggaaagg  24360
aaatggtgtg agtgaaattt acagatgagt gtactaggag gatacttcca aaggagaatg  24420
taagatatgt gcttgagaaa ggtaataagg caatgaccat agaggatacc ctagatgtcc  24480
cctgagactt tatatgaaat aaaaaattta aaaccatatt atatttgatt caaatttact  24540
actcaacaat ttttgaagtt ataatcctta aaacaatgtt gtttcccacc ctgttttgca  24600
gatatttgtc ctaaataagg acatgcatac cttgggtgag tagaaacata atgacagatc  24660
ccattcttac taaaaatcaa tgcttttta ttttatcgc ttcttggcct tttggctgag  24720
atcaagtgta tttttattt gttactttta tgaaaaaaa aatcgatggg tggatgtgat  24780
gtgggtgcag tgctgttgga aaacagaaga tggcaccaga tcccacagac tcacatggag  24840
ctgagacata agtcttgtgc aagatcagag atgactcttt ttttttcttt tccatttttt  24900
attaggtatt tagctcattt acatttccaa tgctatacca aaagtccccc atacccaccc  24960
acccccactc ccctacccgc ccactccccc tttttggccc tggcgttccc ctgttctggg  25020
gcatataaag tttgtgtgtc caatgggcat ctctttccag tgatggccga ctaggccatc  25080
ttttgataca tatgcagcta gagtcaagag ctccggggta ctggttagtt cataatgttg  25140
atccacctat agggttgcag atccctttag ctccttgggt actttctcta gctcctccat  25200
tgggagccct gtgatccatc cattagctga ctgtgggcat ccacttctgt gtttgctagg  25260
ccccggcata gtctcacaag agacagctac atctgggtcc tttcgataaa atcttgctag  25320
tgtatgcaat ggtgtcagcg tttggatgct gattatgggg tggatccctg gataaggcag  25380
tctctacatg gtccatcctt tcatctcagc tccaaacttt gtctctgtaa ctccttccaa  25440
gggtgttttg ttcccatttc taaggagggg catagtgtcc acacttcagt cttcattctt  25500
cttgagtttc atgtgtttag gaaattgtat cttatatctt gggtatccta ggttttgggc  25560
taatatccac ttatcagtga gtacatattg tgtgagttcc tttgtgaatg tgttacctca  25620
ctcaggatga tgccctccag gtccatccat ttggctagga atttcataaa ttcattcttt  25680
ttaatagctg agtagtactc cattgtgtag atgtaccaca ttttctgtat ccattcctct  25740
gttgaggggc atctgggttc tttccagctt ctggctatta taaataaggc tgctatgaac  25800
atagtggagc atgtgtcctt cttaccggtt gggacatctt ctggatatat gcccaggaga  25860
ggtattgctg gatcctccag tagtactatg tccaattttc tgaggaatcg ccagacggat  25920
ttccagagtg gttgtacaag cctgcaatcc caccaacaat ggaggagtgt tcctctttct  25980
ccacatcctc gccagcatct gctgtcacct gaatttttga tcttagacat tctgactggt  26040
gtgaggtgga atctcagggt tgttttgatt tgcatttccc tgatgattaa ggatgttgaa  26100
catttttca ggtgcttctc tgccattcgg tattcctcag gtgagaattc tttgttcagt  26160
tctgagcccc attttaat ggggttattt gattttctga agtctacctt cttgagttct  26220
ttatatatgt tggatattag tcccctatct gatttaggat aggtaaagat cctttcccaa  26280
tctgttggtg gtctctttgt cttattgacg gtgtcttttg ccttgcagaa actttggagt  26340
```

ttcattaggt cccatttgtc aattctcgat cttacagcac aagccattgc tgttctgttc 26400
aggaattttt cccctgtgcc catatcttca aggcttttcc ccactttctc ctctataagt 26460
ttcagtgtct ctggttttat gtgaagttct ttgatccatt tagatttgac cttagtacaa 26520
ggagataagt atggatcgat tcgcattctt cgactcttat ccattgagtc tatcagccat 26580
catactatcc ttctctactt aatttgctcc cttgagatct caagataaag agtcaatatt 26640
ttaattttgg aaacaaagaa atccgtgaga tatgaaataa tgaagtttag cgtgaattct 26700
gggcagccaa atagtttgca gcttttggtg atgcacatat ttatgcattt ttctctgtgg 26760
tataaatctc agtatttacc ttggatatat gaaatctcag gatttgttca gaggtttaca 26820
aaattaatat aattttatga aattcttcaa aataatatcc atacatggca tccatgtaca 26880
cagatggaat cccatgaagc aactttgtca tggacaaagg tccactttgt aatggatagg 26940
gtctactaag atccaacaca actcagacac tgaatcaata cagaaaacaa aaatttattg 27000
taatcaaact gctactgatc aatcagcaac attgaacaga cttgggagct gaactatagt 27060
ccccagccaa aatgtttaca gggctttagg cctgaaagac acaaatatct atgtcaagtc 27120
acagttaaat ttttccatca attgagattc aggtataggg gacttttcta gaaacatttc 27180
tttgtggtac atttatcctg tcctcattgg ttagtttact taactgtggc agagtgactt 27240
gcccagcatt catgtctcaa cttgtcaacc aaggtgtcgg tcaccctggg agatcttaga 27300
aacttaaact ttgtttgaac cctattcaaa atggaagatt tattcaaaat ggctctttat 27360
tacaaatttc cctctgatac attgctcatc aaaggaatca attataaagt tatttaatgg 27420
catataatat ttatatatag aactgagttt cataatgaca ttctttatac atgtatatca 27480
tacattttaa tcatatttcc cccctttatc tacctcttat tctaacctgt tgctttcctc 27540
atcccaacag ccgagtcttc attctacttt cacacacaca cacacacaca cacacacaca 27600
catatatgtg tgtgtatgtg tgtatgcata tatgtattgt atataaattt tattatagag 27660
tatagagcat attatatatt acattcacta tattatacat tgtcttgtgc attatattat 27720
atatatatga actttctggt gacacaatca atttaattag gactgcttgc ataagcatgt 27780
gtacagactt atttacagga gcatggacac aacatcagca tctagatcac taaaaatcat 27840
ctcaggctcc ccctaacaac catgacttgc ctgtaaagtc tcagaaatgt ttggggcctt 27900
gtgagtgagt ctcctgaacc acccagcaac ttttattatc tataatccct cagaagaagg 27960
gggaccacat gaaccctgcc aattccacca atttggttca ggtcttcctt cattgaaaac 28020
ttaaggacat tatgctacta agaagaactc aactaaatta aacattttca ttctcatctc 28080
cacagatatt ataaagaata tttgaaattg taacttctca atggcaattg attcatctct 28140
gtgaagtcta attattctgc tccccatcct atgaagacct aagtcccaat ttattgcttc 28200
ttttctttcc tgcatttatc ccttgtatga cgttactaac ttactgatta aattgatact 28260
gtatgcatac acacatatca gaagcatgct cttaaagttt ccaatgctta aaaatgtttc 28320
actatgcaca actcttaaaa aatatactca tctattatca agcaggataa atgtacttaa 28380
aagaatagtt aaagagttgt acagatgtct tagtcggtgc tcactaaaac ctgtctattg 28440
cctctagctt ctggggtagg atgtgtctca tgagcactcc cctacctagc tataattgca 28500
tggtcaggcc tcgcacacat aaccacatct gctttgagtt catgagcaca catcaccaca 28560
tctgctttga attcatatca atgggcactg cagaaattaa aaaaaaaaaa ccattaggtc 28620
ttacttcaaa agcctgtact tcacaaaatt ggaaaatcta aatgaaatgg atgattttct 28680

```
atatacatac cacttaccaa agttaaatca aggtcaggta aacaacttaa aaagtcctat  28740
aactcctaag taaatagaca aagtcattaa aatattccca accaaaaaaa caaaaagccc  28800
agggccagat tgttttagtg cagaattcta ccagactttc aaacaagagc taataccaat  28860
atgcctcaaa ctattccaca aaaataggaa cataaggaac actacctaat tcattgtatg  28920
aggccaaaat caccctgata cctaaaccac acaaagactc aacaaacaaa agactctcag  28980
accaatttcc cttatgaaca ttgatgcaaa aacactcaat aaaatattag caaactgaat  29040
cagagaaagc atcaaaaaca tcattcaaca tgatcaagta acattcattc aaagggttgt  29100
agggattttt caatgtatga aaataaatca acataattca caatataaac aaactaaaaa  29160
aaaaaactaa tcatctcatt atgtactaaa aaaggctttg acaaaatcca atctctttca  29220
tgttaaaagc cttggagaga tcaggatacg agcacatatc taaatacaat aaaagcaatg  29280
tacagcaagc caatagtcaa agtcaaatag agaaaaactt aaagcaattt tactaaaatc  29340
agggacaaga cacagctgac cactctctcc acatatattc aacattgtac ttgaacttct  29400
agctagagaa ataggaaaat taaaacagat caaggggata caaattggaa aggaagaagt  29460
caaagtatca ctctttacag atggtgtgat agtactcata agtgaaccca agaattatac  29520
cagagaactc ctacatctga taaacacttt cagcaaagcg gctggataca aaattaactc  29580
aaagaaatcg gtagccctct tttatacaaa ttataagtgg gtcgagaaag aagttaggaa  29640
gaaaatacct ttcacaatag ccacaaataa tataaaatag ctaatagtaa ttctaaccaa  29700
gcaggtgaaa gatctgtatg acaagaattt caagtatctg aaaaagaaat taaagaagat  29760
atcagaagct agatcccaca tgcttatgga tcaattgaac taacaatgtg aaaattgcat  29820
ctctccctgc ccttatggat catcagacaa tactggtcca tgtggtcaaa gggaacagag  29880
atgagagacg agaggttaac atgccctgtg agtacataca gtaaataaga tacatcagaa  29940
ccagatgcag ggaggcagac aaactttacc tggggtgatt caagaactat ataatttggg  30000
gatgctagaa aaatccaaga tggccagagg tcattgactg aagacttagg gtactgaaat  30060
aattcactag catgggaaag tatttcacga atctcagatg ctagctgaat gagttcttat  30120
caagagaaat aaagggatat ggactccaca ggaaaaccaa cagagtcaac tgacacagac  30180
ccttgagggc tcccagagac tgaactacca accaaagagt aagcatgagc tgtacctatg  30240
accctacaca catatgtagc agatgttcaa catggtcttt atgtaggtct cccaacaact  30300
agagtgggga ttgtccttga ttctgttgcc tgcttgtgga tcctgtttcc ctgagtaggc  30360
caccttgtct gtcctcagtg ggagaggatc cacctagtcc tgcagtaact tgatgtacca  30420
gagtaaggtg atacccaaag aacacacacc ccttctcaga ggagaaacgg aaggggaggg  30480
gagctgtgtg agggtgagac taggaagaga gagaggctga gattgggata taaagtgaat  30540
aaataaatta acagaaaaat aaattggaga ggaaaaagtc aaagtattgc tagatggttg  30600
gatagtatgc ataatctcta caaaaattct accagggaac tcctacagtt gataaacatc  30660
cttcagcaat gtagctggat acaaaattaa ctaaaaaaaa tcagtatctt ttctttatac  30720
aaatttgaaa tgggctgaga aagaattggg gagacaatac actttacaat agccacaact  30780
aatataagat aacttggtgt aattctaacc aagcaagtgg aagaccccta tgacaagaac  30840
ttcaagtctc tgaagaaggg aaatgtggta catttattaa atgggatact cctccagaag  30900
gggaaataac atagacttgg gaaatgtttt ggaatagtag gacataggac tgagtgagcc  30960
agaggggtca aggacaccac aataagactc acacggtcaa ctaactcggg cctatggtag  31020
ctcacagaga ctaaatcacc aaccaaagag catgcatatg ctggaagtag gccccccctac  31080
```

acatttggag cagatgtata gcttggtctt catgtaggtc ccctaggaat tggagcaagg 31140
attgtctttg actctgttgc ctgcctttga aaccgctcct cttggctggc cttccttgaa 31200
gggctacact gggaatggat gcactaagta cttctgcaac ttgaagcacc aggactggtt 31260
gaggagaaag gatgaggtaa tgggggaagg ggtttgtgag ggtagtacta ggagaagggg 31320
aggttgtaat tggggtgtaa agtaaataaa tagatagata gatgatagat agatgataga 31380
tagatagata gatagataga tagatgatag ataggtagat agatagatag atagatagat 31440
agatagatag atagatagat agatataaga aagaaaattc aaatactaga atccatattg 31500
tgatctaacc atgtaaaatt ctttcttcct acttgatatt ataaggtatt ctttacccaa 31560
agaaaaatat tatttcaagt ctggtttcta ataccatgaa atataaaatg tgattgcagc 31620
attgggaagg taaatcaaat ttcatacagg agaagacatt tttcctgtct gatacttgaa 31680
atagtgtttt catgatattt ttcatgaatt tcactgctgc aaagatatat ttactcttgt 31740
gtttttaaac attatcataa tgaataaagg accttggttt tcaaggcata tacacctcct 31800
tcatggagta tataccactg caatccttag gcatttcaca caatgtaaca aatacaatat 31860
tggcccttaa ttaactacac aagcatgaag catcagggat gaattaatct caaatacaca 31920
cccagtatcc catcaaaatt atttggacaa taacacatca aacttatttc cctaaaggtt 31980
tacttttttt ctaactccat aagctcatcc atcagtcatt gttttaatat acccgatatt 32040
aagtcaatat cttaaatgta atgagatata aatttttttt ctgacaaaca agaagggaag 32100
gattatggat ttctattttg ttgctcataa ggaaacatgg gtgacataat gtgctagttg 32160
agccattcaa acaacatgga cttcagattt tgattttcgc actgagtgga tgatacaaca 32220
agaggtaaaa ttggaagatg cactacctaa aacaaagaga tacaaaccaa atctttaatg 32280
gtttttagac acatctttga ccatgaaaat atggcaaagg aaagttgtct ttaaatgtct 32340
tcattattat ctgaactcaa aaattaattc acatcacagt gttcacactg tgaacactaa 32400
gtcacacata gtctcatctt gtcttcagga gacttttctg ggaattatca ttattttgat 32460
aggggaattt agaagagata gttgggtttt acaaagtgac agacaactga ccaacagatt 32520
ctctatgctg ggttccaaat gacacttctt ccatttcttg ccatcaaatg cagtaagtga 32580
aactaatccc actaaagaaa tgtaaagact atgtaaattg aacaagaaat aaaaaactcc 32640
cataaaatta ttataaatat ctataaagta agtaatagca ttctttttgt ataaaataag 32700
ctgagaccag agaggtttat agattcttga ttccaacacc tgatttacaa aaaactgcat 32760
atatatatgt gtgtgtgtgt gtgtgtgtgt gtgtgtgtgt gtgtatacat atatatatat 32820
atacatatac atatatatat acatatatat ataaaacaaa atcccttaaa gcattgatga 32880
acttcaataa ccttttctct atttgtacat tttaattttt ctcttatttt ttaaaagtag 32940
aacataattt ctttttttctt tagttttaag aatggtgaca ataaattaca taataataaa 33000
gagataagaa agaaaacaca tcagtcagca caatttgagt ttgcttacta agactgtttc 33060
tctcaacaga tgcagagtcc catagcaaaa ccttaggcag agcttgggga gtcctgcaga 33120
ggatggggag gaaggatcac ctaaccagag gagtcaggga caccaaaagg acaaggctca 33180
cagaatgaac tgacatggag gctgtcagag atcagggagc cagtaggggt ctaataggcc 33240
ttgggtgtat atgttatggc tgagtgtagc ttatgttctt ctagggttcc taacaatgga 33300
agtaggacct atctctgact cttttgcctt cttatgggat cctttcactc cttttgggtt 33360
gcctagcaga gccttgacgt gatggtatat gcctgatctt attgtaactt gttataccgt 33420

```
gtttggttta aattgctggg aggcctgctg tttttggaga ggacatggaa gggatggata  33480
tatgaaagag gggaggtaag agagacacag agggaagggg aggaaggaga aactgcagct  33540
aggatgtaat atataacaga agagttaatt aattaattaa attttaaaaa agcctgtggt  33600
ggttttaata agctcagccc aggcagtggc actattagga ggtgtggcct tgttggtgta  33660
ggtgaggctt ccttggaagt agtgtgtcac tgtgggggtg agctttgaga ctcttctcct  33720
agctgcttga aaacagtctg ctcctggatt cctttcaatg aggatttagg gctctcagct  33780
cctccagcac catgtcttcc tggatgctgc catgcttccc acctggatga taatggactg  33840
aatctctgaa cctgtaagcc agccccaaat aaatattgtg cttcctaaaa tttgacttgg  33900
tcatcatgtc tcttcatagc aatggaaacc ctaactaaaa cagagcctct ctggctctta  33960
agccatgctg gctataaagc ctcacatatt acatgacata ttattataga aactttgtat  34020
cacaccctga atatcatatt tacaatattg taggtaatat tttcctctct aattatgaca  34080
tgtaaatgaa ttacgtaatt atactcaaaa gaatttcttc tgacattatt gactacctta  34140
ggttttgttg catttttatg tgtttattat tttatttgtt ttgttttgaa acacattcaa  34200
actatgttag caacggttat cctcaaactc aatatataga tcagggggc ctcaaactca  34260
cagaaaacaa tatgactctg cttcccaaga cacagaatta acagtatgga tcaccatgct  34320
caattaatca caggttaatg tattttagtt tttaattatg tagatattca ggtatctgca  34380
tatgagcaat gttaccaggt gagttcagta cctgacgagg gcagaagagg gagcagattc  34440
ctctggacct aaaattacac atgattgtgc attgcaatat agttgctagg aactgaaccc  34500
aggtcgaaag gaaagctagg actctgaccc agtgagtcat cctaagccag attattttt  34560
aataggtaca gtgcacattt tctttgttgt gtatgatggc tagaatatgc ttgccctatg  34620
gaaattggca gtatgaggag gtgtgtcaat gttggggtag gtgtgacctt gttggaacat  34680
gtgtgacact gtgtgagtgg gttttgaggc tcctatgccc aagctctgcc aaatgaggaa  34740
gagagcctcc tgctggctgc ctgcagaaga aagactctcc tggctgcctt tggatcatga  34800
tgtagaactc tcagctcctt ccccagcacc atgtctgcct gcagactgct atgcttcctg  34860
ccatgatgat aatcatgaac ctctgaacct gtaaggtggc cacaatgaaa tgtttgcctt  34920
taatagagtt gccttggtca tggtgtctct tcacaaatat ataccccta attcagacat  34980
tgtgtattac atcacattga ttgaagacag aatgtgtaca tgaaaaatca atttatttta  35040
tcaacaaaag aatcagtacc atggtaggag tatgggaaac aaatccatga agcagagatt  35100
ctggcttcat aggaaagatg aaaagaaaaa ctaagaaaag gatgagctct cttcattgtc  35160
atgattctga tttcatgaaa gaggtgatgt gggaaatact tctgatcttg ctgtcatctg  35220
tgaagcttca aaagtaaaaa acaagacaaa caaatgaaac agtaagatgt gcatgagctg  35280
gtgcttctga catgagcttt ctgagattgt aaatgaaaaa caaaaattaa tcgacacgga  35340
atatggtgaa aggtttgatt ttaaaaatga cacatgtcac agggttagac ctaggtttgt  35400
tcttggttga cttccataac tctcttccgg catttaaact gagagttttt ggtctaaatg  35460
taatctacca taacacctat gtgcaaggtt gtgtctaagg agactttaca aagttcatgt  35520
acatttacag tatttccaca ttcatgctac actcttggct gtcacaaata tcacttattt  35580
tcaatagtca agtttcatta aattcttacc tattaccttt aagataaaag aaatcaacac  35640
tttggtatag gagagttgct tattcccatg ttataaatat taacagcaac ataaacgata  35700
gctttgccac cttggattat atatgtaatt agaattataa agagatttcc tctactaaag  35760
gcataactaa tagactaaag aatgaatttt tagcagatta aaatattaac aggctctgct  35820
```

gccctgttgt actcacccat attgtgtctt tattggttac aagtgtctgt gagagacaga 35880
aaggaaggaa ataaccacaa acaaaagaca tagttagagc tccttaatat ctccagtgac 35940
tttaaataat tttaaaaatc tgatttagac gactgaaatg atgattatcc tggatatctt 36000
caggtgcatt agtttgctgt gtgaagcaca atgttgttac ctgtgggcgc caagtgctgg 36060
atattctcct ttggaatatt gtattccttg accagcttcc caagctcctg cttctgtgct 36120
ttgctcaggg tctctccttt tcctacatca cataaagcag aaaggaagaa aaagtgtagc 36180
ttacagtact gggtggctca gaacagatgg agttataatg ggttgtgtga tattgatgca 36240
tggaaacatc ttactttgtg ggccctccct caccccatca gtctcattct gatcaaccta 36300
agatctctaa agtaaaaaga acacatttaa tgaagctgaa ctatgatagt ccacacccta 36360
atgaataata tcgttatttg tggtggaatt gttattgttg ttattgccat catcactatt 36420
aatactccta ctactactat tataattatt cgtactttcc atatgaccgt atatttattt 36480
ccaaaaaggc ctgtacataa tcctggtgtt tgaaatactt gaactaaatg tttgtccatg 36540
ctgacttcta ccttacttct gtgtagattc tggagtccgt gccttggata attgataatt 36600
atcaaaataa gcagtgaaat caggctgaac aggctcatga acctgaatca attacgactc 36660
caacaccacc ccacctcacc acttacccaa cctcactacc agattccagt acccagtacc 36720
cagcctccag tcccctgcct ccaggcccaa gcccccaaat tgcctctgct tcctccattg 36780
cccctcacaa ctttggtaaa caaagcaaga ttgttgggtt tatatatata tatatatata 36840
tatatatata tatatatata tatattatca tgacacaaag caaggtcatc tggaaagagg 36900
taacctcaat taagaaagtg ctaccctcag actgctctgt gagaaacctt gtagactcat 36960
tttctagatt gacagttgat atggaagtgt ccacccccact gtaggaaact cagcagcaca 37020
gttttctttg ttagtgtttg atggtagggt gcctagacta tgggtagtgc cacctctggg 37080
gagatggtcc tgggtgctaa gagaaagcat gctgaacaag acctggggag caagccagta 37140
agcagcactc ctccatgccc tgtgcatcag ttcctgcctt caagttcttg gctgtttggt 37200
acagagacag atgggtcaat aattggaata ggattgaaga ccccaaaata cccccaacac 37260
acacacacat ggacacttga ttgttgacta agaagacact accatatagt agaaaaaaga 37320
gagcatcttc agcaaatcgt gctggcctac ctggtggtct gtatgaagaa gaatacaaat 37380
tgatacatat ttctcaccct gtacaaagca caagtccagg tggatcaaaa tcctccacat 37440
aaaatcatat atactgaatc taatagaaga aaaagtagga aatagcttgg aaggtattgg 37500
cacaggaaaa aattttctga accaatggct cagctctaag atcaacaatt gacaagtgga 37560
acctcataaa actgaaaagt gtcttcaaga caaaggacac tgttagtagg aaaaacagca 37620
acctacagat tgggaaagaa tcttcacaaa ccacacatcc aatagagggc taatatccaa 37680
aacatacaaa gaactcatat attagactcc agaaaaccag acaacctagc caaaaactgg 37740
ggtacaaact aagcaaataa ttcttaacta cggagacttg aatggctgag aagcaatgac 37800
ttctttttga aaatgaactg tgttatagga gcttaagcca aatcaaccct ttcttcccca 37860
agttgctttt ggtcatggtg cttatcatat cgatagaaac cctacaagag ggaccactct 37920
caccagcaac taaaatcaca tttgtctcct gtccgctctc atccacatta acgttgtgaa 37980
agaaaagggc gccatcttcc ttcattacaa cttcgaagta atttctacca gagtctgcaa 38040
ttaaaagaga atcagcttag aaatcagtag aatcattgga ggtttcacta ttattttaca 38100
tatgaaatct atgatatttt tatttctttt tcaattattt gacaaatgtc atttacaatg 38160
gtttaaaatt gtaaatgaga attactaagt ggtagagaca ctcttgcatt aattaaaata 38220
ttttttgaa tttaaaaaga atgtccataa ttagacggga atgctggcac acgcctttga 38280
tcccagcact tgggaggcag aggcaggtag atttctgagt tcaaggccag cctggtctac 38340
aaagtgggtt ttaggacagc cagggttata tagagaaacc ctgtctcaaa aaatgaaaaa 38400
aaaagttcat aattacctta tgtctccaca gcctatttaa aaagtgaaca caacgctaat 38460
attaaaatac cacactgaag cagggatggt gactcaaaca tcaaatccca gcaatcagga 38520
ggatctctgg ggctagcctt gtcgcagaac tagttatagg acagccaggg ctatgcagag 38580
taactctgta tcaaaaaaaa ttttaaaaac aaccacaaat gtgtctatgt atgtctgtgt 38640
gtgtgtgtgt gtgtgtgtgt gtgtagcaaa tgtatagttt tccatatatt aaacccttaa 38700
gaaatcagtc ctgtagcttt atgggactgc cttctaaatg tcatttatac ttaaataata 38760
ggcacaaaaa tgtctctaat aatacttttg tatgaatgtg tataatacac cttaactgat 38820
aacataaatg tctggaagtt tagttaggat tttggaagtt gcatcaaaaa ttatcagatg 38880
aaattgttca aggatcctgg ccctttagtt gtgcggcctt gtcaaacctt gcaaaatttc 38940
tctctgtctc tctgtctttc tgtccctccc cccctctctc aattagatta tgcatcccat 39000
taattgatta catactcaca gtcagtagtg taccgcccat cttcttgttt ttctcccaca 39060
acagtgtgtg tctgacactt gccattcatc cttcagaaat aaaaatcaaa aacttgcttc 39120
tgaatttact ctttcaggtt gctcatattt ccttattgtg tggtagtatt aactgtcttt 39180
gggaagtgtt taatttgttt aaataaaccc acatctgaag actgacacca acactctggg 39240
gttatgattg acatggaaag taaatccagg cttccagggg aagacactgt cctcattttc 39300
tacccacatt tcctgttcat gactagtttc aaccagaatt acccaaccct gtaaaactgt 39360
agaacacatt gcattcagtg ttccttaaat caaggacaca actcagaata aatatgccca 39420
ggagatcaat tccatttttt cacatggccc aagtgtcagt gaaaatttca cagacattca 39480
tgtgcccagt ttctcagtcc tgtccatgtg catcaggtga atgtcactta ctggacatgg 39540
aatttgattt tgagtgtccc acagtcgtca ttgcactcca tatgctcaaa gtacgctctc 39600
aggtctccat tcatctttac tttctccacc ttgtccgcag ctatgtaaag ggtgcgccag 39660
tccccattaa cctaaatagg acagacacca ttgcaaaagt tggttagtca atctgttccc 39720
ttttattcag caacatttgt cctaattact acatgacaac aattccataa gtcaacaaat 39780
gaacttggac caagtaaaat gcagatgtct ctctgctaga gagtagatta ggagattgtg 39840
tcatcactca ttcacactag aatatggaac acaggataca gttcacactt tgtcaatcaa 39900
taacaatgca aagtccaatc tgtaattttc tcttcttaac cttctttcat actagacaga 39960
agtcattgaa aacatgcaaa gagttgaaaa tacactagga ctgcattaca gataggattc 40020
agataatgta tatatgctat atataccaca tataatatgt aatgccatac catttatagt 40080
atatgatata tatgctcaaa ccaactacag agtgtacata aacaccccag accctttatc 40140
cccaaatgca cacacctctg agggactgat atcaagagat tcatgatgtg cacaggatac 40200
acctaatgca agcgcaatta gcaggaactt caccatggta gagcctggat tctctccttc 40260
cgaaggagtt cagagaccaa gggcaggtga tggggagacc cagaaccatc tccaccttat 40320
atagtattga ttattggcct gagattggca tggattgcct gtggtaaaat tccagcatat 40380
cctggtggtg gaaacatctg tgatgacaat tctgtttttc tgctactttt gaaataagat 40440
taacttgagt aaagccatga aattgacctt ttagacttct gtggacttgg gctagctgtc 40500
agaaaacaca aatatccatg tccctaaagt ccaagtttct catttggaac actttaaaga 40560

-continued

```
aatgaactta tttgactcag gctattttaa tgatgacaaa ttttccatca atcagaccct  40620
ttgatcacag gttaccatat ggatattaac aattttttat acaattgaat atcaatggac  40680
atatatttct agaacattct agagtgttct agaatgttct acaacattct ggggcattct  40740
tgtaaaaacc tttgtgaaga agtgtactgt tttcctttct gggcaggaat ttgcaattta  40800
gattcatgat tttaaatatt tttataattt gatattttca tcaagatgtg aagattttta  40860
atgatgtaaa attcccattg ttttgtgggt acatttgttg atactatgtc ctggtaatca  40920
gcattgcttt tgctaacatt actttatata ttcaataata tatacacaca cctttgtttc  40980
tgattgctat aagtgtattt tttgacaact gtgtctctaa atcatttatg caatgaaaag  41040
tcagctgcta attttctcat gtttgtgtct gagaaattct caacgttttc tccattgaga  41100
actttgacct gtggatggat ttgcaaatat tcaccgaaat gcatgactca aaactagttg  41160
tcaatgttcc aaggctttaa ataagaaata ttcacccatc ccatgttcag aaaggttctt  41220
gatgtatgtt cttctttttt agtatacccc atacaaatgt gatccttatt atatttttac  41280
atatttttct tgattcattc cttcttctct gtgtttgatt attcaagaga taactcagtt  41340
ccactggaac aagattgggc tgacctacaa acatatttat tttcatccat tcatttcttg  41400
tgaaatctct actttccttc agaattctaa tgtgatttgg aatacagata atgttgggaa  41460
aatgtaatga aaatcaacca gaaaaagctg tcatttaata cttccaaagt ggataattac  41520
ttaagactgt atgtgcactc attaaagtcc ttctcatttc tcctccagac ccagtaacaa  41580
caacacatta atcctattta ttgagtatcc ttctggaaaa ttacctacaa ttttgcacaa  41640
actcaggttc attcttccac atttccaaca gttttattaa aatataagct ttccttcctt  41700
atttattaag tgaagtgagt ttctctccct tctacctgat tacagagaaa ggtgatacaa  41760
cacagcctaa actggagtct tggaaagata aaaacaaatt ctgcctcatg tcaaaacata  41820
catttattcc taaggaactt aaagattatc tctgtctgtt tgaactttaa tattgaagca  41880
tgtacacaaa cacacacaca catgcacaca cacatacata cacacacata cacacatgtt  41940
tcttatgttc ttgtgtattt attcataaat attttatata tggatatggg tttttatata  42000
ttttctatct gtggatatat atttatgtgt aatgtaagta tagctatatt ttacattcag  42060
atttatatat tccaatttat acatgtatga tacatatata catgtgtgat acatacatat  42120
ttgtttccat tttcagtaat ttaccaatta aattcctaat ccacacattt tgtctacctc  42180
agaaaagtga agaaagaatg gaaaatgtag gtgcttcaaa ggacagagtt aaaacataca  42240
aaatactgac acaacggatg ctgttattga agtcatggcc aagcttagaa ctctttgatg  42300
tctgaccttt gagtagaact tggctaaaag tctgtctcct ttcttcttct tttttaattg  42360
gatattttat ttatttacat ttcaaatgtt atcccctttc ctggcttcac ctctggaaaa  42420
cccctatccc atcttcctcc atctctttct gagggtgctc ctacccaccc attcccacct  42480
caccacactg acattccctg acactggagc attgagtcat ttacaactca aatgctatcc  42540
taaatgtccc ttatatcctc cccccaccca gtagccttat ttataatagc cagaacctgg  42600
aaagtgccct gatgtccaag ggcctccctg ccattgatgc caaacaaagc catcctctgc  42660
tacatatgct gctggagcca tggatccctc tatgtgtact ctgtggttgg tggtttagtc  42720
cctgggagct ctggggttac tggttatctc atattgttgt tcctcctatg ggctgttca   42780
tcccttcaac tccttcaagt accttctcta actgctgtat tgtggtcccc atgctcaatc  42840
caatggttgg ctgcaaacgt gtgcctctga atttgtaagg ctctgtcaga gcccctcagg  42900
```

-continued

```
agacaaccat atcaggctcc tgtaagcaag cacttcttgg catccccaat agggtctggg  42960
tttggtgtct gtatgtgatg gatccccagg tcgggcagtc tatggatggt ctttccttca  43020
gactctgatc cacactttgt tcccatactt cttttagaca ggttcaattc tgggttaaaa  43080
atttggatat gagtgggtga ctacgtcccc caacctgggg tcttgcttaa cttctggata  43140
tggtctctac atgttcatcc tccccttttt tgggcatttc agctaatggc atccaagttg  43200
ggacctggga gcctcttaat ttactggcat ctgggacttc ctgatggcta tccctgtttc  43260
ccatcattca ttgctacaca cctctgttca aattcctgac cctctgtaaa atcgtccctg  43320
tctcctagca cacttgttct tacaccccag tccctctcct tctcctctct tccttccaag  43380
tccctcctat cctctacctt ccaagaatat tttgttctcc cttctaagat ggtctgaagc  43440
atccatactt tagtcttctt cttgagcttc atatggtctg tgaattgtat cttgggtatt  43500
ccgagatttt gggttaatat ccacttacca ttgagtgcat actatatgtt ttcttttgtg  43560
actgggttac ctcaataagg atgatacttt tttgttccat tcatttgcct aagaatttca  43620
tgaagtcttt gtttttaata gctgagtagt tctccattgt gtaaatggac catattttct  43680
ctatttgtct gtagaaggac atcagggcac tttccaggtt ctgcctatta taaataaggc  43740
tacttggtgg ggggaggata taagggactt ttaggatagc atttgagttg taaatgaaga  43800
aaatatctaa taaaaattat tataaataaa taaataaatc tattataaat atagtggagt  43860
atgtgtcctt gttatatgtt ggagcatctt ttgggtgtat gttcaggagt ggtatagcta  43920
gatcctcatg tccaattttg tgaagaacca ccagaccagt tataccacca gattagttat  43980
acctccttat aattccacca acaacagatg agtgttcctc tttctccaca tctttgccag  44040
catctgctgc cacctgagtt cttgatctta gtcattctga ctggtctgta gtggaatctc  44100
agggttgttt tgatttgcat tttcctgata actaaagatg gtgaacattt gtttaggtgc  44160
ttcttgtcca ttcaatattc cttagttgag aattctctct tcatgtctgt actccattta  44220
aaatagggtt atttggtcct ctggagtcta actttagaat tatttgtata tttcggatat  44280
tagcactcta tcgaatgtag gattggtaaa gaacttttcc cagtctgttg gtttctattt  44340
tgtcccattg acagtctcct ttcccttaca aaagctttgt aattttagga ggtctcattt  44400
attgattgtt gtttttagat cataagccat tgctgttctg ctcaggaaat tttcccctgt  44460
gcacatgtgt ttgaggctct tacccacttt ctcttctatt agttgcatta tatatggttc  44520
tatgtggagg tccttggtcc acttggagtt gatctttgta caaggatata agaatggatg  44580
gatttgcatt cttctacata ctgactgcca gttgaaccag caccatttgt tgaaaatgct  44640
gtcttttttc cactggatgg ttttagctca ttgtcaaaga ccaggggaat ataggtgtgt  44700
tggttcactt ctgggtcttc aattctattc tattgatcta cctgccttag tctgtaccaa  44760
taacatgcag tttttatctc tattgctttg tagtacaact tgaggtcagg gatgatgatt  44820
tccactgaag ttcttttatt gttgagaata ttttttgcta tcctgggttt ttgcttattc  44880
caaataaatt tgaaaattgc tctttttaag tctatgaaga agtgtctcct tttcagtagc  44940
ctgctgacat tccctactca agaaacaaca aatgtttatt gtttttttcta ttctttgatt  45000
ttgtccccca ttatatttta cacaatgttt gggtttattt gcttccctct ttgttttctt  45060
tcctttctat tgatttaata atctatggat tcttctgtgc attcagtttc gaggaaaaac  45120
agtgaggaaa tgaggcacta gaaattctga ggctttcata gtagtgaggg atggatctgc  45180
taattgtccc atttattggt ggaagatttc tgtcattctc agaatcaggg tttctgtgtt  45240
agaaatttca tggccttggg agaggtgtgg tgactaatgt aaaaactcaa ataaaatttc  45300
```

```
agttaaaacg ttaaaaagaa aagaaactat acaaccttgc ctttttcaga tcatagaggg  45360
aaaatgttca actttttctc atttaatatg tttaaggttg aaatagcata tgttaattgt  45420
attaattata catcattata gatttcattg tgataaataa taatcgggtt tatttcaaag  45480
tgcagcccta ttcactgaca cttaaacgat ttttaatatt ttagatttta atgagctaac  45540
aaattagcag tattcttgat caattttcaa acacttaatt ttgattaaca ctctcatatc  45600
ttcttgtgtg ccctccaact ccactcccca acccagctaa accattcact gtccaacact  45660
ggcatttctt tattacatca tgtttacata gtactgatac tcctttatgc tctattttat  45720
tttaagactt ttgaagatat tttattttag ttttgcaaac atatccacac actttcttcc  45780
tcctatatat gcacatatat gttgcaagct aggttttgtc tactggttgg taattttcat  45840
gattagctga tttcttaaaa ttaataatat gaactttatg tatcagttga gataattacc  45900
atgggtattg cccatagtcc tactgctttt gcacctggtt ttgtcatcaa gtggtgtgga  45960
gctgacctca accaaatcag tttagtagaa tttcttcatc tttggaatct taaaataagt  46020
taagaaaaag tatgcttgct tctttttcaa atgattgcta gggttcggta tcaaaataac  46080
ttggtcttaa atctgctttt ggaggaaaat attttattac tgactcaata aatagttaac  46140
tgaaaaatag ttaatgttgt cctgtgtaat tttatcttaa ggtgtctact gctaggatga  46200
aacaccacga ccaaatgcaa cttggggagc aaagggttta tttggcttaa aaatccacat  46260
catagcccat caattaagga agtcaggaca ggaactcaaa cagggcagga atccagaggc  46320
aggcactatt gcaaaggcca tggaggggtg ctgcttactg agtagctcag cctgttttct  46380
tatacaactc aggaccacca gcatgcggtg gctccatgaa caacaggctt tgctctcctt  46440
catttatatc taatctttaa aatgtcctat aagcttgtct acagcctaat cttatggagg  46500
cattttctca attgagatcc tttctctcag atgactttag tttgcgtcaa gtggcataaa  46560
actcaccagc acacttcatt taattcagtc ttagtgaaat gcatgttagt agcaataaat  46620
ccattttctg cagactctcg gacctgtgtc actgaagttt tcttaataaa acaaatttgt  46680
gtcagtttct gtgttgttaa tgtatgttta tctgatttcc tttcttgatt ttattaattt  46740
atttatcttt ccttctctca ggcactttct cttctctccc ttctctttac ctcatcaaac  46800
aatttcttgc tttgatcttt aaatgtgtgt gtgtgtgtgt gtgtgtgtgt gtgtgtgctc  46860
tttggactgt gtttttgtta tgcctgtact gaaaagaggc gtggagctca aacacgtggt  46920
taaaaataac gtggatctca atgtcagtga caggaaaaaa aaacccatat gattccaaaa  46980
accttcagtc ctcatatgtt tcatgcaaca aatttggaaa aagggtgatt tagtgacaga  47040
attcatacca actcttcaag tgagtaactg tccaaaatta gatcttgtca agtgtcaaat  47100
ttaaatattg agtcatcttt gggaaatatt gagaagtgga gtaataaagg ttttaagaaa  47160
ataagagtga acctatctgc atttcaatat gatagctact cacttctggc agagtgagaa  47220
taaattttaa agggtatggc ctttagtagg tcacacacct gtaagtatgt actgtacaca  47280
aatacaactc caagcataat ttaaaatttt tttttaaaaa aatgagaaag tggaggaata  47340
aaaaaacagc tggaaggaat tagcgggaga aatggggatc aatattatca aaattcattt  47400
tgtatatgta tgaaattttc aaacacttaa taagattatt atatgcatta aaataacttt  47460
aagcatgttc agtgtggata agtcaatatg taaatgaggg actgaaaaag taacagaaaa  47520
caaaaattct gcatagaaat acttaatatc tggaaagaac acagatgtcc ctcaacagag  47580
gaatggatac agaaaatgta gtacatttac acaatggagt agtactcagc tattaaaaac  47640
```

-continued

```
aatgaattta tgaaattctt aggcaaatag atgtatctga aggatatcat cctgagtgag  47700
gtaacccaat cacaaaagaa gtcacttgat atgcactcac tgataagtgg atattagccc  47760
agaaacctag aatacccaag atgcaacttc caaaacacaa gaaaatctag aaggaagacc  47820
aactcatgga tacttcattc ctccctagaa tagggaataa aatatccatg aaaggacttg  47880
cagagacaaa gtttgaagct gagacaaaag gatggaccat ccagagactg ccccacccgg  47940
ggattaatcc cataatcagc caccaaatgc agacactatt gcatatgcca gcaagatttt  48000
gctgaaagga ccctgatata gctgtctcct gtgaggattt gccagtgcct ggcaaataca  48060
gaagtggatg ttcacagtca tttatagcac ggaacacagg gctcccaatg gaggagctac  48120
agaaagtacc caaggagcta aagggatctg caaccctata ggtggaacaa cattatgaac  48180
taaccagtac cccggagctc ttgtgtctag ctgcatatgt agcagaagat ggtctaattg  48240
gccatcactg ggaagagagg ccccttggtc tagcaaactt tatatgcccc agtacagggg  48300
aaagccaggg ccaagaagtg ggagtgagtg ggtagaggag cagggcgggg ggagggtata  48360
ggggactttt gggagagcat ttgaaatgta aatgaagaaa atatctaatt aaaatttttt  48420
taaaagaaag gcttcatata gactctgctc ttctatttac taaatactca aatagcccac  48480
tttacataag ctttatttaa aaccaaaacc agtcatcaaa cacaagatca aacacactct  48540
atccttgtct gtggaaaatg aagattgtca cctgagtttg acatcggaca ttcttcacac  48600
atttgctagg gcatgtgcat gccttcgctc acaggaacat atacacatat gcgcgcacac  48660
aggaattttt ttaaaacaca catttttctg gagaataatt tattcgtttg tttgttattt  48720
ggttggtttt ctggaggcaa gatgtcacta agtagctctg gctgtcctgg cactcactat  48780
gtagaacaga ctagacttga actcacacag atcaacctcc ctctgcttct acagtgccag  48840
gattaaaatg tatgcatccc catgcctgat taagaccatt gtattttcaa aacaaacttc  48900
acattcctgt gggaaatgct cacaagtata gctataaatg cagataaata gagtcattat  48960
ttttctgtat caacattggc tctggaacaa atgtttaaag agctgatcca aaaattagat  49020
ctcaggagga ggagtattgt tattttctaa aatgttcaga tttctgcttt acttttcaac  49080
tgtatgctga agtatctttt tttcacagca ttaaaatacc tttatttgta attagatttt  49140
aaaatactgt caaaaattat gccaggaaac aggaaggaca cagcttaccc tagagggaaa  49200
aacaataaat ccaagacaga tgatttcctc tacaagggtt tttcttggca aacagatata  49260
taagcagaac cagggcactc acagtagata gcaactgcac agacaggttg ggagtttaca  49320
aaaccaaaac ttgcattgtt gaggaaaggg aaatgacaca gaggagcata ttgactggag  49380
aatacccatt gtctgaattt tttttctctc ttttctgttg tgacatttac tacttagtaa  49440
cacagtaagc taaacaacca gtgccatggt aggcttgagt cagctctttc aggttcatgt  49500
ccatcaaaga tctacatctc tcccctggta gcttaagaga agccatggtg gttggtattt  49560
cctactgcca gacagctggt tgttaagtga atattttgaa gtcctaaaaa ttgtgttgaa  49620
ttttatagca ttatccatca ctttgcatta tttactttt tcaaaaaaat tgacaatctc  49680
atgactgcac ataatatatt ttgatcaatt ccactacatc ctctttaata ggacaatagg  49740
aggtgctgtt tgggttccta tagaggactg atctcacagg aggaagtatg ccactttgag  49800
gaattggatt tgaggtctca atgcaatgct tgtctacttt tctctgttta ccacttttgg  49860
atcaagatgt aatctcttag cttctggatc gagacagtgc catgataaag atggaaactc  49920
atacctccga aacagtgacc ttgaagaaaa acttccttct gtatgttgca ttttctactc  49980
taacaaattt acttttgtag tgctccaatg agtaactgac atatcaatta aaagtggggt  50040
```

-continued

```
taggggagac atactgactt gaataatttt tgcactatag tgtaggtttt gacaatttct  50100
acagtgtttt atatttcaga actgtgttcc tgagatgtgc gatatctcag gggtaatga  50160
tgactgagtt ttgtgaccta cttagtagga gaagaaagaa ccagtatcca ccagctatct  50220
tctgacctcc acacacatgc caaggtatgg gcatacccag tcccatgtac aaaataaatg  50280
ataaagtttt aacatgtatt atgcacaaat ccaaaattaa taaggacact tactacgtgt  50340
ataactgaaa cccaaagtaa ttgtaaaatc aagtatttca tatttctctt tcatgtgcag  50400
atggataaca gaagtcaaaa ctgtctttct ggctgtttta atataacata taattctatg  50460
caaaaaatac tgatactatc ttttaaaaag aaaaaaactg tatatgcata cattatttca  50520
tattaaacac tattaagaag aaatgagtgc aaacattgta tttcaaattt cagattaatg  50580
gattctgaca tgtggaaggg ttacatttcc caaatgtctc atcagcacag gttcctgaaa  50640
actggggaaa cccaggacta atgagatgga ttttcacata gaggtggata ctgccaagcc  50700
tgggtacctg agcccacaca cccatgaact caaaataatt tttaaaaaga agaaatttaa  50760
aatttaacta tatatattat gattatccaa taagctttct agatgtttct ttggttatat  50820
gtcataattg tcgtgattga caagctgtta aatttgagtg atgtttgtaa agaaataaca  50880
ataaattata tctatagaag caagacttca tctttaggat caagactgta tgctccatgt  50940
tatcacagct gtttaaccag acaaaggcta gaacctccag ttccacaaac aaatgtgaat  51000
tctactgtgt ccagtttact gccatgtttt tggtcatgtg aacaatgtgg tttgtgccaa  51060
cattagagca gagttcacaa gtgcattttg cctccccagt attgctgatg aatccatggt  51120
tcaggttcaa gggtgttgaa aacttgattg aaaatggtca gacttgatat tcttccagta  51180
tatctgattg gaggaactga taatagatat cagatttaaa cctctaccat tccagttaag  51240
ataatatgat agcatcttgt tcttcatctt cctttttctt aatagggaca taaaaccaat  51300
gaataaaaat atacctgaaa catgggatag gcactgggca ttggaaatga caataaaagt  51360
aaattttcca tccctagtaa agttctccag gaacctattt gtatactaaa tgacacaatg  51420
tcaatgtcag tgcacaactg ccaactggga tgcagaacac tgctcacgcc aaccatcctg  51480
aaagccaact ataaaaagca gagagatact ctgcaccttt tcagtgaggt ccagataccc  51540
acagagcaga gacagtcgct cacacatgga taaagtttta aacagagagg aatctttgca  51600
gctaatggac cttctaggtc ttgaaaggag tgcctggggg aatattcctc tgatgagaaa  51660
ggcatattta aaaaaatgca aggagtttca tcctgataaa ggaggagatg aagaaaaaat  51720
gaagaaaatg aatactctgt acaagaaaat ggaagatgga gtaaaatatg ctcatcaacc  51780
tgactttgga ggcttctggg atgcaactga ggtatttgct tcttccttaa atcctggtgt  51840
tgatgcaatg tactgcaaac aatggcctga gtgtgcaaag aaaatgtctg ctaactgcat  51900
atgcttgctg tgcttactga ggatgaagca tgaaaataga aaattataca ggaaagatcc  51960
acttgtgtgg gttgattgct actgcttcga ttgctttaga atgtggtttg gacttgatct  52020
ttgtgaagga accttacttc tgtggtgtga cataattgga caaactacct acagagattt  52080
aaagctctaa ggtaaatata aaatttttaa gtgtataatg tgttaaacta ctgattctaa  52140
ttgtttgtgt attttagatt ccaacctatg gaactgatga atgggagcag tggtggaatg  52200
cctttaatga ggaaaacctg ttttgctcag aagaaatgcc atctagtgat gatgaggcta  52260
ctgctgactc tcaacattct actcctccaa aaaagaagag aaaggtagaa gaccccaagg  52320
actttccttc agaattgcta agtttttga gtcatgctgt gtttagtaat agaactcttg  52380
```

-continued

```
cttgctttgc tatttacacc acaaaggaaa aagctgcact gctatacaag aaaattatgg  52440
aaaaatattc tgtaaccttt ataagtaggc ataacagtta taatcataac atactgtttt  52500
ttcttactcc acacaggcat agagtgtctg ctattaataa ctatgctcaa aaattgtgta  52560
cctttagctt tttaatttgt aaaggggtta ataaggaata tttgatgtat agtgccttga  52620
ctagagatcc attttctgtt attgaggaaa gtttgccagg tgggttaaag gagcatgatt  52680
ttaatccaga agaagcagag gaaactaaac aagtgtcctg gaagcttgta acagagtatg  52740
caatggaaac aaaatgtgat gatgtgttgt tattgcttgg gatgtacttg gaatttcagt  52800
acagttttga aatgtgttta aaatgtatta aaaaagaaca gcccagccac tataagtacc  52860
atgaaaagca ttatgcaaat gctgctatat ttgctgacag caaaaaccaa aaaaccatat  52920
gccaacaggc tgttgatact gttttagcta aaaagcgggt tgatagccta caattaacta  52980
gagaacaaat gttaacaaac agatttaatg atcttttgga taggatggat ataatgtttg  53040
gttctacagg ctctgctgac atagaagaat ggatggctgg agttgcttgg ctacactgtt  53100
tgttgcccaa aatggattca gtggtgtatg actttttaaa atgcatggtg tacaacattc  53160
ctaaaaaaag atactggctg tttaaaggac caattgatag tggtaaaact acattagcag  53220
ctgctttgct tgaattatgt ggggggaaag ctttaaatgt taatttgccc ttggacaggc  53280
tgaactttga gctaggagta gctattgacc agtttttagt agtttttgag gatgtaaagg  53340
gcactggagg ggagtccaga gatttgcctt caggtcaggg aattaataac ctggacaatt  53400
taagggatta tttggatggc agtgttaagg taaacttaga aaagaaacac ctaaataaaa  53460
gaactcaaat atttcccct ggaatagtca ccatgaatga gtacagtgtg cctaaaacac  53520
tgcaggccag atttgtaaaa caaatagatt ttaggcccaa agattattta aagcattgcc  53580
tggaacgcag tgagtttttg ttagaaaaga gaataattca aagtggcatt gctttgcttc  53640
ttatgttaat ttggtacaga cctgtggctg agtttgctca aagtattcag agcagaattg  53700
tggagtggaa agagagattg gacaaagagt ttagtttgtc agtgtatcaa aaaatgaagt  53760
ttaatgtggc tatgggaatt ggagttttag attggctaag aaacagtgat gatgatgatg  53820
aagacagcca ggaaaatgct gataaaaatg aagatggtgg ggagaagaac atggaagact  53880
cagggcatga aacaggcatt gattcacagt cccaaggctc atttcaggcc cctcagtcct  53940
cacagtctgt tcatgatcat aatcagccat accacatttg tagaggtttt acttgcttta  54000
aaaaacctcc cacacctccc cctgaacctg aaacagaggg cagaggaagt ctgctaacat  54060
gcggtgacgt cgaggagaat cctggcccca tggaagatgc caaaaacatt aagaagggcc  54120
cagcgccatt ctacccactc gaagacggga ccgccggcga gcagctgcac aaagccatga  54180
agcgctacgc cctggtgccc ggcaccatcg cctttaccga cgcacatatc gaggtggaca  54240
ttacctacgc cgagtacttc gagatgagcg ttcggctggc agaagctatg aagcgctatg  54300
ggctgaatac aaaccatcgg atcgtggtgt gcagcgagaa tagcttgcag ttcttcatgc  54360
ccgtgttggg tgccctgttc atcggtgtgg ctgtggcccc agctaacgac atctacaacg  54420
agcgcgagct gctgaacagc atgggcatca gccagcccac cgtcgtattc gtgagcaaga  54480
aagggctgca aaagatcctc aacgtgcaaa agaagctacc gatcatacaa aagatcatca  54540
tcatggatag caagaccgac taccagggct tccaaagcat gtacaccttc gtgacttccc  54600
atttgccacc cggcttcaac gagtacgact tcgtgcccga gagcttcgac cgggacaaaa  54660
ccatcgccct gatcatgaac agtagtggca gtaccggatt gcccaagggc gtagccctac  54720
cgcaccgcac cgcttgtgtc cgattcagtc atgcccgcga ccccatcttc ggcaaccaga  54780
```

-continued tcatccccga caccgctatc ctcagcgtgg tgccatttca ccacggcttc ggcatgttca 54840
ccacgctggg ctacttgatc tgcggctttc gggtcgtgct catgtaccgc ttcgaggagg 54900
agctattctt gcgcagcttg caagactata agattcaatc tgccctgctg gtgcccacac 54960
tatttagctt cttcgctaag agcactctca tcgacaagta cgacctaagc aacttgcacg 55020
agatcgccag cggcggggcg ccgctcagca aggaggtagg tgaggccgtg gccaaacgct 55080
tccacctacc aggcatccgc cagggctacg gcctgacaga aacaaccagc gccattctga 55140
tcacccccga aggggacgac aagcctggcg cagtaggcaa ggtggtgccc ttcttcgagg 55200
ctaaggtggt ggacttggac accggtaaga cactgggtgt gaaccagcgc ggcgagctgt 55260
gcgtccgtgg ccccatgatc atgagcggct acgttaacaa ccccgaggct acaaacgctc 55320
tcatcgacaa ggacggctgg ctgcacagcg gcgacatcgc ctactgggac gaggacgagc 55380
acttcttcat cgtggaccgg ctgaagagcc tgatcaaata caagggctac caggtagccc 55440
cagccgaact ggagagcatc ctgctgcaac accccaacat cttcgacgcc ggggtcgccg 55500
gcctgcccga cgacgatgcc ggcgagctgc ccgccgcagt cgtcgtgctg gaacacggta 55560
aaaccatgac cgagaaggag atcgtggact atgtggccag ccaggttaca accgccaaga 55620
agctgcgcgg tggtgttgtg ttcgtggacg aggtgcctaa aggactgacc ggcaagttgg 55680
acgcccgcaa gatccgcgag attctcatta aggccaagaa gggcggcaag atcgccgtgt 55740
aataattcta gagtcggggc ggccggccgc ttcgagcaga catgataaga tacattgatg 55800
agtttggaca aaccacaact agaatgcagt gaaaaaaatg ctttatttgt gaaatttgtg 55860
atgctattgc tttatttgta accattataa gctgcaataa acaagttaac aacaacaatt 55920
gcattcattt tatgtttcag gttcaggggg aggtgtggga ggttttttaa agcaagtaaa 55980
acctctacaa atgtggtact cgagataact tcgtataatg tatgctatac gaagttatat 56040
gcatggcctc cgcgccgggt tttggcgcct cccgcgggcg cccccctcct cacggcgagc 56100
gctgccacgt cagacgaagg gcgcagcgag cgtcctgatc cttccgcccg gacgctcagg 56160
acagcggccc gctgctcata agactcggcc ttagaacccc agtatcagca gaaggacatt 56220
ttaggacggg acttgggtga ctctagggca ctggttttct ttccagagag cggaacaggc 56280
gaggaaaagt agtcccttct cggcgattct gcggagggat ctccgtgggg cggtgaacgc 56340
cgatgattat ataaggacgc gccgggtgtg gcacagctag ttccgtcgca gccgggattt 56400
gggtcgcggt tcttgtttgt ggatcgctgt gatcgtcact tggtgagtag cgggctgctg 56460
ggctggccgg ggctttcgtg gccgccgggc cgctcggtgg gacggaagcg tgtggagaga 56520
ccgccaaggg ctgtagtctg ggtccgcgag caaggttgcc ctgaactggg ggttgggggg 56580
agcgcagcaa aatggcggct gttcccgagt cttgaatgga agacgcttgt gaggcgggct 56640
gtgaggtcgt tgaaacaagg tgggggggcat ggtgggcggc aagaacccaa ggtcttgagg 56700
ccttcgctaa tgcgggaaag ctcttattcg ggtgagatgg gctggggcac catctgggga 56760
ccctgacgtg aagtttgtca ctgactggag aactcggttt gtcgtctgtt gcgggggcgg 56820
cagttatggc ggtgccgttg ggcagtgcac ccgtaccttt gggagcgcgc gccctcgtcg 56880
tgtcgtgacg tcacccgttc tgttggctta taatgcaggg tggggccacc tgccggtagg 56940
tgtgcggtag gcttttctcc gtcgcaggac gcagggttcg ggcctagggt aggctctcct 57000
gaatcgacag gcgccggacc tctggtgagg ggagggataa gtgaggcgtc agtttctttg 57060
gtcggtttta tgtacctatc ttcttaagta gctgaagctc cggttttgaa ctatgcgctc 57120

-continued

```
ggggttggcg agtgtgtttt gtgaagtttt ttaggcacct tttgaaatgt aatcatttgg  57180
gtcaatatgt aattttcagt gttagactag taaattgtcc gctaaattct ggccgttttt  57240
ggcttttttg ttagacgtgt tgacaattaa tcatcggcat agtatatcgg catagtataa  57300
tacgacaagg tgaggaacta aaccatggga tcggccattg aacaagatgg attgcacgca  57360
ggttctccgg ccgcttgggt ggagaggcta ttcggctatg actgggcaca acagacaatc  57420
ggctgctctg atgccgccgt gttccggctg tcagcgcagg ggcgcccggt tctttttgtc  57480
aagaccgacc tgtccggtgc cctgaatgaa ctgcaggacg aggcagcgcg gctatcgtgg  57540
ctggccacga cgggcgttcc ttgcgcagct gtgctcgacg ttgtcactga agcgggaagg  57600
gactggctgc tattgggcga agtgccgggg caggatctcc tgtcatctca ccttgctcct  57660
gccgagaaag tatccatcat ggctgatgca atgcggcggc tgcatacgct tgatccggct  57720
acctgcccat tcgaccacca agcgaaacat cgcatcgagc gagcacgtac tcggatggaa  57780
gccggtcttg tcgatcagga tgatctggac gaagagcatc aggggctcgc gccagccgaa  57840
ctgttcgcca ggctcaaggc gcgcatgccc gacggcgatg atctcgtcgt gacccatggc  57900
gatgcctgct tgccgaatat catggtggaa aatggccgct tttctggatt catcgactgt  57960
ggccggctgg gtgtggcgga ccgctatcag gacatagcgt tggctacccg tgatattgct  58020
gaagagcttg gcggcgaatg ggctgaccgc ttcctcgtgc tttacggtat cgccgctccc  58080
gattcgcagc gcatcgcctt ctatcgcctt cttgacgagt tcttctgagg ggatccgctg  58140
taagtctgca gaaattgatg atctattaaa caataaagat gtccactaaa atggaagttt  58200
ttcctgtcat actttgttaa gaagggtgag aacagagtac ctacattttg aatggaagga  58260
ttggagctac gggggtgggg gtggggtggg attagataaa tgcctgctct ttactgaagg  58320
ctctttacta ttgctttatg ataatgtttc atagttggat atcataattt aaacaagcaa  58380
aaccaaatta agggccagct cattcctccc actcatgatc tatagatcta tagatctctc  58440
gtgggatcat tgtttttctc ttgattccca ctttgtggtt ctaagtactg tggtttccaa  58500
atgtgtcagt ttcatagcct gaagaacgag atcagcagcc tctgttccac atacacttca  58560
ttctcagtat tgttttgcca agttctaatt ccatcagacc tcgacctgca gcccctagat  58620
aacttcgtat aatgtatgct atacgaagtt atgctagcta gtgactcaac aagatcagga  58680
ttaggtgagt caaagcacat taattttata tcttgaagtt ttaattttaa ttttatttta  58740
atatttaagt tattaatatt taatatttaa agtaaataat attttatttg ttctttatcc  58800
ttttcatata tttatataat gtatatttat ctttcatact tccacacacc tcatccaagc  58860
aacacatctc cctctatact tcatggcttt taaattttat tattatttat tattattatt  58920
acctcaatga atccaattgg tgctatttct gaatagggta tgtcaattcc tggaggcatg  58980
agtaatgtaa tataccaggg ctattatgta atataaaaaa atggactgca gggagctggt  59040
ggcacatgca tttaacctag cgctcaagag gcagaagcaa gcatatgtct gcgttttaga  59100
taaccctagt ctacagagtg agttccagga cagcaagggc tactcagaga aaccctgtct  59160
cataaaacca aaaagtatat tttttaaagg cagaagagga aaggagggag ggagggaggg  59220
aaagaggcag acagacagac aggcaggcag gcaggcaaaa agaaggaaaa agaaaaatat  59280
ggaccctccc tctcccagaa actatcaact ggcaatagct ctttggtggg gggggggggt  59340
cctgaatccc tctctgctca attctagaat gttaattagc ttgatctgac cagggtcttg  59400
tgcagaacac cacagttgct gtgagttcat gattgtaaca gatctgtcat gttcagaaaa  59460
cagaatttta tggctctact ccccatccag atgataattg atggctaagc atccacagtc  59520
```

acttgtcctc atcctttgac cagctacaaa tttctgcaca aaccactccc cactgtaaaa 59580
agttgagcag aagtcaaaca tggaggcaca caccccttaat cccaacactt gggaggcacg 59640
ggtagatgaa tctctgtgag tatcaagcca gcctgatcta catactgagc tccagaagat 59700
ccaggtacat agtctctatc taaacaaaca aacacaaagt taaaaagttg atttgaccaa 59760
aattgagaga agcataaatc tatgagtatt tttaagaccg tggcttggaa acatgacagt 59820
tcatcaccac tggtctcctt cataggctcc atgagctcca ttgtcacagg cttttgactc 59880
gaattacaat agaaacccac ccttacccct gttcttccat agatatgaag ttccttccat 59940
ggagctggca tgaaatttaa tcagagagtg cttggctccc caatacagcc tttattgcac 60000
cagtggacgc aaggatgatt ttatagtgtg ttggggaagc atggtgacat cactgacatc 60060
ttatcccaca tacacagcct attaagtaca tctaagcact gtgaacgagt ttcctagtcc 60120
atttgacatc gatttcttga tgccctacag ccacagcatt tggtgtcttc agcaatagtg 60180
ccctaccatt tagatatggt gtatagtcaa gagatatggc aatagccaag ttattttggt 60240
tattccaagg cttccttcca ttaataaata tcatggtggt acccccatga ctaaaaatta 60300
gattttcact gaataaacca tgtcttctgg gaacagcatt ataccattgc agggatcctc 60360
tgctgaaact tttttaatac tatattttta cttagcttac aaactagtgg atttctgtaa 60420
gacttcattt accttcagtt tcagttgacc ctcccctacc ctgttcttcc ctatgcccaa 60480
acacatccac acctactcct ctagcccaca gctctcactt tctaatcttc cctgtcacca 60540
gtgcccaatt atatcgcctg tattattata ttttaatcac acaaccatag gtttccatat 60600
gaggttttaa taacccttca ttctggttaa accttccacc acaccctgat ttccccattc 60660
cacaaccaac tccatgatta agccttcctg ccccaagtat tcttctttat acttcatttt 60720
aatggcatta catttgatgg acccacttcc ttgatggacc caattcaaac cagtttctaa 60780
ttacctggat tccttacata ctccatatta tgcatacaaa ataaaagatt caagtctaat 60840
gtccacatgt gagatagaat gtgcagtttg tctttctgag cctgagtggc ctcattaagt 60900
ataataattt ccagttcctt ctatttactt ggaaatttca tattttcatt gttctctatg 60960
gctgagtaat attccatctt atacattaca ttttccttat ccattcatta gttgatgaac 61020
agttgggtca acttcgtttc ttagctatta tgaacttaac ctcagtgagc atggacattc 61080
aaaggtctct gtaacagaat ataaacccct ttgtgtacat atctagaaat ggaggaacta 61140
gagaaagcac ccaaggaact aaagggaact gcaaccctat aggtggaaca acaatatgaa 61200
ctaagcagta ccccggagct cttgtctcta gctgcatatc tatcaaaaga tggcctagtc 61260
ggccatcact gcaaagagag gcccattgga cttgcaaact ttatatgccc cagtacaggg 61320
gaatgccagg gccaaaaagg ggggatgggt gggtagggga gtgggggggg gttggggact 61380
ttttgtatag cattggaaat gtaaatgagc taaataccta ataaaaaatg gaaaaaaaaa 61440
gaaatggtgt aactgagtca catgggaagt ctttttctaa tctttggatt tgtttatttg 61500
atgttcatag tttttgggtt ttggttggtt ttgttctaag ttctttgtat attgtagaca 61560
ctaatcctcc atcacatgtg tagttggcaa agatctccat tccccgagat acctgtgcat 61620
ttaattgaca gcttcctttg ccgtagtttt taattccatg atatctgaca agtgtttgtc 61680
ttactttctt gctacaagaa tcctattcaa agaatccata cctgtgtcta tggttaacac 61740
acactccatg ctttcttctc tatcagcttc aggttaccat gtcttatgac acggtctttg 61800
aatcatttgg agttgaggtt tttttcaagg tgacagggaa gagcccaggt tcatttctct 61860

-continued

```
gtatcctgat gtccactttt tcctattcgg tctatttatg gaattatata tttttatgtt  61920
aggtcatttt tcagtggagg cattaacaat atccagaagg ggactatttc ttactagtgt  61980
tgagatggta ttctcctata tggggctggt actgaaggca gcaagttcta cccctagtct  62040
tcctgtgaga ttcaactact atctgggacc tcgagtgaga ctctgtctgt aggatacatg  62100
gggcttggta aactccaatg tgaaacaaaa aatatataat tttagtttag attcatagaa  62160
actacatcct caaataaaca cataagttct aaaaagtacc aatttaggtc ttgatataag  62220
atcatttgtc atataaaaat tttccatata aggaaaattt ccatacaaag ttcatgtata  62280
tttccaaata tacaaaattc tgtaaaatgt ttttgcatga tacatcttgt cattgtttgc  62340
ctctttaatg gcttgtattt gtttcatttt ctactctcat caaatatcat gtattactat  62400
cctaaatata tgaaataatt ctgttccagc attacagatg acatcaggaa ttttccagta  62460
tatttttcct ggaacctgaa acatcaatat gaagatgaag caatcttgtc tctcagatca  62520
tattttccta tttattgcaa attacaattc ctgtctctgt actttctctt tcactcattg  62580
tttcccatgt tctaatcggt attagtgcat ctttgaatgt ttaaataaat ttattttact  62640
tgcatacgtg ttgttaaaag gggaagctaa agtacaatgc acataaatac ctatttgact  62700
ttttttaaag gagaggaggg ttggaggggt ggcatgtgat tgctcacgcc tgtaatttca  62760
gcaccgggga aagaggtaga gacagttgaa tcctctgatg tcaccagtag ccagcctaga  62820
ctacatgaaa tattgcaggc cagtgagaga tcatcccaga aaacaaggca gggacatgac  62880
aggcagctca gtggtcaaga gcactagctg ctcttccaca ggacctgggt tatattccta  62940
acactcacat gacaactcac aactttctgt aattccagtt cccagggatt tgacatatat  63000
atggacaacc atgcaagcaa aacaccaatg cacataaaat tttaaaaaac taattcaatt  63060
aaggcagatg tgaatgaagg atgccacctg acataatcct gtggcactca acatttacat  63120
gcacacactt gtgtccatga acacaagtgc aaaaatacag agagagagag agagagagag  63180
agagagagag agagagagag agagagaaca tacaccaaag agtctcatca ttcctacatg  63240
ttacaaactc caatattgta attttgactt tagaaaggaa ggtaaaatat tatattggtt  63300
gtttaaagta aacatttaaa aactttgtag cagaaaatgg cctagttggc catcattggt  63360
aggagaggcc ctttgtcttg caaagattat atgccccagt acaggggaat gccagggcca  63420
ataagcagaa gtgggtgggt tgggaagcag ggtggggaag tgtataggga actttcagga  63480
tagcatttga aatgtaaatg aacaaaatat ctaataaaaa aaaagctttg tgtgctagta  63540
gtttgtcaac ctgacacagg ccatagtcat ttgggaaagg agacactcaa gaaaatacct  63600
ccaccaggtt caactgtgga gcatttcttg actggtagtc aatgtgaggg caggtcctac  63660
tcactgtgga aaacactgcc aagcaaacca tgaggaacca gacagtaagc agaactcttc  63720
catagcctct gtatcagttt ctgcctccaa gtctctgcct tgacttcccc aaggtgataa  63780
gctacaagtg gtcagatgaa ataaaccctt ttctccctaa gatgcttttg gccatggagt  63840
tcacaaaagc aatagaaacc ctaagacaca gagtaatgtt gaagagctta gatcacaaat  63900
catatcttaa agttgaaaga aaccacccca cacacttgta tgcatatata caaattcaca  63960
tgtggacaaa catacatata tactcaaacc atacatgtat gtatatttaa aaatttgaaa  64020
tgtcacagga agaattattt tgtagtcttt gaactacttt gatttattta ctttaaccac  64080
ttgcctgcta ttgttgggtt caatggtcat gctttcataa tgccttctaa atattaattt  64140
gcatctctgg accaggatca tgctcaactt ttgtcagaga agcttgtttt tgtggtgaga  64200
tgaatgttat gacactgaag tttttgcatc acgttctgac atatgtctat ccacctacca  64260
```

tttgatcacc cactacgtgt gtgtgtgtgt gtgtgtgtgt gtgtgtgtgt gtgtgtgtgt 64320
gtgtgtgtga tttgaatgag aacagccccc gtaggctcat agatttgatt gcttgatcac 64380
taaggagtag cactatttga aaggataagg agatgtggac ttggaggaag tgagtcactg 64440
aggatgagct ttgtggtttc aagagcccaa gccagaccct gcttcctcat cctacttgct 64500
atggactcag atgtaaaaat ctccactcct tcagcaccat gtctgcctgt gtgctaccat 64560
gccaaaaaat ggaataaatc tctgacactg tgtgaccctc cctgccccga gaattgttga 64620
cctatattgg tccatgagga gcagagacaa tggggaaaga gcaggggctt agaaaccctg 64680
tatgtatggt aataacgata cacagggacc agcttcagag agacaggtca agtttacttg 64740
tggtgattca agggtgatat agttgtctta gttagggttt ctattgctgt ggggagaaac 64800
catggccaaa aacacaaatg aggaggaaaa ggtttattgg gcttacactt ccacagcact 64860
aattatcatt gaagaaagtc aaggcagaaa ctcaaaccag acaagaaccc agaggcaata 64920
gctgatgcag aaaccatgga agggtaatgc ttacatatta ctcatggctt attcagcttg 64980
cattagcttt ttattattat taatcattcc attagtttac atctcaaatg atatctcact 65040
ttcaggttaa cccctccacc aatccccatg aataataacc caattcctgg atacccctcc 65100
attgaccccc atcccacatc caccctccac cttccccttt gcttgtatga gatttctccc 65160
ccatccactc acattctctg aacccactgc tccagcatcc acctacactg gtgcatcacc 65220
cctcccattg ctgtcaggca aggccatcct ctgctacata tgtatctgga gccatggatc 65280
catccaggca cactccttgg ttggttgtct agattctgga aaaactaggt gatcaggcca 65340
gcctaagttg ttattccatt ggggtagcaa ttcccttctg ttcctccagt tcttctgcca 65400
gctcccccac caggttccct gagctcagtc tgatggttgg ctctaagcat ccacatctgc 65460
attggtcagt tgctagccag acttcccaag gaactgccac accaggttcc tgtcagcaag 65520
cacctcttga ccatggcaac agtgttaggt ttggtgtctg cagacagggt ggatctccag 65580
gtggagcttt ccccaaatgg cacttccttc agtctctgtt caatttttttg tccctgttct 65640
tcttttggat aggaacattt atgggttgaa aatttgagat gggtgggtag cttcatccct 65700
tgacctggag ctgtgcctat ctattggagg tggtctcttc aggttctgtc tccccccttct 65760
ctgtgcattt ctgctaatgt catctccttt gggtcctggt agcctcatgt ttccctggtg 65820
tctgtgaccc tccagtgact gtccccagtt cctcatttct tactgctaca tattttttgt 65880
tcgatatctt gaccttctgt atctctttga catctcctcc agttcctgat acttccctcc 65940
ttatttcctc accctcctct ctccctccca ggtcttcctc taatagaaca aaaaatgggg 66000
aagagactca aatacttggg cacagaagaa aactccctga agataacacc aatgtgttat 66060
gctttaagat caattgacaa atgggacctc agaaaatgaa aaagcttctg taaggcaaag 66120
gacactgtca ataggacaaa acagtcaccc acagattggg aaaaaatctt taccaaccct 66180
acatctgata gagggctaat atccaatata tacaaagaac ttaggagtta aactccagag 66240
aatcaaataa ctctactaaa aaatgagata aacagagaat tcatgactaa agaaacttga 66300
gtggccaaga agctcctaaa gaaatgttca ccatttgtag tcatcaggta aatgcaaatg 66360
aaaacaaccc tgagttccta ccccacacca gtcagaatgg ctaagatcaa aaactcaaat 66420
gacagcagat gctggtgagg atgtggaata agatgaacac tcctccattg atggtggggt 66480
tgcaagctgg tacaaccact ctggaaatca gactggtggt ttctcagaaa attggacata 66540
gtactacctg aggacctagc tataccactc caggaagtat acccagaaaa tgctccaaca 66600

-continued

```
tgtaataaag acacatgctc cactatgttc atagcagtca tatttataat agccagaagc  66660
tggaaacaac ctagatgtcc ctcaacagag gaatagatac agaaaatgtg atatatttac  66720
acaatggagt actatgcata gatttaaaac aatgacttca tggaattcac aggcaaatgg  66780
atagaactag aaaatatcat tctgagtgag gtaatcaaga cacaagggaa cacacatggt  66840
atgtactcac taataagtgg atattaacgc aaaagctcac aattgccata atacaatcca  66900
tagaccatat ggagcataga aagaaagacc aggatgtgga tgcttcagtc ttgcattgag  66960
gggggatcag cttgcattct taagaaaccc aagactatca gcccaagggt aacaccactc  67020
agaatgggct ggtccctcac ccatcaatca ctaattaaaa aattgcccta caggcctatt  67080
gaggcacttt catttttttc ttttttttatt agatattttc ttcatttaca tttcaaatgc  67140
tatccactat accctccccc caaccctgct ccccaaccta cccactcctg cttcctggtc  67200
ctggcattcc cctgtactgg ggcatatgat ccccgcaaga ccaagggttg aggcactttc  67260
ttaattgggc ttcctttctc tcatatgact accacttgtg tcaagatgac ataaaactat  67320
gcaacacaga cagtatatac atatgtatta tctatcatct agaaattcat catctatgca  67380
ttcatcatat atctatccat catctatcaa tacatcattt gtttatccat catttatcta  67440
tgtatcatct attgtcgctc tgttcaccct ctacccatct atctattaaa aaattaactt  67500
gatcagggcc atagtgacac aaacttttaa tcccagaatt tgggaggcag aatacggcta  67560
gcctgatcta catacagagt aagctccagg atagccagag ctacacagga aaaggttgtc  67620
tcaaaacaac aaaaaataaa ttaatgtgta taatgatcaa ggaagacact taacataaat  67680
ttcatcatct atgggaatcc atgaacctgc acacataaaa acgtatgttt actgaatata  67740
catacacctg gagtatttaa tttctgaagt acactagtga aatgtcccat ctatccacac  67800
aactctaggg atctgggtta aattcctggg acacaagtaa atgagggagg ggggagaaca  67860
gagtctccaa aagtgtcccc tgaagtccat acatgtgctg gctatggtgt atacacccac  67920
tcctagacat gcacaataat aaataacttt cctaaataca gaagaatcta attacctcaa  67980
aaagagatct ttattacaga tttgttcaaa tgctagacta taaaagttta ctcagatagc  68040
atgtaacttt ttgatatcct gttgttcttt tctcaacata ccagagatga acataaaaaa  68100
gaggtatgtt ttcctctttt ttgaatatat atttaattgg ttgtattgat gacacaagat  68160
tccaatacac ctgatcatgt atgacatatt agtttctttt ggccaactac ttggcataaa  68220
cagtttgaga aaggaagtgc tgattcactc atgatttaag atagtgtaca gcccatcata  68280
gtgggacaga aactggggca tgtaggccta ctctgtgaca caccattaag aaatatcact  68340
gactgtccct actgcaaaag ccattactcc tccatagtgc ctcagttagg agtagaccta  68400
taagtgacat ccataactat gcatatatat taatcatctc tttattgatt atttcatcta  68460
tgcatgcatc caaccatgca tctatctatc tatctaatct attacctatc tatctatcaa  68520
tctatcaatc tacccatcat ctattatcaa ttgatctatc ttatagtgat atatcatttc  68580
attctctata atctacccac ttataatcta tcacatattc ttccatcatc tatatcaatc  68640
catcatctgt ctatcatcta atcagtcttt ttttcacctg tcatctacca atatgtttcc  68700
tttactacta tcatgttcta tattgtgaca cagcctcact aagaagccca gaaacttact  68760
ttacaacact agctggactt gagttccatg atcccacatt ctcagactta caagtatatg  68820
tgattacata gataaataga taggtttata ggtaggtagg taggtaggta ggtaggtagg  68880
taggtaggta gatagataga tagatagata gatagataga tagatagata gatagataga  68940
taaatagaaa gaaatatatg tgatagattc ataattgata gatgattgat agatcaattg  69000
```

-continued

```
agagacagat aagtacatat ataagaagat agatggatag agagatatca atacagaatg  69060
tatagataga aatagataca tatagatgat atagatagat taattagatt gataaacaca  69120
gaatatacat agatgcttat atagatggta gtagatgtat agataacagg tggagagtta  69180
gatgatagat tttatgttag acaagcatat gatatctata aacatatgtg tctatgttat  69240
gtagataggt aatagattaa tgatacacaa ataaatggtt gatatatgga tgagtgaatg  69300
gatagatata tccataagta tatttcagta tatattaaac tgaaatattt ctattgatat  69360
atgaacatat atacttttta taagtatact aatatgtttg taaatattta gatatctgat  69420
gtatatacat gtctatctta tatatagatg tcatcttcct atctatacct catatatcaa  69480
taatctgtca tctacctatg ttataactca ttaacccagt taatcataca caaattcaac  69540
taaaataaat tcttcctctt tttattggat attttattta tttacatttc aaaagttatc  69600
cctcttcctg gttttgcctc tgaaaacccc tatcccatct gccctccccc tgcatctatg  69660
agggtactcc ccaacccacc caccctccca ctcccacctc accaccttgg cattctccta  69720
cactggtgca cctagccttc acaggaccaa gggcctctcc tcccatgatg ccagataagg  69780
ccatcctctc ctacatatgc agctggagcc ttgcaaaccc cttcaattcc ttcagtcctt  69840
tccctaattc ctccattggg gtccctgtgc tcagtctaat caatgattgg ctgctagaat  69900
ccatatctgt atttgtcaga ctctgtcaga gcctctcagg agacagccat accagggtcc  69960
tgtgagcaag cacttcttgg cataggctgg gtttggtgtc tatatatggg atggataccc  70020
atctctagat ggtctttact tcagcctctg ctccacactt tgtccccata ttccctttag  70080
acaggagaaa ttctgggtta aaattttaga gataagtggg tggccatatc ccccaactag  70140
gggccttgcc tatcctctgg ttatggcctc tacaggtcct ccctccactt tgttgggcat  70200
tttagctact catctccact gggtcctggg agtctcttgc tttcctggca tctgagacat  70260
taaggtagct attcccagtt cgccatcccc cattgctaga cacctctctt caatttcctg  70320
accctctgtg tatcataccc atctccttcc atacctgatc ctgtccccct ttattgtgtc  70380
tcctttctct cttcctccta agtcctttgc accctctacc tcctgtattt tgttccccat  70440
tctaaagagg actaaagtat ccacacttgc tcttccttct tcttgagcct catatggtct  70500
gtgagttgta gcatgggtat tctgagcttt ttacctaata tccacctatc agtgagtaca  70560
tatcatgtga ccatgtatgt tcttttgtga ctgagttacc tcactcagga tgatattttc  70620
tacttccatc catttactta cgaatttcat aaagtcgttg ttttaatagc tgagtagtac  70680
tccattgtgt aaatgtccca cattttctgt atccattcct ttgttgaagg gcatctgggt  70740
tatttccagc ttctggctgt tataaatatg tctgctatga acatagtgaa gcacgtgtcc  70800
atataaatatg ttggagcatc ttttgggtat atgcacagga gtggtatagc tgggtcagca  70860
ggtagcacta tctccagttt tctgaggaat agccagactg atttccagag tagttgtacc  70920
agtttgtaat tccaccagcg ttgggagagt attcctcttt atccatatcc acaccagcat  70980
ctgctgtgac ctgaggtttt gttcttagcc attctgcctg gtgtgaggtg gaatctcaag  71040
gtcattttga tttgcatttc ccagatgatt aatgatgttc aatatttctt aaggtgtttc  71100
ttggccattc gagactactc agttgataat tttctcttta tctcactacc caattttaat  71160
agggttattt gattctcagg actctaactt cttgaatctt tgtatatatt ggatattatt  71220
cctctattgg atgtaggatt ggtaaagatc tttcccaatc tgttggttgc cattttgacc  71280
tattgacagt gccctttacc ttatgctttg caattttatg aggagtgtaa aatattatgg  71340
```

-continued

```
agtgtaaaaa tgtgaattaa aaataaaatt taaaaaagtc taaatttttt agtctctttc  71400
tctatttctt ccctgcccat gttatcattg agtagagagt tgttcagctt ccattcctat  71460
gtgagctttc tgttgatttt gttgttattg aagaccagcc ttagtcggtg gtgatctgat  71520
aggatgcata ggattatttc aatcttcttg tatctattga cacctgtttt gtgacctatt  71580
atgtggtcaa ttttggggaa ggtactatga ggtgctgaga agaaggtata ttcttttgtt  71640
ttaggatgaa atgttctata gatatctgtt aaatccattt ggttcataac ttctgttagt  71700
ttcactatgt ctctgtttgg tttctgtttt catgatctgt caattgctaa aagtggggtg  71760
ttgaagtctc ccagtattat tgtgtgagtt tcaatgtgtg ctttgagctt tagcaaagtt  71820
tcttttatga atgtgggtgc ccttgcattt ggaacataga tgttcagaat tgagggttca  71880
ttttggtaga ttttttcctt tgatgtgtat gaatgttatc tttttgata actcttggtt  71940
gaaagtcgat tttatttgct attagcttgt ttctttggac cattttcttg gaaaattgtt  72000
ttccagcctt ttactctgag atagtgtttg tctttgtcac tgaagtgcat ttccagtata  72060
ctgcaaaatg ctgggtcttg tttacatatc cagtctgtta gtctatgtct tgttattgga  72120
gaaatgagcc aattgatgtt aagagatatt aaggaagagt ggctgttgct tattgttgtt  72180
tttcttgttg gaggtggaat tatgtttgtg tgtctatctt cttttgggtt tgttgaaaga  72240
agattacttt cttgcttttc ctagttataa tttccctaca tgtgttggtg ttttccacaa  72300
attatccttt gtaggactga acttgtggaa agatgttgtg taaatttggt tttgtcatgg  72360
aatacttggg tttctccatc taccgtaatt gagagttttg ctgggtatag tagcctgggc  72420
tggcatttgc attctctttg ggtctgtata acatctgtcc atgatcttct gactttcata  72480
gtatctggtg agaagtctgg tgtaattctg ataggtctgt ttttatatgt tacttgacct  72540
ttttgcctta ctgcttttaa tattctttct ttgttttgtg catttggtgt tttgactata  72600
atgtaagaga aggaatttct tttctggtcc agtctatttg gagttctgtg gtcttcttgt  72660
atgttcatgg acatctcttt ctttaggata gggaagtttc cttgtataat tttgttgaag  72720
atatttactg gcacatttag ttaggaatct tcagtctctt ctatacctat tatccttagg  72780
tgtggtcttc tctttgtgtc ctggatttcc tggatgtttt ggattaggag ctttttacat  72840
tttgcatttt gcattttctt tgactgttgc ataaatgttt tctatgctat cttctgcccc  72900
tgagattcta tctcttgtat tttcttggtg atgcttgcat ctatgactcc tgatttattt  72960
cctaggtttt ctatctccag agttgtctcc ctttgtgatt tctttattgt ttctatttcc  73020
atttttagat cctgggtggt tttgttcaat cccttcacct ctttggttat gttttcctgc  73080
aattctttaa gggattttttg tgtttcttct taaagggctt ttacctgatt acctctgttc  73140
tcctgtattt ctttaagtga gttatttatg tccttcttaa agtcctctat catcatcctg  73200
agatgtgatt ttaaatcata atcttgcttt tctgatgtgt tggggtatcc agggtttctg  73260
atgactccaa gtagccttgg tttctgttgc ttatgttctt atgcttacct cttgccatct  73320
ggttgtctct ggtgttagct gaacttgttc tctctgaatg gatcttatcc ctcctatgag  73380
cttgtgagcc tgtgatctta ggtctatcag cactcctcag agaccagttc tttctgggtg  73440
gggtttgggt aaggagaact gtagcacagg gttatctcag gggcacagat ggaaaccaga  73500
agctaagttc ttcctcttat atctgcgcct caacataccc acatcacctt gaacctttcc  73560
taaatatacc atcatgattt atcccattcc agtagttgct ttacactata tatttatttc  73620
aattttatcc tggagctatg tatagcaata aagtcaattt ggcaagagag ttcactgaca  73680
tcttttattt aaaatgtgca tagaaccctc taaaattggc tgcttaatat ggtttttgat  73740
```

-continued

```
ttggtttgat tttgattttt tttttttttt ttttggagac agggtttctc tgtgtagccc  73800
tggccttcct gaaccaggct gggcttggac tcagaaatct gcctgcctct gcctctgttg  73860
gaattaaatg tatgtgctac gaccacctgg caagataata tgtatttaac tcagtctgaa  73920
acttcttata atctactgtt cctgtattac ctggaaccaa cctccctagg caccattgac  73980
catgtgttgt gaggattaat tcttcactaa acattaattt agtatcacaa gtatgtttta  74040
catttttttc taaaagtgtc aaatcacttt acaccacttt ccaaactgct tcataattta  74100
gtttgttttt atttaattct gtgcacactt gcaaacaaaa gctttcaagg atttcgtcag  74160
agttgaaaaa tctgtatttg tagattttta tttgcatttt tgcaaaactg cataaattaa  74220
tatttgcatt ttatgactac aagcgagcct gataaatttt gctactaaca cacattctga  74280
tatgtttctg tgttaagtaa atgttttaat tctcaaatct taatctcata catctggaag  74340
aggaggtgaa gaggatctca aagaagttgt ggaggggaac cataatcaga ttatattgca  74400
tgaaaaagag tatattttca attaaaaaaa tgtaaagctc atctatctgc cataaaagtc  74460
aattcgctta taaaataaca tttttaaatt ttttatttga tattttcttt atttacattt  74520
aaatgttatc ccctttccca gtttctcctc tgaaaacccc ctatctcttt ccccctcccc  74580
ctgctcccca acccaccgac tcctgcttcc tagccctgac attctgctat actggggcat  74640
agaaccttca caagaccatt gatgaccaac taggacatcc tctactacat atgcaactag  74700
agccacaagt cccaccatgt gtttttcttg attggtggtt tagtacctgg gagctctgag  74760
ggtatgaatt ggttcatatt gttcttccta ggaggctaca aaccccttca gctctttggg  74820
tcctttctct agctccttca ttcggggccc tgtgttcagt ccaatggatg actgtaagca  74880
tctgcttctg tatttgtcag gcactggcag accctctcag gagacagcta tatcatgctc  74940
ttgtcatcaa gctcttgttg gcatccataa cagtgtccgg gtttggtggt tgtttatggg  75000
atggatcctc aggtggggca gactctggat ggtcattcct tcagtctctg ctccgaattt  75060
tgtctctgta cctccttcca tgggtatttt gttcccccttt ctaagaatga tcgaagtatc  75120
cacactctgg tcttccttct tcttgagttt catatgcttt gagaaatgaa tcttaggtat  75180
tctgagcttc taggctaata tccacttatc agtgagtaca tattgtgtga gttcctttgt  75240
gattgtgtta cctcactcag gatgatgccc tccaggtcca tccgtttgcc taagaatttc  75300
atgaattcat tgtttttaat tgcagagtag tactccattg tgtaaatgta ccacattttc  75360
tgtatccatt cctctgttga gggacatata ggttctttcc agctcctagc tattataaat  75420
aatactgcta tgaacgtagt ggaacatgtg tccttattac atgttggtgc atcttctggg  75480
tatatgccca ggagtggtat ttctggaccc tccgctagta ctatgtccaa ttttctgagt  75540
aaccgtcaaa tggatttcca gagtggttgt accagcttgc aatcccacgg atactgtcaa  75600
taagacaaaa aggcaaccag cagattggga aactatcttt atcaatccta catcagaaag  75660
aggggacata tccaatatat acaaagaact ccagacatcc acataaccct atttaaaaat  75720
ggggtacaga gcttaacaaa gaattctcaa ctgaggaata ccgaatggct gagaagcaac  75780
taaaaaatgt tcaatatcct taatcatcag ggaagtgcaa atcaaaacaa ccctgagatt  75840
ccaatacctc acaccagtca gaatggctaa gatcaaaaac tcagttgaca tcagatgatg  75900
gcaaggatgt ggaaaagaat aaaatgacaa tattaactgt gtctgtttta caagagtttc  75960
tctataatgg cactttcttt ccacagctca atgagaattt gatatattga tttttaatgt  76020
gtattatcat gtacagttgg catatgtgct gatatgtggt gtgacagaaa atacagtgaa  76080
```

-continued

```
aaatattcac aggcctacta ttttgaaaat tctggtttta tgtgcataat ttggaataga  76140
ttctcagacc ccttctgtgg ggaaatattg gccgctctat ggttctggtt atatacccca  76200
gagcctttgg ggacaaatac ttctaaatat taatttttca gctatatttt tataataaaa  76260
tttgagtgtg ttcacaggca tatttccttt ctgtctgcca tcttcataat atgagcatgc  76320
ctagtggtgt tgctatgctt tcaaacaaat gatgcataat tttacaggaa tcatgaccaa  76380
acatgcatca tgctattttg tttctgaaac aaagaacttt aaactgagca tggtcatgaa  76440
tgtgcatctt cactgtgcat tttcagaaat gtgtctgctc acaaatcatt tttctatatg  76500
aatatgcaaa ggtcccctga ttaaatgtca ctctttaatt gttgaaggaa ttgtcattac  76560
tttggaaata acctcatgtg tcatctatta cacaaaataa atatttttgt actatgttca  76620
ctctgtaaac accaaaatgt gaattcacag accaaaagaa caattcttat caaatatgta  76680
ttacacacat aacagattca aatactttta gggtgtattg tgttattatt attctcttat  76740
accatcatag gcttctcagt gttctccatt gtttacttca tagcttcgtg ctacatcctg  76800
gttagcatga aattggaatt ttctgtgctg ggcatatttt tgtttttctg aacagaaaat  76860
tccccattca ggctcctgaa aaactttctg catttgagta gaacagatac atttttaaaa  76920
cttacattta aatgttcttt cttttcctat ctaaagaatg ttgttagctt tctggaaact  76980
tctaaacaaa aacctggtcc aaatcaataa acttttataa aataactccc tatggtttag  77040
ccaatgcaca gtaatttata tatttcacca aactaagtga tgatacacag acatttttta  77100
tattatgctg actgaaactt attatcagat gattgagaat tttgagcact agtttgaatg  77160
gaaaattaat aataacaata ataataaata aaatttatta taattttcta aggatatctt  77220
tgttaacatt ttgtgtcagg acactattgc tctaatatga aaatttgagg tttcttttct  77280
ccttttgaga catttgaaag agtttgtgaa gcaggaatga tgtgttggct cagtggacaa  77340
tgaagcttgt caccaatcct catgacttga gttatagcac aaggaaccat gttgtagaag  77400
gaggggatca acacccaaaa gtgatcttct gggctctgtg gcatagacat acatatacac  77460
acagtaaata ttttttaatt aaattaaatt aaaaggtcat aaagtcaagg tattaactac  77520
cactgattat ccaatccctg actttgcttt gaggatgaaa aattttttct aagagaggtt  77580
tttaattaat ttatttattt gtttgtttgt ttattatgta caatgttctg tctgcatgta  77640
tgcctccatg ccagaagagg gtaaaagatc tccttataga tggttgtgag ccaccatgtg  77700
gttgctggga attgaactca ggacctctgg aagagcagtc agtgctctca acctctgaac  77760
catctctcca gccttgttat agatctattt ggttacctgt ctatctatac atgtatctat  77820
ctctctatct gatactttct gccttgcagg agtgtgttca ttttaactgt gcggcctaga  77880
caccaccaaa agattagtta tcaccattct tacagtttag atttcagcaa attcaaacta  77940
atgtagcttt gatttctcat tgtatttgct actctgtcaa tatgacttat ttttttcctc  78000
atgttgatct ctacataata tcagcctttg actttgttga ctttctccct acttctttat  78060
ttttccttaa ttttactata atatgacata tgcagcttcc tctaatacgt ggtttaattt  78120
ggtgttaatg atggaccata ttgagatgag tgtttagatt gttagccatg caatattaca  78180
gtcctgacat aaagacgttg acaactgtac attgtccatt tgctaccatg agtcctagat  78240
aaaatgtaca aaatcctaca aatttggcca gattccattt tcttggaaac attgaaatca  78300
aatgttattc ttttctcctt tgacagtgga ttttgtgtga ccaggctgtt ttatttacac  78360
atatttgcaa atttcaaaat tttcctttta ttcacgactt ccagtttagt ctctatgctg  78420
gtgtttgtca acttgttaca aatctatgca tacctacaaa gttggattct caattgaaaa  78480
```

-continued

```
aatgcttcca tcacatgggc ctgtaggaaa tcctgtaggg cattttattg attggtggtt  78540
gatgttgaag gcccaaaatc aatgtgggtg ataccacccc taagctggtg gtcctggaat  78600
acataagaaa gcaagctgaa aaagttatgg ggagcaagta agtaagaagc acccctccat  78660
ggcctgtgca tcagttctgc ctccaagatc ctattttgag ttcctgtcct gacttccctc  78720
agtgatggac tgtgatttga aagtggaaga caaatgtacc ctgggttata attgtgtcct  78780
tcatccagcc caaacccatt gcttcctgat tcaccaagat atcagaaaaa aatgtagcaa  78840
tctcttccca acacacacac acaaaattag tttgctttct attgctgtga caaaccccta  78900
taactaaaac ctaacttaga aaaggaaagg gttaacccat cttacacagg tcaccatcta  78960
ccattgaggg aagttagggc agaatcttca atcaaaaacc atgtatgcta tgtattggct  79020
tgttttttaa ctcatgctta accaacttcc tagtacagcc cacaaagcct gactagggaa  79080
tgatgagccc acactgagat gagtcatcca tatcaatcat caatcaagac attccccaac  79140
agacaatccc acagaaaaaa acatgagctg ggcaatccct caattgagac ttccttccta  79200
aatgattcta aactgtgtca aattgaccat taaagttgac tacgaaaaaa aaaatagaga  79260
ctcttcatct gcgccatgtt tcccaccatg ataggccaca ccttcaaact agggaccaaa  79320
ataaggcctt ccctcaattg actactgtca ggtattaaat caaagtacca aaaagatatt  79380
tatatgggtc tctaagtccc ctctctagta ttaacaacaa actatatcaa caactgtcta  79440
aactatcagt tgtagtaaga aagtgaaata actctggatt aaaagtctct acagttaaca  79500
agcactaaat acttccagaa caactgctgt aattactgtt gaatatcaac ctgacaggat  79560
ataggatcat ctataacata aacccctttgg tatatctgtg agaatgcttt tagattggta  79620
taactgaggt gggaaatccc tccctaagtg tgggcactac tatttaatgg catttgattt  79680
tgtataccct ttcctgcttg tatcagagga gttaggggaa aaacaaaggg gtaagtgaca  79740
aggggaagaa ggggtgtcct tccccacttg ggtaccacag aacttaatat ccatcaaagc  79800
ctacctgatc agtggctttg aggatcttct ttaatgaatt tgaagaatat tatttgagga  79860
ccccagaggg tggattattt gtcttgaatt gggtacttgg gtgaccagtg ggtgggcact  79920
ttagagtgag aaagagacat agcagagctg ggcaaggtca gggctttggg tgataacatt  79980
atgatctgaa gggattttga caggatttat ggtaattctg aggtgcttca tagtagtgaa  80040
tgagagggat taaaactcag gctgacatcc aatttcaggt acaacaggac tgaatgggac  80100
atcatcgcag tattatttta acaaaccacc caccatgaat ggcatggaaa aaaggctggc  80160
aagtgaattc tttatggttg ccaccctctg gcttggagta ttgcccatgc tgacctctaa  80220
ttcctggaaa aacaaaaact taagaaaaca aaactagttt cctattttca aataaaaatt  80280
gaatgactta cttacaagaa aattctcccc attctaatat tttatgtgag agtttgaaaa  80340
gcgttttttt ccccattttt tattaggtat ttagctcatt tacaaaattt gtatattctt  80400
ttttttcttt tttttgtttt ttttccattt tttattaggt atttatttca tttacatttc  80460
caatgctata ccaaaagtcc cccataccca cccacccact ccccctttttt ggccctggcg  80520
ttcccctgta ctggggcata taaagtttgc aagtccaatc ggcctctctt tgcagtgatg  80580
gccgactagg ccatcttttg atacatatgc agctagagac aagaactccg gggtactggt  80640
tagttcatat tgttgttcca cctatagggt tgcagttccc tttagctcct tgggtgcttt  80700
ctctagctcc tccattgggg gccctgtggt ccattcaata gctgactgtg agcatccact  80760
tctgtgtttg ctaggccctg gcatagtctc acaagagaca ggtatatctg ggtcctttca  80820
```

-continued

```
gcaaaatctt gctagtgtat gcaatggtgt cagcgtttgg aagctgatcg tgagatggat  80880
ctctggatat ggcaatcact agatggtcca tccttttgtc acacttccaa attttgtctc  80940
tgtaactcct tccatgggtg ttttgtttcc tattctaaga aggggcaaag tgtccacact  81000
ttggtcttcg ttctcttgag tttaatgtgt ttagcaaatt gtatcttata tcttgggtat  81060
cctaaatttc tgggctaata tccacttatc agtgagtaca tattgtgaga gttcctttgt  81120
gattgggtta gaaaagcgtt ttttttccct aggtttattc atattaaatc tttggctgta  81180
aattctcagc atttttgcca gtggatttga acaactttgt gtgctgaact gttgaactgt  81240
gaatgaatga atatgaatat gcaggaaaca gatttttgcc tgacatctta atcatttctc  81300
agccacttaa caaggccaaa ttcatactga aaaacaaagg cttattggat tatctacatt  81360
gggaagatga acaaagagat ccagtaacct accctcactc accccctttac accaccccac  81420
ccaaccctaa cgctacccca ccctcattcc cttaccactg ctaccacatc accacgccac  81480
cattacccct atcctcaccc ctggtaacaa acccattgtc agggtcctga cataaggtta  81540
aagtagcagt tctggtgaag ctgtggtccc acccatacct gaccccgcag agagtctatt  81600
atcctaaaat gtgaacttaa aagctgtcaa actctctcag ggaaaaattt accttctacc  81660
tagtctgggt ttctggattt gtcttctctc gggatgatat ccctgaggaa atttcagact  81720
tttgagtccc attatttgga tattccagaa actagaggga atggtacaaa gtccttaccc  81780
ctacccccaa ggctggttaa agcatctctc tatagaaaac tatcatggga ggcttaactc  81840
tgtgtagaaa ctcgcagcaa aaaacaatgt tttgtctacc ctcaaattat ttccatttaa  81900
atatttatta cagtattctc attattgttt taaaaataaa actgtggtta tgtagtggaa  81960
acactgcctt aacaactatt ttaagattta ttgtatatgt taggtctcaa aactgacctg  82020
gctgtcaggt tctctcacca tctctaagtc gttacctgtt acagggtatg gccaactccc  82080
tacacaaaat ttctctagct gggctgctct tccctatata atgcatccat tttgatcatt  82140
cagccccttt ttgtctagcc tttttccctc ttgagctctt gatctcctgg ctttccactt  82200
cccactctcc cctctccctc tgtttacatg cccctgctca gggacctgtt gactctggac  82260
tctcccagat gtgcctgcct ctgcttatgc tctcctgata tctacaataa acctatcatc  82320
tatatctaca ataaacctat ctatcatacc taggagtagt cacgtcctga tttttatttt  82380
ttcattcaat atatgcatat aaaatttatt tcagtgcctc aaaagacgat ggagtaaaca  82440
tggctttgtg actggtttta catttatatt taggaatatg tatgtatata catatatgca  82500
tgcaatataa ttcatttgaa atggggcatg gacttgaaag agagcaagga ggggtatatg  82560
gaagggttta gagagaggaa atggaggggc aatgatataa ttatattatt attatctcaa  82620
aaaaataaaa aggagatttt aaaagtaata caatattgga ggtggagtga agaaccctgt  82680
tcattcccca gcaccctggt gggcagcaca caaccacctg caaatccaat gcctatggat  82740
cctacaccct ctttcagact tcacacacac ctgcaaaaag aaataaatgg cccacacata  82800
aaaaagaaat tcaactttga aaaagtagtc ccacattaga aacattttta aacacacctt  82860
cttcctggaa tcactatgtc accttttatc tggttttact gaagaacttt catcaatgca  82920
tcaataacat tttattaatg tcataaaatg aataaacgcc ttgaactcta ggaaggaagg  82980
aaggaaggaa ggaaggaagg aaggaaggaa aggagggagg gagggaggga gggagggagg  83040
gagagagaga gagagagaga gaaagagaga gagagagaaa gaaagagaga gagagaaaga  83100
gagagagaga aagaaagaga gagagagaaa gaaagaaaga gagagaaaga gagagagaga  83160
aagaaagaga gagagagaaa gaaagaaaga aagaaagaaa gaaagaaaga aagaaagaaa  83220
```

gaaagaaaga aagaaagaca gacagaccaa agcatatatt tcaggaaggg gaatgcaagt 83280
gccaattcag aggtcacaga gggaaaaaag atcattggta ataaatgaaa atgaatgagt 83340
tgttatctgg cctggctgta tccattccac tggttagaaa caaaactgaa tgtcaccata 83400
gactgtaatt gtaacaaccc ttcacttttg gcatcaatct cactgtaaga aatccacatt 83460
gggaataaat caattcagga agtgtgagtc cttgaaggga atactaggac cccagtatca 83520
tttttcctct ctctctctct ctctctctct ctctctccct ctctctctct ctctctctct 83580
ctctcctaca cacacacaca cacacacaca cacacacaca cacactttca gtcatttatt 83640
tattgctaga acctcctgta gttccctgtg gcctccacta tgtaactgag catgaccttg 83700
aagtcctgaa ttcctgaccc cttcccctgc ctatgcctct catatactga gaagatggat 83760
gagacacaca caccagacct tgacatttat tattattgtt attgttgttc aaagtctgac 83820
ttttatgtaa tttacatgat ttctccttca atagttaaat aggaaattac tgattccaat 83880
tctctatcat taattcaatt acttggaagc taatgctaaa cagcacatga taggaatata 83940
tattttgtgc acttgtcagc atgcacctaa caaaaattga ttaccctgtg tagtgatagc 84000
ttttgtactg gctggttttg tgggtcaact ggacacaagc tggagttatc acagagaaag 84060
gagcttcagt tgaggaaatg cctccatgag atccagctgt ggagcatttt ctcaattagt 84120
gatcaagggg gaagggtcgc ttgtgggtgg taccatccct gggctggtag tcttgggttc 84180
tataagagag caggctgagc aagccaggag aagcaagcca ataaagaaca tccctccagg 84240
gcctctgcat cagctcctgc ttcctgacct gcttgagttc cagtcctgac ttcctttggt 84300
gatgaacagc agtatggaag tgtaaactga ataaaccctt tcctccccaa cttgcttctt 84360
ggtcatgatg actgtgcagg aatagaaacc ctgactaaga cagctttata gagatcttgg 84420
catagaaact ggaattttag aagaaaaaat aagtggaatg ggttaaagtt tgaccttcaa 84480
gtgtggattt ctgcttcact cttatctcag caaagcaaac acctggcaga accttccaga 84540
aggagtgatg ggcacagcta cctgaaaaga ttctgtttgc ttagaaagga attgttcctt 84600
tattgttccc tgccagccca gtcctggaag ccttgataac aaatatttgt acatttttat 84660
tgttccccgc aaaatcatcc tctcataact gcagatcctg tcaacatgcc tgccagatgg 84720
cagaaatcac ctatcatgtg acctataaaa gctgtgagaa attatggggt gtttgggaac 84780
ttttcaaagc atcagcccag tcatagctac aaaatttctt gtgtctccca gggcctgctg 84840
ggttgattcg tggttggagt tttccatagc agcacacaag tggaaaatac attttggtag 84900
aatcacctca ttggtgtcaa ttgatttcat aagaaaaatt aacagtcaca ataagattgg 84960
gtactttcaa agttccctat gtccaaatag tatcccattg tactctcaga acaagtgaac 85020
attgcaacct ttatttcaaa agattaatat tctaattatg tttatatcta ttatatattg 85080
tattatacac acacgtatgt actatgagct ttatttttac acttttattt tagtattaat 85140
tgtgtatatg tgtgtatatg caatacatat tatattacac atatatatgt acattacaat 85200
ttttatttta aaatttttca tttcagttat atgtatatgt ggagtggggc agggtgggca 85260
catgtgagta tagtaccatg agaggccagt agagggtggt gagcccccag gatcaggaac 85320
aacaggtgtt tgtgggcttc ctgtgtaggt gttggaagct gaacttggtc cctatttgtt 85380
ggccttgctt gtgggggatt acatgctaca ctttgctgga ggaattacat cagtggggga 85440
gagctatttg agattctgaa acattcagca agttctgttt ggttggagat gggagctctc 85500
agctccttgt tggtgccacc ttgccagccc cttcctgctg tacttgtccc ttatgtgtgc 85560

-continued

```
ttctgtcaca gccatgccca cccctcacca ctatgcttcc ctgtgccaac gaactcatca  85620
ccctttggat cttaaatgca taagtcaaaa tatttcttgc atacactcat tttgtttgtg  85680
atatcttgtc acagcaacag aaaactctta ttgcttaaca ctaagctacc tctccagccc  85740
ctagaggttt ttggtttggt ttggctttta atatcatttt tttttattt atgtgtaggg  85800
gtgtgtgcct gtgtgagttt tccccattta atttatttat ttattcattt tacatgcccc  85860
cctccttgtc cccactcaca tcgtctcttc cccattcccc ctccccttct cttctgaggc  85920
ccctctgggt attccccgat cctggcacat caagtctctt cagagctagg tgcatccact  85980
ccctctgagg caagacaagc agctcagtta ggggaacagg ttccacgaag atttgagaga  86040
aggaatgaag gccctaaagg ggatagaact ccacaagaag accaacagag tcaaataatc  86100
tggaccccga gaggctctca gagactgaac caccaaccaa agatcctaca tgagctggac  86160
ctagccctcc ccaccccac cccccacata tgtagtagat attcaattcg gacttccaat  86220
aggagctgtc cctaaagctg ttgcctgtct gtggaatctg agagattagt tttttgtttt  86280
ttgtttgttt ggttggttgg ttggttgttt tgggtttttt gggaggattg gggggctgtt  86340
tgtttttgtt tttgtaccct gaaagttctt caatggaata gttctcagtg ttgcttctat  86400
ttcattcatg ctacccacag gcttgctttt gaaattacat gtatttttcc catttcttc  86460
tctctaaatt tgagtcaatt tctggtatca gcatgtttga aacaccaagc agaataatgt  86520
gtctgcttta ttttatattt tgtcgtactt atgcacatgg aaacacacac acatgttatg  86580
tgctcaatta ttggaacaaa tgttttcctt ttttatctac tctcactatg tgacccttta  86640
tttgtttcaa gtaaataaaa taacaaactg ataatcaaac taataaaact gtaacattta  86700
cagatgatgt cattatttgc atcatctaat tctcatggaa aaggtgccct ttttcttact  86760
aatgctactt acaggtagac actcttagcc aaaaataatc cggaagtgaa actgcctgcc  86820
aacacaaacc actgatgact gataagattc ctgaggatta ggaaaaccac acggttctta  86880
cagggaacaa ctgattcttc agagactgcc taagaaaaca ctgacacatt tgcagaaaag  86940
ctattgagtt ggataaaagt tttacaaaat gcccacaatg aattttaata ctaaacctgc  87000
aaaagaaata tgctaaggaa atcacacaca cacacacaca cacacacaca cactaccacc  87060
accaccacca ccaccaccac caccaccacc accaccacac aaataaatgc ataagccaag  87120
tcctgagggc ctgggatatc agccccaaat tcagtaggct gggtaagaag gaagccagga  87180
ctctgtttta agatgaattt ctttcaaaat ccacaggaac acatcatgca tatcacatca  87240
tgtgctatat cctggccctg gggttgtgga gtgtccaaga aggatgcgga ggcacaggtt  87300
atgattaatt atctgagcat atcaagcagc aaactcagac actccttcct cttctgtctt  87360
ccaaaggatg tttgtttcgg gacattttct agaaagacag gtaccaatgt atattgacag  87420
atgaggcaca ccaatgatag tcaaaggaaa tttttcacat gagtctttct gggttgactt  87480
acaggagggt gttttccacc atcacatatg gaatgtttca ctttctgcca tttcacatca  87540
gtaaatataa atattgatga gtgggcgtcc ttccttcaag acatgcattt aattgggttt  87600
tgatcaaatg ttcaggcact gggaggaagc cagtggcatc aaagttgtcc acaaacccaa  87660
catcacacta ggggactagt gtgaaaactc agtaaaagtt gcccaagtca tgtatctgtt  87720
gttgttgttg ttgttgttgt tgttgttgtt gttgtcatcg tcatctttgg aggtggtggt  87780
ttggtttggt ttgggagtgt ttgtttattt tgtttgagac agagtctcac ttcatagctc  87840
tgactgatct ggaactcact atgtagacca cactgaccct gaatttggag agatcctgcc  87900
tgcctctgcc tcctgagagc tgggattaaa ggcatgcacc actgtgacat gcaagttaat  87960
```

```
ttttttaat tatatttttt ctacaactaa cattcatcag tgtttcagcc tggaaggaag  88020
aaaacttgca tgcaatcaat gttttaattg aacaagaaca tatgcaaatg gcacaggcat  88080
ttctatcatt tggatttaga agaaaatccc aagatgatgt tgcagttttc ccacctcagc  88140
tgtgaacact tactattcgt gattgagtct gcaggcagtt ggcgggcaaa agcctgtcag  88200
gggtattatt agccttcata ccagatcata aagaaggatt tgccaaaaat cctagtttcc  88260
agaagagctc tgttgtacca aggcagtgga gcatcgccac cttacgactg taccttgcaa  88320
tgcaactagc tcgcacaaat tacaaatgct atttattgat tggggcaggg aggggaaaaa  88380
aggggagggc agaggcagac tgttggttgg tttggttggg ttggttggtt ggtttgttgg  88440
ttggtgattt ttcaagacag gatttctcta acagtcttcg ctgacctgaa ctccttctgt  88500
acagcagtct agcctcaaat tcacagagat ccacctgcct ctgattctcc agtgctgggc  88560
tcaaaggcaa gcgccactac tgcctagcct gtgttgtttt ttggttaagc aaaacatctt  88620
taaatgtcta gattagatat ccagattaaa tgtctagact aagatctcta aacattttct  88680
aatataaatt ttatcagttg aaacttgtcc acttttatgg gatgctaagg atgtatggaa  88740
ctcaggactt tgtgcattca gtcccactgt ctggtagaca ctgttatgct gtatattcct  88800
aatggggagc agccaaaaac aaaaacaaaa caaacaaaaa atccaaacct caattcctta  88860
attaattaat taattaattt tttagaacta agatttaatc aggaaagttg cattatatgc  88920
atacccctgg ttattcaggt aagcatagta agaatataat taaaagttgt ctgcacattt  88980
gaatttagat ggatatgaaa gtgtttcaga tttcctactt aagtaaagtg aaacaatatt  89040
gaaatttttc gaaggttgtt actgtgggat cccgggtcca cagacacata aaataaatct  89100
ttgaaaaaat aatattaata tttagtaatg tgacatgaaa ttaaattaaa ccaatgtttt  89160
tcctctggca agaaacgcag aaagtaaaaa tgatacattg tattcgtggt aaaaatccta  89220
atctcattta atcgatacac attgcatcca ttatgagttg cagtcattaa taataaaata  89280
atattattaa gcagcaagca aatagtctta aagcagcacg tagtgagacc tcagagctgt  89340
taatttccta ataaaagaat acacttccca ggaaacttta cggccaggcc aagcacttcc  89400
ggaaggaggg actacgggac ggcaatagga ccccttctgta agaaaaggga gaaatgtggc  89460
ttcaaaagaa accatactta ttcatgtgag tggcgatttg tcacatgtgt gtgacgatag  89520
ccaatatgtc tgaagagaaa gaccggttgt ggcgctaact ggggggacct actgcctccc  89580
tgtaagcctt ccttacaagg ctatctcggc gcaaggaatg ctggaaagtg tagtgatttg  89640
gctggaaact accagctatt aagtaaaatc gcgtcatcac cccgaccagt tctgttccca  89700
agcctgctga tctagacctt atcccacctc cgttcctgct ccattctgag ccctgactgt  89760
gaaggtttca ctctcttcac ttacaggagc tttagggaag aagtctccca caggagctga  89820
gggtgggggg cgggcggtct ccctcttctg gcctctatcg gtactgcaag gaggggccac  89880
caattacatg caatttttat gccacactaa gatgcacaaa taaataaggc cagagattcc  89940
ccagagtcag gatttgaggc tttggggacc aatgagagtt gttggattga atgcaaaatg  90000
tacacacttg gaaacaagac tgggcaaggc tgcattttct agtctgcagg gagacctgaa  90060
aagttagtag aagtacatgt gtgtgtcagt tctaaatgaa acgacggggg acaaatgcct  90120
gaggtgcctg ttagcatacc aaagcacatg atggcctcta gactcacttg ggaccgctga  90180
ctatgctcta ctcttctgat ctggccccat aacttaatcc aagccagacc ttctcctagc  90240
atcttttacc tatataacca gccatttagg ccatgctccc acttggtcct ctcagtctcc  90300
```

-continued

```
tctgttccct ctcttttctt cttctcttat tctcctcacc ctttccacct ctgtcctctc  90360
atggctgggt tcagtctact gtccaggttt agtccactac tttctctgct ctggactctt  90420
ccagaagcct ctggctgttc ttatccgtac ctgggagtgg ccatacccto atttgtacag  90480
tatcttcctc cagcgtctcc ctgtggctga ccctggaggc ctttatgctt tctccctgga  90540
aaaattctaa ttgggggggg ggggggaatc cagtttgttg caatgaccag acagctgaag  90600
gggtggctca agggccgggg cataggtcat tgaaatatac tcagggctac taggagtggc  90660
agtcagtgtt caagtacaca ggaagcaact ttctctgcaa aggtataaag aaaagtaaaa  90720
agttttgaaa aagctaaaaa tttaaattaa attaaagaca atcatctggg cagtgatggt  90780
gcatgcctta aaaaccagca gattagggct ggagagatgg ctcagcgatt gagagcactg  90840
actgctcttc cagaggtcct gagttcaatt cccagcaacc acaagatggc tcacaaccat  90900
ctgtaatggg atccagtgcc ctcttctagt gtgtctaagg acggctacag tgtactcaca  90960
tacattaagt aaataaatag atttaaaaaa aaaaccagca gattatacat gggagacaga  91020
ggcaggtgaa tctctgagtt cgaggccagc ctggcctaca gagaaagttc caggacagca  91080
aaggctatac agagaaaccc tgtcttgaaa aactaataaa ttaaattaag aggacaacaa  91140
aggtgagctg agtgctttct gggccagtga gtccaggtcc tcttaccctc tgaaccacat  91200
ctccagtccc aaattaacct ttagtttcta ctccccagga acataaaaca agccctggac  91260
cttataaaag gtgtcaggag ataagagcag cctaaggctt ctttatttct ttcctctaca  91320
ctcctggaaa agaaagggta gcaggaaagc cagtggtcag ataaaataca aattgtcaga  91380
ttaaaatctt aattctggtt gtatttattt tacactctct gaggactcat tgccctacag  91440
tatgtttggg gactagaaag gaaatgaaat ctcagtgtca gtagcccaca aagagacaga  91500
agcaaaagta gtttgcaaag gacagtgaga aagtcctctg atgttctctc cctctccctt  91560
tccttctacc ctcttctttc tgcatttttt tttgacccag ctcctgtgac ccccatctcc  91620
aaccctttga tccagtagga ctttcaagtt ttctgaacag tgctcaaaga aaacacttta  91680
cttgtggttt tccatatcct ctgaggtctg gactttctgt ccccagccag caggtggtgc  91740
tgttactaca gctggaagca aagttcccaa aacgtagctg aacacctggg aggctgattg  91800
actggtagtg tgtggagatg tgcagagttg gaatcctgag agtccagagc ctaattatga  91860
tttctcttgg acaattttca gctctctaga tagatgtccc taagccacct atgtcagacc  91920
tgacgtcctg tgactaacag atttaaaaaa caaacaaaaa taaaacattt ttttttgtct  91980
gtctaatttg atcaaattgt tctttcacag caaagggcct agtaaaagca aggacttctg  92040
gctctgcttc atccacctgg cttaatattc ccactcatgt attttgaaaa gaaccttgat  92100
tgatgttcct ataaaaactt catgaaactg tgtctatgtc cctccatggg atttggggat  92160
gcagtttacc atgccttacc gcaacctgat gtgtggaacc ttcaaactgt ggcttaaaac  92220
aaactcttct ttcctttaaa gtgcttgact caagtatttt gtcgaagcaa tgtgtagggt  92280
aactaatacc cttggataga ttaaatcagt ggaaatacac tctctgtcac tggatgagaa  92340
cgtgctttta gcaaggctca atggcatctt tcatcctacc cagcacttag gaagcagagg  92400
caagggaatc tctgagctcc tggcctgcct gatctacata aaggatttca gtccctgtga  92460
cacttactca ataacagtga caggagagaa tttggttccc aggaacttgg agatgggggc  92520
gggatattgg agaggttggg ggaggatgtt ggacagctgg ctaccatgtg agttccaaat  92580
ttaggtggac agtgatagag gggggtattc catgcccccct ctacatttcc atatgtgcac  92640
atatgtgctt atctaaatga gtcattttat tactctttga ttcccatttc ccaatttcct  92700
```

```
tctatcaaga gagtaaagac aaaaaacaaa tccattattt tttttgtgtg taaattcttc  92760
tgctcatgaa tattctatgt attttagttc cctaaaaaca aaacttcatt aaaaattttg  92820
aaagctgccc ataatttttt tgacatagag gaattcaagt tatacattca attttacatt  92880
ttgattgcat tttaaagcat gggactactg cagctcaaag cagctgcaaa tctcaaacct  92940
tcctgcctcc acttcccagg cactgtttac aggcatggag ctccattatt ggatatagaa  93000
acacacaaag agaaacatac acacagacat acatacacac atataaaata ggctttgctg  93060
gaagaaaata aacaagaaca aaacagtgat tattcagttt ggtcaggccc aagttccaag  93120
gctatacaca tctgtgacaa gaatttcaga tataaacatg tgaaggaaat tttataggtg  93180
caccttttttt atttattttt gttagatatt ttctttatat acatttcaaa agctatcccg  93240
aaagttccct ataccctccc tccaccctgc tcccctactc acccactccc acttcttggc  93300
cctggcattt ccctgtactg ggacatataa agtttgcaat accaaggggc ctctctttcc  93360
agtgatgacc aactaggcca tcttctgcta catatgcagc tagagatatg agctctgggg  93420
acactggtta gctcatattg ttgttccacc tatagggttg cagacccctt cagctccttg  93480
ggtgttttct ctagcttctc ctttgggggc cctgtgttcc atcttatgac tgtgagcatc  93540
cacttctgta tttgccaggc actggcatag cctcgtacaa gacagctata acaggggctc  93600
ttcagcaaaa ctttcctggc atatgcaata gtgtctgggt ttggtggctg attatgggat  93660
ggatccctga gtggggtagt cactggatcc tttcgtctta gctccaaact ttgtctctgt  93720
aactcctttc atgggtattt tgttccctat tctaaggagg aatgaagtat cttccctctt  93780
cttgattttc ttgtgttttg caaattgtat cttgggtgtt ctatgtttct ggactaatat  93840
ccacttatca gtgagtgcat atcaaatgac ttcttttgtg attgggttac ctcactgtct  93900
tagtcagggt ttctattcct gcacaataat catgaccaag aagcacctgg ggaggaaagg  93960
gtttattcag cttacacttc cacattgctg tttatcacca aaggaagtca ggactggaac  94020
tcaaacaggt cagaaagcag gagctgatgc agaggccatg gagggatgtt ctttactggc  94080
ttgcttcccc tggcttgctc agcctgctct cttatagaac caagactacc agcccagaga  94140
cggtcctact cacaaggggc ctttcccccct tgatcattaa ttgagaaaat gcagaaaatc  94200
aagaatttca cacacaacta tgacaggcat ttcatacaca tacacatatg acaagaattt  94260
ctctctctct ctctctctct ctctctctct ctctctctct ctctcacaca cacacacaca  94320
cacacacaca cacacacaca cactcctgtg acaagaatac catacataaa actctggtag  94380
gaatttcaca tacaaacctg tgacaggaat ttcacataca cacataccca cagacatctg  94440
ttaaatgaat tttaaacaca catgtgacca gaatttcaca cacacacaca cacacacaat  94500
cacctgatac aggagtttca ctcatacaac tgtgacatga attttatata cacacgtatc  94560
tgtgaaatga attttacaca ggtacatgtg acaggaattt cacacacaca cctgatataa  94620
aagtttcaca catatacatg tgacatgaat ttcacataca cgcatatcag tgaaattaat  94680
tttgcacaca cacatgtgac aggaatttca cacatacaca tacctatgac aagagtttca  94740
cacacaacac tgcaatagga aatttaacac ccatacaaaa cagtgatatg gattttatac  94800
acacacacac acacatacac atgtaacaaa aaattcacac acaaaactgc aacaggactt  94860
tcacacacac acaaagctgt gaccagggtt cacacacaca cacacacaca cacacacaca  94920
cacacacaca catctgtgaa atgaatgcta cacacatgcc tgttaccaga aattcacatg  94980
cacacacata cacacatacc tgtgatggga atttcacaca cactgtgaca ggaatttcac  95040
```

-continued acatatgcac aaactcctat ttcaggagtt tcacacacac acctgtgaca caaatttcac 95100
acacatacac acacacacac acacacacac acacacacac acacacacac tgtgataggg 95160
ttgttaataa gtagctagct agatggatag ttgaatgatg ggtgggtggg tgtctgtact 95220
gatggaaaga tacccagagg tgatgaattg acatccagag gtggacatat ggatggaaag 95280
aggaaggcat gaatactgaa caaatggaag cattggtgaa tggatgggtg tatgaatgga 95340
tttgtcgtgc atgtactggt agagggtcta atgagtgtat atatgagtgg gtggctggct 95400
ggctggctga atgagtgagt ggatggatgg gtgtttggga ggattgttaa agttcctttt 95460
gttctcctga tataactatt gttttaaagg cttattgcct ccatctgcta acctaagcct 95520
agtcttggaa gcttctagcc tccatacaat cttatctagg cctagaatct tttcaacatt 95580
tgagacttgc tgctgaatat gctcaccttt tctagttatt tctgaactcc tgctagctgg 95640
tcaattcagc agttctggct cagaactctt ttccatgcta actgattcaa tcttgcttct 95700
cttggcttct cttgaatttc tctacttggc ctcataataa ctttggcaat atgttctata 95760
cagaagtata tggctccttc tcattctctg actcattctg tcttctcctg tgtcttgctt 95820
ggtctctctc tctctctctg caatctgcct ctgtacaact gtcccagtaa aactgcctcc 95880
ttcctccccc ctccactctc tgcactgctc tcttaagtag cttccctttc ttctctcttc 95940
ttataggata tgttacttcc tcctacaaac taactttacc ttcattgttt gggattaagg 96000
gtgtatacca agggcatgtc tatattccag caagggggat taagggtgtg tgctaagggt 96060
gagccacacc acaactagaa acaggttttt ccagtaaata attcaatctt gggtttccca 96120
gtgtgatcaa atatcctaca acagtgaatg gatagtaaga tgggtggatg gattggtgga 96180
ttgtgagtag atagatgaat aggtgaatgg atggataggt ggttggatag gtgggtgggt 96240
gaatgaacag gtcatgtatt gtggatgtgt ggatatatga gagggtggat agatagatgg 96300
atggatgggt gggtggatgg atggatggat ggataggtgg atatatgtgt gagtaaatga 96360
atgggtgggt ggatgaatgg ataggtggat atattggtgg atgtgtggat tagtggtaga 96420
tgggtatgtg gacacatgga taaatggatg gatggatgga tggatggatg gatggatatg 96480
tagatggatg tataaatgga tggataggtg gatggattga tggatgtgta ggtgtcagta 96540
aatggatgga taaatgtata ggatgatgaa tgaagggtaa acggatgtgt gggtgggtgg 96600
ataaataggt gtgtgtgtgt gtgtgtatgt gtgtgtgtgt gtgtgtgtgt aggtgtttgg 96660
atggatggtg gatggatggt ttagtggatt ggttgattgt gaatatgtga gtgaattgat 96720
gactagatgg gaatattgaa gtttgaataa atggatggat gggtttatgg atgaatggat 96780
ggataagtat atgtatggat atatatatgt gtgagtgggt ggatggatga atggatgagt 96840
gaatgggtga gtggatggat ggatggatgg atggatggat ggatggatgg ataggtggat 96900
gagttggtag atatgtggat gtgtgagtgg atggatgaat agatggatag tgaatggatg 96960
gtgtagtggc tattcctggt tgtcaacttg acaatatttg gaatgaacta caatccggaa 97020
ttggaaggct caccagtgac ccttatctgg aggcttggag atccttatct ggatcttggt 97080
ttgaagatct tgagccatag tggctatgga ttccagaaga ttgaatctcc gagtttaagg 97140
aacacaccct taatctgggc tacgcctttc atctgggatt aaaggtgtgg tggaacacac 97200
ctttaatctg ggctccacct tctgctggag acaatataag gacattggaa gaagggagtc 97260
tagctcttgc tcttgctcct ttgcctgctt gctgcgtgag actgagtaac tgctagatcc 97320
ttggacttcc attcacagct gcgactgaac aattgttggg aattcggctg ccgactgtaa 97380
gtcatcaata aattccttta ctatttagag attatccata agttctgtga ctctagagaa 97440
ccctgactaa tacagatgga taagtagatg gattgatgga tggatgtttg agtgggtggg 97500
tgtatgtatg ggtgggtggg tggatggata gaagaatggg tgtactgatg gagaatatgt 97560
tcatcaatgt tgctttgtaa caacccaatt gtaagcttct attcaacaat gtactgcttt 97620
ctttgttccc aaggtcatgc cttatctgtg atgttcaaaa tgaattcaca gccagatctt 97680
aacttcccat ggccgactgt gagcaccaag gatcttaaat cactgacacc acattccttg 97740
aaccttgacc ctgaaacatc ctggtatgga tgtgacatca gctcagctgc aatcaggact 97800
atatgagagg gaactgagaa tgttcatttg tagagcagag agacaatctc tacacagccc 97860
acatgaagaa gaaagtggag aaaggggagg cagaaaggaa aagggaagag ggatggactg 97920
aatgaaggga agggaaaaga tcagtaggga gactacctcc agaggtggtt caactacaga 97980
agcacagcac agaagtctct gcttcaaaaa tagaattgtt tgcaaactcg ttcctctttc 98040
tcatttctcc aaaagaaggg aggggctgga atcacaccca tggtttaatg ctaaccagga 98100
acaatggagt agatgctgct aaaagtgaag gacctgctac aacttctgag aaactacaaa 98160
gtcacaatca agtaccctaa gcttggcctg gatcacaggg tgcttctaga agtgtgactc 98220
ttctaaaaga ttctacttca tacaaggccg tgacttttca aattcacctt taatttgaag 98280
ggctggtttt atgtatttat cattgtcagt tctttatcca tttacttaat tttttgttgt 98340
gtttatttct ggtttttcaa gacagggttt ctctttgtgt agccctgcct atcttggaac 98400
acactctgta gaacaggctg gcctcccact gaaagatcag cctcccaagt tcttgtctta 98460
caggattaaa ggcatgcacc accactgact ggttatttaa atatttttaa gatttttaa 98520
aattgtatat agtttttcc cataatcact gtgggaggta catggggttc agattttgga 98580
taacacatta caaaatctac cacaggagga tactcccttt gaggaggcag atgttttcta 98640
aagaaaagta tttatttctg tcgcccactg tccagtcaga ctcatttaaa gaggaatcaa 98700
ttgacaagaa aactaactgt gcaggggtct ggccagaaga gggtcacttg gaaggttctg 98760
tgaaaggctg agtcaacaac aggaagttga tctgtgtggt ttgagatagc atctggcctg 98820
gcctcatagc agtgacaaac atttcctcaa aaaagatact gtgagaatga gttaggttga 98880
gtgagaaagc taataccaaa actcacctat tatgatttat tctgtaagag taaacatgtt 98940
tttaataagg aaaaaataaa aaagttgtgg agaacaaaaa acaacccagc actaactaaa 99000
catatttcct gattttaaca ttcacaattt tggggccagc taggtggctt aggaggtaag 99060
agtgtttgtg accaagcctg ggaatcagag ttcaattctg ttgtcccatc cagaagctga 99120
ctttgatttt tacttttatg tattgttatg gcatgactgt cagaggacag cttcattgcc 99180
atcagctctg tctgtccagc tttccatggc ttctgaaaat tgaattcatg tttccaggct 99240
tgagtatagt cttaggatat ctaatattga aactttttct tttttttttt cactaaaaaa 99300
gtgaatttag cttgtgacta tgtcctcgca ctttcgagtg tgttgagtgt gtgtgtgtgt 99360
gtgtgtgtgt gtgtgtgtgt gtgtgtacac cttttctcgc tgtatcaaga atctaaataa 99420
ttttggcatt ttctgccacc cactgtaagg atcacaccaa ggtgaggaat ttctcctctt 99480
ccaatccaag cacacatttc tgcaatttta tcaaaactgt ttatcattat tggactgaag 99540
ttcatcaaac ttcacctcct attcccctca tctgagcaga agcaatgtgc atttttcctt 99600
attgtgtttg tttgtttgtt tgtttatatt ttggattttc gagacagggt ttctctgtgt 99660
agcactggat agtctcaaac ttgtagacca ggctagcctt gaactcacag agatctacat 99720
gtctctgcct cctgggtgtt attttcttta gattctgcaa tattattgta aacacttccc 99780
aggtagggaa ctcaaactta aaaattcgtt tacaatttcc tcataataca cacctatacc 99840
ctcagtagaa tttcatgtag tgttctttgg ggatttgggt ggtttgcttt gttttatttt 99900
tctgtcaaga gacaaggtct caccatgcag ccttggctgg cctagaattt acagaaatcc 99960
ctctgtctca gtttccttag tgctggcctc acaggcatgc aatatgcacc ttttagcaag 100020
tttttaagtg agggtctgta aagtttccca agtttactta gtttatagtc cttgaccctg 100080
gcctgcagcc accaagtagt cacctgaaag aaaagaaaat agaatttgca gctatttttc 100140
atgagaaacc aaggtggtat ctgcagagat ggagactgag tcatgaaaag gagatagagt 100200
tgccacagag aaggttgctg cccaagggaa acttactctg ctgagctcca tgctgtgacc 100260
ctgaaaacta gagtttcaca gatgatctga gactagggga tatgttcgag tgtcttcaag 100320
gattgtccca agtgaatcca tagtaaagca gggataatcc atggatctaa aaggaaacaa 100380
caggtgccca tccagtcatg aaatagttaa tatccagact tgtaaaagca ggaagttcct 100440
agacactaaa cgaatgaatg aatgaatgaa tgaatataat aaaagtatgt atggggctag 100500
agagacagct tggcaattac aagtacaacc tacctttgca gccaacccaa attcagttcc 100560
cagcacccac aaggaggctt ataaattcca caacttcagc atccagatct ccatggtcaa 100620
tgacttctga cttttagaaa acagatccaa cttccagtga cataaactct gaagctttaa 100680
ccttcctggc tgttttgttt tccactagaa cctgtgactg aagccctact acaacacaac 100740
ccccaccata catacataca cacacacaca cacacacaca cacacacaca cacacacacg 100800
taacttgatc cctgactgaa agcaagttct tactttcacc agagtacttg agctccaccc 100860
acctcctcgt caatcactta actgaccaca agaaaatcca aatgctttgt tgacaagatg 100920
catctatgga cactacaaca aacccacaaa cccttcttaa acatagtttt taagtctaca 100980
gaagattcgt atctcacctt tccgaggcta tttggagcta ggctatactc actaggtagt 101040
gcttacagct cagtggcaaa aatgcttata gctactagga taaggtgttc aatagctcag 101100
tggatagggt gcttgaagat tagtgagtaa tgtgcttgta gctcagtgtc ttagttagtg 101160
ttctattgct gcagtaaaac accaagaagc aagttgtgga ggaaagggct tattcgtctt 101220
acactttcac actgctgctc atcaccaaaa gaagtcagca ctggaacaca cagggcagga 101280
gcctagaggc aggaactgat gcagaggcca aagaaagatg ctgtgcactg gattgcttcc 101340
tctggtttgc ttagcatgct ttcttataga acccaaggct acctgggccc tccccctctt 101400
gatcactaat tgagaaaatg ccttacagct ggatctcatg gaggcattgc ctcaactgaa 101460
gctcctttct ctgtgatatc tctagcttgt gtcaagttga cacacaaaac cagctagtat 101520
gctcagtttg tagggtgcat acctagcatg cagggagtca tcagttcagt tctcttagct 101580
ttgtgggtcc aaggactgaa ctcaggccat taggcatgat gcaagtgcct ttacagaccc 101640
agccatcaga cccgatgttt ttaatgcttt cagatagcac ccaggtgggt gtactagcac 101700
acatctggaa tcttaagaat cttcagcctc acttaagaag ctgaggctga agaactcctg 101760
catttgacat cagcctcact gatgtagctt gtgtttcgat ttcttgcctg ttgctgtgac 101820
aaactccctg accaacagca aaagaacatg acttttattt gaaaacaaga accctctgaa 101880
gctcacttgc aatgtcactg ccaaatatag aaactgaaca aagggtagaa agcagcagca 101940
ttttcccgaa aatcactgat agggaagaga aacccatcca cccatgagga gaaaaggggc 102000
cactcatgag tcactcagaa tctggaaggg actgaaagaa ccctccctgg ggcctgacaa 102060
ggaagcctca tacattgtgt gctacctaag agtgcctgca ccatcttgta gcacacctgc 102120
tctgtgccat tttggatccc acccttagat tcaacccaac ctgcaccatc ttagatctga 102180
tccaccctgg gtcatcttgg atgtcattca ctctgggcca tcctgggtct aatactctac 102240
caaacaagct cccagtgctc taccctctga gctagaagaa ctctactcaa tgagtcacaa 102300
atactcaact acaagcactc tacctactga gccccatccc tagccccata tccaaccttt 102360
gactgcccat gtttcctttc atttattttt ctgtatttct acctgttagg agcagattcc 102420
ttgccaccat gaatcctttg tgctgtgtct gaggcagttt cacttcagtt atcagtgaca 102480
gttggttttt aacaaaccag ctctgcctgt cagagtttga ggtgccaata aataatgcac 102540
agggtcatga ccttttttca ggccaaagca catgctgctt tcaggtgcat gtgcaagtgc 102600
tgtgaccccc cccagctcca ccctctgagg ccctgaagcc atgtgatcag caatcatcaa 102660
gcccatgatg tcagcagagc acccaattca agaggcctga gtccacaaga ttgtggggac 102720
taagtgatgg ctatgtggga acaaaacaag actgcagaga gcaaagcatg aaaaaagaga 102780
cccactatgt gatgaggggg aggagaaatc acagtcacag tggagcagcc ctagatactg 102840
agtctgcagc actccctggg tgctctgcct gacatcaccc tgggtttctg gaggatgata 102900
cctgttaggg caatggcaga ccctagggtg agtggtaatg tgcacatgca gaagaaggtg 102960
ggcagaggag cacactggaa caattctggc catcctcctg ccttaggcac atgtatatat 103020
gcttcatgtg ggcttagaga ttcgaactca gatcctaatt gctagagcac ccattctcat 103080
agagtatctg tctcatcaga agatcaatgt ttgcagagtt gaataaatgc tttttgttgt 103140
tgagatgttt accaaagact gcatggacat gggtttgagg caatagaaat tctttattag 103200
ccagccagag actacatttg ggtacttggg ttccaagtgt accctaagcc tttctcaggg 103260
tgagctttta aaacagaaac tatgttctag gttgacatgt tttaacaaga acaattagcc 103320
agaagtggaa ctacagaaac caaaatgcaa gcttagtaga tttagaaact ttcccagaac 103380
taagggcttt gatggactag tcttttagtt ttggtaggtg gcgctgtctt cattttgagt 103440
gttataacct gaatgatact tccatcatgg agtcagctgt ataaagtctg gggtctact 103500
aaggtctggg atcaggctac agttttgtca tagtgtaacc aaactcaaaa taatagcagg 103560
ctctgtgcat tctgactagt ggagtatcag gtcctagcat gtgtttattg aatgagaaaa 103620
tgttctcaat gtgaaacaat aaaaaaaaat aataataaat aaagcagcca gcagactttc 103680
ttgttgccaa ggtcagtgta cttgccacct acgggcatca tcggggcaac tggttccgaa 103740
tggatggtcc ccacttcatt cctgacttgg ggccctattg gccctgtgtc ttctaggacc 103800
cagtgcctca aagctaggag cggtgcagtg cagtgagcat gcactgagca gccgggagac 103860
cacattcttt gcattccagg ctcagggaaa caccgccctc accttgcagg tggtggctgc 103920
ggtctgtgaa gcacccagtt ctcagcactg cctacgagcc caggcctgtt tgaagccgca 103980
taacaagtcc ctggaaaccc ggtctactca ggagccccag ggctcaggat cagcaggtgc 104040
tgcagggcca ctgagagccc gggctttcgg gagggcggca ctcggggact acagaacacc 104100
aggagttcaa tcccctgaga ttaaggagaa accgagaaac cctgcccaac ccggactcct 104160
tctggtgcct ttacccactg ctaaggctct gctggtaaat atccaagcag cagccggaag 104220
ttcctgcacc tcttccttcc cgcttcctgc caagggggag gaaccaggca tgcggtgtgt 104280
gtgtgtgtgt gtgtgtgtgt gtgtgtgtgt gtgtgtgtgt gtgtgagaga gagagagaga 104340
gagagagaga gagacccatg gtgtgcgtgc gtgtgtgtgt gtcaagctgg accccgtggc 104400
cccagtgcag ccccctccat tacttttact ttggtgcagg tacatcccat gggcgtgggc 104460
cccgcgggtg agtaacaata ggcagggttg ggccaacgcc gggctcctcc ccgtcggtta 104520

-continued cgcaacaagg cggagcgaga tgaaggctct tccccctcgc gtcatccaga caccccactc 104580
ccccgccgtc acaagccggt cgccgcccag ccggcttccg ccgggaatga agagggttgc 104640
ggttggctcc ggtcccgcgg accccacgcg cgtccgtgga gccctcgggc gacttccatg 104700
agcccctccc atcgctctga gacccgctga gtttgcttcc attgtcctct cggccgcggg 104760
ctccggaaca cccgtgcgag cccactgctg atgcacagac tgccattgcg ccgctgtcac 104820
accgtgcgtc ccccgcccca tggagccgcc cgctggtgcc gcggcgaccg taaaagatcc 104880
agaccatgac cccgtgaaga ccaaggtctc ggcgcccgcc gcggacccca aacccaggac 104940
atcgtcacag aaggcggggc actcgttaca agattgggac accatagcca ccgtgggtga 105000
gtgagaactg agtaagaact tatgtgtggg gacgcggctt gggagcgacc ctcagatttc 105060
tgtctcccac actctcatta ctgggcctcc ggaaacgggg cagccccacg tcacagagct 105120
ttcaggaggg tgacttcacc ttagggactc ggaggctccc tactggggtg ctagccaccc 105180
ttgggacacc acgcccggcc tccctggcgc ttgcgcaccc gctcatgccc aggatttctc 105240
gggatcgcat ccagcctccg cactgtagac ccctggcggg actcgaaggg acgcgtgacc 105300
cccaagggac ccttcgggga cgttttccca gcatctattg tgtgcctggg tctcgttttt 105360
tctttagtgg ctcaaacttg gtaccctcgt gaccccgaaa gttgctaggg aagccggtag 105420
atccccaaac gtgccggagt actggggagg gaggctagga tcttgcgaat catgggcgcc 105480
agcttctcaa gtctgaagcc caggagtccc gggcttctca gcaaacttgg tcactaggac 105540
agttgtgcct ggtgtgttga tgattaggaa agtgttccgg gaggatggag gaaggacaga 105600
gggagggatt ggcgtcctcc gatcagctgt gagcagagat tctagaggct tctgtgttca 105660
ccctggtgtg gaagtcaagt cagggttcag gaccaggatg aggggcaata aacactttct 105720
cagctgagca ggtgagatgt taaaaaaaaa atgtgtgtgg gtaaaagggc ttgcaagttt 105780
gatcctggtt ccctcttgga ggctggctga cactcgctgc atcttggctt ttgattgact 105840
tttgagggaa actgagctgc ttgaatgaat gtcgtttatt tatgtatcat gttgtattct 105900
aggctggcct ttccatcact gtgtagccag gatgacctta aactacacat tctccgcctc 105960
cccctctttc tgagtgctgg gaaccgagcc ccactccacc acagattggt tatggggtgc 106020
tgggaatggg gactgccctc tatatgtttg agacattgac ctgaaagtca ctgcatagcc 106080
taagctgact ggagatgcca gacaatcctc ctgtcttagc tttcccagtg ctgagacttc 106140
agggactcat tcacaggcac ttggcacctc aactggttct ccaccctttt ctttctgtct 106200
gtcttccttg ccctctccct ccacgcccca tctcggcacc ttagctggtt cttctctcct 106260
tccttccttt tttctttcct tcttcttcgt cctttttttgt gtttgtttgt ttgtttgtct 106320
gtttgtttgt ttttgaaaac aaggactctc tccatagctc tgggtcacta actcctagag 106380
atgtgcctgc ctctgcctcc caaaatgtta ggattaaata tctgtgccac cacacctggc 106440
tcttttgtta attttaaaat ttacttattt actgtgtgaa cgaggggagg gggcagcaca 106500
agtgtggggt caaggttcaa cttttagaag tctgttgttt tgccaagtaa gtccatggta 106560
tcaaactgaa gtccttagac ttggcaacaa gcctattggt ctgctgagcc ctcttactgc 106620
cccactgtgt ccctagaata gacctcatgg gacatcttgg gagcgtcctt gtcctgaagt 106680
cctccaactt cttcaccttt tccttaccat gaccctgttc cctcggaatc ttttagaagg 106740
acctgggcac acacatcagc ctcccctctc ccctactcat cctttcatat atatacacac 106800
ataactgagc tataagcgct ctcttcactg agccctcaca taaatttaga tggtgtctat 106860
gaccaacgga gttttgtggg tgtttgagac agggcctcca tgtgtagctc tggctgtcca 106920
ggtacttgct gtgtagacca ggtcttgaac tgcaggtgcc taacaagtac ataccaccca 106980
aattaacatg gagcacctcc gtactctctc tctctctctc tctctctctc tctctctcac 107040
acacacacac acacacatac acatactcac acacaaagac aactcctgcg tccctagtcc 107100
ccagcacaca ctgcgttctc caggaaataa gtgttgatgc ttttgtctct gacctaaagc 107160
tcatttctcc attcattagg agactcaagt agagaacatt tcaggctggg gatgtgattc 107220
agtggataca gtgtttatag cttagttgag ataatgttta tagcttagtt gggatgggga 107280
gactgcttgt gattacagta catgtgactc agtagacaga gtatttatag ctcagtgggt 107340
agagtgcttg tagctcagta caatgcttgc attcagtggg tagaattaag tgggtagagt 107400
gcctgtagct cagtggacag agtgcttgta attcagtgaa tctcatatct aaatttgctg 107460
aacaggcccc ctctgtccag caggtctaat gtagtcttgt ttccctgtac tcagctgtga 107520
tctcttgagt cctgtgcctc agtttacttt tcagtgcttc catggcctgc tgccttatgg 107580
aaagccagta ctaaatcttc agtcttacaa gggcagaaga tctccagtct gtctggatgg 107640
gaacatcctc cttagatgaa gagtcacatg agcagctgtc agatgctctg acagatcact 107700
acaggctagt gtcttttaca ctagagagga attactgagg gtcctgtggg ggatggggga 107760
gttggcatct gagatacatt gaggccatct ggtagtccat agtgacatta atacaaattt 107820
agaactatct aggagacact tgaagtccag atcattgagg aagaagaatc ctgtgcatgg 107880
gtggggaccc agagtgctta aaagggaaat caattaccca ttaatattgc caagtcacca 107940
gcgttcatcc ctattgatgt aaggagagca actatgtcct gcttttgcct ccatgaagtc 108000
atctcccctg gaaggcccac tctcaccacc atacaaccct agtcattagt aatggtgtag 108060
gctgtgggag ttgcattaac attcatgaat atgcagatat acactctgta tatacacacc 108120
cacattgtac aaggccagcc tctgcctctt tctagaccag tcccattgtg cagaggagag 108180
attgtaatca cccatagtac acttggctgt tcttttgcaa agtccctaaa ggtggaatgc 108240
tgtgcacaat gcctcccacc atgtcatcac ttccctgagt gctaccttct aattcattgt 108300
ggtttatgag atggggcttc actgtcattc aaaccaggca tccactccaa ccgaaactaa 108360
aggatcatgg gttggaggga tatgaccaca ggatgtctgg aacacccaga agcaggacat 108420
ggttgggagg gtcttctttg aggcctgcag gagatgggga gtagggggct gatggacctg 108480
tacctcatat ttccaccctt ggacaaagga taacaggtga gcctacccac tttgtgccac 108540
cttggatgtc ttctgttcta tgtcatcctg actgaaccta tctgggccat cttgaacccc 108600
acccaccctg agccatctta aattccacct aacctgtgcc attttgcctt gaagctatgt 108660
atgctatctt gaatagcacg taacctttgc catttgaatg ccacccaccc tggaccttct 108720
taactaaacc atctagaaac ccatccaagg cagccatctt gaattgctca ctgtcttgat 108780
atattctttc aggtttcttt tcttgactgt tttctcctga tagtataaag aacctgtcct 108840
gtcctccttc tcaaccccta aaccttgtct gtgtatctgt ccatttcctg ctcagccctt 108900
agcatcctca tcctgaatca ccaagggtga taaatcacac tctctctctc tctctctctc 108960
tctctctctc tctctctctc tccctccctc cctccctccc tccctccctc ccccatgccc 109020
cctgcccctg ccccctctcc cctctcccct ctccctctcc ctctccctct ccctctccct 109080
ctctctctcc ctctgaaagg cacttgtcct gagccactgg tggtcctaga gtgagtttca 109140
ggatgatttt cctacaagga catcacccaa aaggagagca ggaagtcaca gcttcagtca 109200
cgcaggccaa agcttcttgc ttcaatctcg tttagagcct ggatgctcta gtcttagtct 109260

-continued aaccacacac taaggacagc accttcattc tcttgaggac ttatgcatcc ttaggcgttc 109320
tctgtattga cattttcatt taattttatt tttgaagtgc tgggtgttga atatagagcc 109380
tcactcacat taagaaaatc tcctagtctc tcttaagtct cctctgtcct cccttttttct 109440 ttccagagtc tcccagagta gctcaagctt tcctggaact cactgtgtat tccaggctgc 109500
cctcaaaccg ctgttaatcc ttctgcctta ctttagaagt gctaggatta aagcctaccc 109560
tactaggctg aatttatgca aagcttggga ttgtgtcctg ggcttcatgc atactacact 109620
taaatatcct acttttagtt ttatttccta tctgaaataa ccaccatgcc atcacacttc 109680
ctttatttta aaaagatttc tccctgaggc tgagggtgga actcagtgat acagagcttg 109740
taattctgtt gatagggtgc ttatggctta gtagattggc tcttcctgtg ggaggccatc 109800
caagctaatg acacactgct gtacctgata cttggctcct tcaggaatta tctgggttgt 109860
gtttccagtc cactcttctg tttatatttt cctttccaag gctagggtta gaatgtgagg 109920
ggaatagtaa taataatagc cacagtaata acccacttat tattattata tctattattt 109980
ggggggttgg actggaaccc agtgcctcat gcatgctagg taaccagcca ctgagctgct 110040
acacacagag cccaagagca aacttgttag tagtagtatc atcacttttt ttttgtttct 110100
tacatttatt ttattgcata ttgttagtaa atattccatt taatacaatt atgttgtcaa 110160
aataaagcaa gaaatagtgc tatgactcat tgttgacata taccacaaat gataacataa 110220
aactccagta taagagaaac acacacacaa tatatatata tatatatata tatatgtata 110280
tccagtgttc taattttatg tacagtttta agtgggggta aattttaaac atttctattt 110340
tttccaattt ttttattgga ttgttattgc tcttattgtt gctgtgtgag gtgctgggaa 110400
tgcaaccaag gaactcattt atgccagtcc tgagttccag cgctgagttg catccctagc 110460
ccatccttcc tgcctctata tcaaatgctg tattgacctt ggacaaaaat cacaatttcc 110520
caatatgatg gggaaaagga aaggacctgc atctatcttc acagcctgct gcaattgttc 110580
ctgcttgtgc atgttggatt ttgaaaccca gttctgggta tctgggcgac ttccatgtaa 110640
catcttcctc agctacccca ggagccttgt tacccacata aaagtttaca tttcctcctc 110700
accatgtcag acacagaaaa ttatgtctga aaggttacag gtgttcatgt atggaacact 110760
tgactaccat ttgtagagca tgtgtgtaga ttagatcttc ctctgaggta gtcatttggg 110820
gtttttgttg ttgttgtttg tttgtcttat tggcaaaggc attcatcctt gtggaaggca 110880
accttggaat ctataagggc tgtaaagtaa tttgcaatga atttaggtgg tgttgtttgt 110940
taccttgatg acctgtgacc tctgagtcac cttataggtc aagggactct gctgtagtga 111000
ctgttgtaaa tggctggggt atgagcatca aagatggagt gattttgtat cacataggga 111060
tgctgggaca ttgactggga taggcatata caacatacat ttgagtgaat gtaggttgtg 111120
ttgatggctt acaaccaagg gattgggggt ggaggaggag gagagacaag caacttaggt 111180
ttgggtccaa tgacaacaca attctttctt acagactttg aatattggtg tggaatgtgt 111240
attagctagc ttcccattgc agtgacaaga tctctgacat tataaaatta taaagaagaa 111300
tgatttgtgg tggcttgtgc tgtcaggcat ccatccatgg ctctgttggt ttggacctgt 111360
ggagatttag agcatcatgg gagcttgtag tagaacagag ctgcttacca cgtagtggcc 111420
agtacacata gaaaagagaa gatgagtccc agtgtctcct tcaatgtcat gcccccaatg 111480
agctaagttt ctcccactag gcagtaaata gcaccttacc ctgagacttt ctggtccttt 111540
tgcttgactt tgttctgaca gcttctggca gttggcactc tgctgtactg ttcttttcca 111600
cagtgttagg tttctctctc agcctgtgct ctgctctgtg taatcaacac caccagctgt 111660

-continued ttctgcaccc acaagtctca ggcacaagtg tgaaggaaac aagtcggtag ccatctgata 111720
cagaagtcat cctgtggact gcgcatcgca gtacagctgt cacaggctct cttcacctac 111780
tgtactttga acacaaaggt gacatgtgat ccaccaatca gaagcacagg caagggttcc 111840
agtgtcaaga cccttgcttt tctcattttg ctgtgacaaa atgcctgata ataggaattt 111900
aaggggagag ggattattc tgactcagac tgctgctggt ccatcatgga ggcaggagca 111960
aagagaagga atgctggggc tcagcttact ttctggatcc aggaccccag caaagggatg 112020
gtgatgccca tattcagggt aggatttcct acatcagtga actagatgtt ctggggtagc 112080
ttggagcaaa ctgaggttat tttaagcatt ttcagcttga ttatcccgtt cctcattgaa 112140
atgtctataa attctcaccc acactttcta tccatctgat ccactgtagg ccagtcttgg 112200
cttccactca ggctatgact ctgtgtccct cctccattcc tatgtattct gtggcaggtg 112260
tctcctgact gatagacatc accttttctt taaagaacaa aacaaaacaa aaaaccaaca 112320
aaccccaaaa atccctaagc acccaagacc aattttatat cccaattaat tcattgtaag 112380
cttagatagc agaagtaaaa gaatgttttt tgaggctggg catgacagag gatgcctgtt 112440
gtccctttta aataacttta gtactaaaca tggttttttt gtggttattg ggctgttcgg 112500
cctgctgtct agctgtgggt gtgtccttct tgatcctgca tctggatcta gcttgctgtg 112560
gggagcattc tgtatttttt cccctttta ttggatattt tctttatgta tgtttcaaac 112620
gttatcccct ttcctggtcc cccctcctgc aaaacccctg tcccatttcc cccttcctct 112680
gattctgtga gggtgttcct ccacccaaac acccacctta ccgccttcac actccctata 112740
ctggggcacc tagccttcac aggaccaagg acctctcctc ccattgatat ctgacaaggc 112800
catcctctgc tacatatgca gctagagcca tgagtccctc catgcatact ctttggttgg 112860
tagtttagtc cctgggagct caggcagtgg aggcttctgg ttggttgata ttgttgttct 112920
tcctgtgagg ttgcaaaccc ctttagctcc ttcagtcctt tctctaactc ctccattgga 112980
gaccctttgc tcagtctaat ggttggtttt gagcatccgc ctctgtattt gtcaggttct 113040
ggcagggcct ctcaggagac agctatatca agctcctttc agcaagcact tcttgtcatc 113100
ctcaatagta tctgggtttg gtgactgtat atgggatgga tccccaggtg gggcagtctg 113160
ctccacactt tgtctccata tttgttctgt gagtattttg tttccccttc taagaaggac 113220
cgaagcatcc acactttggt cttccttctt cttgagcttc atgtgctctg tgaactataa 113280
cttgggtatt ccgagctttt gggctaatat tcacttatca gtgagtgcat attttttaat 113340
ggtgagaaaa gaatgaaatt gtatgaggtt tgcatttttt ttggagtaca tcataagatg 113400
tccttttcta catcataaga cagaaagcaa ctgtgtttaa aggctgggat ggggagagag 113460
gtgggggatg gatgaaggaa tgggggaatg gatgttggtg cgtgagggtg gatgagttag 113520
tatatagatt gaaatggaag agaaagagta agaggaaaag aggacaagat ggatatggag 113580
ctagaagaga aaaggaacac agggggcata gggagagata cagatggagg aagatgaaga 113640
ataattagga ggaaaatagg gaagagatga tgaaagggca gatgaggcag aaagttcagt 113700
ggaggaaaaa aaggaggagg agcagagaga ttcagaaaga gaagaagcag gaagtcttgg 113760
aagaagagga ggggaggggg taggagacaa tagaggcaga tagaggtgga agaggaaggc 113820
agacagagag agcaaggatt caaagttccc caccaggagt caccaagtcc agcatttcag 113880
ctcttcccat ggctgtgttt caatctccaa tgcacatagc aggcaattat ttgttttagg 113940
ttttagtcat tattattact gtgcatattt gtggttgtag gcaatagcat gcttgtggac 114000
agacatcaca ggaaactttg ttgagtgact gtccattcat tccccaaagc aagctcttta 114060
ccctcagagc catctccctg gccccttgat tgacagttgt gtgtgaaaaa atatctatac 114120
agagctcaag tgctcatcta agtttctttt cttgtattta tctttaaggc cccagattgg 114180
catgatgtcc attcctcagg tatgtttcct tttcctgatc cttgactgaa tgcattgtct 114240
tcctcaggca ctgggacctt tggccgtgta aacctggtga aggagaagac aggcaggcaa 114300
tactgtgcct tgaagattat gagtatccca gatgtcatcc gcctgaaaca ggaacagcat 114360
gtgcagaatg agaaagcagt cctgaaggaa ataaaccatc ccttcctcat taaactgtga 114420
gttcctggct ccttcctttc cacctcctca cctccctaac gttattctcc caagagtgcg 114480
atgtaggggt gctgccaggg ctgtagctca gtggatagag tgcttttagc tcagtggata 114540
gagtgtttgc agctcaattg gtagagtgct tgcaactcag ctaatacagt gcttgtagct 114600
tagagggaag agtacttata tatagctcac cttatggaac gcttgcagct caattgttag 114660
agtgcttata gctcagtggg taaagtgctt gcagctcagc taatacagtg tgtgagtagc 114720
ttagtgggaa gagtgcttgc agagcagtga taagagagta tgtagctcag tggatagagt 114780
gcttgtagct cagtggtgtg aggtgggaga tactatccag attttgtctt gatttattat 114840
tgtgtgtgac catgcacatg ggcacagtac cacacaaagg ccacaggaga gcactatatt 114900
tccttggaac tttagttaca ggtggttgtg cactgctcaa ttgggtgctt ggaatccaat 114960
ttacatcttt aagagcagca agtgttctta aattctggtc catacctcaa cccttaactt 115020
aggagttttt ataacaacta ctttttgtgt gacctgacca ggagccatga ttctaacagt 115080
ctcttcaatg tttatgccca aacattgctt atgttatgta aaagtccaag acctgggtct 115140
tttattacgg cttctagtca aggtgacaga gtaagctaat tattcatttg atattcatat 115200
aaagcaactg gtgatttttt taacaatatt aaatccctct ttgaatttga gaaatataga 115260
tgtatataaa aatacttata tacatatata gtatgtgaag gtccatatgg gcgtatgcat 115320
gtggagatct gagaacatct gctgtcattc cttaatttaa agtgtttgag acaaggcttc 115380
ctgatagccc aggacacaga aagtccaggg agcttcaggg agggtaaatt acccagcatg 115440
tcgttattga aacaccactg cacaattgtc atgctattct agagtattct atgttgtcag 115500
aacattacat aagtgcacta tagtcaaaat tcattagata gtgtagaaac tagagcatcg 115560
ggctgaagga gaaggatcag gttgagtact tgttcctttt gcagagcacc tgggtttggt 115620
tcccagcact cacagcgcac agtcatctgt aattctaatt tggggacaca tacacacaaa 115680
taaatatgta aataagatac aaataaatat gtatttttaa tatttgaaac acagggcatt 115740
taaattctac acagacttca atattagcca aaatatgttc ctgttagcca cagcaccaac 115800
tgaggctcat cgctctgtga gtgtttgtgt cccagtctcc tctccttatg aggacccagt 115860
cctgttaggt catgtctacc ccaaagacct cattctaccc cagtttcccc atttaaagat 115920
ccatctccac acagctctgt cccaaggtcc taggtatgca gacatttaat acaggaattc 115980
tggcagaaag aatcctgagt gcttagctaa gtcagactgg acaattctac ccaccactgt 116040
gtaattacac atgccttaaa ggaatctttt ctttttgct ttctttatct tgcatttaca 116100
ggattcagca ggtgggttaa aaactatgtc aaagtgactt agtgctatag agatttgcac 116160
ttggcctgca tgctgtattc acagcatggc agagcacact gtatatctgt ccagctgtag 116220
gaacacaact tagcaggtct ttgaacttca aaggatgata tgcatgctac ttaaggcctt 116280
taaagtctta tactctgtcc tttaactgtg aacacttgtg aggtcatcca tccaacttgt 116340
gcatgttgcc tatgaacatg gagtagtctg tcttgaggaa acatgggatg cccagcatag 116400

-continued tgggaaaggc ttcaaacggc tgatgaaaat cacagcttac attgctgcag aaatctggac 116460
ttatttacaa atggttttaa caagagtcag tattaggctc agcctactgt acatggcact 116520
attcccagga cagggaaaaa tgtgtgataa gcttcaacta tcaattggca caacccaaaa 116580
tcccctggga atggtttcac tgagggattt cccacatcag tccagcttgt gaatatgtct 116640
gtgagagtgt tctaattgat gattgacata ggactccacc caccatggac aagatgaggg 116700
tgtagtgtca atttgacaca gaaagtttgt gctctacatg cataccatga cccttcatct 116760
gtgctttcat tcctttatgt cagaggtatt tgcacataga ggtataacaa gaaatgaagt 116820
cttgactggg ctgcactgtg cactcttgaa aggtccagtg cctttgggtg ccctactgtg 116880
ggtgctgaga gaagaaacct ctcatcctag gggcttataa tcagagtgct ctttagacat 116940
tgctttgtac ccctggagag caatgatgtt tctggatgaa aaccttgtgg tagttgggtg 117000
ggaattactt gcatgatata tgatagatag atagatagat agattagata gatagataga 117060
tagatagata gatagataga tggatggatg gatggatgga tggatggatg gatagatagt 117120
atatgtagat gatagcagat agatgtacgt agataacata gatgatagat catgaatgga 117180
aggacaatag atggtagaaa ggtgatagat ggttggatag ataggttaaa tagctagata 117240
atagatgact gactgataga taatgataac atacatacat acatacatag tattgacggt 117300
aatattgaag gtctcaccta gggcaccatc tcttagcata tactctcctt gtgaattcca 117360
ccctcaggtt gtcaccacag ttttagcatc ctctgatatt ctaatatcaa cctgcatcta 117420
cagtccagct aagcacaacc ttatgatctg ggttgactga catcagatat cttatcaaac 117480
atcttgatta cttgctggtg agctttgatt ctgttgtgat taaacaatga ctaagaggga 117540
ctgagggtag gaaaggctta acttggctac ttggctttca ctttgctgtc acaggccatc 117600
tgagaggaaa gtcagagcag gaaccagaag cataaagctt tcatccagcc caagaaccca 117660
gtccatgatg ggtggggctt cctatgtcaa ttatcaaaca ggacactccc cacagacacc 117720
cacaggccaa tctaatgtga gaaatgactc actgagaccc tacctaggtg acttcaagct 117780
gtgttagagc tgacagcaca tcttccccct gctagggact ggcgccaccc tccatggaga 117840
tgatcgtcat acttcaatca actaatcagc tgaataaaga catcccccca tagacatgcc 117900
cacaggctag gatgatatgg gaaattcttc actgagtacc ttcccaagtg actctgggtc 117960
ataaaggtga tggttaaagc taaccaggac acattcacat gtttgcatct gtttatgtgt 118020
ttatcttgat atctgtattt atattttgat atttgcatat atgcacctgt tagtgtctgt 118080
gtataccagt atattaatgg gaacatctac ctctgtatat ctggagtctg tacacatatc 118140
ttgtcatcag tgtctgtcaa tcaccaacat acatccatcc atgagtatcc acttctgagc 118200
acccaactta ttacccatcg tgcactctgt tgtgtctcgc aggctttgga caggccatga 118260
caaccgcttc ctatacatgt tgatggagtt cgtgcctggt ggtgagctct tcacctacct 118320
gcgtaatcgt ggccgattct cctcagttgc ttcagtcttc tacgccacag agattgtgtg 118380
tgccatagaa tatctacact caaaggaaat cgtatacagg gacctgaagc ctgaaaacat 118440
ccttctagac agggaaggac atattaaact gacagacttc ggcttcgcca agaaactggt 118500
ggataggtga gtgggaacag ccattggctc atcagaggtt aattaaaaaa taaaggtttg 118560
atttaaatgg gtggacagaa aggggcagaa gatgtatggt gggctctggt gtgatgcact 118620
tctccctcca tctatttaga tgggtctccc atttttcccc cattggtata gtaataaaac 118680
catctttaaa aagcagatta aggaagaaca gggataaagg tgccaacagg agcatgtgta 118740
gaggacagct gtttacattg tagccacata taggaagagc aagcaggaag tagagcaggg 118800
ttattgtctt agttagggtt ttactgatat gaacagatac catgaacaag gcaagtctta 118860
taaggacaac atttaattgg ggctggctta ctggttcaga ggttcagtcc attatcatca 118920
gggcaggagc atggcagcat acatgcaggc atggtgcagg aggaactgaa aagttctaca 118980
tgtttggctg aaggcttctg gaagactggc tttaggacat ctaggatgag agtctcaaag 119040
cccaatacca gagtggcaca cctactccag tagtgcccct ccctgggcca agcatataca 119100
aaccatcaca ttctactccc tggcccccat aggcttgttc aaacatgagt catccacggg 119160
ggccatgcct aaacatagca tattaaaaaa atacatttag tccaacttcc aagtccccac 119220
agtctatagc agtctcaata atgctaaaag tccaaagttc aaagtctcat ctgagattca 119280
cccaatcaat taactgtaat ccccaaatca aggcaggaaa ccagctgggc aaactcaaac 119340
tctgaattcc catgtctgat gtcaaaggag tcttcagatc tccagctcct ttttcatcat 119400
tgttgactgt aacaaatttc tttgcctggg ctggttccac tcccttttag caactttcct 119460
caacatgtat cccatgaccc tggcatcttt aacatcttgg ggtctccaag tcaacttcag 119520
cttcacagct tcttgttcca gtgtctggga tctacacatg atcttctggg ctcctccaaa 119580
ggacttgcat tgccacaggt ccttcattcc cgctgcaaca ggaacttcat ggacaccaag 119640
tcgggttcac acaatgactt ctttacttgt ggctttttcc tttacagctc tcttccccag 119700
cagcttcttc ttagggcaag ggctaaacta caactcctat tacaatagct tctcttactc 119760
ctacttctac tcacagcaag ggctaaacta tattcaaacc gactcacctc cttctagctc 119820
caccccacct catccaatca gaattcacac acgctctagg catgagctca gatcgttcac 119880
agataggctg acaggtcctg atcacaaggg atagtctagc ctggcaggca gcccacgcat 119940
gcagcctcac tgcacatgct cgggcaaggc agtaaacaac ttggcccatg cagccacatc 120000
tgcttcccgc gtcgcatcac ttcttcaact ctgccctcta tagcactata gtctctggtt 120060
gactccactc cactgctgct gccattcttg gtactgacat cttaaatatg ctggcatctt 120120
ccacagcaac taggcttcac caatagcctc tcataggctc tcttcatggt gccaggcctc 120180
aactttgcat ggccccctca gtcccaggcc atcaactata actgagactg caccttcacc 120240
aatggctccc catggcctct cacagtgcta agcctcagct gctctccatg gccccttcat 120300
accttcaaaa ccagtaccac ttgggtgatt cttatgcatt atcaagtcca gctgcaacat 120360
gacatacaac ctcggctatc tctggaacac agcttctttg tgctttcaga aaatacttct 120420
cagaagattt cacttcaatg atgctggtct taatcactgc taatatctta gctccagcta 120480
accagcaaca attgttcctg tagtcccttt tattcttgac tctgaagcta gagccacatg 120540
gttgaaactg ccaaattctg cagcttgcta gtgccggaac attctgccca cttattctat 120600
tagcagcttt ctattttcca actccctcaa ggcttggctg tccttgaact tgcactgtag 120660
attgaccttg aactcagaga tctgcatggc tctgtctcct gaatgcccct ccagattgtg 120720
agcagaagag aaaattgttc tgccatcaag atggttgaat atgttccaga aaattccaat 120780
attgtatgtg tgaatgtttt cataattgca tatagataga tatatagatt acttatatca 120840
tcatataatt tatatatcta tataatccta ccattcctgt acttaagctt ttcttcacct 120900
agaacttgct ctgtaccagg ctggccttga acttagaact gcttgacttt ttctcctggg 120960
attaaaagta tgtaccagca tgcctgggcc taagcttttc atagccactg tttctcaaga 121020
tccagatcaa aagcctgtgt cttctagcct caagatctgg atcacaagtg taccettcat 121080
ttctagattg tagtttattc cagattaaaa gtccacacta ttccttgttt aactgcaaac 121140
acaagcagta ggtttagcta ggtgggttct tgcagtgaga ttaccactcc ctgaatgtct 121200
ttatctcctt gaacaccgga ttcagctcca tttcacttcc tggagtccct ttataacttg 121260
gaccatacat tttatatttt tcctttctca gcttgtttct cttgttcaaa acacccttcc 121320
tgagacttaa tcagagaaca aagtttctgt tgggcttttt gagacttcct ttgtcaatgc 121380
aattaatata aatctcttta cgttaacctc aggtagacgc ttcaggcaag ggcaaaaagc 121440
agccccattc ttcaccaaaa tatcacaagt ctctcagcca catattaaaa ttgttctcct 121500
ctgaaatctc tataaccagg cttccacagt tcaaatcact cacagcaata acatcttcca 121560
tattcctacc aggatggccc attgagcccc acataaagca ttccagtgct ttccaaatac 121620
aaagtcccca aatccacatt cttccaaacg aaggcatggt cagacctatc acagtaatat 121680
gccagtccct gataccaact tctgtcttat tactgctata aacagaccaa ggcaactctt 121740
ttaaaaacat ttattggggc tggcttacac gatcagaggt tcagtacatt atcaaggtgg 121800
aagcatgaca gcatctaggc aggcatggtg caggcagagc tgaaagttct acctcttcat 121860
ctgaaggctg ctagaagact ggctttcgga catccaggat gagggtctca aagcctatgt 121920
ccacagtgac acacctactc aaacaagggc acaaatactc cagcatttcc actccctggg 121980
ccaagcacat atagaccatc acatttaaaa aaaaaaacct tgagccccac tgctactgac 122040
atactttctc ctgtgaggct ccactttacc taaagcttat ccagaacttt cccaaacaga 122100
gctgcctgct ggaccaagtg ttaaaatacc tgagcctgtg ggggacagcc cacacctagt 122160
gtacagctat gggagtggag aggcccctcc agattgtgag cagaagagaa aattgttctg 122220
ccatcaagat ggttgaatat gttccagaaa attccaatat tgtgtgtgtg aatgttttca 122280
taattgcata tagatagata tatagattac ttatatcatc atataattta tatatctata 122340
tacatttata tataactata ttatatatat ttgtatattt tacacacagt aatatgctca 122400
gggatactat agctggatca catggcagtt caattttttt agtgttgtat ttttccccat 122460
aagatacatt tattttatgt ctctatggtg tgcctatatg catgtcatac ccacagaggc 122520
cataagaggg catcagatac cctagacctg gagttacagg tgaatgtgtg cagtcttatg 122580
ggtactaggt gttgaaccca ggttctctgc aagggcagcc agcaatctta aagctaacat 122640
gcctctccag cctctgtctt agagttttct atttatagaa ctcagtcctt agggtccttt 122700
gcccagggct ccttccccta ttcatagcta tggaagttct ttactgataa tgaagaagat 122760
ggtgtcatgt tcctgttaac ccatagccgg ggtagggggg gaaaggctca atattgaggg 122820
aatcagatac tttccagcct caaagggtgt ccatgctgtg tacagattct ctatgatccc 122880
agtattgctg tggtgtgcta agtaccctta accagccagc cagccattgg tgcattttgt 122940
aaaaaaaaaa aaaaaaaaaa aaaaaaaaaa agaatgtgtg cagaaaggtt caaagctata 123000
ggaacaagcc agaactagaa aattccacag cctgaggcat gcaggcctcc agcctggggc 123060
agacacaaaa agactcagct ttcagtgggg taagcagagc tgcctccggt agagttacct 123120
gtgacctcat cagctcatta gctctatctg ccctgatctt gttctgagac aaggctacaa 123180
ggatcaaaat ctgagttatt gggcccaggg gcaaatggaa tgttgggagc ctgtgatgga 123240
ctgacttcta gttgatttcc attacggaga gaagagagga ggcagagggt gtatgtgcag 123300
cccaggctgt catagcactc actagggagc caaggatgac cttgaactga tccctcctat 123360
ctggacctct ggcgtgctag tatgacaagt aagcatctcc acatcttgtt tatgctgggg 123420
ttgggatctg ggctcagtgc ctacaaggca agcactctgc ccattgagct acaagcattc 123480

-continued tgttcctggt cctaccctat agttctatcc cttctgagtt ggatcagttc tttacaggtt 123540
cttgactcga atccccttct atctgttccc tgtgctgtac tgctcagaag ctcttgagtt 123600
ttgggccctc atctctgtca gttccttcct gagccctaga atccttatta ggaagtcttc 123660
ctgatatgtc cgtctgtggg tatcagggtt ggagcaaaat ggatggaact gagcaatgga 123720
taaattcaag gaaacatgta ggcttgaaat tgtcttaata gaatcagtta tttcttcttt 123780
ctcttctaat tcatatcttt gccccttttc tttttaattg cacagtcttg ccatacagcc 123840
caggcacccc caaatgtcat tatccctttg cctgagtctt ctgcatagtt agattgccag 123900
tgggagcccc agactgagca tagaattttc cttttaaaaa cattacttta ttattttatg 123960
tgtgtgactc ttgtctgcat gtctattatg tctgtaagtc tatgtaacac atgcattcct 124020
ggtgccccca gaggtcacaa gaggccatca ggtcctcctg aaactggagt tagaggtgat 124080
tttatcacca ctatgtggat gcttagaatc aaactcaggt tcccacaaga acaagtgctc 124140
ttattcactg agccatctct tgatcccact ttaaaaaata attacattta tttatcttgg 124200
atgggggaga gtacagttca gaggtcaact ttcagaagtc agtgttctgt taccatgagg 124260
gtcccaggaa ttgaactcgg gttgtcaagc ttgacacaat tgtttgacct gctgagaatc 124320
tctgcttcaa gcatgcttag gcctctctca actttaccat ggtcctagct tcaggacatt 124380
ttgatcatat gtaaacatct ctcctcattt gtgcctcatg accctgtggt atgcctctct 124440
ggatcttcct agcctacata ctttacacac acagcatcat tacaatattt ttttttatt 124500 ttttgttcca gcttatgtaa tggcattgtc tatctatgag gtaccactgt caaacttact 124560
gtccttttca tggctgaata atattccttt ttatagttgg accacatggt gtttattaac 124620
cttgtataac ttaatttact ttttatttga atctttcttt tgaagaaaga aacaatcatt 124680
ttttcctatt ttatctttct ttaaaagaaa caaatcaact tttcattttg tatactctgc 124740
agcttgcagc tgcttgccac accaattggc tcttttaaat ataaattaaa gcaggacaag 124800
gtagcacttg cctttgatac cagatagcat tcaatgggca gaagaaggta gatctctgta 124860
cgtttgaggc tagcctggtc tataagacag ccaaggctac acagagaaac cctgtctcaa 124920
aaaaaaaaaa aaaaatagag ctttttgttc tttcaaatgg gttctttctt taaaattatt 124980
cttttctcct gtgaggacac agtagaaagc ctgaagctat agttttgtgg tagagcagtt 125040
taccaaggat agagcttcat ggtaaaccag ttaggtaatg tataaggccc tgggttccat 125100
ccccaggact gtaggatctg ctggtggaag agtaggatgt agtctccatc ccagcaggga 125160
gagatgggga gaattttttt taaaaagaaa caaacaaaaa tcctagattt gtccaaacat 125220
cctactgtcc ttcatctttc ttgtctgtgg gtggcaccaa aagctaaact caacctccaa 125280
tcctgccaac tgtcctaatt tcttttgaca aaaatgtttc ttgatgaggg attggagaga 125340
gaaattatca acattctgga aatttttctc ttcagaaagg agcttgttgc cacacaagca 125400
ggaagtgctg gcacagcaga gttgatgagg agaggagagg ggtcatatta tttttttattt 125460 ctttgatttt tgacacaagc ccctgatccc accacttggg aggcagaggc aggtggatct 125520
ctgtgagttt gaggccagtt tgagatctat agagcaagtt gcaggacagc ataagtacat 125580
agagagacct tgtctcaaaa tacacaaaaa ctctgaagtc ctgatcctcg tgcctctacc 125640
tccatgctat gctggaaatt gaacccagag tctaaacacc agccatgctg gtaccaacga 125700
tgctgtacca actgagttat atccctagcc cctatcacta atgttaaaaa ttattaatac 125760
tgcatattga tttacccacc catgatggtt tgtatattct tggaccaggg agtggcacct 125820
tttgaaggtg tgaccttgtt ggaattggtg tgacctggtt ggagtaggtt tgtcactgtg 125880

-continued ggtgtgggca taagatcctc accctaggaa agagaggccc attagtcttg caaactttat 125940
atgcctcagt acaggggaac gacagggcca agaagtgcga gtgggtgggt agaggagtgg 126000 ggggggtat ggaggacttt tgggatagca ttggaaatgt aaatgaagaa aatacctaat 126060
aaaagtaaat aaataaataa aataaaagca aaaaaaaaaa agcctcaccc tagttgcctg 126120
gaagtcagtc ttccactagc agcctttgaa tgaagacata gaactctcag ctcctcctgc 126180
accatgcctg cctagatgct gccatgttcc caccttgatg gtaatgaact gaacctctga 126240
atctgtaagc cagacccaat taagtgttgt tttttataag acttgccttg gtcatggtgt 126300
ctgttgagtt ttgtttactt tttaagtgtt tttattttaa gttgtgtatc tctgtgtgta 126360
tgtgtatgcc agtgcagtac tagctgagga caagaaatga tcatgggatc atctattaac 126420
taaattaaat tgaagttaat gcttgtaagt aaagaacatt cagcaaggaa cttgccatta 126480
cagggtcagt ttatgtgata aatatagatg gagcaactag aggtgatggt ctatgcatat 126540
aatccaagga gtgggcaagt ttgaggccag ccaggcctaa aaacaaggaa aagagtatag 126600
aatcaggagt gttgttgtat atatgctgag tgtttggaca catggtacaa gtgtaggagt 126660
cacagcatga acaaaagcat tttgcactct gttctttcct acctctcacc cgccccagac 126720
aggatttttc tgtgttcccc tggctgtcct ggaactcact ctgtagacca ggctgacctc 126780
aaactcagag atccacctgt ctctgcctcc tgagtgctgg gattgaaggc gtgtatcacc 126840
accactcagc ttcttctacc tcttctgtag atctatctta tacttgtaca ataatctacc 126900
agctaagcca tgttcatgta cctaggcaca tgtaacaggt tcatgtacct aggcccatag 126960
gccaatctga tgtgggaagt cctccactga gacccttccc aggaaattct ggattgtgtc 127020
cgctgacagt taaagctcac agcacagctt cgtgtgcctg gggaatgggt ctacccatgg 127080
tgactatgac ttgtgcctct ttcaaatcat ggaatcttat acttgtcaca tcattgatgc 127140
ttagaaagtt ttagatttag gagcattttg ttttagttag aagtgttcaa cctataaggc 127200
catatgttaa ttttttgcac agtggccaca cttgtagtgt gatctttatc gctgtatctt 127260
ttagcacctt ccaagtttca tggattcatg cttttgttac ccccacagga catggactct 127320
ctgtgggaca ccagaatatc tcgccccaga agtcattcag agcaaaggtc atggaagggc 127380
tgtggactgg tgggcactgg gcattcttat attcgagatg ctgtctgggt gagtgaccct 127440
cctgacagac atggctgcat acacggccta tgaagaacct tagcatcccc tttttcctaa 127500
gtctgcagat acatggcata tggatgcact cacataatgt actgtcaaga ttgaagggtg 127560
attgggtgtt tagtttactt aaacaagact ttaacgtttc atagacatcc atagttactt 127620
atgtataaca tccatcttct ttatgtgatg gacacccaag gctaatcagt acccaaggtg 127680
aacaaatgac actaatcaga aacagctttg taagtagtga tggaagagca gatgaggaag 127740
gcaagctcag ttgttttatt caccctaatt tccctctctt ggcaatgcac aagatacagg 127800
agtgtgggct ctgtctctgt ctcccagttg atgggaaggt tggttgttcc tgatggtcac 127860
tggtagctgt ggaggcaagt atacacctga taaaaattgt gtaaacattg aaagcaagat 127920
tcccaagatc taggtgtagc cgagggaatt gtaggccaat accatgggag agttattcct 127980
ctggggaggt gacagttttc ccagtcccag gggcttttct ctggtactga gataaaggaa 128040
aattcatcct ttggtagatc aacccaggta ggaaaaaagc ttgaaggagg attttactaa 128100
aatagtgtga gatctgtcaa gagaaagaaa gcatctcctt acccacccac cagtcatcta 128160
tctacccact catctatcca catgtctatt cacctaccta aggcattaat ccacccaccc 128220

-continued atccatccat ctatccactc tttcagctcc tggaggtgcc aggtgtgctt ggcttttgta 128280
gccccatcac ccccatctct gcagggcttc tgtgagtctg catctctttt tttgtctgtc 128340
atgaggtcac tgtcattgca tttaaggtca tctgcagcca gggtgtgctc atgtcaagat 128400
ctgtcactca ttctctaggc agagacccta tatgcaaatg atgtcacagt catgtgttct 128460
gaaaaatgta cacatattgt atgtgtttgt aatccatgaa gcttattttc ttaaaaattt 128520
acaaatataa aaccacattt atttatatac acataattta taatatagaa cataatttat 128580
tatatatata tataaaatct atggagtcta ccacatttat ttatatacac ataatttata 128640
atatagaaca taatttatta tatatatata taaaatctat ggagtctagt atatacctga 128700
taaaattgta taatcataca cacacacaca cacacacata tatatatata tatgtgcata 128760
catatacaca caagagaatg atttagaatc aacaaaaaat gatttttca cattgaagtg 128820 attgtgaaga gcctggggtc ccagtgtctt tgaagagggc atctccagca atctaacttc 128880
ttcccactaa acctggcttc ttgaaggttt ataatgatca cttccacccc ctgctgggaa 128940
ggaagctatc aactgaagct ctttgggagc cctcaggacc ctccatgctg tctctctcct 129000
cctgtggcta taccatctcc taagatcatc tgtttcccat ctgtcttcag atggtcatgt 129060
taacagttat caagcagtgg atccatttga caaaaaaaaa aaaatgtttg catccattaa 129120
gaaaaaataa tagttaacac aaaatagata taattctgta tttaactctc tactaaatat 129180
ccatgcttct ctctgtgaca ggtttccccc atttttcgat gacaacccgt ttgggattta 129240
ccagaaaatc cttgcatgca aaatagattt ccccagacaa ttggatttca cctctaagta 129300
agtgcactcc cggcccggtt tcctgccctg cccccatgtc tactttcaaa gttgtgtgaa 129360
atcacactgc aagcatacac tcctggcaaa ctggatcagt acaattctgt cagtcatttg 129420
tttccaccag gaaagaaaaa cgtttcagtt attctcattt tactgaaatt taatattcaa 129480
aagacctgct acatatctca tttcttttga gatggacagt gttgaaatta acgcagattt 129540
gggacaagtt gtgtaagcga tcagtttgtc catccatcca tccttccctc tatccaacta 129600
tctggttttt ttttcattta ttagttatta actaacttat tgaaacaggg tctcaattta 129660
tagccctagc tagcctggct agtcttgaac tcatagatat ctgacccctg agtgctgaga 129720
taaaaggtat gcaccaccat acacagcttc tttattaact ttttaacttg tctaaatttt 129780
taacttttct ttgaactgtt aagaagggct tagaggaaaa gttagtttat gggaagtatg 129840
accttgaagg agacaatgga ccctaggctc ttcttcatga tcatttccat gtgtaaatat 129900
agtatttttt attaattttt tgagatactt ccacacatat ggtgtgtttt aatggcattg 129960
gtttatttac tgagctagga gaatctttgt gaatgaatct ctgtgccacc acaaaagtta 130020
actttaattc attttttct ttttactgaa attgtacata tcataaagaa ttccttttta 130080
ttaatcattt tgtttacatt tcaaatgtta tccccttcc tggtctcccc tccacgaatc 130140
tctcaccccc tcccctcct ctttgcctct aataaggtgc tcccctacc cactcctgcc 130200 tcaaccctct agcatccccc ttctctgggt cattgagcct ccacagaacc aagggctgcc 130260
cctcccactg ctgccagatg aggcaatcct ctgctacata tgtagtggga gccatggacc 130320
aacccatgta tactctttgg ttggtagttt agtccctggg agctctgtgt ggtccagtta 130380
gttgatgttg atcttcctgt agggttgcaa tccccttcac cttttcagcc tttcccctaa 130440
ctcttccatt ggggaccccg ggctcaatcc aatggttggc tatgagtatc tccatctctt 130500
gtagtcaggc tctggcagaa cctctcagag gatggccata ccaggctcct gtctgcaagc 130560
acatcttggc atcagcaata gtgtcagggt ttggtgtctg cagatgaaat ggatcacatg 130620
gtgggacagt ctccagatgg cctttccttc agcctctgct ccatttttg ttgctgtatt 130680 tcctttagac agggagaatt ctgggtaaaa atttttagat aggtggatag ccccatccct 130740
ccaaaggagg ccatgcctat ctactggagg tagtctcttc aggttctgtt tccctgctgt 130800
tgtgtatttc agctaatgcc atccctattg ggtcctgaga gcctgtttca tccctggtgt 130860
cttggacgtt tgagtggttc cccaagttcc ccacctacca ctgctatttc tgtctattca 130920
ttctccttgg ccctctggag ttctctcctg tctcttctca tacctggtcc tgttctcctt 130980
tctttttcct ccctttcctc cctcccaccc aggtctttcc ttccctttgc ctcctgtgat 131040
tattttgttc ccccttctat gtgggagtga agcatccaca agttggcctt ccttcttgtt 131100
aaggttctat ggtttattat ttatatgggg gtattctgag cttttgggct aatatccact 131160
tatcagtgag tacataccat gaatatcctt ttgggtctgg gttacctcac tcaggagttt 131220
atttgcctac aaaactcatg aagttatcat tctgtagagc tcagtagtat tccattgtgt 131280
aaatgtacca cattttctgt atccattctt cagttgagag acatctaggt tatttacagc 131340
ttctggctat tataaataag gctgctatga acatagtgga gcatgtatcc ttgttatatg 131400
ttggagcatc ttttgagtat atgcccaaga gtggtatagc tggctcttca ggtagatcta 131460
tttcaaattt tctgaggaac cacagattga tttccagagt ggttgtacca gtttgcaatc 131520
ccaccaacaa tggagaagtg ttcctctttc tccacatcct tgccagcatc tgctgtcacc 131580
tgagtatctc agccattctg actggtgtga gatggaatct cagggttgtt ttgatttgca 131640
tttccatgat gactaaggat gttgaacatt tctctaggtg cttctcagcc attcggtatt 131700
cctctgttga aaattctctc tttatctctg tgccccattt ttaaattggg ttatttggtt 131760
ctctggagtc tttctttctt gagttctttg tatatattgg atattagccc tctattggat 131820
gtagggttgg taaaaatctt ttccaaatta ccaggttgct gttttattct gttgtccttt 131880
gccttacaga agtttttcag ttttcaaaat gagatcccat tttgtcaatt gttgatctta 131940
gagcctgagc cagtggtatt ctgttcagga aaattttccc tgtgccaatg tattcaaagt 132000
tctttcccac tttctcttgt attagattga acatatctgg ttttatatgc aagtccttga 132060
tccatttgga ctggaacttt gcacaaggag ataaaaacgg atcattttgc attcttctac 132120
atgcagacca ccagttgaac cagcaccatt tgttgaaaat gctgtttttt tcactgggtg 132180
gttttagctc ctttgtcaaa gatcaagtaa ccataagtgt gtgggttcat ttctgggtct 132240
tcaattctat tccattgatc ttcctgcctg actctgtacc agtaccatgt agtttttatc 132300
actattgctc tgtagtacag cttgaggtca gggatgatga gtcccctaga agttctttta 132360
ttgttgagaa ttgttttcgc tatcctgaat ttttggttat tccagaggaa gttgagaatt 132420
gattgctctt tctatctctg tgaagaattg agttggaatt tttatgggga ttgcattgaa 132480
tccatagatt gcttttggta agatggccat ttttactata ttaattctac ccatccatga 132540
gcatgggaga tttttccatc tcctgaggtc gtcttcgatt tctttcttca gagacttgaa 132600
gttcttgtct tataggtctt ttacttgccc agttagagtt aagtcaacat attttatatt 132660
atttgtgact attgtgaagg gtgttttctt gatttctttc ttagcccatt tacccttagt 132720
gtagaggaag gccactgatc tgtttaactt aattttatat ccagctactt tactgaagta 132780
gtttatcaag tgtaagagtt ctctgctaga atttttgggg ttgcttatgt atactatcat 132840
attgcctgca aatagggata ttttgacttc ttcctttcca atttgtatcg ctttgaccta 132900
attttgttgt ttaattgcta gctagaactt caagtactat attgcataaa tagagagaga 132960
gtgagcagcc ttggcttgac cctgatttta ctgagattgc ttcaagtttc tctccattta 133020
gtttgatatt ggctactggt ttgctctata ttgcttttaa tgtgtttagg tatgtacctt 133080
gaattcctga tctttccaag acttttagca tgaaggggag ttgtatttta ttggaggctt 133140
ttttcagcat ttaatgagat gatcatgtgg ttattttttc atttgagttt gtttatatag 133200
tggattatgt taatggattt gcatatattg aacatccctg catccctggg atgaagcctg 133260
cttgattgtg gtgaatgatg gttttgatgt gttctttgca agaattttat tgagtatttt 133320
tgtaacaata ttcataagca aaattggtct gaagttctct ttctttgttg ggtctttgtg 133380
ttgcataaat atcagtgtaa ctgtggcttc atagaacgaa ttgcgtagag taccttctct 133440
ttctattttg tggaatcgtt tgagaaatat tggtatttgg tcttctttga aggtctgata 133500
gaattctgca ctaaaactat ctggcccagg gctgtttttt tttttggggg ggggtgggac 133560
ttttaacgac tgcttctatt tccttagggg tttggggact gtttagacag tttatctggt 133620
cctgatttaa ctttcgttcc taaatctgtc tagaaaatca ttcatttcat ctagattttc 133680
cagtaggctt ttgtagtagg aactgaagat tttctaaatt ttttcagttt ctgttgttat 133740
gtctcccttt tcatttctga tgtaagatgt ttagaggtca acacactgct tcacaaacaa 133800
ttactcagta ttcatgttga ccatgcattt catgaagatt atggcaaaaa tagtgaaaaa 133860
gaaaaaacac agagcatatt tatatattta aaaaacatat aaataccttc aactttcttt 133920
gatttgaatg tggtcagatt tgagcatttt ctaaccagaa tgagctttgg tttccaattg 133980
tttctttagt tagttaggca gcaggatccc acatagccca gaacttctga tcccttttcc 134040
tcagccttct gaaggcaggg tgacaaacag acttgtgccc ccagtgatgc aacagatgag 134100
atccagggct aggtgaagac tgtactcact gagtataaga actcagaaag cactctgctc 134160
actgagctaa gaacatcctt ttcaccgagc tacagtccct gctggatatt atcataggtt 134220
ctatggattg cagggtgttt gggtatatga gtgctcagac atgtgcgcgc tcacacacac 134280
atacacacac acagccataa cccatggcat tctgtctcta ccctgcttta acttctctaa 134340
gtctttgatt taatccacct taccatcctt tgcattctct tgtcttttgt cgacaataga 134400
gacacaggag aataacagat atttgggaac tcattccata ggtgtgtgca gcctgcaaac 134460
tcagtttccc tgtacagaac tgtgtaaatg aacacaggtg tggtcttcaa aacagcctcc 134520
tcagttagtt acacaggaag gaacaatact ggaatggata aatgctaaag ggttgcaggc 134580
gaaacactgg cttatagctc agtgggtgga gtgcacataa ctcagtggag agagtgcttg 134640
aggcagagtg ggctgagtac ttgtagctca gtgggtagag tgcctgtggc tcagtatcta 134700
gaatgcatat agcttagtgg gcagagtgct tgtaactcag tggggagaat gtttatacct 134760
cagttggtag agagtttgta actcactgtg tagactgtct atagctcaca tggcatagta 134820
cttaactcag tgggtagagt gctggtggcc gagttggcac taacatgccc caagggctgg 134880
gctccatttc ttaccatgta aatggaaagc cagtctgcat ccgtggcata taggagattg 134940
aggctggaag acaggggttt aaggtcattg ttaggggttg gagcccagag tgcaagctgc 135000
ctacctgctt gctctcacaa atcctggtaa gtctttttcc cacaatagag ataccatgtg 135060
gtggtgtggg tggaatgagc acctcagttg attctggcat tttctggatc caagtggagt 135120
cttctctgct aacacaggga cctcatcaag aagctgctgg tggtggacag gacccgacgc 135180
ctaggcaaca tgaaggtgag tcatgctaga gcattccagt ttgcacactg acggtgatgt 135240
catccactaa gaggatccca gaccatgctc aatgttaaat tagtttttgg cttgtttgtt 135300
tgttgctggt ttgtttttat taattctgtg tatgtactac tcaggtttat tacctgccac 135360

-continued agtggactca ggtcccctgc agctgcagtt acaggagatt gtctacttcc atatagatgc 135420
tgtgaatcta acctgggtcc tctgaaagag cagccatctc tctggcccct atttgctgtt 135480
ttcctgtagc ccagactaca atcaaaatca ctatgttgta gctaaggata accttgaact 135540
tgtgacccac tcaacctccc acctcccagg actgggatga catgcatatg cctccactca 135600
tggttgactt attctttatt tttgagtatt tatttattta taagacaggg tctcagtata 135660
tacttctgag tgtcctagaa atctcttttg tagactaggc tggcatcaaa gttatcatct 135720
gcctccttct ccagagtgct agaattaaag gcatgtgcca ccaaacctgg ccacttaatt 135780
tatttttaaa ttgctttatt ggagatttta gaaatgatac acatgcacac gcacatacac 135840
acacactttt tttttcaaat gctttttact gagtgtttat gtttcctctc aagaatgggg 135900
cagaagacat caagcggcac cggtggttcc gaggtgtgga gtgggaatct gtgccacaaa 135960
gaaaactgaa ggtgggagta ttatacaccc ttgaattaaa tgaacagctt catatatggt 136020
cctaaccacc cagtgagctc ccactactgt gtctcagtct tccaaattaa tttactagag 136080
gtttattgtc atttattttg cgcttgatgt atgtgtattg tttctgtgtt catgcgcacc 136140
atgtgacttc agtactggag taccttcagc ctctcataaa atttgtattc caagtgacag 136200
gcattacatg tccccactgg gctacccagt gtcacctcat tcacttattt tatttctttg 136260
ttgctttgtt tattttgaat gactctcagc cacccattgt gcccaagtta tcgggtgatg 136320
gtgacatctc caactttgag acttatccag agagtgaatt ggacaagaca ccttctgtat 136380
ctgacaaaga cctggaaaca ttcaaaaatt tctgaggatg agaactcatg tctgaaaggt 136440
aaaacttttt tttttctga atttctaagt agggtgtcat gtagccaaag atagctttta 136500
atttaccatg tagttgagaa aatatacatt cagtgcaact gagaatgatg aattaaccag 136560
tctgcagggt ttcttactat gtatgattgt caggtaactc agtagtaaat gttgataatc 136620
tctgaaccct ccccccttcct tttctttgcc agatgtatgt gaagacatcg ataccacacc 136680
ataccacacc acagcacaac ataccacacc aatggccaga accttttttg tcgtacgttt 136740
ccatttccta ctatgaaact agaaggtttg gtgtgtgtat tccagttcct gaaagatcaa 136800
tacaatcatc acccttggaa cccagcctca tttcaacaac tggaaacctg cccaatgaga 136860
attcgcaaaa cctgttaaat tgtaggtttt ctccttcttc atgagtcttg tgtttgtgct 136920
gtgaattttg tttctttttt tgtttgtttg tctttctact gaacttttta agtttgaatt 136980
tgacccattt ggttttatgg ctgtcagtgt atatgtgcac agaaattgtg caaactggaa 137040
attttggcac tttgtgcttg tgacatgttc attttttaaa gctttctgaa aaatctttca 137100
ccctacaggc aaaaaaaaaa agggtgagat atatgctttt taaaaatgcc tttctatgca 137160
ttttgcaatc atttgtgtac attgtttatt tagttactgt ttgtttattt agttcctttc 137220
tggtcacttt aaacttggaa gtcaggaagc cacatgccct gcagaccctt attcagatat 137280
agcacaaatg tgtggctttc ctccaatctt ccagtttaga tgttttcagt aaaatatccc 137340
ttcctaaagt taagccagaa ctctgcatac agcatggcac ctgggtgcaa agattgcctt 137400
tttatgataa tacaaatgta cccacatccc cacaagggaa ctttaaggat ccacccctta 137460
agcccctccc tcctctgttg taaatggcat tttcttctca ccatcttaac tttgttctcc 137520
cagccatgtc cgtccgtgaa aactcaggtt ccaggccggg aacttctatg aaagtttgta 137580
cagagctgta tttttggtga gctttctcag tgctttccaa tatgcaaact aactgggtta 137640
tgtacctcaa acaaacaaac acatacagga gatagaatgc aggattataa tcaagtcctg 137700
tcagtagatg tttgctatta agtaggaaat aacatgaaat tagcatagga aatattgcct 137760
taattctaaa cacacatggg gagatcacac atgcgcacat gcaccctctg tgtgctccta 137820
aagcaccttg caatctgact ccaatcctaa aaatcaaata aaaaaccctt aatcaggctg 137880
taaatcaaat gacactatgc gatgtcacta cagtgacatc agacatcata taggaatcat 137940
aattttctat tttaagattt ttaattctgt gtgtacatgt gactgcagta cacacagcca 138000
acaagtgcac cagagaccct acagctggac ttataggcag ttctatgccg ccctgcggat 138060
gctgagaacc aacccaacct cgatcctctg cagtccatgt agttaacatg caagaagggg 138120
tggtaaggca aaagcagcca tgaaaaaggg tgagggaaat atgtcctgtt cttaactctg 138180
agtccaggga gagttgtgca cccaacacct tctcatgaaa caatggaata gttaataaat 138240
ttcaaatttc tctggtggta gcttgattcg aaccaaagta taaaagataa tcactagcaa 138300
ataaaaattt aaaaacaaat ttctgggctg gagagatggc tcagcggtta agagcagtga 138360
ctgctcttcc ggaggtcctg agttcaaatc ccagcatcaa cctggtggct cacaactatc 138420
tgtaatggga tccgatgccc ttttctgatg tgtctaaaga cagctacaat gtacttacat 138480
ataataaata aataaatctt aaaaagcaaa aaaaaaaaaa aggaaatccc ctcttttaaa 138540
aaaaaaaaaa acaaatctct atgctcttca actaagactg actttaatgt ttagtacaga 138600
taaagtacta cgtgctgtgg attggtgctt gtctcactaa actagctgtt acatgttaca 138660
ctgtagaatg tgatttgatg gcttaatact gttcacagga ccctctggct gtgcaaatat 138720
cccaacattg gaccaaaaca taccaatcac cactgtgttg ctaggtgaac cctagtgaaa 138780
atttagcatt gtgtgggtct tgatgttgag gtgaaaatca cagaaagggt ctcacttctg 138840
actgtagatt tgaaatatgt tgatttcctg ggatttgttt gtttgttttt gttattgttt 138900
tggatgaagc tccgtaggaa gcatttgatg aacattcaac acctgtcatt cttatttgtc 138960
agaacactgt aaaccacctg aaacttataa tgcaaagtca aggtttatgt gtgagttggt 139020
gcccccatta ggttgtgttt gttcccatca gtttaggggg aggatctgct tcccaactgt 139080
taaatgttac tatcaaatct gcctttgagt ctcacaccct tgcatctggc ctcacagtta 139140
tttgggagag ggaggttgct ccagttggtt atgtaataga catcatgaca tcattatctg 139200
tgtgacttag agaaagtgag caccccagcg ctcctggtcc tcacatgtca gactaaaacc 139260
ccttgtcacc tccgttcttc tcagagtgtg gggctcatca cttgacctgc tataacacag 139320
gtcccacgtg cactgttcag gtgcaccccc ccccctgctg ccgagcaacc gtcagcttgc 139380
ctgaaattat gcagaatgaa aaagcctgtt tctttttcct tttttatcct gatgcatatt 139440
aaaaaaaatc actgtgattt gtgtgtatat ctctctatat atttgcccca ggaaaacttt 139500
ctgctgtcta atttataaaa tactattact gagtccaggt ttgtttaata aaagtttgta 139560
tgttttaaga aatctgtttc aggtcgtttc ttgacttttc ctgtaacaca gggtaacacc 139620
ataaaacaca agtcattgac catggttaat gacctcagtg atccagtcac caacagtagt 139680
tggtgcccat ttctcagagg cagaactagt gaagctgaaa tgaagttggg ttaatcaagg 139740
aaattggtct gcacccctgt aacaggttga tgattgtttt gaggaatatt agtacccagg 139800
atagtggaag tattacaaac ttcagacgtc attaacttgg gggatggggg tagggtggtg 139860
cataacctaa gtcacaagag tgtgctatgt gggatttctt ttctggtcct tatacgtttc 139920
tgtgcatctc tttattttc ttttactttt tttaatgaat aatatcttta tttacattac 139980
aaatgttatc ctctttccca gttcccctcc ccagaagccc cctatcccat ccctctaccc 140040
cctgcttcta tgagggtgtt ccctcaccca cccaccaact cctacctccc tgccctcgat 140100
tcacctacac tggggtatcg agccttcaca ggaccaaggg cctctactcc cactgatacc 140160
taacaaggcc atcctctact acatatgcgg ctggagccat gggtccctcc atgtgtactc 140220
cttggttggt ggtttagtcc ctgggagctt tgggggatct gggtggttga tattgttgtt 140280
cttcctatgg ggttgcaaac cccttcagct ccttcagtcc tttctctaac tcctccattg 140340
gggaccctgt gctcagtcca gtggttggct gtgagcatcg cctctgtatt tatcaggctc 140400
tggcagggcc tctcaagaga tagctatata aggctcctgt cagcatgcac ttcttggaat 140460
ccacaatagt ttctgcattt ggtgactgta tatgggatag atccccaggt ggggcagtct 140520
ctggatgacc tttccttcag tctctgcttc atactttatc tccatatttg ctcctgtgag 140580
tagtttgtta cttcatctaa gaaggaccaa agcacccaca cttcggtctt ccttcttgag 140640
catcatgtgg tctgtgaatt gtatcttggg tattccgagc ttttgggcta atgtccactt 140700
atcagtgagt acataccatg ggtgttcttt tgtatcttgg ttacctcact caggatattt 140760
tctagttcca tccagttgcc taagaatttc atgaaattat tgttcttaat agctgagtgg 140820
tactccattg tataaatgta ccacattttc tgtatctatt cctctgttga aggacatctg 140880
ggttctttcc aacttctagc tattataaat aaggctgtta tgaacatagt ggagcatgtg 140940
accttgttat gtgttggaga atctttgggg tatgtgctca ggaatggttc tcttagtttt 141000
aatctattgg tttctgccct gactttgatc atttcctgct atcgctcctc ctgtgtgtgt 141060
ttgcttcttt tttctaaagt cgtcagatat acttttaata tgttagtatg agaactctcc 141120
aatttgttta tggaggcatt tggtgctata aactttcctc ttaaccctgc ttttagagtg 141180
tcccataagt ttggatatgt tgtgccctca ttttcattga attctagaaa gttattcatt 141240
cctttctttt ctctgacccc agtgatcatt gttgttgttc agttttgatg aggagtatgt 141300
ggactttctg ttgtttctgt tgttgttgtt gttgttgttg ttgttgttgt tgttgttgtt 141360
gaagttcaga tttaatccat ggtgatctga taggatggga ttatttcaat cttcttgtat 141420
ctgttgagac ttggtttgtg acagactata tggtcagttt cggagaaggt tccgtgaggt 141480
gctgagaagg tatattcttt tgtatttggg tgatagatat atgttaagtc catttaaatc 141540
ataacctctg ttagttttgt tatttctctg tttagtttct gtctcaatga cctgtcaatt 141600
ggtaagagtg gaatggtgaa gtctcccact attagcgtgt gggattcatg tgtgattaat 141660
ctttagtaat gcatctttta cgaatgtggg tgcctttgca tttgaggcat agttgttcag 141720
aactgagatg ccttcttggt tgattttcct ttagtgagta tgaagtattc ttcctggtca 141780
tttctgattg cttttggttg aaagtctgtt ttattagata ttaaaatggc tagtccatct 141840
tgtttcttag gtgcatttgc ttgaaaaacc tttttttcag cctttattaa tatctatctt 141900
tttgctgaga tgtttcttgt gtacagcaga atgatggatt ctatttacac atccattcag 141960
ctagcctgcg tcttttaact ggggaattga atctatggat gttaagagat attaatgatc 142020
aatgattgtt ataactttct gttattttga tggtggtagt ggtggtagta tgtgtgtgtg 142080
tttctcttct attttaatgg tgtggatcta tttatttatt tatttattta ttcattgtat 142140
tttctttagt gtagttagcc tcattgggtt tgacttttcc ttctagtatc ctctgaaggg 142200
ttgggatagt ggaaaggtag tttgaatttg gctttgtcat agaatatctt agtttcttca 142260
tctatgttga ctgaaagttt tgctggggca gtgagccccg tctgccagac cttcaaggtt 142320
ccaccatgtt ctcgaaggtg agtattgtca ggctgtcggc ctgtgccacg cagccgcaat 142380
ggatccaagt ttgaaacatg gcaactctga aagatattac caggagactg aagtccatca 142440

-continued

```
aaaatatcca gaaaattacc aagtctatga agatggtggc agctataaag tacacccggg 142500
ctgagcggga gctgaagcct actcaagcgt atggaacagg gacctgagga caataagaag 142560
cacctcatta ttggtgtgtc ctcagataga gggctttgtg gtgctattca ttcctcagtg 142620
gctaaacaga tgaagaatga agtggctgcc ctcacagcag ctgggaaaaa agttatgatt 142680
gtttgagttg gtgaaaaaat caaggtcata ctttatagga ctcattctga tcagtttttg 142740
gtgtcattca aagatgtgcg acagaagccc cctacttttg gagatgcacc agtcattgcc 142800
cttgagtttt taaattctgg atatgaattt gataacgact ctatcatttt taatcagttc 142860
aagcttgtta tctcctacaa gacagaagag aaacccatct tctctctcaa taccattgcg 142920
actgctgaga ccatgagcat ttatgatgac attgatgctg atgtgctgca gaattaccag 142980
gaatacaatc tggccaacct catctactac tccctgaagg agtccaccac cagtgagcag 143040
agtgccagga tgactgccat ggacaacacc agcaagaatg cttctgatat gattgacaaa 143100
ttgacgttga ctttcaacca cacccgccag gatgtcatca caaaggagtt ggttgaaatc 143160
atcatcatca tgctgctctg aattaatgaa aatcaagttg tatcctcaga caagaggtaa 143220
agaagaagaa tgtgcaggct gattttaact gattgctatc tttgtcagaa gaaacttggt 143280
ccactgagtt acaaagatag caggatgttt gttgagaaat tgggtgtaag tataatatat 143340
ccatctttat attttacttg gccttttttcc cttgcagctt ttaatattct ttcttctata 143400
tatttagtgt tatgattatt atgtgacagg aggactttct tttctggtcc aatctgtttg 143460
gtgttcttta ggcttcttat acatttatat ccatctcttt ctttaggtta gggataattt 143520
cttctatgat tttgttgaag atgtttctgg acctttgagc tggcaatctt ctccttcttc 143580
tatttctatt attcttaggt ttggcttgtt catagtgtcc caagtttcct ggatgtttcg 143640
tgtcatgaac tttttagatt ttgcattttc tttgacataa atattgatat ctactactac 143700
tactgactca tctcttgtat tctgttgatg aggcttgtat ctttagttct tgttctcttt 143760
cctaggtttt ccatctccag gatttcctca gtttgtgttt tctttattgc ttctatttct 143820
cttttaaagt cttgtacagt tttattcata tccttcacct gtttggtcgg attttcctgt 143880
ctttctttat atttatttgc ttccttgttt aatgcttcta actgtttgaa tgtacttttc 143940
tgtagttgtt tgtttgtttg cttttcaaga cagggtttct ctgtgcagtc ctggctgtct 144000
tggaactctg tagaccaggc tggcctcgaa ctcagaaatc tgcctgccac cacctcccaa 144060
gtgctgggat taaaggtgtg caccaccact gcccggcttc tgtatttctt tatgggattt 144120
attcatgtcc tctttaaagg cctctatctt tataagactg gatttaagat cctcttcttg 144180
tgtttcagtt tccttagggt atacagggtt tgttgtggca gcacagctga gctctggtgg 144240
tgccatacta ccctaggtct tgttggttgt gttcttaagc tagcttttag gcatctgctt 144300
ttccctggtg ttggctgtat gatcctgatg ccagcaggac ttctctggaa gatgggggag 144360
ccatagtaca gacaatggag gtcaggttac acaattctgg gggctgtgcc tgaggtggac 144420
cccactgata agggattggt ggagcaatgc tccaacctgg aagttcttgg ggtttccaca 144480
ggcctccaca tagaaacagg atgctcttga ggtcccctaa ggctcttcag gactgaagag 144540
caagcccaga actaggcagt agagttcagg ggactgtgca caactctgcc tgctgtatcc 144600
caggtggacc caactgagaa gggattggtg gagcaggttt ccaagctggt tagttttggg 144660
gtctggaagt cttccacagg aaagcatgac agtcttggga tcctccaagg ttctgtcagg 144720
actgaagagc taattcagag ttagataatc aagttccctt tgatttttca tgtgactttt 144780
ttgtataaca tacatttaca tttattaatg aatatctcta aaatcagcaa ccattaaaaa 144840
```

-continued gtgattgcat tatgtggtca agcagaacta gcaactttcg tttttaaaa agcacaaatc 144900 ttaaaaatct caatttattc acatacataa tacagcatac tagttatgtt aaatgctaca 144960
aaccaatgtg agtctaatcg gatggggaaa agcacacatt taagctttaa gaaacatttt 145020
tccctatata ttagcatttt cttaaataca tacatgagat aaatgaggta actataaaat 145080
atacagggaa caaccatcca tcttgtgtat atgtatatgt atatgtatat atatatatat 145140
atatttatat ttatatatat atatatatat atatatatat atatatatat acacacacac 145200
acatgcatac atacatctat aaaacctttc taacacagaa aacagtgctg ggcccacatt 145260
gttaggaaaa gataactact attatgacta ggccagaagt tggtaaataa agagtaaaca 145320
atgccaagcc cccaccacag gaaaccattg gtaacatgga gtctatagca aggtcagcaa 145380
atcacaaaca tcctaagtaa ttgtgttcca agatatttga tcacattgtg aaccccaaga 145440
ttgtgaactg gaaaaaaaaa aactttcttg ttgttgtatg gcttagccct agcacacacc 145500
tttaacccaa gagctttctt tttttgttgt tgtttctttt tttttccatt ttttattagg 145560
tatttacctc atttacattt ccaatgctat accaaaagtc ccccataccc acccaccccc 145620
actcccctac ccacccactc cccctttttg gccctggcat tcccctgtac tggggcatat 145680
aaagttccaa gagctttcta taaataagag ctaaataaag tcaactgtag gtcaagaggc 145740
agagcaaaca accaattgag agagagtgaa catagaaagt agaatggacg gacattgagt 145800
tgaaggttat ttaagacagt ataaagaagg aaaaggaact ttttccttct gggacactgg 145860
tggaatagaa aggtcaactg ggtgcttttt tctgcctctc tgaactagca ggctctcatc 145920
ataatgtctg gcttttgagt cttcatttgg caaatagaac atttgggatt ctgtttttaa 145980
aacaacataa ctgtttcata attagttttt aaataatttt aaaaagtgta taccccctcag 146040 acctgcttgt tggtattact gtagccaaca caatccatga gccaattctg ctgtcccagg 146100
gtttcaaatc acagggtttg aattttttttg ttgttgttgg agtgaggaag agatagaggt 146160
tggagaaggt ggttctctgt gtaaaacagg tagataaata tagtgtaacc atcacctggt 146220
tacatacagt aaactttagg ttcttgtagg gtgggccaat gggcccctgg caggctgggt 146280
gggatgcagg aaacctgggc tgctgcatga gaatggggtt tgttggaaca ggcctgctat 146340
caggtgctgg ccccacaagt ggtttattca cttagggcaa caaccccaga tggggatagg 146400
aaaggaaata aatgggactt gaaagtgtag ggaactcaga cttctccaga ccttgagggc 146460
aggagtcagg ccaggaaggg ccataagata gaggttcatg ccctccttgt ctctgtcctt 146520
atgggattcc taggagactc acccaggcag gtgagagaca ggccctgact ggagaggaaa 146580
tgccttgaaa atcaaacagt cctggtagtc tcatgtgact tataaacact tttattaaaa 146640
cactcccttg gtttttcttt tctttttaag atttatttat tattatatct aagtacactg 146700
ttttagctgt acttcagatg caccagaaga gggtgtcaga tctcatcatg gatggttgtg 146760
agccaccatg tagttgctgg gatttgaact caagaccttc ggaagagcag tcagtgctct 146820
taaccactga gccatctctc atcacaggtt tttgtgtctt aaatgctgtc ttgttacata 146880
accagagtgg tctgaagctc agattggcat tagacacact gttgtcttcc tcctaccaag 146940
gctttgcagc tggagttagg gatggttgta aactactatg tgggtactgg gagtcaaacc 147000
aggggcctct actagagtaa ccagtgttct ttaaaaatga tttatttatt tgttttatat 147060
aagtacactg tagctgtctt caaatacacc agaagagggc atggatccca ttacagatgg 147120
ttgtaagcca tcatgtggtt gctggggatt gaactcagga cctctggcag agcagtcaat 147180
gctcttaacc actgagtcat ctctccagca cctaaatgct gaaattctaa tttgtacctt 147240
ccctacaaag gtagaaacaa atgctaatgt atgctttgta tgaattattg tgactcagaa 147300
tgaggtagtt gactgtgtct tgcaagcccg aggccctacc tttgatcttc agtgccatac 147360
agaaacaaaa caaacgtatt aaagagtcct cagattttca gtagctcccc tttctgcctc 147420
tatacatgtg gccatagatt ggattggaca aataggcaga tggagaccct gtgaggggtg 147480
agatgagcaa aattattcta gaagtagtac agggggtaca ctaaggctga ctggtctttg 147540
gggtaaaatg gtttgttata ccacagaaag acagcaaggc aagaagagct cttgagggga 147600
actctggtcc atgtgggaaa gtaggaatcc ctccttgtac gcttaggagg aggggtaaaa 147660
atccatgcta catacacaaa agattttatg cttgtaactg acatgattgc agtagttccc 147720
acagaccacc ttcactgcaa gacagaagtt ctaagcatag gctgtgatct gcagaaagga 147780
cccttgacaa tgtcaaatga cagttttgct tccactttgg agaaggcatt tttcccaaca 147840
tggagaggta tccattgctt ctcagaattc tagagtgctt agaatggcct tgctacttgc 147900
aatatgccca agggtcctta ctctcaactc cagaaactct ctgtatgact attatcaaca 147960
ataatattaa ataatgcatt actattattt atttgtctaa atttttattg aatctctata 148020
tagtatattc catctattta cctgtcaata tttatctcat ttttttctct tgaaaatatt 148080
tctgtgcatc aatgtttttc ttgcaggtat gtatacctag tgccgatata gactgtaagg 148140
atcccatgga attgaagttg cagatggttg taagaggcca tgtggaggct gtaaatcaag 148200
ccttggtccc acagaagagc agcaaatgca ttttaatagg tgatccatca gtccaggact 148260
cattcttccc ttttctattt gagggagcat ctgtaagcct aaaggggcct tgaagtcaca 148320
atcctcctgt ctcagcttcc aggggactgg gagtgtagtt gagtctgctc taactaaact 148380
taacaggctt ttatggtgct tagtgccaat aagtaaaatg atggagatga gaaaatgaaa 148440
agagcccaga gcagaagata gatgcccaag gccaacccag atttaaatat ggattaggct 148500
caggaggcca gggtacattt accatgctag aggctcatca ggggctatag acacctgttg 148560
tgtactggat ctgatcctgg attgggtcca caagtgctct ggaatttttt ttaattaggt 148620
attttcctca tttacatttc caatgctatc ccaaaagtcc cccataccct cccccccatt 148680
ctcctaccca cccactccca cttcttggcc ctggcgttcc cctgtactga ggtgtactga 148740
ggcatataaa gtttgcaagt acaatgggcc tctcttccca atgatggccg actaggccat 148800
cttctgatac atatgcagct agagacacga gctccggggt actggttagt tcatattgtt 148860
gttctaccta taggactgca gatcccttta ggtccttggg tactttctct agctcctcca 148920
ttggggaccc tgtgatccat ccaatagctg actgtgagca tccacttctg tgtttgctag 148980
gctccagcat agtctcacaa gagacagcta tatcagagtc ctttcagcaa aatcttgcta 149040
gtgtatgcaa tggtgtcagc gtttggaggc tgattatggg atggatcccc ggatatggta 149100
gtctctagat ggtccatcct tttgtctcag ctccaaactt tgtctctgta actccttcca 149160
tgggtgttta gttcccaatt ctaagaaggg gcaaagtgtc cacactttgg ttttcattct 149220
tcttcagttt catgtacttt gtatcttgta tcttgggtat tctaagtttc tgggctaata 149280
tccacttatc agtgagtaca tgtcatgtga gttcttttgt gattgggtta cctcactcag 149340
aatgatgccc tccaggtcca tccatttgcc taggaatttc ataaattcat tctttttaat 149400
agctgagcag tactccattg tgtaaatgta acacattttc tgtatccatt cctctgttga 149460
ggggcttctg ggttctttcc agcttctagc tattataaat agggctgcta taaacatagt 149520
ggagcatgtg tttttcttac cggttggaac atcttctgga tatatgccca ggagaggtat 149580

-continued tgctggatcc tccagtagta ctatgtccaa ttttctgagg aaccaccaga ctgatttcca 149640
gagttgtaca agtttacaat cccaccagca atgaaggagt gttcctcttt ctccacatcc 149700
ttgccagcac ctgaattctt gatcttagcc attttgactg gtgtaagatg gaatctcagg 149760
gctgttttgg tttgcatttc cctgatggtt aaggatgctg aacatttttt caggtgcttc 149820
tcagccactc ggtattcctc aggtgagaat tctttgttta gctctgagcc tcattttta 149880
atggggtttt ctgattttct ggagtccacc ttcttgagtt ctttatatat gttggatatt 149940
cgtcccctat ctgatttagg ataggtaaag atcctttccc agtctgttgg tggccttttt 150000
gtcttattga cggtgtcctt tgccttacag aagctttgca gtttcatgag gtcccatttg 150060
tcaattctca atcttacagc acaagacatt gctgttctat tcaggaattt tccccctgtg 150120
cttttcccca ctttctcctc tataagtttc actgtctctg gttttatgtg gagttccttg 150180
atccacttag atttgacctt aatacaagga gataggaatg gatcaattcg cattcttcca 150240
catgttaact gccagttgtg ccagtaccgt ttgttgaaaa tgctgtcttt tttcccattg 150300
catggtttta gctcccttgt caaagatcaa gtgatcatag gtgtgtggat tcatttctgg 150360
gtcttcaatt cttttccact ggtctacttg tctgtcagta taccagtacc atgcagtttt 150420
tatcacaatt gctctgtagt acatctttag gtccggcatg gtgattccac cagaggttct 150480
tttatccttg agaagagttt ttgctatcct atgtttttttg ttattccaga tgaatttgca 150540
gattcctctt tctgattcgt tgaagaattg agttggaatt ttgatgggga ttgcattgaa 150600
tctgtagatt gcttttggca agatagccat ttttactata tcgatcctgc caatccatga 150660
gcatgggaga tctttccatc ttctgagatc ttctataatt tctttcttca gagacttgaa 150720
gttcttttca tacagatctt tcacttcctt atttagagtc atgccaaggt attttatatt 150780
atttgtgact attgagaagg gtgttgtatc cctgatttct ttctcagctt gtttattctt 150840
tgtgtagaga aagggctctg gaatttttac atcttccagt gggtttagca gagtccataa 150900
acctaggctg gtgactagat ccaacattgg gttaggtcat cctggtctac agaatgagtt 150960
ccaggacagc cagagctaca tagtaattcc ctgtctcaaa aaaaaaaatt aaaaagaaag 151020
aaacaaagaa agaaagaaag aaagaaagga aggaaggaag gaaggaagga aggaaggaag 151080
gaaggaagag agaaagaaag aacaacatga gttagggaac tgtagagctg gctttctaat 151140
gcaaacactt acactagatc taaagctctg actatagtcc cctaaacctt aacatgacaa 151200
agtatacact catacaccta gacccagacc taccttacat ctcaaagata atttacattc 151260
acaagtattg taattgaatg ctacaggaaa aaatggacaa aatatgaaac ctatcagatt 151320
ttggtataaa aatcaatttt aatgctttca ctaaccctaa gaccatgacc ataatcccct 151380
aatgctaatc ctaaccttaa cacagcagac cacaaaacac tccttactta taaaaaaaca 151440
aaactaacat aaccttacct tgcatcatag acataactta tattaagaga catggtaact 151500
tgatgttagg tcaaaaaaaa tggatagat tatgaaacct attggatttg ggtgtaaaac 151560
tttcccaaat atcaagatta gaaactcagg ttttgagaag catgattgaa tcttttttga 151620
ggcaataaaa aatttaaacc tggaggatga tggtggcata tgcctagaat cccatcactc 151680
cggagacaga ggcagatgga actctatgag ttcgaggaca gcctggtcta tagaatgagt 151740
tcaaggacag tcagagccac acaaagaaaa acctgtctca gtaaaatcaa aaaacaaaac 151800
accaaaaaac ccaccactgc cactaccaac aataaataaa taaataaata aataaataaa 151860
taaataaata agtttaaacc tgcggttact agactaatgg gtaactctat gatgctttat 151920

-continued agctctattt ccttgagtca gaatgactgg agaagtgctc tgcagattcc agatggaatg 151980
aaagctatta acctagaaat ggtacactga ggcaaaggaa cccaggcagg gtggtagagt 152040
gaagaaattg cagccataga agtctctaca ccaaaggtga agactaagga gcagcactca 152100
acatctatag ggtcttgggg gccccttgag ttcctacaaa atgcctctgc ctcataaaca 152160
atatgtttgt ctggaagtca gctactttca gccccctatc ataaaacgat aacggaacct 152220
gccatgtcca ggtctgtctg acatgcagaa gtccaagtaa caagatttgg ctatacactt 152280
cttaaagatt ctctgtctcg ctgtctctct gtctctgtct gtctccttct gtctctgtct 152340
ttctgtgtgt atttatatac aagtgtgtgt gtgtgtgtgt gtgtgtgtgt gtgtgtgtgt 152400
gtgtgtgtgt gtggtgagta cctatttact gactcttggg ccttagtaaa atatattgca 152460
atctgctcta aaactagaag gcaagttttt acaatcagta gatatttgtt ctaaagaggc 152520
ctggattttt aaagcaaaat ctgatatcaa aatatctgtg agggaggcat gacactagca 152580
aagatataga agaagccaga cataataata ccattatgat caactatcca agataagtgc 152640
caccagatat aagattaaca aggaacaaat acctagaacc agaatcaaag gggaaaatga 152700
cacatgggaa taaatactac ctaccattaa gctacagaag atcacttgtg tttattgcca 152760
ctataccaaa aactaggaca tcaaggaaca caaggactaa aacactgaat agactaatgc 152820
aatattcagg aatcctggca tgttattaag aatactatta gctagatggt tgtggaacac 152880
acctttaatc ccgacactca ggaggcagag gcaagagact ctctgagttt gagatcaccc 152940
tggtctacag agtgagttcc aggagagcca gggctacatg gagaaactct gtcttgaaaa 153000
acaaacaacc aaatactatt aaaggttgtg aaaaaagttc tcacggatac tttttaacta 153060
gatacaactc tattggtaag gctacacact gtaagatata tgtatttaac tatacaatac 153120
aaatacactt cgtaggacca ttgatcaaat atagaagtaa atatacatgc acaatggcaa 153180
acacctttat aggattaggc attgtagtgc gcatacccta ctcagcaagc ctccatgaac 153240
aatctttggt tctggtacac agcctttgat tgtcctaagt ttataataga ctctgacaaa 153300
ggctcatact tcgcaggcaa aatgacacaa gaaacggcaa ataattagat atctaatgga 153360
atttctatat accatatagc cctagaacat caggaaacat gagagatgca atgctttgat 153420
caaagaataa ttaatgttgt ctggttaaat ttacctgcaa ttggctttta ttaataaagc 153480
agcttatacc ctgacccagc tgggacttag cctgtctata ttggcttgtt cttttccaaa 153540
atctggactt cagcaacatc tccaataaaa cctggagata ttaagcactg actacactat 153600
ttgcttcagt ggcacattgg ttgaaagatg aaatgaaaga taaaggtggc attgccacct 153660
tcaaatcaat gttctcacaa cttagtggga catagtataa gactaatttg cacaggccct 153720
aattggtcta aagcagctct catcactctt tgtgacttta ctaccttaat taagttttat 153780
cagttccatt cactttatat gcaaattgtt tttgagattt ggcctctcag acatatttaa 153840
gttaggagaa gaactaccag atataccatt atttgaaagc ataataacct ttctagaact 153900
tataaacaaa tttactatac aacctcatat tgggagcaga ttttgttttg gtcctggaag 153960
acaaagaatg gaactagatc ttaagacgta atggtagata cacacccctt cactctcttc 154020
acactttata ttgccttaat tgtagtctta ctcagttttg aactggctct atatcaaata 154080
ctatgaacac ctctctccaa gcaccacgca cctactggga tacaacacac taacatttag 154140
aaagaagtgg atcaaacctc tctttgtgtt gatgataggt agaaggccct ctttgaagct 154200
actaccacta ctgtcactgt agccatctgg acctagctca ctatattcat ttccccagaa 154260
ctccccaata ttgtaggatg gaaggactta atgtaaccat cagacttgat aataacaata 154320

-continued gccgcctatt ggaatgttac agaattggca cataaacctg ttgtcttagg atctccattg 154380
ctgtgaagag acaccacagc aacttttata aaggatatca tttaattggg gctggcttac 154440
aggttcagag gttcagacta ttatcatcat gatggaaaac atgacaacat ccaggaagaa 154500
atgatgctga agtggtaact gagagttcta tatcttgatc cacagacagc agaagactga 154560
tgtgacacac tggtcagact tgagcttttt agacttcaaa gctcataccc agtagcctac 154620
ttcctccaac aaggccacac ttactccaac atagccacac atccttattg tgccacttcc 154680
tatgaccaaa cattcaaaca catgaatcta tgtgggccac cacacctgtt gagatgcaca 154740
tgataataaa tgcaaacagg ctatgcagaa tagtaagcat tttaactcac aacttaagag 154800
ctttaccaac ctagacaaat gcaataatcc tactaaagcc tctagcaata ctaattgttg 154860
aaaataactg gaggattaca gaaaggcaca aaaaagcaat ttatgcagac cactggatat 154920
acttagaaca aatggagctc ttgtctctag ctgcatatgt atcaaaagat ggcctaatag 154980
gccatcactt gaaagagaga tccattggac ttgcaaactt tatatgcccc agtacagggg 155040
aacgccaggg ccaaaaaggg ggagtgggtg ggtaggggag tgggggtggg gtgggtatgg 155100
gggacttttg gtatagcatt ggaaatgtaa atgagctaaa tacctaataa aaatggaaaa 155160
aataaaaata aataaaagag taaaaaaaac ataaaaaatc aatgttgatc aacacatttc 155220
gtctgctaag atgccctacc tacaagatga gtttttaatt attccaagct ggtactctga 155280
tggaactctt acaagtaaca cagctatgga agtcagcttt atactaattc tggtacccat 155340
atgggatgga aaagataagg actataaata tgtagaaact gaggtatcca acaataagga 155400
tgacacagca acaataacaa ccaaaccata ttttaatcct ctcaagccat attttaatcc 155460
atctaatgac agtatatcct tcatatttag aatacaagaa ggaacagatt taaaaagaaa 155520
tgagcaatga gagtatatat tatgttttag gcttcattaa ttttccatac tttggacatc 155580
tctctctctc tgaccaccca tgaggtgaag gagttcacag aagtctcatc ttgggacagc 155640
tgatctctaa tacctcttaa tcccccatca ttatgggatt ctaatacttt tggaatatat 155700
tgggacatat accaattccc acttgtgcct actgaaccca aatgtctgcc ctactcttta 155760
gaaagattac aacaaaagtc tttaagacag aaccaggcac ttactctcct aaattcctat 155820
cccattattt catattatta gaaaccaagc tagtggcaca tgtaaattta attttatcac 155880
agccccaaac tataactcta cattgcctaa ctttgaaatg atttgtgtat gtttagaatt 155940
aaaacaaaac cttccacttt tacggggtca caattggaca atatttgggg caatcaactt 156000
gtagaaaact ggttagctta ggcagaaaat cgcaactcta aaatcactgt ccaacacaga 156060
tggaacatgt ctggagaagt gtatctccta gtggtatggg gtggtactac aatgagatga 156120
gcactcatac tactttggct caatgtaaca atcctggctg acaaacataa tccagcaata 156180
gtcaaaacac tatcaaaagc atctagtttg atacatcagg catcaaatat acacagtgat 156240
caaatatata cagctatcac caacagttaa tcaggaactc aaatccattt aatttgatgt 156300
tggctattgg cttgctgtat attgctttga ttctgtttat gtatgtgccc tgtatccctg 156360
atttctctaa tacctttaac atgaaggggt attggatttt atcaaagtct ttttcagtgt 156420
ctaatgagat aatcatgtga ttttctttgt ttatatggtg gattatattg atgatattaa 156480
tatattgaat catctctgca tccctgggat gaagcttact tgatcatgtt ggatgatggt 156540
tttaatgtgt tctctgattc agtttgctaa tattttattg agtatttttg catcaatgtt 156600
cataaaagaa attagtctga gaatcttttg ttgagtcttt gtgtggttta ggtatcaggg 156660

-continued

```
tgactgtagt cacacaaaat gagtttggca gtattctttc tatttccatt ttgtggaata 156720
gtttgaggag tgttggtatt aggtcttctt tgaaagtctg gtagaattct gcactaaaac 156780
catctggccc tgggctttgg gtggaggatt gggagacttt taatgactgc ccccccacac 156840
ttaggggtta tagggctgtt taaatagttt acctgatctt gatttaactt tggtaagtgg 156900
tatctgtcta gaaaattgtc catttcactg agatttcccc gttttgtgga gtataggctt 156960
ttgaagtaag acataaaaat tcttttaatt tcatcagtgc ctgttgttat gtctcccttt 157020
tcatttctga ttttgtttac ttggatactg tctttctgtc ttttggttag tctggctaag 157080
ggtttgtcta tcttgttgat tttctcaaag aaccggctgc tggtttcatt gattatttgt 157140
actgctttct ttgtttctaa atgaatgatt ttagccccaa ttttgattat ttcctgcctt 157200
ctactactct taggtgtact tgcttctttt ttctatagct ttcaggtgta ctttttttaaa 157260
cttaatttta ttttttactt attcacttta catcccactc actgccccct cccacagtcc 157320
ttcccccatc cccctccccc ttctcctctg agcagttggg agccttcctg gctatctccc 157380
aatcctggca cttcaagtct ctgtgaagtt aggtgcttct cccactgagg ccagtcaagg 157440
gagcccagct agaagaagaa catataccac atacaggcaa cagctcttgg gatagcccct 157500
gctccagttg tttgggaccc acacaaagac caagctgcac atctgctgca catgttgggg 157560
aggcctaagt ccagcctgtg tatgttctct ttgattggtg ttcagactct gagagctcca 157620
agagtccagg ttatttgctc tgttggtctt tctgtggagt tcctatccct ttctgggcca 157680
caatccttcc tcctagtctt ccaaaagagt ccccaagctc catccactat ttggttctgg 157740
gtgtttgtat ctgtctgagt cagctgttgg gtggagcctc ccagaggaca atatgcacct 157800
gtgtgcaagc ataacagagt accattaata gtgttaggga ttggtgcttg tccataggat 157860
gggtctcaag ttgggccagt tattggatgg ccaattcctc aatctctgct ccatcccctg 157920
tccctgcatt tcttgtggac cggacagatt ttgggttgaa atttttgtgg gtgagttggt 157980
gtctctgtcg ctccactgga ttcttgcctg gcttcaggag gcaggttcca tatgcccaat 158040
tttgtgagtc acagctaagg tcactcccat tgattcttgg gtgcctccct tatcccaggt 158100
ctctgtcttg tcctggagat gccccccccc atctcctcat ccttgtcagt tgcaaagttt 158160
tttatggttt aaaatattac ttttactaaa attaaagcat gctatagaat accaccataa 158220
gatatttaga attgtgtgtg ttgtttgctt gctttgtcct tctcaatgtc tttggctatg 158280
gcaggtatca aatgaggaaa tgaaaatgat ttgtataaaa atatgctttt gataagactt 158340
tttagatgga ggagagttgc tgggtattaa accagtgcct catgcagact atttcctctg 158400
cttttgaaaa aaaaaaatct taaaaacatc tttcatccct tgtaaagctc ctaaaatgta 158460
gatatatcat atacttatct gggcaatgat ttcatctgat ttggaattct atcaatagca 158520
agtgatggtt aattcatgtc ccaaaatcaa agaggatcag gaatatatat gtggctagta 158580
ggagagatct tgcccagagt gtgagcctag aatatcacca caagcctcac agcaaaagag 158640
aaaatggctt caaactgaat cttaaatgac taaatactta acatctgaaa tgattgagaa 158700
tttgtgccta ggggaaacat agttctacat aaattataaa attattcatg gaacttgtta 158760
gaaaaaaaat ttcatgctac ataagacaca agccatgaaa accatatagc tttacagcta 158820
aaatgattta aaacaatttt taaaatactt aaaaattata aagggagaga ttggttaaga 158880
gcacaaattg ctcttccagg ggatgcagtt tctaatttcg gctaccagat ggtgactcac 158940
acctgtctgg ccacttcagt ggatctgctg ccctcttctg gccttcttga gcaccagaca 159000
tgcccatagt acacatggta ccaaacaccc atacacttaa ttttcttaat aaataaaaag 159060
```

aaaacctaga gtcataaata tgaaagaaaa atgattgtaa gatgaatttt tggatatttg 159120
attccatctc actttaatgt acattcccag aaatcatttt acaccctaaa aaaagggagc 159180
atatactact agatagtaaa agctttaaga gtttggaaat agatctcact gttaaagcat 159240
ttgcttagca tgcatatgac tttggattca attctcagca ctgaaagagg ctctacaaga 159300
aaggaaaata caaactgcat taagatgaga cattaaagtt catttctatc aaattcatta 159360
attatattag tctttttttt caatgctaag gattgagccc aaggaagaat tatttcactc 159420
agatgagttt tctttaaact ttgctactaa agattcaaat actgggctgg aaatatggtc 159480
tggtgacata gtgtttaccc agcatgtttg gttcctgaat ttgatcctta gtagcggcac 159540
tttcccctta agtaaccctc ccttcgagga gaggcccttg gtccggtgaa ggtcctctgc 159600
cacagtaaag gggaatgcca ggtccaggaa gtgggagtgg gtgggttggg gagcacgggg 159660
aggaaggagc ggataggggg ttttcagagg ggaagccagg aaaggggata acatttgaaa 159720
tgtaagtaaa gaaaatatct atttaccctt tcttagaaat gggaacaaaa cacccatgga 159780
aggagttaca gagacaaaat ttggagctgt gacgaaagga tggaccatct agtgattgcc 159840
atatgcaggg atccatccca taatcagctt ccaaacgctg acaccattgc atacactagc 159900
aagattttgc tgaaaggacc cagatatagc tgtctcttgt gagactatgc cggagcctag 159960
caaacacaga agtggataat cacagtcagc tattggatgg gtcatacggc ccctaatgga 160020
ggagctagag aaattaccca aggagctaaa gggaactgca accctaatag gtggaacaac 160080
aatatgaact aaccagtacc ccggagctct tgactctagc tgcatatgta tcaaaagatg 160140
gcctagtcgg ccatcactgc aaagagaggc ccattggact tgcaaacttt atatgcccca 160200
gtacagggaa atgccagggc caaaaagggg cagtgggtgg gtaggggatt gggggggggt 160260
gggtatgggg gacctttggg atagcattga aaatctaaac gaggaaaata cctaataaaa 160320
aaaaagaaaa tatctaataa aaaaaaagag taaccctccc ttcaaaaaac tcaggaagac 160380
aaaaccacta attttctttc tgaagaaaac aaatcttcaa aaccttagac aaacagtgca 160440
cacctacact ctctacctgc tgaaaagcaa gaacttcact agagcctggg aagagagcct 160500
gatcctgcat gtacttccaa attctctgcc atccctccca agaaaatcat tagtcctggg 160560
accagcacta ataggctttt gaaacttcat aacagtttat caaactttgg agacatgttt 160620
ccactggcat taagacgtgt tttactgctg ggcagtggtg gcacatgcct ttaatcccag 160680
ctctcgggag gcagaggcag gcggatttct gaatttgagg ccagcctggt ctacagagtg 160740
agttccagga cagccagggc tatacagaga aaccctatct cggaaaaaca acaacaacaa 160800
aaaagatgtg ttttactgta tgaagccagg ttcttcccac tatggaatgc ctggatctaa 160860
cttggcacac tgcgtaagca atgcattttg agaagcacag gaatcaatgt gacagacatt 160920
agaggccaac ttgtctatct gtgaagacta attggcatcg ctcctggaga tacagacaga 160980
ggttccgctt ctgttgaatg acaagtggtg gcagtagtga tatcctccag gaagcacgaa 161040
gtcctgctga acactgacaa gctagcagca aatgctgtct gtgcttgctc agctagaaca 161100
ccaccttcag cttctttgcc aatctttgcc aatcaaagat taaagaaata gtatggactc 161160
aggaggcaga ggcaggtgga tctctgagtt tgagtccagt ctggtctaca gagaatttaa 161220
ggacaacaca gagaaaccct gtcttgagga gaaaaaaagc aaagaaacca aaaagtaatg 161280
tgtatttgcc ctttgcaaaa gcatcagtgg aaaatggaaa actttagttt taaaagttct 161340
gaaggtaggt gtggtaatcg tgtacctcag cagttgtctg agagaagaca gttatatcgt 161400

-continued

```
gagggttata tgttgagaga cacctacagc taggtagcac cagccagaac tacatagtaa 161460
aacattgttt caaacaaaag tttctataca atttctgaag gattttcaaa gttcttacac 161520
acacacacac acacacacac acacattctt ctttcactgt tggactcatt ctagacttgg 161580
tgggttctta caatttcctc tgatattaga gaattctcta aaaaacaaat tgaaagtaag 161640
tagtggtaac acccctgtgt tcatagcact caggggggctg agacaaccgg cgtgtaagtt 161700
aaagcccaac ctggccttct taaccagacc ctatctttaa tgggctgaga gtgggtctaa 161760
aatttgaggt tattgaaaaa tgtctgaaca ctaaaactat ttgcatagca ttttgagttt 161820
gatacttgcc ccagaatagg caaaggcata taaatacaag aagggtaaaa accttgacaa 161880
aactttccca ctgaaaatga cttgggatgg gggttgccaa agatgtacaa catatttata 161940
gttttacttc tccagtaagg gaacaactaa taaagtagca gttgctacaa aaagaactaa 162000
ttctaggtct gggaaggtgg ttcattgatt aagagccctg attgctcttc ctgaggacct 162060
aagttcaact tccagctcac aaccatcggt aactggcgtt ccagggatcc aatgccttct 162120
ggcctttgta tgtactggga catggatggt gcaaagacac acatgcagac aaaagaacac 162180
atacatataa aataaaaaaa aatttaaata caaataattc tgttaggttt gttgaatgtc 162240
cacttttctt cataatcaac gtataactta taacatgtcc atttatatgt cccatgtatc 162300
tttctctgcc tgtgccccat ctaagctatg atagaacatg aggaatgagg gaaaaggaaa 162360
gggaggagaa atagaaggaa gaaatttcca acactctcgt cctttctctt ccccactttc 162420
attttattat tttgtttccc tttttcatct ccctgtccct ttaaggtgat gtcgattgta 162480
tctcaggcag gcctcaaagt tgatttgtag ccaaagatgc ccttggattt ctgatccccc 162540
tgcttccaat ttccagatgt taagattatg ggcttgtgac atctcatccc tagaaaagca 162600
taagcttgta gaagtcaagg gacactttta tttactgctg cctctctaga aacttcctgc 162660
cagtttggca cttacaaaat attttttaga aagaagagga aagtagataa tctatatact 162720
aaataagtac ttgataactg agtggaactt aaaattaaaa aaaaaaagca gtgtttgtga 162780
acaggtttca gtacctcccc atttttctca aagcaaatgg tcctggcggc tgtgtctcac 162840
acgtgggtaa tgaaatctcc ctgcctaaag atgtacaatg tgaaagtctg tttccccttg 162900
tgatagaggt taacattgta agccctgcag caccacatgg ctcaggtagt gttgtggtta 162960
aaattgtgtt tggccaaaag aaactccaac acatatatgc catcgctact tctatttttt 163020
ttcttaaaca taataaaatt taaagaaaga aaaacctcac aattgttagg atttagtggc 163080
agaaggtcct tgatgggttg gggcagagat gtgctgcaaa gagatcacac catgcaaaca 163140
gatctcagga gagaggccat ctcagagtgg ggacataaaa gagagagtta gagtcagaga 163200
gccagactga aagagacaga ctgagagact ggaagacaaa gagaatgggg gtgtgttggg 163260
gggggggttg gtaagggttt tgtaacttgt ggaaacagtg taaagagtgg catttgggga 163320
agggaggtga tgatgtgcct tttggcgctg agttcctgag ggcaggcttg acaagtgcct 163380
gctttctaac attaatggcc attgatactg gaaaaaaaaa ctattttatt actacattaa 163440
ttgaaatttg caactatatt tataaataat atttatacat ttatggagtc atgttaactt 163500
tcagcccaag gagagataac attaaaaatg aaatatattt tataaagaaa atattttctt 163560
aacctcgtaa aagtatacac agtaaactat ggttatctgt aacatttaaa gtaaataatt 163620
ttagcttaca atttaattat gatgctgatg gggtatgttc agaaagttat tcatgaaaag 163680
ttccaattcc ttacacatag attttccaac tactttcttt tgtttattca gaaaggatgg 163740
gaaactacga gggctaacac cctacctcct tgtttaaggg actgactcaa tcttctactg 163800
```

```
gagatgcccc attgcttttg acttactatg ttcattcagc cttctatttt aggtttgatt 163860
agtttgattc tacacttaac tttctcctga cataaagctc tcaataagaa agtatattca 163920
ttaacattgg cctcagaaag agagaggttt taggctgttc actggatata tgatcagaat 163980
aaaagagata caatacatac acatcagaga gagctgctgt gttggtgcca gaaattgaat 164040
ccaggtcctc tgaaagaaga gccagtgctc ttaagcacct agtactgtct tcagctccaa 164100
caagtaggtt taaatcttat tttgcaatgg gacctggtgg ctcatgcctt taatcctagg 164160
tgaatgactg tgatcttgaa ggtagcttgg tctacataat gaattccagg acagccaggg 164220
ttatgtaaaa aaaaaaaaaa atgtgtcaaa acaaaacaaa aaaaaacctt attttgggag 164280
ggaaaaattg gggtttctgt cctgacaaat ccctagcctt tctgttgaat tctttataaa 164340
aaatgtattt gtgtaaaagc tcttttgttc cttttgcacc caactctcct gcatgaaagg 164400
tcaacatgaa aatattaaaa atcacaacca agatcggatg aaatttaaat tataattact 164460
aaatgggcac atccaaatta ttatgacaga gaaaacaaaa gccctaggac tagggagatg 164520
tggaaaaatg aagcagtcat gaaatactaa aaccattctt aactgtcctt attctggaag 164580
gggaaaatca acatttccct gaaagctgct gtaatcatgt gaagttcaaa tggtttgatg 164640
agccttcctc caatcaaaca gatatgatag caactaaatt tctccaacta aattatttac 164700
aactgactga gacagtccct ctgaagccag gtactcagct aaactattca gaatgaaata 164760
ggaacggaga agagggtgga aggctctgta atgacagacc acactggaat agtagcccac 164820
tacctgactt cgtagatgtc ctgatatgat gggaatgata gacaagcatg acagtaaggt 164880
tatgaggtgg gaagaagtga gtggaattac acaaaatcta taaagaggaa gtgaagcaaa 164940
tgatgtagca agccaccctc ataggatttt gcatctgatg attgagatgg ttactaggat 165000
ctctagctat gaaatctaaa acagcttttt tggggggggg gaatcaatta cctgtagttt 165060
tatttcttgt tcatttttct ttctttgaat agcatgtttg tcctgagcca tgaaagtctc 165120
ccacatacaa accaaaagaa ggaaaaacaa acattcgata atccagttca ctgaaggaaa 165180
gtacagtggt ttaaatatgc ttaccccagg gagtggcact attagaaggt gtgccttgta 165240
gaaggaggtg tggccttgtt ggagggagcg tgttactgtg ggtgtgggct ttgagaccct 165300
ccttctagcc atgtggaaga cagtcttctc tttgccttca aaacaagatg tacaactcag 165360
ctttcccggc accatgtcat gcttcccact gtgatgataa tagcctgaac ctcagaacct 165420
gcaagtcagc ctcaattaaa cgttgtcctt tataaaagtt gccttggtca tggtttttct 165480
tcacagcaat gaaaacccta agaaagaagt gataatgaaa tttataaaga gaaataatat 165540
gtattttatg aggtatcaca tgctgtaata ttcagtagca catgaggatt gaaaattcac 165600
taaaattcag tggctacttc tggtggttct acctggaatg cttttatttt taaaagaaca 165660
tcaactcagt gcaaagtggt ttccattgtt tttatgtaac ttttctagat atgaacctct 165720
gtttcggctt tcctgtctca ccaatttgtc tctagacacc cattctacta agaaattcca 165780
cagagtgtct tatacatata ctgttttata caaggtctct attcctctat tccatacacc 165840
ccataacttg tttctctcct atttccttac aaatgaagga taaagttaaa gcaatttttg 165900
gaaaagaatt ttattctcac atgaaagcac aggttgcggc ctatgtgggt gctgcctccc 165960
ttcctcttcc tcctccccac tcctctctgg ttgccatgga gaatacagtt gatggaaaca 166020
tacaattaca agcaacgata                                             166040
```

<210> SEQ ID NO 16

-continued

<211> LENGTH: 475
<212> TYPE: DNA
<213> ORGANISM: Mus musculus
<220> FEATURE:
<221> NAME/KEY: misc_feature
<222> LOCATION: (330)..(330)
<223> OTHER INFORMATION: "g" one of 2 alternative transcription initiation site
<220> FEATURE:
<221> NAME/KEY: misc_feature
<222> LOCATION: (427)..(427)
<223> OTHER INFORMATION: "a" one of 2 alternative transcription initiation site
<220> FEATURE:
<221> NAME/KEY: misc_feature
<222> LOCATION: (470)..(472)
<223> OTHER INFORMATION: the start codon of the mouse Pbsn gene

<400> SEQUENCE: 16
cagtattgct gatgaatcca tggttcaggt tcaagggtgt tgaaaacttg attgaaaatg 60
gtcagacttg atattcttcc agtatatctg attggaggaa ctgataatag atatcagatt 120
taaacctcta ccattccagt taagataata tgatagcatc ttgttcttca tcttcctttt 180
tcttaatagg gacataaaac caatgaataa aaatatacct gaaacatggg ataggcactg 240
ggcattggaa atgacaataa aagtaaattt tccatcccta gtaaagttct ccaggaacct 300
atttgtatac taaatgacac aatgtcaatg tcagtgcaca actgccaact gggatgcaga 360
acactgctca cgccaaccat cctgaaagcc aactataaaa agcagagaga tactctgcac 420
cttttcagtg aggtccagat acccacagag cagagacagt cgctcacaca tgatg 475

<210> SEQ ID NO 17
<211> LENGTH: 4282
<212> TYPE: DNA
<213> ORGANISM: Mus musculus
<220> FEATURE:
<221> NAME/KEY: misc_feature
<222> LOCATION: (1)..(3)
<223> OTHER INFORMATION: the stop codon of the mouse Pbn gene
<220> FEATURE:
<221> NAME/KEY: misc_feature
<222> LOCATION: (4)..(23)
<223> OTHER INFORMATION: Exon sequence and 1st part of the 3' UTR of the mouse Pbn gene
<220> FEATURE:
<221> NAME/KEY: misc_feature
<222> LOCATION: (24)..(3768)
<223> OTHER INFORMATION: intron sequence of the mouse Pbn gene
<220> FEATURE:
<221> NAME/KEY: misc_feature
<222> LOCATION: (3769)..(3982)
<223> OTHER INFORMATION: Exon sequence and 2nd part of the 3' UTR of the mouse Pbn gene
<220> FEATURE:
<221> NAME/KEY: misc_feature
<222> LOCATION: (3983)..(4282)
<223> OTHER INFORMATION: intergenic sequence

<400> SEQUENCE: 17
tgactcaaca agatcaggat taggtgagtc aaagcacatt aattttatat cttgaagttt 60
taattttaat tttattttaa tatttaagtt attaatattt aatatttaaa gtaaataata 120
ttttatttgt tctttatcct tttcatatat ttatataatg tatatttatc tttcatactt 180
ccacacacct catccaagca acacatctcc ctctatactt catggctttt aaattttatt 240
attatttatt attattatta cctcaatgaa tccaattggt gctatttctg aatagggtat 300
gtcaattcct ggaggcatga gtaatgtaat ataccagggc tattatgtaa tataaaaaaa 360
tggactgcag ggagctggtg gcacatgcat ttaacctagc gctcaagagg cagaagcaag 420

```
catatgtctg cgttttagat aaccctagtc tacagagtga gttccaggac agcaagggct    480
actcagagaa accctgtctc ataaaaccaa aaagtatatt ttttaaaggc agaagaggaa    540
aggagggagg gagggaggga aagaggcaga cagacagaca ggcaggcagg caggcaaaaa    600
gaaggaaaaa gaaaaatatg gaccctccct ctcccagaaa ctatcaactg gcaatagctc    660
tttggtgggg gggggggtc ctgaatccct ctctgctcaa ttctagaatg ttaattagct    720
tgatctgacc agggtcttgt gcagaacacc acagttgctg tgagttcatg attgtaacag    780
atctgtcatg ttcagaaaac agaattttat ggctctactc cccatccaga tgataattga    840
tggctaagca tccacagtca cttgtcctca tcctttgacc agctacaaat ttctgcacaa    900
accactcccc actgtaaaaa gttgagcaga agtcaaacat ggaggcacac acccttaatc    960
ccaacacttg ggaggcacgg gtagatgaat ctctgtgagt atcaagccag cctgatctac   1020
atactgagct ccagaagatc caggtacata gtctctatct aaacaaacaa acacaaagtt   1080
aaaaagttga tttgaccaaa attgagagaa gcataaatct atgagtattt ttaagaccgt   1140
ggcttggaaa catgacagtt catcaccact ggtctccttc ataggctcca tgagctccat   1200
tgtcacaggc ttttgactcg aattacaata gaaacccacc cttacccctg ttcttccata   1260
gatatgaagt tccttccatg gagctggcat gaaatttaat cagagagtgc ttggctcccc   1320
aatacagcct ttattgcacc agtggacgca aggatgattt tatagtgtgt tggggaagca   1380
tggtgacatc actgacatct tatcccacat acacagccta ttaagtacat ctaagcactg   1440
tgaacgagtt tcctagtcca tttgacatcg atttcttgat gccctacagc cacagcattt   1500
ggtgtcttca gcaatagtgc cctaccattt agatatggtg tatagtcaag agatatggca   1560
atagccaagt tattttggtt attccaaggc ttccttccat taataaatat catggtggta   1620
cccccatgac taaaaattag attttcactg aataaaccat gtcttctggg aacagcatta   1680
taccattgca gggatcctct gctgaaactt ttttaatact atatttttac ttagcttaca   1740
aactagtgga tttctgtaag acttcattta ccttcagttt cagttgaccc tcccctaccc   1800
tgttcttccc tatgcccaaa cacatccaca cctactcctc tagcccacag ctctcacttt   1860
ctaatcttcc ctgtcaccag tgcccaatta tatcgcctgt attattatat tttaatcaca   1920
caaccatagg tttccatatg aggttttaat aacccttcat tctggttaaa ccttccacca   1980
caccctgatt tccccattcc acaaccaact ccatgattaa gccttcctgc cccaagtatt   2040
cttctttata cttcatttta atggcattac atttgatgga cccacttcct tgatggaccc   2100
aattcaaacc agtttctaat tacctggatt ccttacatac tccatattat gcatacaaaa   2160
taaaagattc aagtctaatg tccacatgtg agatagaatg tgcagtttgt ctttctgagc   2220
ctgagtggcc tcattaagta taataatttc cagttccttc tatttacttg gaaatttcat   2280
attttcattg ttctctatgg ctgagtaata ttccatctta tacattacat tttccttatc   2340
cattcattag ttgatgaaca gttgggtcaa cttcgtttct tagctattat gaacttaacc   2400
tcagtgagca tggacattca aaggtctctg taacagaata taaacccctt tgtgtacata   2460
tctagaaatg gaggaactag agaaagcacc caaggaacta aagggaactg caaccctata   2520
ggtggaacaa caatatgaac taagcagtac cccggagctc ttgtctctag ctgcatatct   2580
atcaaaagat ggcctagtcg gccatcactg caaagagagg cccattggac ttgcaaactt   2640
tatatgcccc agtacagggg aatgccaggg ccaaaaaggg gggatgggtg ggtaggggag   2700
tggggggggg ttggggactt tttgtatagc attggaaatg taaatgagct aaatacctaa   2760
```

-continued

```
taaaaaatgg aaaaaaaaag aaatggtgta actgagtcac atgggaagtc tttttctaat   2820
ctttggattt gtttatttga tgttcatagt ttttgggttt tggttggttt tgttctaagt   2880
tctttgtata ttgtagacac taatcctcca tcacatgtgt agttggcaaa gatctccatt   2940
ccccgagata cctgtgcatt taattgacag cttcctttgc cgtagttttt aattccatga   3000
tatctgacaa gtgtttgtct tactttcttg ctacaagaat cctattcaaa gaatccatac   3060
ctgtgtctat ggttaacaca cactccatgc tttcttctct atcagcttca ggttaccatg   3120
tcttatgaca cggtctttga atcatttgga gttgaggttt ttttcaaggt gacagggaag   3180
agcccaggtt catttctctg tatcctgatg tccacttttt cctattcggt ctatttatgg   3240
aattatatat ttttatgtta ggtcattttt cagtggaggc attaacaata tccagaaggg   3300
gactatttct tactagtgtt gagatggtat tctcctatat ggggctggta ctgaaggcag   3360
caagttctac ccctagtctt cctgtgagat tcaactacta tctgggacct cgagtgagac   3420
tctgtctgta ggatacatgg ggcttggtaa actccaatgt gaaacaaaaa atatataatt   3480
ttagtttaga ttcatagaaa ctacatcctc aaataaacac ataagttcta aaaagtacca   3540
atttaggtct tgatataaga tcatttgtca tataaaaatt ttccatataa ggaaaatttc   3600
catacaaagt tcatgtatat ttccaaatat acaaaattct gtaaaatgtt tttgcatgat   3660
acatcttgtc attgtttgcc tctttaatgg cttgtatttg tttcattttc tactctcatc   3720
aaatatcatg tattactatc ctaaatatat gaaataattc tgttccagca ttacagatga   3780
catcaggaat tttccagtat atttttcctg gaacctgaaa catcaatatg aagatgaagc   3840
aatcttgtct ctcagatcat atttcctat ttattgcaaa ttacaattcc tgtctctgta   3900
ctttctcttt cactcattgt ttcccatgtt ctaatcggta ttagtgcatc tttgaatgtt   3960
taaataaatt tattttactt gcatacgtgt tgttaaaagg ggaagctaaa gtacaatgca   4020
cataaatacc tatttgactt tttttaaagg agaggagggt tggaggggtg gcatgtgatt   4080
gctcacgcct gtaatttcag caccggggaa agaggtagag acagttgaat cctctgatgt   4140
caccagtagc cagcctagac tacatgaaat attgcaggcc agtgagagat catcccagaa   4200
aacaaggcag ggacatgaca ggcagctcag tggtcaagag cactagctgc tcttccacag   4260
gacctgggtt atattcctaa ca                                            4282
```